US009823109B2

(12) United States Patent
Garrepy et al.

(10) Patent No.: US 9,823,109 B2
(45) Date of Patent: Nov. 21, 2017

(54) CHEMICAL ANALYZER

(71) Applicants: Mark Christopher Garrepy, Windham, ME (US); Stephan Hersey, Scarborough, ME (US)

(72) Inventors: Mark Christopher Garrepy, Windham, ME (US); Stephan Hersey, Scarborough, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 43 days.

(21) Appl. No.: 14/804,212

(22) Filed: Jul. 20, 2015

(65) Prior Publication Data

US 2015/0362352 A1     Dec. 17, 2015

Related U.S. Application Data

(63) Continuation of application No. 12/451,304, filed as application No. PCT/US2008/005909 on May 7, 2008, now Pat. No. 9,116,129.

(Continued)

(51) Int. Cl.
    *G01F 23/14*         (2006.01)
    *G01N 35/00*        (2006.01)
    (Continued)

(52) U.S. Cl.
    CPC .............. *G01F 23/14* (2013.01); *G01N 21/78* (2013.01); *G01N 35/00029* (2013.01);
    (Continued)

(58) Field of Classification Search
    CPC ......................... G01F 23/14; G01N 2035/1025
    See application file for complete search history.

(56) References Cited

U.S. PATENT DOCUMENTS

| 2,058,516 A | 10/1936 | Schaaff ........................... 141/24 |
| 2,204,471 A | 6/1940 | Campbell, Jr. et al. ........ 141/29 |

(Continued)

FOREIGN PATENT DOCUMENTS

| EP | 0042337 | 12/1981 | ............. G01N 35/06 |
| EP | 0042340 | 12/1981 | ............. G01N 35/00 |

(Continued)

OTHER PUBLICATIONS

The Notification Concerning Transmittal of International Preliminary Report on Patentability (Chapter I of the Patent Cooperation Treaty), in English, dated Nov. 19, 2009, the International Preliminary Report on Patentability (Chapter I of the Patent Cooperation Treaty), in English, dated Nov. 10, 2009, the Written Opinion of the International Searching Authority, in English, dated Sep. 17, 2008, and the International Search Report, in English, dated Sep. 17, 2008, which were issued by the International Bureau of WIPO for Applicants' corresponding PCT Application No. PCT/US2008/005909, filed on May 7, 2008.

(Continued)

*Primary Examiner* — P. Kathryn Wright
(74) *Attorney, Agent, or Firm* — Bodner & O'Rourke, LLP; Gerald T. Bodner; Christian P. Bodner

(57) ABSTRACT

A chemical analyzer includes a slide transport mechanism having a slide track adapted to hold a plurality of reagent test slides, a sample metering device, an incubator formed as a part of the slide transport mechanism to precisely maintain the temperature of the reagent test slides, a slide ejector mechanism to remove the slides from the slide transport mechanism, a sample preparation station, which includes a centrifuge, and associated electronics and software. The slide transport mechanism holds a plurality of trapezoidally-shaped reagent test slides about its circumference, which slides are loaded onto the transport mechanism by the slide (Continued)

inserter mechanism. The slide transport mechanism positions the reagent test slides under the sample metering device, which device deposits a predetermined volume of sample onto each slide. The slide transport mechanism also carries the slides above a reflectometer. After testing has been completed, the slide ejector mechanism automatically removes the reagent test slides from the slide transport mechanism.

3 Claims, 87 Drawing Sheets

Related U.S. Application Data

(60) Provisional application No. 60/962,869, filed on Aug. 1, 2007, provisional application No. 60/928,131, filed on May 8, 2007.

(51) Int. Cl.
*G01N 21/78* (2006.01)
*G01N 35/10* (2006.01)

(52) U.S. Cl.
CPC .............. *G01N 2035/00049* (2013.01); *G01N 2035/00138* (2013.01); *G01N 2035/1025* (2013.01)

(56) References Cited

U.S. PATENT DOCUMENTS

| | | | |
|---|---|---|---|
| 2,363,474 A | 11/1944 | Schlesinger | 222/179.5 |
| 2,586,513 A | 2/1952 | Butler | 210/94 |
| 2,598,869 A | 6/1952 | White | 141/113 |
| 2,665,825 A | 1/1954 | Poitras et al. | 222/209 |
| 2,692,820 A | 10/1954 | Alway et al. | 210/659 |
| 2,721,008 A | 10/1955 | Morgan, Jr. | 222/334 |
| 2,797,149 A | 6/1957 | Skeggs | 436/53 |
| 2,802,605 A | 8/1957 | Parker | 222/215 |
| 3,036,893 A | 5/1962 | Natelson | 436/170 |
| 3,106,845 A | 10/1963 | Dimmick | 73/864.11 |
| 3,164,304 A | 1/1965 | Jager et al. | 222/192 |
| 3,190,731 A | 6/1965 | Weiskopf | 422/102 |
| 3,300,099 A | 1/1967 | Marona | 222/207 |
| 3,323,689 A | 6/1967 | Elmore | 222/385 |
| 3,341,087 A | 9/1967 | Rosin et al. | 222/422 |
| 3,367,746 A | 2/1968 | Maurukas | 422/100 |
| 3,449,081 A | 6/1969 | Hughes | 422/61 |
| 3,460,529 A | 8/1969 | Leucci | 600/580 |
| 3,526,480 A | 9/1970 | Findl et al. | 422/66 |
| 3,533,744 A | 10/1970 | Unger | 436/63 |
| 3,572,400 A | 3/1971 | Casner et al. | 141/1 |
| 3,574,064 A | 4/1971 | Binnings et al. | 435/286.4 |
| 3,615,240 A | 10/1971 | Sanz | 73/864.13 |
| 3,616,264 A | 10/1971 | Ray et al. | 435/287.3 |
| 3,618,829 A | 11/1971 | Elmore et al. | 222/209 |
| 3,645,423 A | 2/1972 | DeGraw | 222/207 |
| 3,650,437 A | 3/1972 | Binnings et al. | 222/136 |
| 3,659,934 A | 5/1972 | Costanza et al. | 353/103 |
| 3,675,488 A | 7/1972 | Viktora et al. | 73/863.72 |
| 3,748,044 A | 7/1973 | Liston | 356/409 |
| 3,754,866 A | 8/1973 | Ritchie et al. | 422/73 |
| 3,756,920 A | 9/1973 | Kelbaugh et al. | 435/287.3 |
| 3,758,274 A | 9/1973 | Ritchie et al. | 422/50 |
| 3,788,816 A | 1/1974 | Rohrbaugh et al. | 422/64 |
| 3,790,346 A | 2/1974 | Ritchie | 422/64 |
| 3,810,779 A | 5/1974 | Pickett et al. | 422/256 |
| 3,832,135 A | 8/1974 | Drozdowski et al. | 436/47 |
| 3,855,867 A | 12/1974 | Roach | 73/864.18 |
| 3,856,470 A | 12/1974 | Cullis et al. | 422/64 |
| 3,873,273 A | 3/1975 | Moran et al. | 422/64 |
| 3,883,308 A | 5/1975 | Matte | 422/64 |
| 3,904,372 A | 9/1975 | Lightner | 422/63 |
| 3,915,651 A | 10/1975 | Nishi | 73/864.16 |
| 3,918,913 A | 11/1975 | Stevenson et al. | 73/863.72 |
| 3,926,514 A | 12/1975 | Costanza et al. | 353/113 |
| 3,942,952 A | 3/1976 | Atwood | 73/864.91 |
| 4,041,995 A | 8/1977 | Columbus | 141/275 |
| 4,043,756 A | 8/1977 | Sommervold | 436/43 |
| 4,052,161 A | 10/1977 | Atwood et al. | 436/34 |
| 4,059,405 A | 11/1977 | Sodickson et al. | 436/44 |
| 4,061,469 A | 12/1977 | DuBose | 422/64 |
| 4,067,694 A | 1/1978 | Blakely et al. | 422/63 |
| 4,090,791 A | 5/1978 | Siddiqi et al. | 356/414 |
| 4,118,280 A | 10/1978 | Charles et al. | 195/127 |
| 4,119,381 A | 10/1978 | Muka et al. | 356/244 |
| 4,142,656 A | 3/1979 | Smith et al. | 222/325 |
| 4,152,390 A | 5/1979 | Nosco et al. | 422/63 |
| 4,160,646 A | 7/1979 | Furutani et al. | 436/169 |
| 4,161,508 A | 7/1979 | Jänchen | 422/100 |
| 4,198,483 A | 4/1980 | Sogi et al. | 435/309.1 |
| 4,198,485 A | 4/1980 | Stark, Jr. | 521/55 |
| 4,210,724 A | 7/1980 | Sogi et al. | 435/309.2 |
| 4,219,529 A | 8/1980 | Tersteeg et al. | 422/65 |
| 4,224,032 A | 9/1980 | Glover et al. | 436/46 |
| 4,234,538 A | 11/1980 | Ginsberg et al. | 422/64 |
| 4,234,539 A | 11/1980 | Ginsberg et al. | 422/64 |
| 4,236,894 A | 12/1980 | Sommervold | 436/43 |
| 4,264,560 A | 4/1981 | Natelson | 422/58 |
| 4,271,123 A | 6/1981 | Curry et al. | 422/64 |
| 4,272,482 A | 6/1981 | Jessop et al. | 422/65 |
| 4,277,440 A | 7/1981 | Jessop et al. | 422/100 |
| 4,287,155 A | 9/1981 | Tersteeg et al. | 422/64 |
| 4,296,069 A | 10/1981 | Smith et al. | 422/64 |
| 4,296,070 A | 10/1981 | Montalto et al. | 422/65 |
| 4,298,571 A | 11/1981 | DiFulvio et al. | 422/65 |
| 4,298,575 A | 11/1981 | Berglund | 73/864.13 |
| 4,302,420 A | 11/1981 | Jakubowicz et al. | 422/63 |
| 4,303,611 A | 12/1981 | Jessop | 422/65 |
| 4,308,231 A | 12/1981 | Kolber et al. | 422/64 |
| 4,321,122 A | 3/1982 | Whitcomb et al. | 204/400 |
| 4,325,909 A | 4/1982 | Coulter et al. | 422/63 |
| 4,335,620 A | 6/1982 | Adams | 73/863.11 |
| 4,340,390 A | 7/1982 | Collins et al. | 436/54 |
| 4,347,750 A | 9/1982 | Tersteeg et al. | 73/864.31 |
| 4,351,799 A | 9/1982 | Gross et al. | 422/63 |
| 4,359,447 A | 11/1982 | Welch | 422/63 |
| RE31,150 E | 2/1983 | Ginsberg et al. | 422/64 |
| 4,387,990 A | 6/1983 | Yazawa et al. | 356/244 |
| 4,392,195 A | 7/1983 | Inoue | 700/162 |
| 4,399,711 A | 8/1983 | Klein | 73/864.16 |
| 4,420,566 A | 12/1983 | Jessop et al. | 436/46 |
| 4,424,191 A | 1/1984 | Jakubowicz | 422/65 |
| 4,429,373 A | 1/1984 | Fletcher et al. | 422/55 |
| 4,430,299 A | 2/1984 | Horne | 422/64 |
| 4,441,532 A | 4/1984 | Hrubesh | 141/1 |
| 4,451,433 A | 5/1984 | Yamashita et al. | 422/63 |
| 4,452,899 A | 6/1984 | Alston | 436/46 |
| 4,455,280 A | 6/1984 | Shinohara et al. | 422/63 |
| 4,475,666 A | 10/1984 | Bilbrey et al. | 222/14 |
| 4,488,810 A | 12/1984 | Hatanaka et al. | 356/244 |
| 4,503,011 A | 3/1985 | Hubeau | 422/73 |
| 4,512,952 A | 4/1985 | Blanding et al. | 422/63 |
| 4,522,921 A | 6/1985 | Ogawa | 436/47 |
| 4,539,855 A | 9/1985 | Jacobs | 73/864.25 |
| 4,540,549 A | 9/1985 | Manabe | 422/64 |
| 4,549,809 A | 10/1985 | Minekane et al. | 356/436 |
| D282,203 S | 1/1986 | Leonard et al. | D24/1.1 |
| 4,568,519 A | 2/1986 | Hamilton et al. | 422/64 |
| 4,584,275 A | 4/1986 | Okano et al. | 435/287.3 |
| 4,586,546 A * | 5/1986 | Mezei | G01N 35/1011 141/2 |
| 4,599,219 A | 7/1986 | Cooper et al. | 422/61 |
| 4,615,360 A | 10/1986 | Jacobs | 141/18 |
| 4,627,014 A | 12/1986 | Lo et al. | 702/25 |
| 4,629,703 A | 12/1986 | Uffenheimer | 436/45 |
| 4,644,807 A | 2/1987 | Mar | 73/864.62 |
| 4,647,431 A | 3/1987 | Sekine et al. | 422/63 |
| 4,656,006 A | 4/1987 | Assmann et al. | 422/63 |
| 4,656,007 A | 4/1987 | Douchy et al. | 422/64 |
| 4,670,219 A | 6/1987 | Nelson et al. | 422/63 |
| 4,675,301 A | 6/1987 | Charneski et al. | 436/180 |
| 4,678,755 A | 7/1987 | Shinohara et al. | 436/43 |

(56) References Cited

U.S. PATENT DOCUMENTS

| | | | |
|---|---|---|---|
| 4,680,164 A | 7/1987 | Kelln | 422/72 |
| 4,681,741 A | 7/1987 | Hanaway | 422/100 |
| 4,695,430 A | 9/1987 | Coville et al. | 422/65 |
| 4,706,207 A | 11/1987 | Hennessy et al. | 701/21 |
| 4,710,352 A | 12/1987 | Slater et al. | 422/63 |
| 4,713,974 A | 12/1987 | Stone | 73/864.23 |
| 4,719,085 A | 1/1988 | Jacobs | 422/56 |
| 4,731,058 A | 3/1988 | Doan | 604/155 |
| 4,737,344 A | 4/1988 | Koizumi et al. | 422/100 |
| 4,738,826 A | 4/1988 | Harris | 422/100 |
| 4,752,449 A | 6/1988 | Jackson et al. | 422/73 |
| 4,757,449 A | 7/1988 | Kurihara et al. | 701/51 |
| 4,761,268 A | 8/1988 | Andersen et al. | 422/72 |
| 4,769,009 A | 9/1988 | Dykstra | 604/155 |
| 4,770,053 A | 9/1988 | Broderick et al. | 73/866.5 |
| 4,774,055 A | 9/1988 | Wakatake et al. | 422/64 |
| 4,785,407 A | 11/1988 | Sakagami | 702/22 |
| 4,794,085 A | 12/1988 | Jessop et al. | 436/54 |
| 4,795,613 A | 1/1989 | Azuma et al. | 422/64 |
| 4,798,705 A | 1/1989 | Jakubowicz et al. | 422/63 |
| 4,808,380 A | 2/1989 | Minekane | 422/64 |
| 4,814,279 A | 3/1989 | Sugaya | 435/303.1 |
| 4,821,586 A | 4/1989 | Scordato et al. | 73/864.18 |
| 4,823,992 A | 4/1989 | Fiorentini | 222/333 |
| 4,826,659 A | 5/1989 | Akisada | 422/63 |
| 4,837,159 A | 6/1989 | Yamada | 436/45 |
| 4,841,208 A | 6/1989 | Itoh | 318/561 |
| 4,855,109 A | 8/1989 | Muraishi et al. | 422/63 |
| 4,863,695 A | 9/1989 | Fullemann | 422/100 |
| 4,928,540 A | 5/1990 | Kido et al. | 73/864.11 |
| 4,931,257 A | 6/1990 | Quenin et al. | 422/100 |
| 4,935,374 A | 6/1990 | Jacobs et al. | 436/103 |
| 4,943,415 A | 7/1990 | Przybylowicz et al. | 422/56 |
| 4,963,333 A | 10/1990 | Shaw et al. | 422/568 |
| 4,970,468 A * | 11/1990 | Ishizawa | G01F 23/263 324/662 |
| 5,034,191 A | 7/1991 | Porte | 422/64 |
| 5,037,613 A | 8/1991 | Shaw et al. | 422/64 |
| 5,039,615 A | 8/1991 | Takahata | 436/44 |
| 5,049,359 A | 9/1991 | Azuma et al. | G01N 35/00 |
| 5,049,487 A | 9/1991 | Phillips et al. | 435/4 |
| 5,075,079 A | 12/1991 | Kerr et al. | 422/64 |
| 5,089,229 A | 2/1992 | Heidt et al. | 422/64 |
| 5,102,624 A | 4/1992 | Muraishi | 422/64 |
| 5,126,952 A | 6/1992 | Kildal-Brandt et al. | 702/91 |
| 5,141,871 A | 8/1992 | Kureshy et al. | 436/47 |
| 5,149,501 A | 9/1992 | Babson et al. | 422/58 |
| 5,174,960 A | 12/1992 | Shaw et al. | 422/63 |
| 5,174,963 A | 12/1992 | Fuller et al. | 422/82.05 |
| 5,182,083 A | 1/1993 | Barker et al. | 422/64 |
| 5,213,764 A | 5/1993 | Kerr et al. | 422/100 |
| 5,250,262 A | 10/1993 | Heidt et al. | 422/64 |
| 5,257,212 A | 10/1993 | Kildal-Brandt et al. | 702/25 |
| 5,283,195 A | 2/1994 | Muszak et al. | 436/48 |
| 5,304,343 A | 4/1994 | Meserol | 422/100 |
| 5,314,825 A | 5/1994 | Weyrauch et al. | 436/43 |
| 5,336,467 A | 8/1994 | Heidt et al. | 422/64 |
| 5,340,540 A | 8/1994 | Miller | 422/64 |
| 5,425,918 A | 6/1995 | Healey et al. | 422/64 |
| 5,455,008 A | 10/1995 | Earley et al. | 422/100 |
| 5,463,895 A * | 11/1995 | Brentz | G01F 23/14 73/61.71 |
| 5,474,910 A | 12/1995 | Alfano | 435/34 |
| 5,478,750 A | 12/1995 | Bernstein et al. | 436/164 |
| 5,483,843 A | 1/1996 | Miller et al. | 73/864.23 |
| 5,525,514 A | 6/1996 | Jacobs et al. | 436/46 |
| 5,525,551 A | 6/1996 | Ohta | 438/789 |
| 5,645,798 A | 7/1997 | Schreiber et al. | 422/58 |
| 5,653,942 A | 8/1997 | Terashima et al. | 422/634 |
| 5,654,200 A | 8/1997 | Copeland et al. | 436/46 |
| 5,658,532 A | 8/1997 | Kurosaki et al. | 422/64 |
| 5,730,939 A | 3/1998 | Kurumada et al. | 422/67 |
| 5,753,512 A | 5/1998 | Riall et al. | 436/50 |
| 5,772,962 A | 6/1998 | Uchida et al. | 422/67 |
| 5,811,306 A | 9/1998 | Komatsu | 436/54 |
| 5,837,546 A | 11/1998 | Allen et al. | 436/169 |
| 5,879,944 A | 3/1999 | Komatsu | 436/50 |
| 5,897,837 A | 4/1999 | Mizuno | 422/100 |
| 6,013,528 A | 1/2000 | Jacobs et al. | 436/54 |
| 6,136,270 A | 10/2000 | Maes et al. | 422/64 |
| 6,183,693 B1 | 2/2001 | Bogen et al. | 422/64 |
| 6,268,162 B1 | 7/2001 | Phillips et al. | 435/14 |
| 6,296,809 B1 | 10/2001 | Richards et al. | 422/64 |
| 6,326,160 B1 | 12/2001 | Dunn et al. | 435/14 |
| 6,352,861 B1 | 3/2002 | Copeland et al. | 436/46 |
| 6,372,485 B1 | 4/2002 | Clark et al. | 435/288.7 |
| 6,387,326 B1 | 5/2002 | Edwards et al. | 422/63 |
| 6,458,324 B1 | 10/2002 | Schinzel | 422/65 |
| 6,531,094 B2 | 3/2003 | Seto et al. | 422/64 |
| 6,531,095 B2 | 3/2003 | Hammer et al. | 422/64 |
| 6,663,832 B2 | 12/2003 | Lebl et al. | 422/64 |
| 6,783,733 B2 | 8/2004 | Bogen et al. | 422/64 |
| 6,797,518 B1 | 9/2004 | Jacobs et al. | 436/46 |
| 6,830,731 B1 | 12/2004 | Buechler et al. | 422/82.08 |
| 6,890,761 B2 | 5/2005 | Ishizawa et al. | 436/180 |
| 6,913,933 B2 | 7/2005 | Jacobs et al. | 436/180 |
| 6,919,044 B1 | 7/2005 | Shibata et al. | 422/63 |
| 6,937,955 B2 | 8/2005 | Barnes | 702/94 |
| 6,984,527 B2 | 1/2006 | Miller et al. | 436/180 |
| 7,198,956 B2 | 4/2007 | Uffenheimer et al. | 436/180 |
| 7,256,045 B2 | 8/2007 | Jacobs et al. | 436/43 |
| 7,270,785 B1 | 9/2007 | Lemme et al. | 422/64 |
| 7,616,317 B2 | 11/2009 | Misener et al. | 356/466 |
| 7,632,468 B2 | 12/2009 | Barski et al. | 422/561 |
| 8,287,823 B2 | 10/2012 | Sellers et al. | 422/563 |
| 8,585,989 B2 | 11/2013 | Rich et al. | 422/563 |
| 2001/0019826 A1 | 9/2001 | Ammann | 435/6.11 |
| 2002/0054830 A1 | 5/2002 | Bogen et al. | 422/64 |
| 2002/0182108 A1 | 12/2002 | Ishihara et al. | 422/63 |
| 2003/0022380 A1 | 1/2003 | Jakubowicz et al. | 436/54 |
| 2003/0027206 A1 | 2/2003 | Ammann et al. | 435/6 |
| 2003/0104634 A1 | 6/2003 | Jacobs et al. | 436/180 |
| 2004/0072363 A1 | 4/2004 | Schembri | 436/174 |
| 2004/0191923 A1 | 9/2004 | Tomasso et al. | 436/180 |
| 2005/0036911 A1 | 2/2005 | Sellers et al. | 422/65 |
| 2006/0148063 A1 | 7/2006 | Fauzzi et al. | 435/286.4 |
| 2006/0211253 A1 | 9/2006 | Chen et al. | 438/714 |
| 2006/0275892 A1 * | 12/2006 | Shibazaki | B01L 3/508 435/287.2 |
| 2007/0166194 A1 | 7/2007 | Wakatake | 422/64 |
| 2011/0093207 A1 | 4/2011 | Ingber et al. | 702/19 |
| 2011/0304722 A1 | 12/2011 | Nilsson et al. | 348/79 |
| 2013/0132006 A1 | 5/2013 | Gwynn et al. | 702/55 |

FOREIGN PATENT DOCUMENTS

| | | | |
|---|---|---|---|
| EP | 341438 A2 * | 11/1989 | |
| EP | 0353592 | 2/1990 | G01N 35/02 |
| JP | 62-194464 * | 8/1987 | |
| WO | WO 96/05488 | 2/1996 | G01J 3/30 |

OTHER PUBLICATIONS

The Notification of Transmittal of the International Search Report and the Written Opinion of the International Searching Authority, or the Declaration, in English, dated Mar. 25, 2015, the Written Opinion of the International Searching Authority, in English, dated Mar. 25, 2015, and the International Search Report, in English, dated Mar. 25, 2015, which were issued by the International Bureau of WIPO for Applicants' related PCT Application No. PCT/US15/10671, filed on Jan. 8, 2015.

The International Preliminary Report on Patentability (Chapter I of the Patent Cooperation Treaty), in English, dated Nov. 7, 2006, Written Opinion of the International Searching Authority, in English, dated Aug. 23, 2006, and the International Search Report, in English, dated Aug. 23, 2006, which were issued by the International Bureau of WIPO for Applicants' related PCT Application No. PCT/US04/25073, filed on Aug. 4, 2004.

* cited by examiner

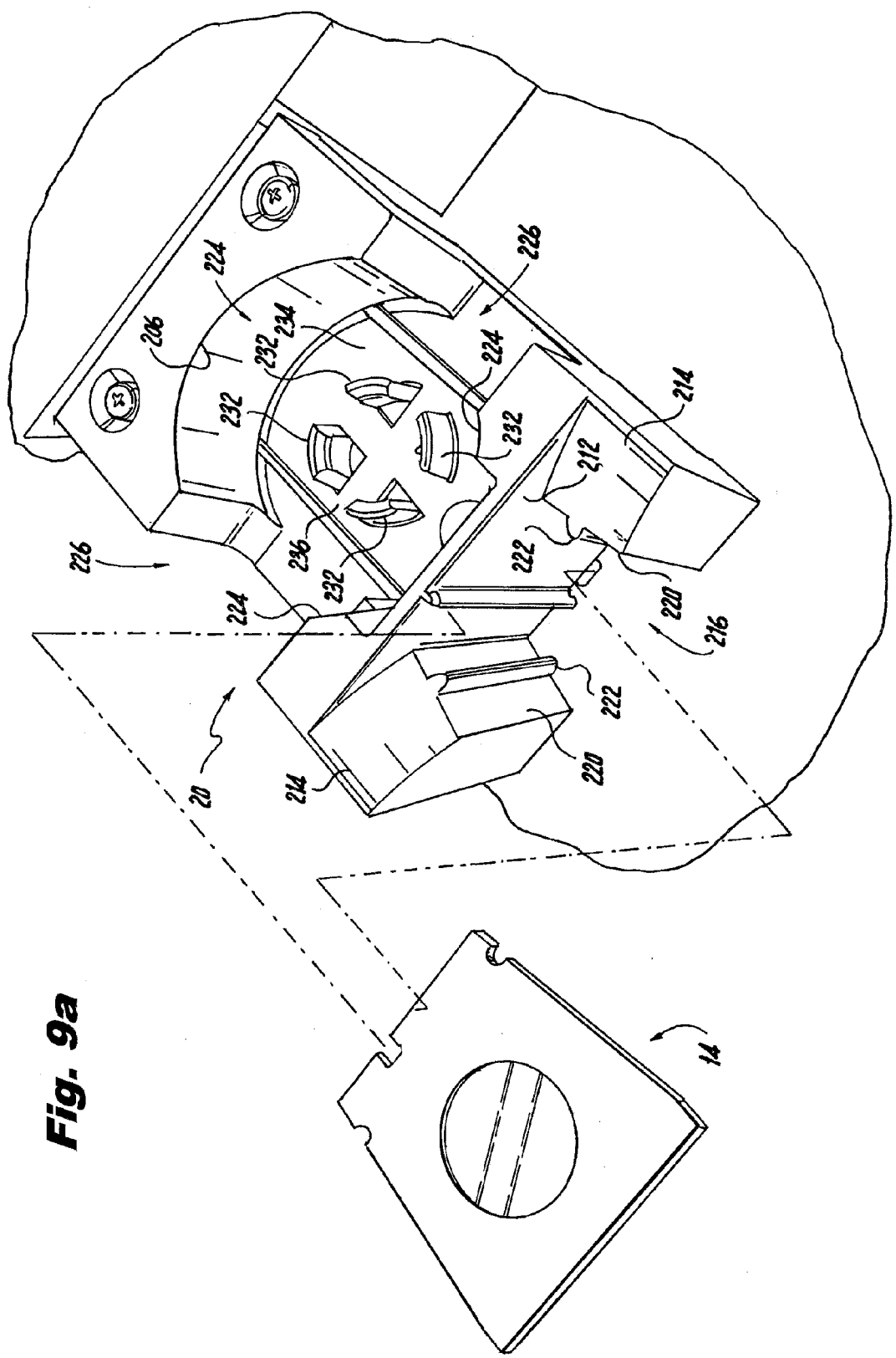

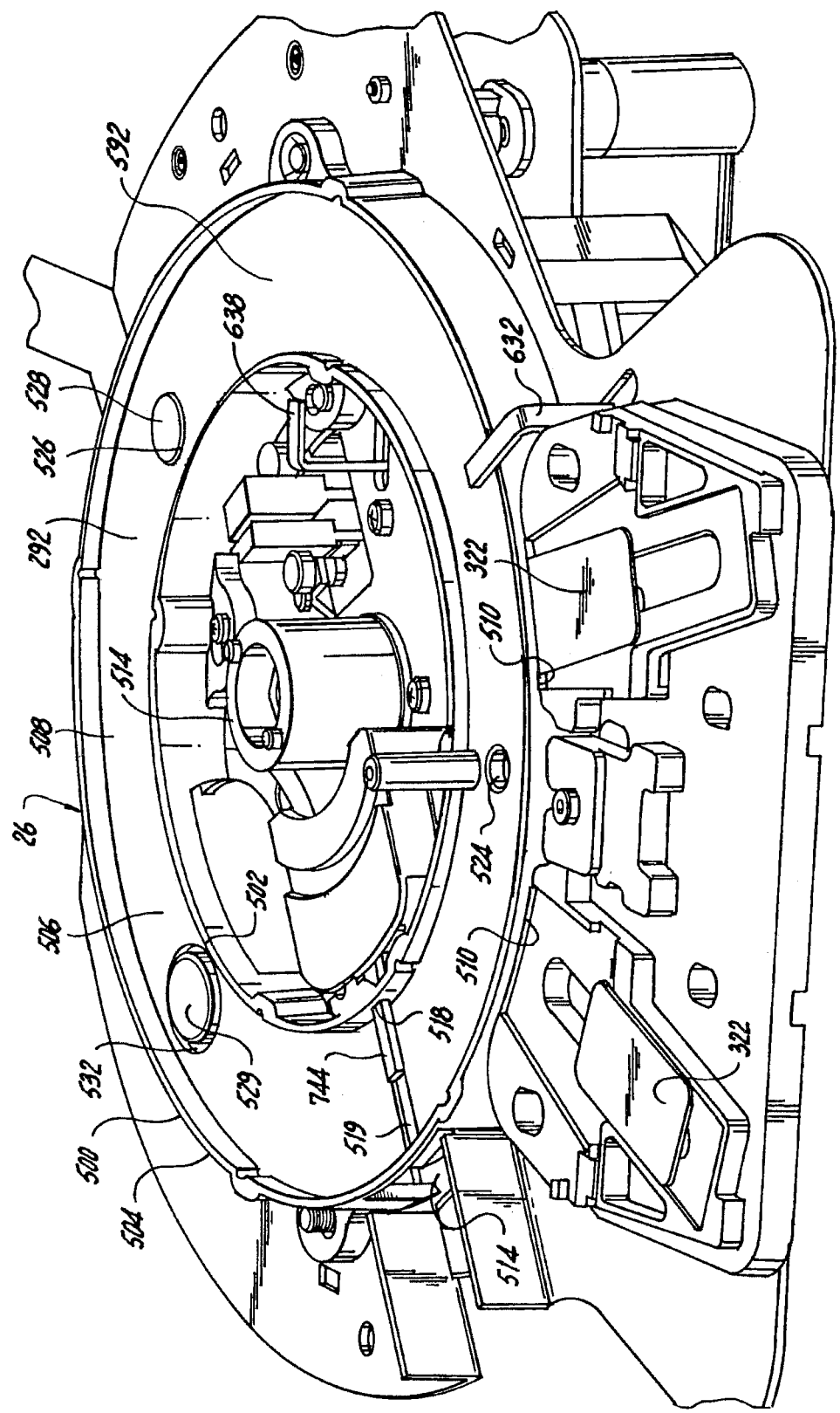

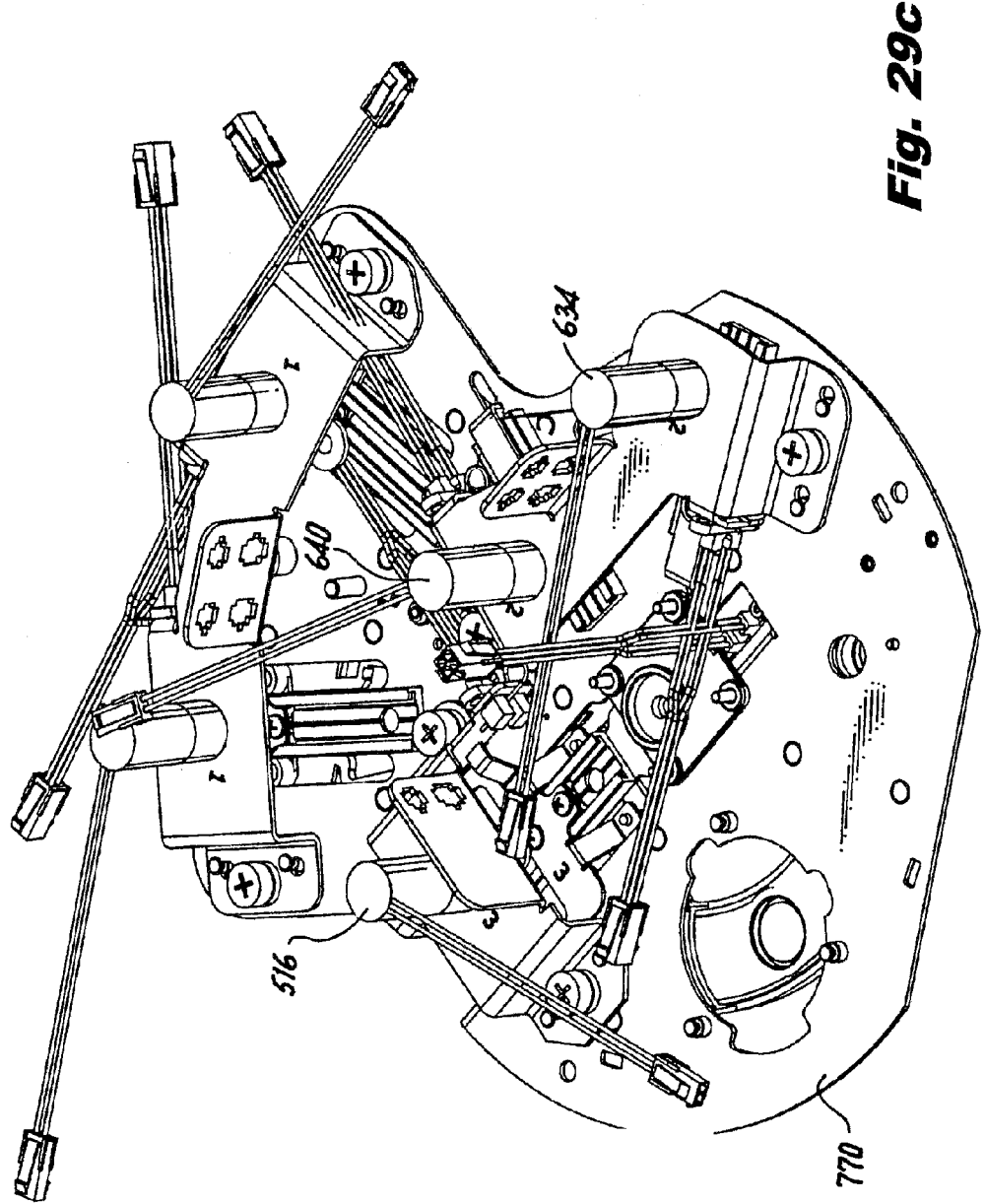

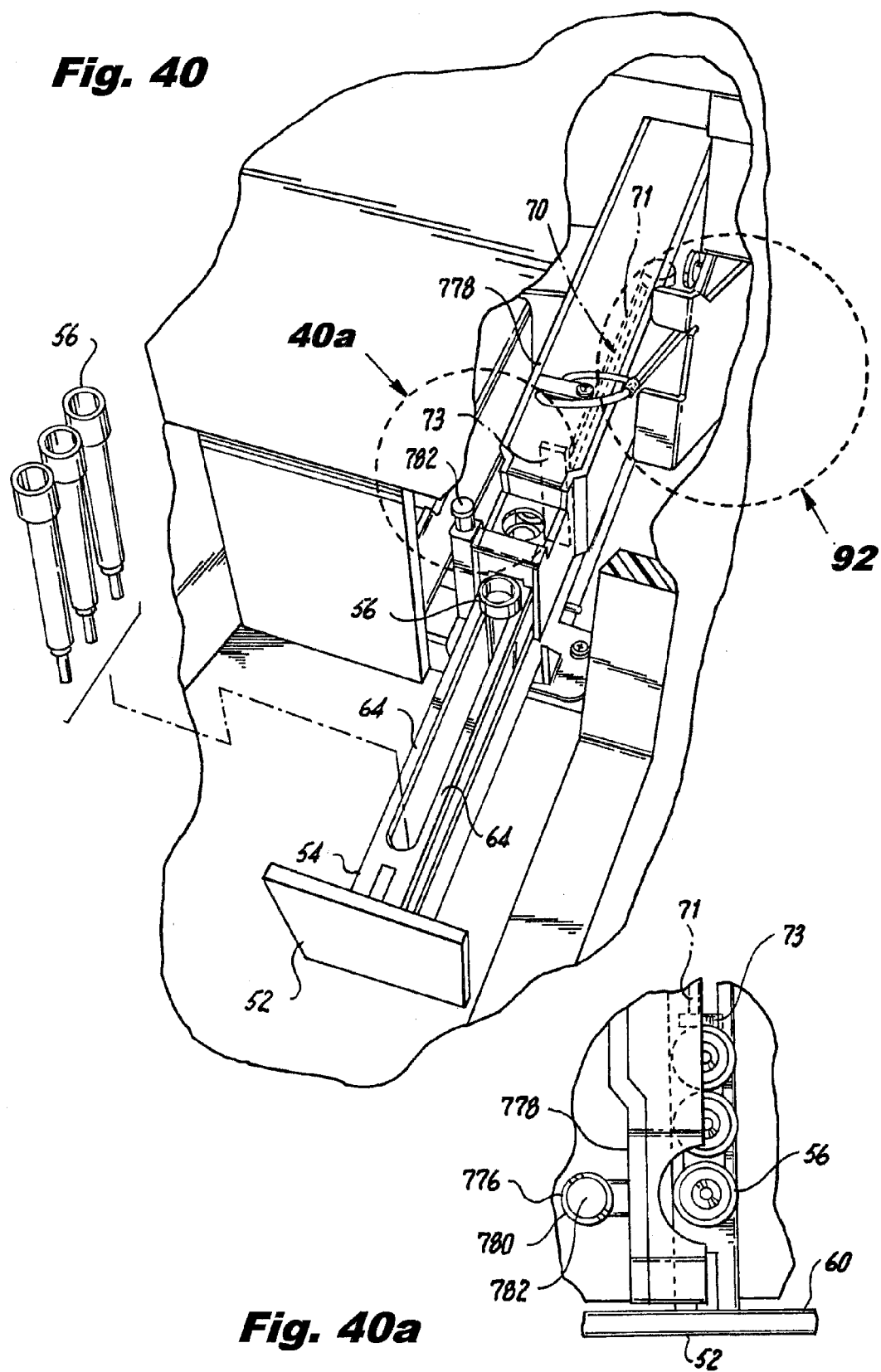

Fig. 44
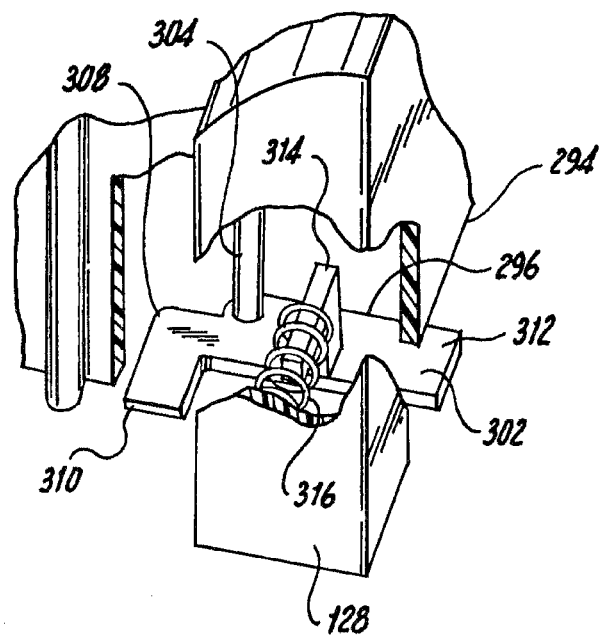
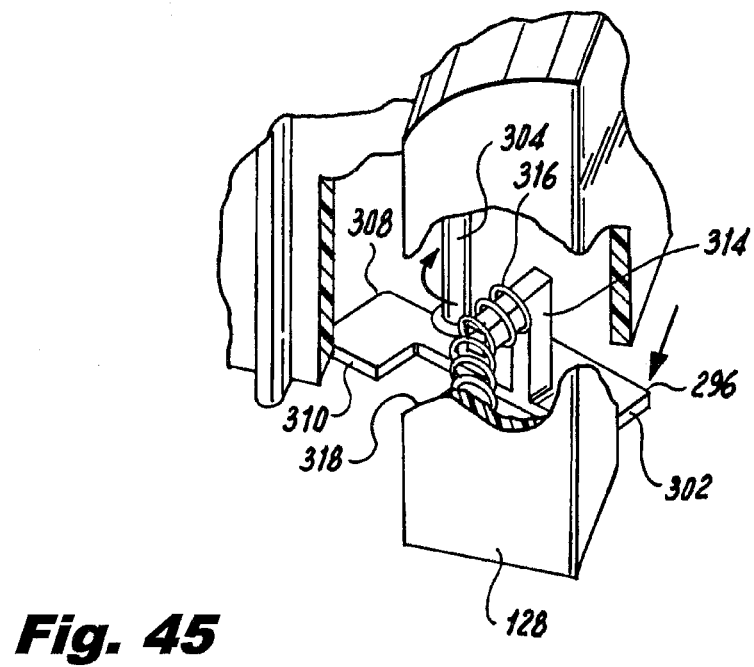
Fig. 45

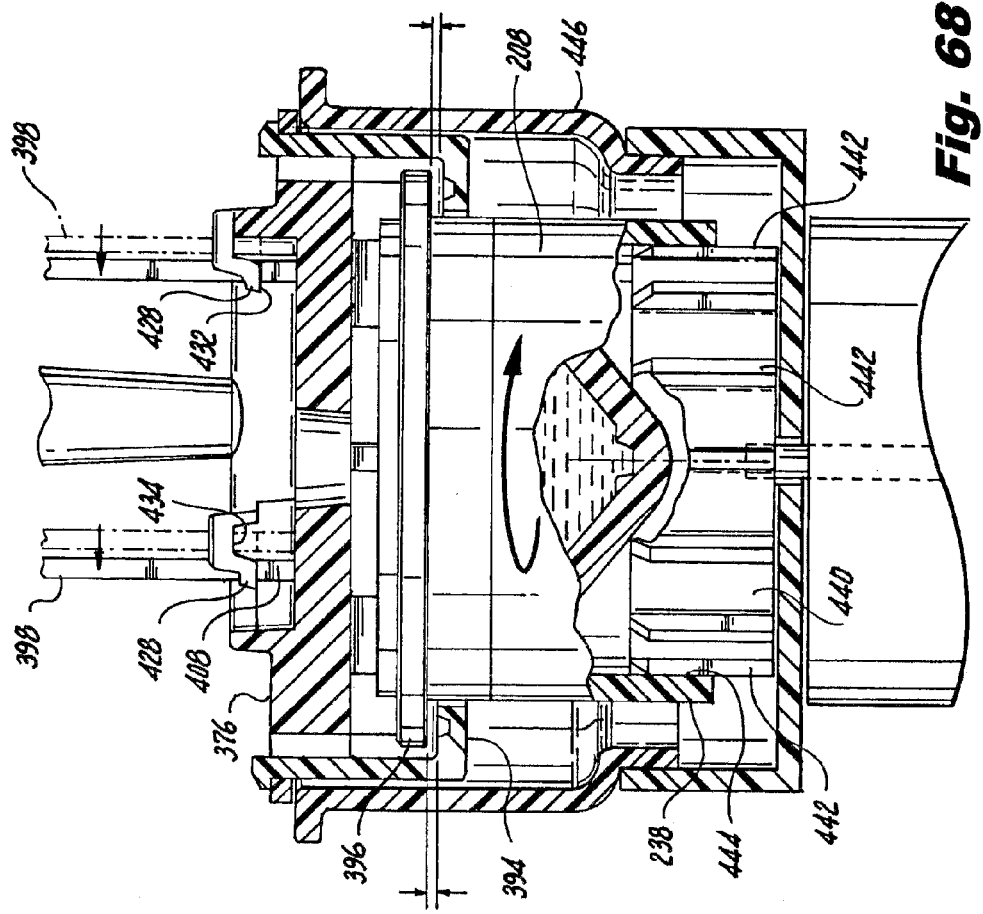
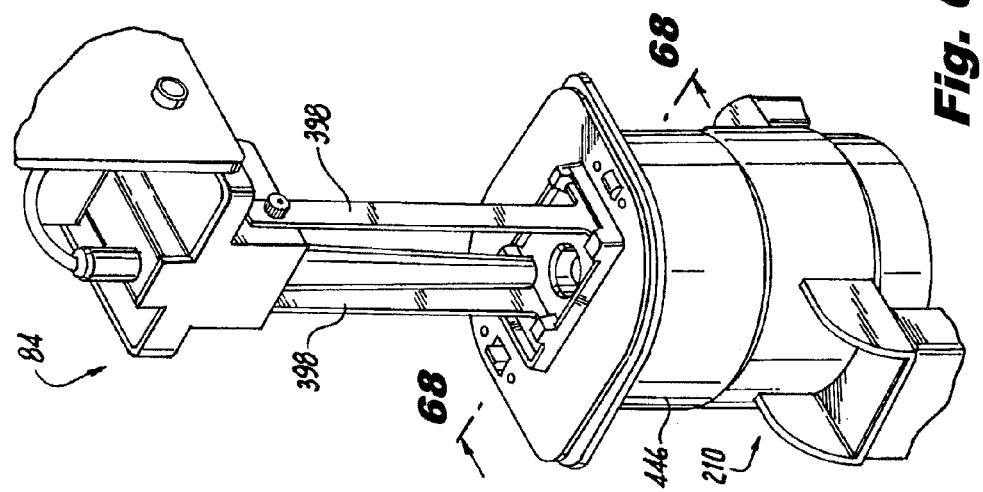
Fig. 68
Fig. 67

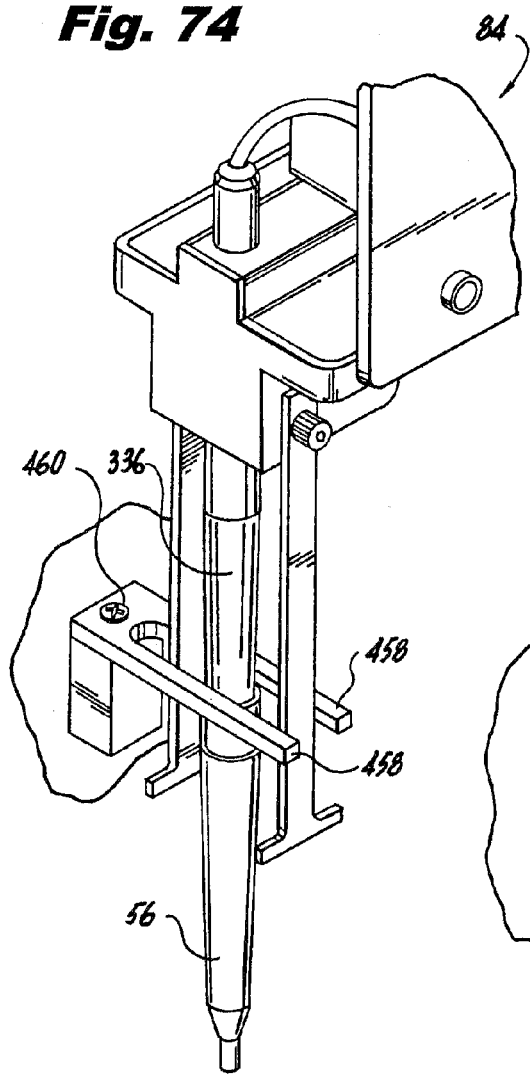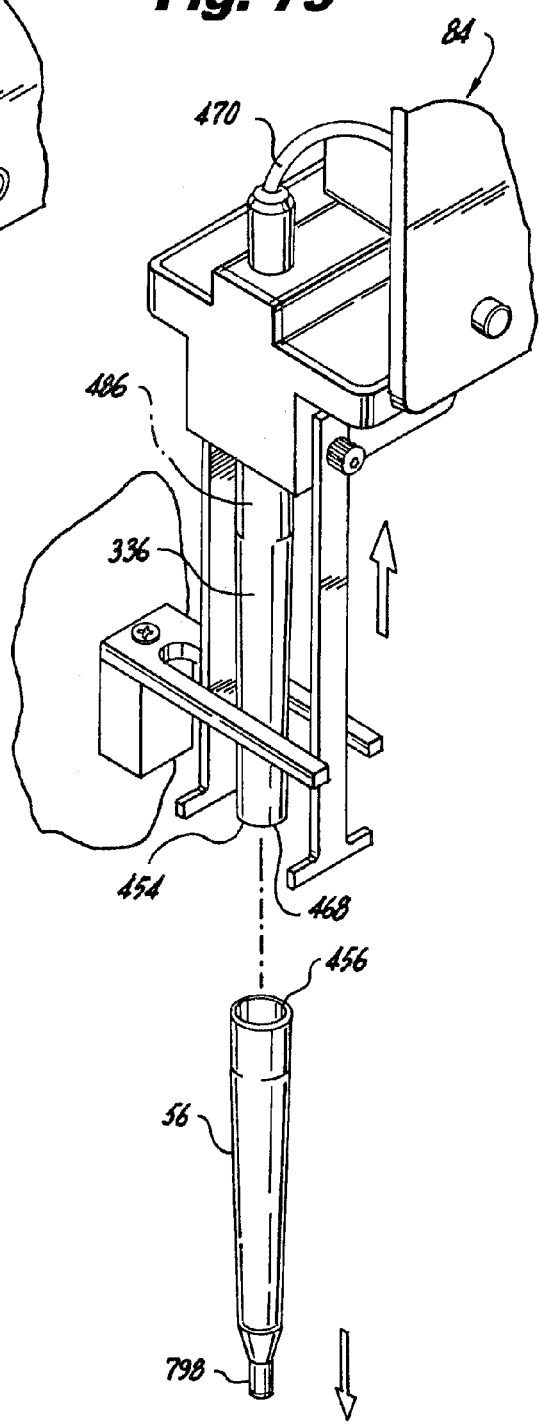

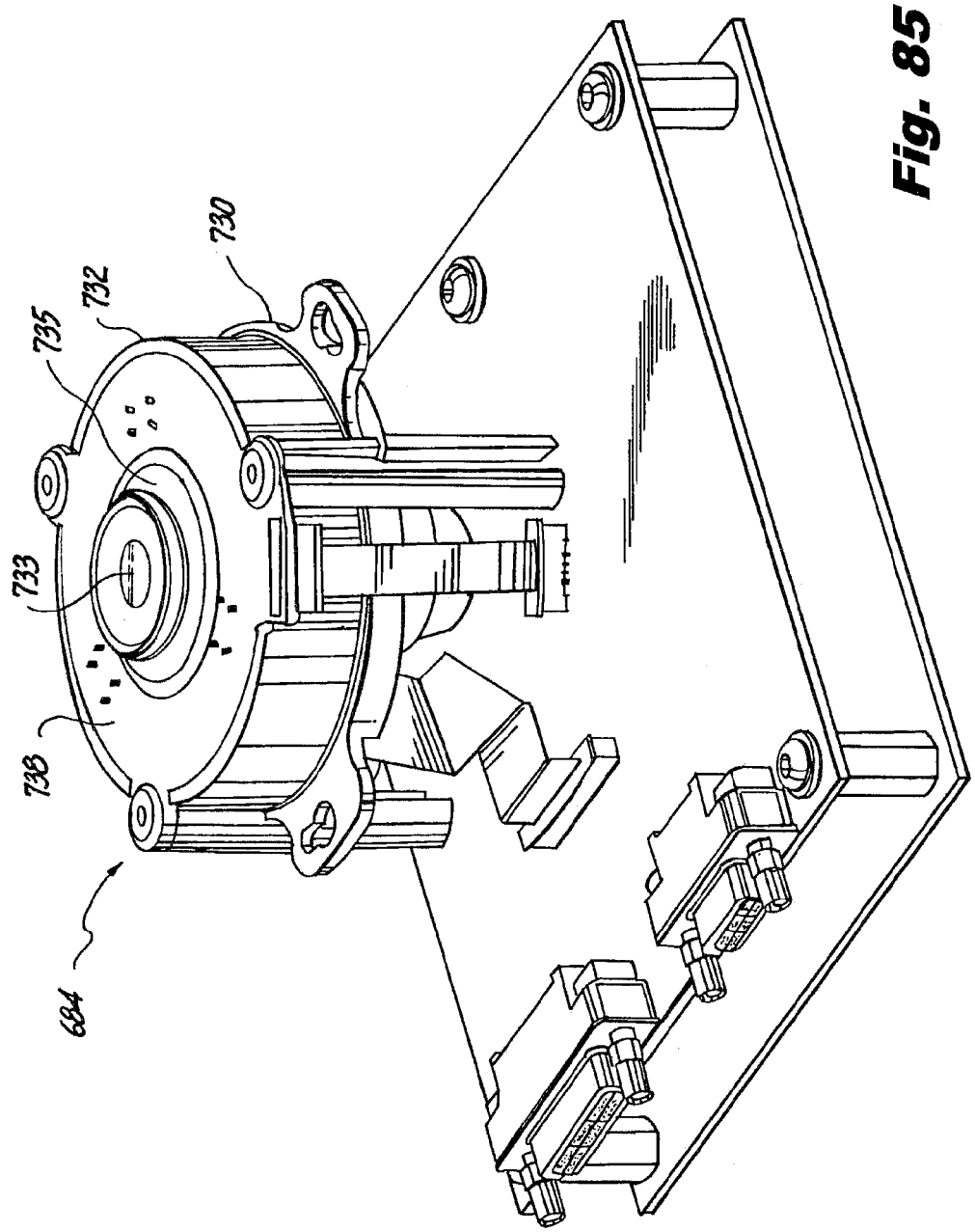

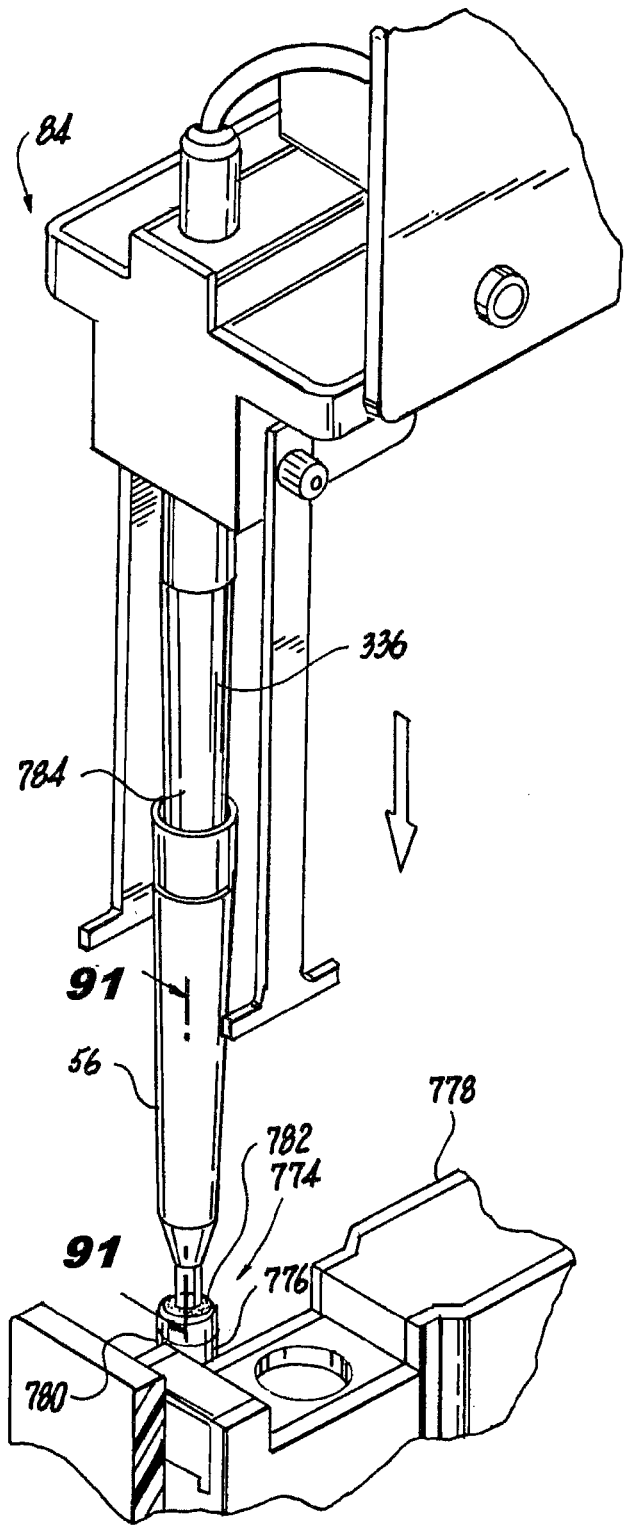
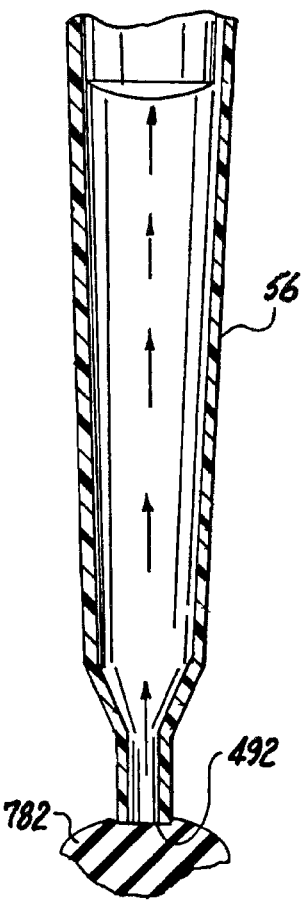
Fig. 90
Fig. 91

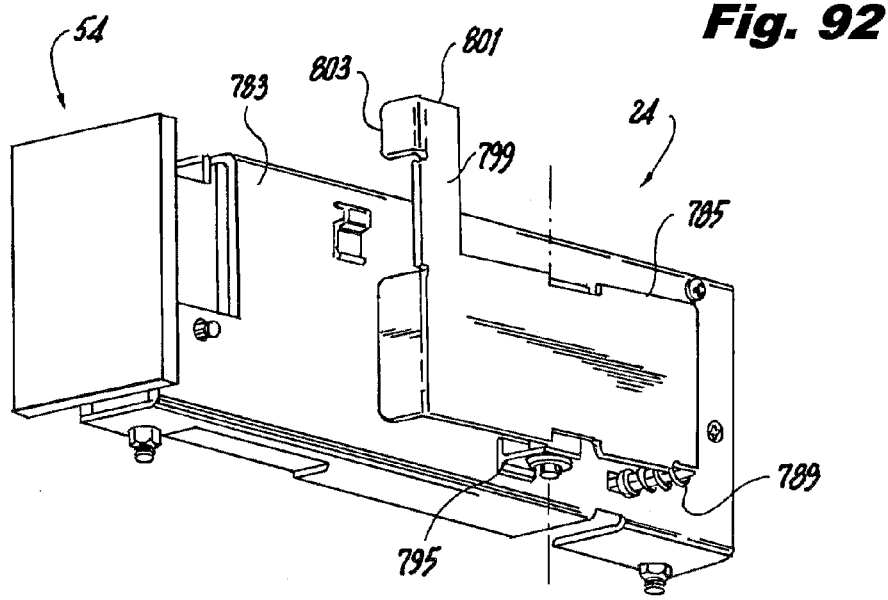
Fig. 92
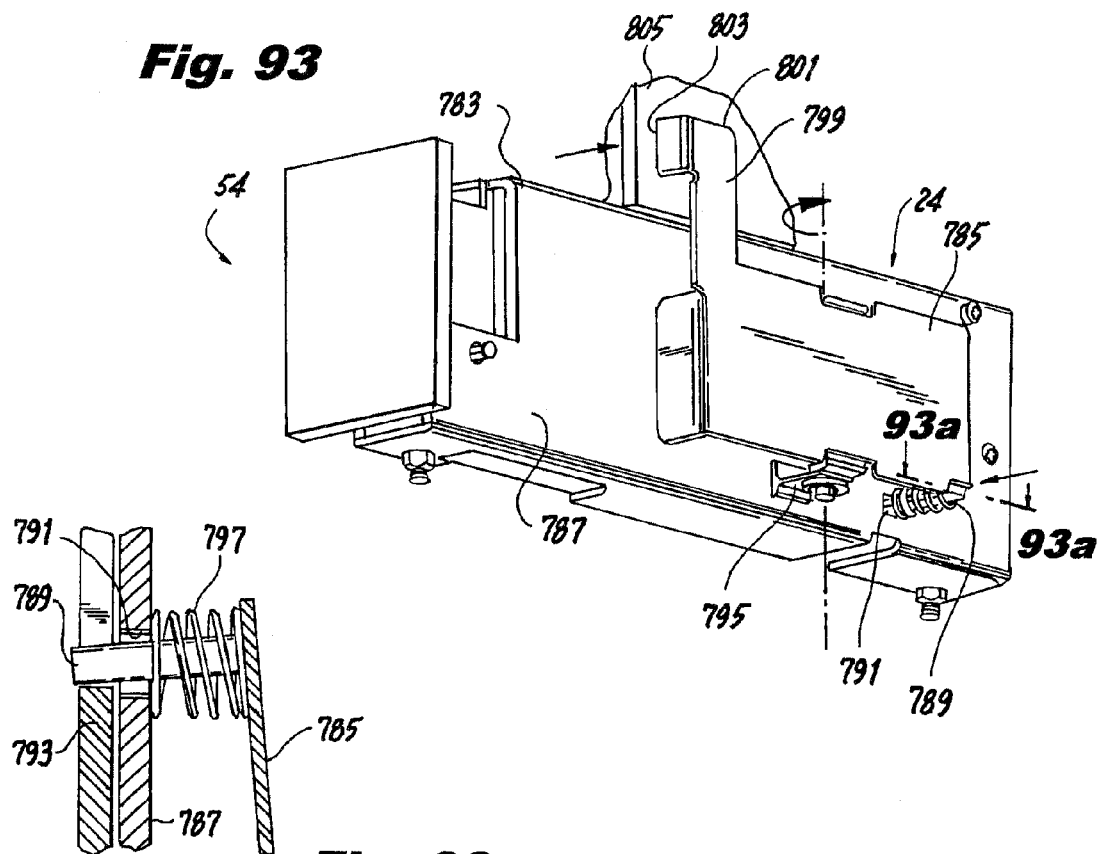
Fig. 93
Fig. 93a

CHEMICAL ANALYZER

CROSS REFERENCE TO RELATED APPLICATION

This application is a continuation of U.S. patent application Ser. No. 12/451,304, filed on Nov. 5, 2009, and entitled "Chemical Analyzer", which claims the benefit of priority, under 35 U.S.C. 371, to international PCT Application Publication No. PCT/US2008/005909, filed on May 7, 2008, and, under 35 U.S.C. 119 and/or 35 U.S.C. 120, to U.S. Provisional Application Ser. Nos. 60/928,131 and 60/962,869, filed on May 8, 2007 and Aug. 1, 2007, respectively, each entitled "Chemical Analyzer", the disclosures of each of which are incorporated herein by reference and on which priority is hereby claimed.

BACKGROUND OF THE INVENTION

Field of the Invention

This invention relates to chemical analyzers which automatically analyze fluids, and more particularly relates to "dry chemistry" analyzers. Even more specifically, this invention relates to chemical analyzers that are particularly adapted for biological fluid testing purposes wherein a change in an optical characteristic of a sample is sensed and analyzed automatically by the analyzer. The analyzer of the present invention has particular utility for human and veterinary applications.

Description of the Prior Art

Various analyzers have been developed for automated test procedures involving essentially dry, analytical elements, which elements offer substantial storage and handling conveniences. The "dry" analytical elements are preferably in the form of test slides. The test slides are formed as a multi-layer element containing the necessary free agents for reaction with components of a biological fluid, such as blood serum, deposited thereon. Certain reactions colorimetrically produce a change in optical density, which is sensed by a reflectometer or other device, the amount of light reflected from the test element varying in accordance with the reaction and being indicative of the amount of a particular component present in the fluid. Such test slides containing a dry analyte are well known in the art and are described in U.S. Pat. No. 4,647,431, which issued to Takasi Sekine, et al. Instruments utilizing dry slides are also known, such as the VETTEST® analyzer available from IDEXX Laboratories, Inc., Westbrook, Me. and the VITROS® analyzer available from Ortho-Clinical Diagnostics, Inc, Rochester, N.Y.

A very capable "dry chemistry" analyzer is described in U.S. Pat. No. 5,089,229, which issued to Thomas Heidt et al., the disclosure of which is incorporated herein by reference. The chemical analyzer described in the aforementioned '229 Heidt et al. patent includes a rotatable turntable which is adapted to hold a plurality of reagent test slides, a sample metering device, an incubator or temperature controller, a reflectometer, a slide inserter mechanism, a slide ejector mechanism and associated electronics, computer or microprocessor, and software. The rotatable turntable preferably holds up to 12 slides about its circumference. The dry analytical test slides come individually prepackaged, and are inserted by the operator onto the rotatable turntable one at a time by using the inserter mechanism. The turntable positions the reagent test slides under the metering device, which device deposits a predetermined amount of sample onto each slide. The turntable also carries the slides above a reflectometer. After testing has been completed, the ejector mechanism automatically removes the reagent slides from the turntable.

OBJECTS AND SUMMARY OF THE INVENTION

It is an object of the present invention to provide a chemical analyzer in the form of a small, desktop unit.

It is another object of the present invention to provide a chemical analyzer which can run a series of tests simultaneously in a relatively short period of time.

It is still another object of the present to provide a chemical analyzer which is relatively inexpensive to manufacture and has a relatively low operating cost.

It is yet a further object of the present invention to provide a chemical analyzer having a slide analysis portion which provides high resolution and good short-term stability.

It is a further object of the present invention to provide a chemical analyzer which includes a metering device which can dispense fluid with high accuracy.

It is yet a further object of the present invention to provide a chemical analyzer having a metering device which accurately aspirates a sample of fluid into a dispensing pipette.

It is yet a further object of the present invention to provide a chemical analyzer having a metering device which provides full wetting of the chemical reagent test slides.

It is yet another object of the present invention to provide a chemical analyzer having a metering device which minimizes or eliminates capillary action that would otherwise wet the outer side walls of the dispensing pipette of the metering device.

It is a further object of the present invention to provide a chemical analyzer having a metering device which includes an automated and managed aspiration of sample into the dispensing pipette of the metering device.

It is yet another object of the present invention to provide a chemical analyzer having a metering device in which an extremely small volume of air is aspirated into the dispensing pipette of the metering device.

It is yet a further object of the present invention to provide a chemical analyzer having a metering device which includes a dispensing pipette that automatically receives a pipette tip from a pipette tip storage tray.

It is yet a further object of the present invention to provide a chemical analyzer having a metering device in which fluid sensors are advantageously positioned on the metering device to accurately control the aspiration and dispensing of fluids by the metering device.

It is still a further object of the present invention to provide a chemical analyzer having a metering device in with the positioning of the pipette tip of the metering device is continually adjusted with respect to the level of fluid contained in the sample vial or centrifuge rotor from which the fluid is drawn to minimize wetting of the pipette tip which could have otherwise led to inaccurate metering.

It is still a further object of the present invention to provide a chemical analyzer having a metering device which aspirates a small quantity of air after each sample drop is deposited on a reagent test slide to provide a fluid meniscus within the pipette tip that is slightly withdrawn from the pipette tip orifice.

It is still another object of the present invention to provide a chemical analyzer having a metering device in which the amount of sample deposited on a chemical reagent test slide is automatically adjusted depending on the type of test slide on which the fluid is being deposited.

It is another object of the present invention to provide a chemical analyzer having a metering device incorporating an extremely accurate mechanism for aspirating and depositing sample fluid.

It is a further object of the present invention to provide a chemical analyzer having a metering device which incorporates a pressure sensor so that, as ambient temperature changes, sample fluid will not be forced by air pressure out of the pipette tip.

It is yet a further object of the present invention to provide a chemical analyzer having a metering device which includes a pump that may be controlled to increase volume and lower pressure within the pipette of the metering device.

It is still a further object of the present invention to provide a chemical analyzer having a metering device which includes a fluid sample pump having a backlash control for more accurately aspirating and dispensing fluid samples.

It is yet a further object of the present invention to provide a chemical analyzer having a metering device in which a relatively minute volume of sample fluid is deposited on a reagent test slide to prevent overwetting the reagent test slide.

It is yet another object of the present invention to provide a chemical analyzer having a metering device which forcefully ejects fluid sample from the pipette tip of the metering device rather than having the fluid sample being drawn therefrom by capillary action, which avoids pipette tip backwetting.

It is yet a further object of the present invention to provide a chemical analyzer having a slide transport mechanism which is mechanically simplified from prior art slide transport mechanisms in conventional chemical analyzers.

It is another object of the present invention to provide a chemical analyzer having a slide transport mechanism incorporating an incubator structure that accurately controls the temperature of the reagent test slides situated on the slide transport mechanism.

It is a further object of the present invention to provide a chemical analyzer having a slide transport mechanism in which the reagent test slides situated thereon are uncovered sequentially to minimize evaporation of the fluid sample deposited on the chemical reagent test slides.

It is another object of the present invention to provide a chemical analyzer having a slide transport mechanism which incorporates no slip rings.

It is a further object of the present invention to provide a chemical analyzer having a slide transport mechanism in which a plurality of heating elements and sensors are strategically placed to provide precise temperature control of the reagent test slides situated thereon.

It is a further object of the present invention to provide a chemical analyzer having a slide transport mechanism which minimizes or eliminates any smearing of fluid samples deposited on the reagent test slides during the transport of the slides.

It is still another object of the present invention to provide a chemical analyzer having a slide transport mechanism that includes structure for cleaning a window of a reflectometer used in the chemical analyzer to ensure accurate colorimetric measurements.

It is yet a further object of the present invention to provide a chemical analyzer having a slide transport mechanism which includes structure that removes sample fluid which may inadvertently be deposited on the slide transport mechanism.

It is yet another object of the present invention to provide a chemical analyzer having a slide transport mechanism which may receive a relatively large number of chemical reagent test slides.

It is still another object of the present invention to provide a chemical analyzer having a reflectometer and fluorometer incorporating a single light source.

It is another object of the present invention to provide a chemical analyzer having a reflectometer/fluorometer with optics that provide off-angle LED (light emitting diode) illumination of reagent test slides to ensure more accurate readings with Z-axis variability in the position of the reagent test slides on the slide transport mechanism.

It is yet another object of the present invention to provide a chemical analyzer having a reflectometer/fluorometer which eliminates the need for a reference test slide on the slide transport mechanism.

It is a further object of the present invention to provide a chemical analyzer having a single centrifugation station for processing blood samples from multiple patients.

It is still a further object of the present invention to provide a chemical analyzer having a centrifugation station incorporating a centrifuge rotor with an overfill indicator.

It is yet a further object of the present invention to provide a chemical analyzer having a centrifugation station with a safety drop wall and interlock to prevent injury to a clinician during processing of a blood sample.

It is an object of the present invention to provide a chemical analyzer having dual slide inserter mechanisms.

It is yet a further object of the present invention to provide a sample preparation station in which a single, linear drive mechanism is used in the sample preparation stage and which cooperates with a two-patient loading system of the chemical analyzer.

It is another object of the present invention to provide a chemical analyzer having a slide inserter mechanism that cooperates with reagent test slide clips that eliminates the need for a clinician to touch any of the reagent test slides.

It is a further object of the present invention to provide a chemical analyzer having a slide inserter mechanism that has the capability of intermixing stacks of different test slides.

It is an object of the present invention to provide a chemical analyzer having a slide ejector mechanism which incorporates a single push bar that cooperates with a slot in the slide transport mechanism to eject slides therefrom.

It is another object of the present invention to provide a chemical analyzer having a slide ejector mechanism that ejects slides to a slide drawer, where the slide ejector mechanism includes an interlock and is prevented from ejecting slides if the slide drawer is opened or removed from the housing of the analyzer.

In accordance with one form of the present invention, the chemical analyzer comprises a slide transport mechanism, a slide inserter mechanism which inserts a plurality of chemical reagent test slides onto the slide transport mechanism, a reflectometer/fluorometer which is positioned in proximity to the slide transport mechanism and the chemical reagent test slides situated thereon, a sample metering device that aspirates a sample fluid from a vial or centrifuge rotor and deposits a predetermined volume of sample fluid onto a plurality of chemical reagent test slides, an incubator for maintaining the reagent test slides situated on the slide transport mechanism at a predetermined temperature, and a slide ejector mechanism which removes the reagent test slides from the slide transport mechanism.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 9a is a top perspective view of a portion of the slide inserter mechanism of the present invention shown in FIG. 9, and illustrating the placement of a chemical reagent test slide thereon.

FIG. 28c is a cross-sectional view of the rotor carrier and the portion of the picker mechanism shown in FIG. 28a and taken along line 28c-28c of FIG. 28a.

FIG. 29 is a pictorial illustration of the slide transport mechanism, slide ejector mechanism, and first and second bar actuators for covering and uncovering reagent test slides used in the chemical analyzer of the present invention.

FIG. 29c is an isometric view of the underside of the skull plate on which is mounted the slide transport mechanism, slide ejector mechanism and first and second bar actuators for covering and uncovering reagent test slides used in the chemical analyzer of the present invention.

FIG. 40 is a top isometric view of a portion of the chemical analyzer of the present invention, and illustrating in greater detail a portion of the clean pipette tip tray encircled by dashed line 40 shown in FIG. 6, and illustrating the placement of clean pipette tips thereon.

FIG. 40a is a top plan view of a portion of the chemical analyzer of the present invention, and illustrating in greater detail a portion of the clean pipette tip tray encircled by dashed line 40a shown in FIG. 40, and illustrating the placement of clean pipette tips thereon.

FIG. 44 is a detailed top isometric view of a portion of the slide inserter mechanism shown in FIG. 41, that portion being encircled by dashed line 44 in FIG. 41.

FIG. 45 is a detailed top isometric view of a portion of the slide inserter mechanism shown in FIG. 41 and FIG. 44, and illustrating the portion of the slide inserter mechanism in a different position from that in which it is depicted in FIG. 44.

FIG. 67 is a top isometric view of the rotor carrier, centrifuge and picker mechanism of the sample metering sub-assembly, and illustrating the picker mechanism situating the rotor carrier and centrifuge rotor mounted thereon on the centrifuge of the chemical analyzer of the present invention.

FIG. 68 is a cross-sectional view of the rotor carrier, picker mechanism, centrifuge rotor and centrifuge of the present invention shown in FIG. 67 and taken along lines 68-68 of FIG. 67.

FIG. 74 is a top isometric view of a portion of the sample metering sub-assembly and a portion of a pipette tip removal member formed in accordance with the present invention.

FIG. 75 is a top isometric view of a portion of the sample metering sub-assembly and pipette tip removal member shown in FIG. 74, and illustrating the removal of a pipette tip from the sample metering sub-assembly by the pipette tip removal member of the present invention.

FIG. 82b a top isometric view of a portion of the slide carousel portion of the slide transport mechanism constructed in accordance with the present invention and shown in FIGS. 82 and 82a.

FIG. 85 is a pictorial illustration of a reflectometer constructed in accordance with the present invention and used in the chemical analyzer of the present invention.

FIG. 90 is a top isometric view of a portion of the sample metering sub-assembly and the engagement of a pipette tip mounted thereon with a vacuum test member formed in accordance with the present invention and used in the chemical analyzer of the present invention.

FIG. 91 is a cross-sectional view of a portion of the pipette tip and vacuum test member shown in FIG. 90 and taken along line 91-91 of FIG. 90.

FIG. 92 is a bottom isometric view in greater detail of a portion of the clean pipette tip tray and a mechanical interlock formed thereon and constructed in accordance with the present invention, the portion of the clean pipette tip tray shown in FIG. 92 being that portion encircled by dashed line 92 shown in FIG. 40.

FIG. 93 is a bottom isometric view of the clean pipette tip tray shown in FIG. 92 and illustrating the operation of the mechanical interlock thereof engaging a portion of the sample metering sub-assembly of the present invention.

FIG. 93a is a cross-sectional view of a portion of the mechanical interlock and clean pipette tip tray, and illustrating the operation of the mechanical interlock shown in FIG. 93 and taken along line 93a-93a of FIG. 93.

DETAILED DESCRIPTION OF THE PREFERRED EMBODIMENTS

Initially referring to FIGS. 1-7 of the drawings, it will be seen that a chemical analyzer 2 formed in accordance with one form of the present invention is a compact, desktop unit. Because the unit is relatively small and lightweight, it is quite portable and may be set up conveniently on a desk or table, requiring very little space.

Figure 1:
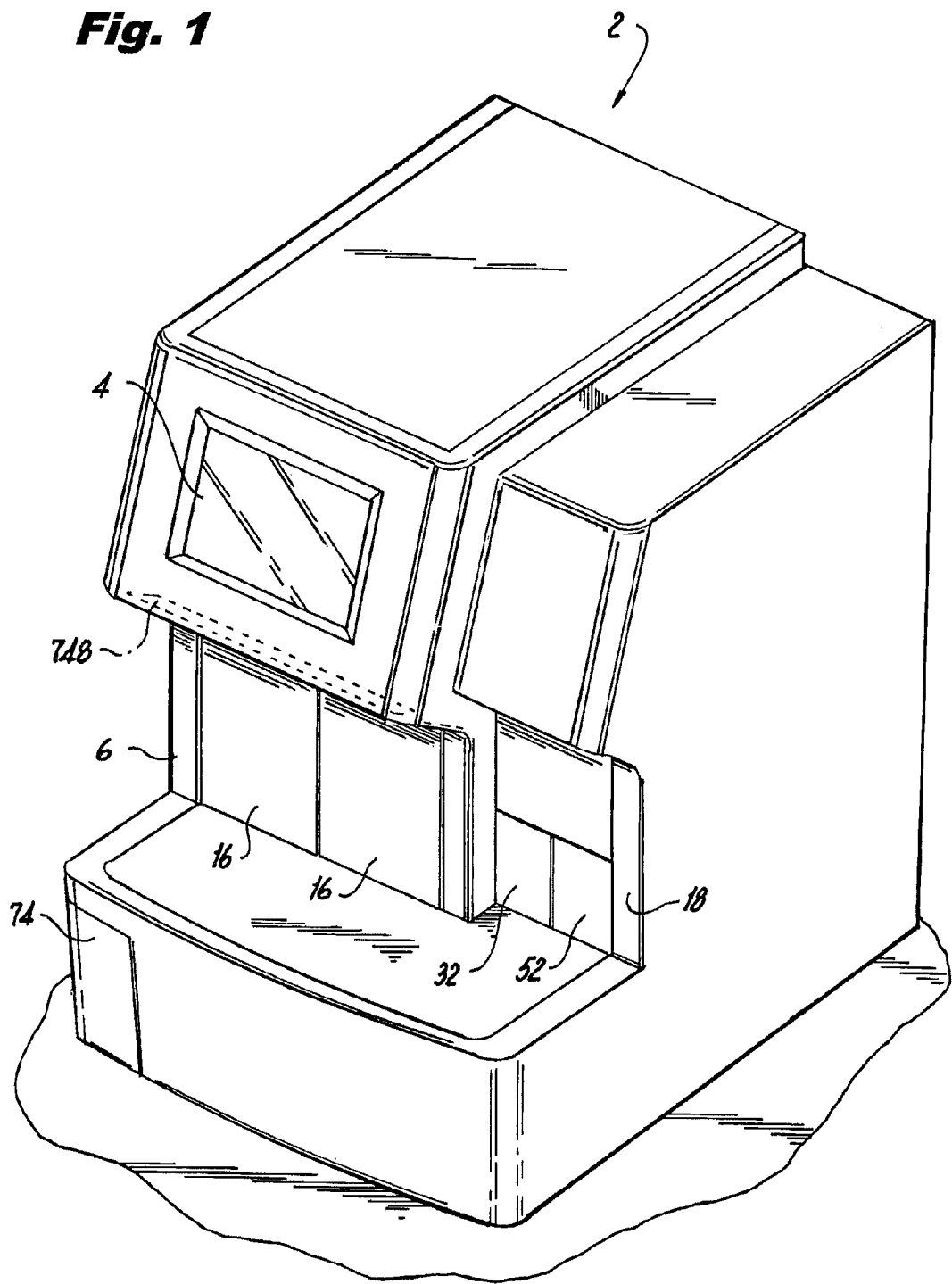
FIG. 1 is a front isometric view of a chemical analyzer formed in accordance with one form of the present invention.

As can be seen from FIG. 1, the chemical analyzer 2 preferably includes a display 4, preferably a touch screen, liquid crystal display. The display 4 provides the user with diagnostic information as well as with instructions relating to the operation of the analyzer 2, and allows the user to input information and to control the operation of the analyzer 2.

The chemical analyzer 2 includes a housing 6 in which are preferably flush mounted a series of doors, trays and drawers. Certain of the doors 8 are preferably mechanically interlocked to prevent their opening during operation of the chemical analyzer 2 to insure the integrity of the test being performed on the reagent test slides 14 and to prevent injury to the clinician operating the analyzer 2. More specifically, there are preferably two sliding doors 16 which move vertically on the front face of the housing 6. The sliding doors are movable vertically to uncover, and allow the clinician access to two respective slide inserter mechanisms 20. The sliding doors 16 are operable in accordance with the operational software programmed into the electronic circuitry of the analyzer 2 and in accordance with commands entered on the touch screen display 4.

Figure 38:
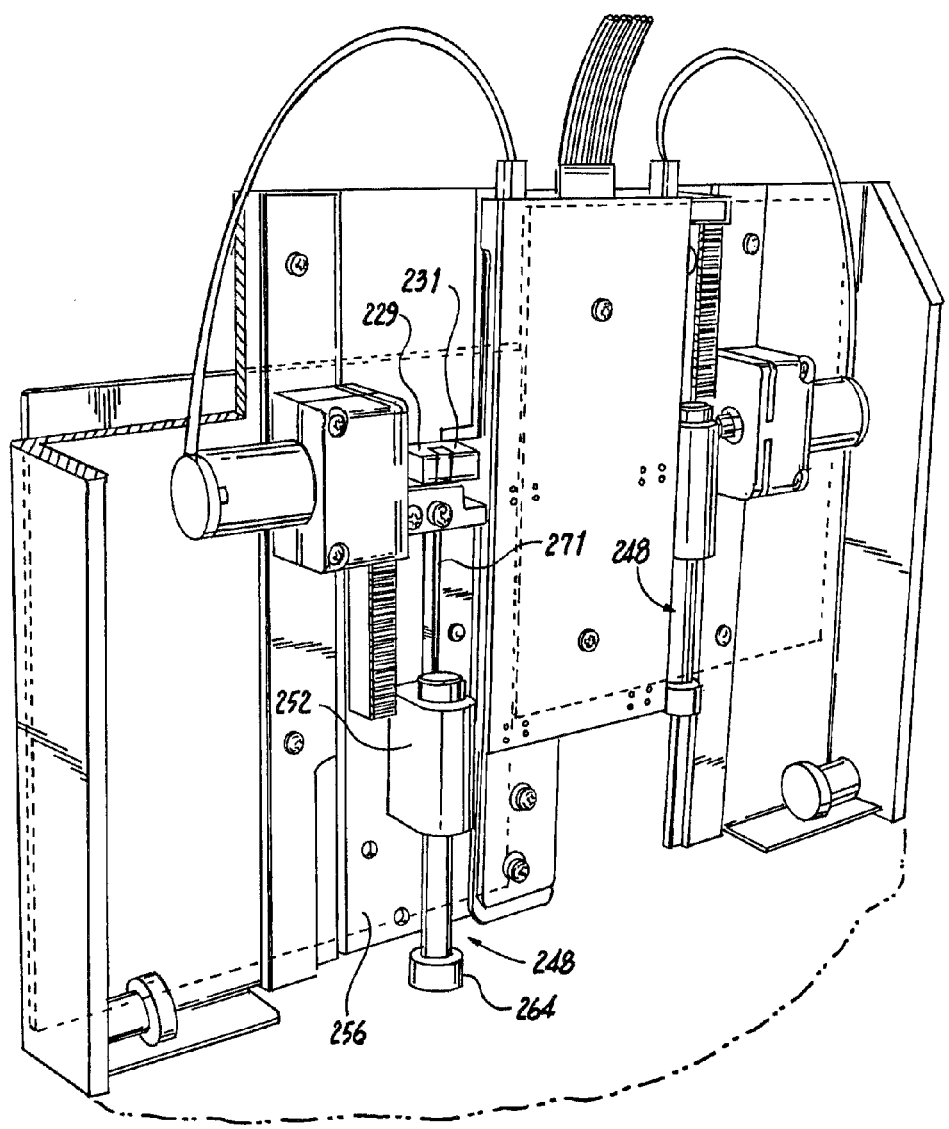
FIG. 38 is a rear isometric view of a portion of the chemical analyzer of the present invention shown in FIG. 3 and taken along 38-38 of FIG. 3.
Figure 38A:
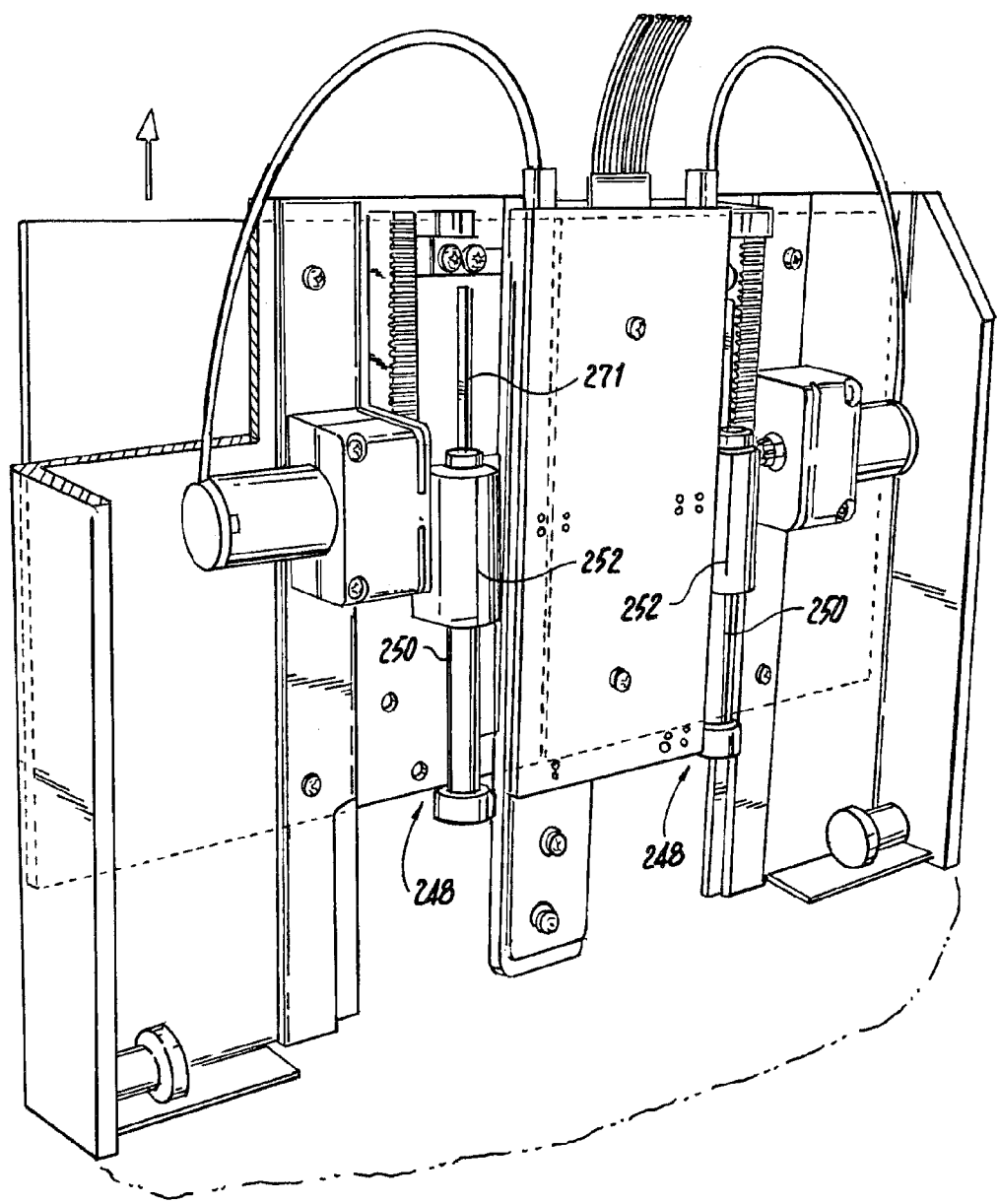
FIG. 38a is a rear isometric view of the portion of the chemical analyzer shown in FIG. 38 with a door of the analyzer shown therein in a different position than that depicted in FIG. 38.

A pair of electrical sensors (not shown) positioned in proximity to or on each door 16 at a low position and at a high position with respect to the doors 16, with each sensor preferably including a light source (not shown) and a light detector (not shown), detects the position of the door 16 and provides door positional signals to the electronic circuitry 22 of the analyzer 2 which, in turn, processes those signals to either allow the doors 16 to open, or prevent the doors 16 from opening at an inappropriate time during the operation of the chemical analyzer 2, such as during incubation of the chemical slides 14 mounted on the slide transport mechanism 26 or when colorimetric measurements are being conducted. The electronic circuitry 22 of the analyzer 2 also provides control signals to electric motors 30 (see FIGS. 38 and 38a) which are operatively linked to the doors 16 to cause the doors 16 to open and close (or to maintain the doors in an open or closed position) in accordance with the operational software programmed into the analyzer's electronic circuitry 22 or in accordance with a command entered into the touch screen display 4 by the clinician.

Figure 39:
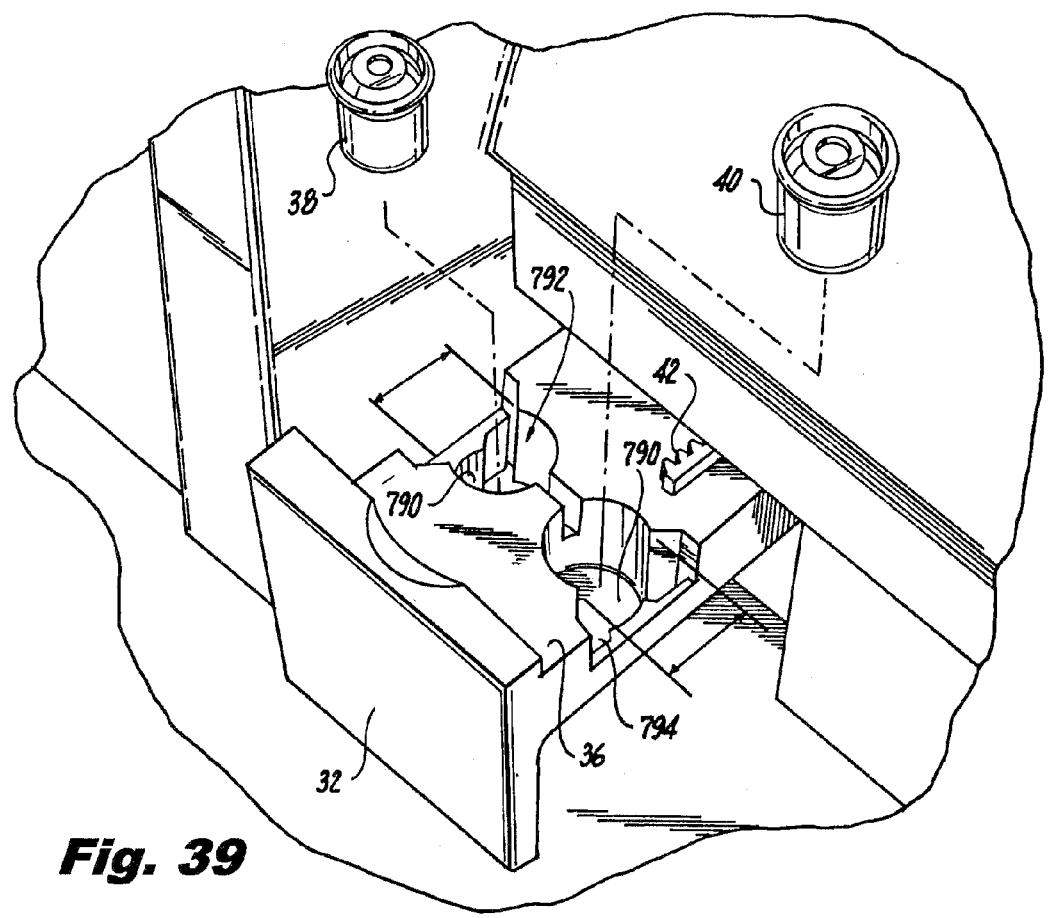
FIG. 39 is a front isometric view of a portion of the chemical analyzer of the present invention shown in FIG. 5 and illustrating in greater detail a portion of the diluent cup and mixing cup drawer encircled by dashed line 39 in FIG. 5.
Figure 39A:
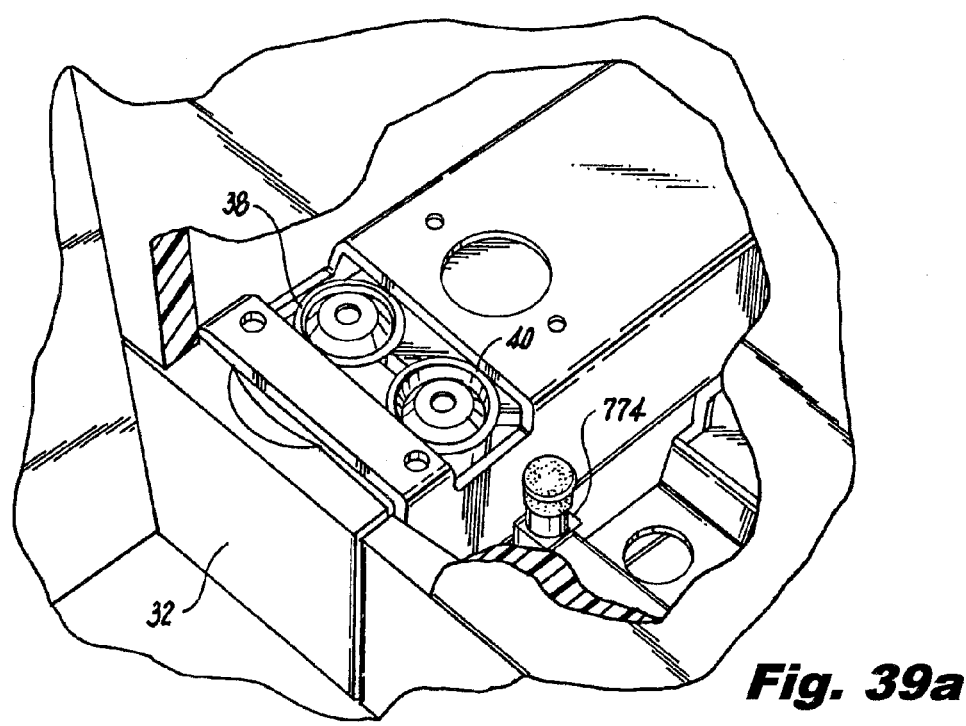
FIG. 39a is a top isometric view of the diluent cup and mixing cup drawer shown in FIG. 39 retracted within the housing of the analyzer and with the housing of the analyzer partially broken away, and illustrating the placement of a diluent cup and mixing cup thereon.
Figure 39B:
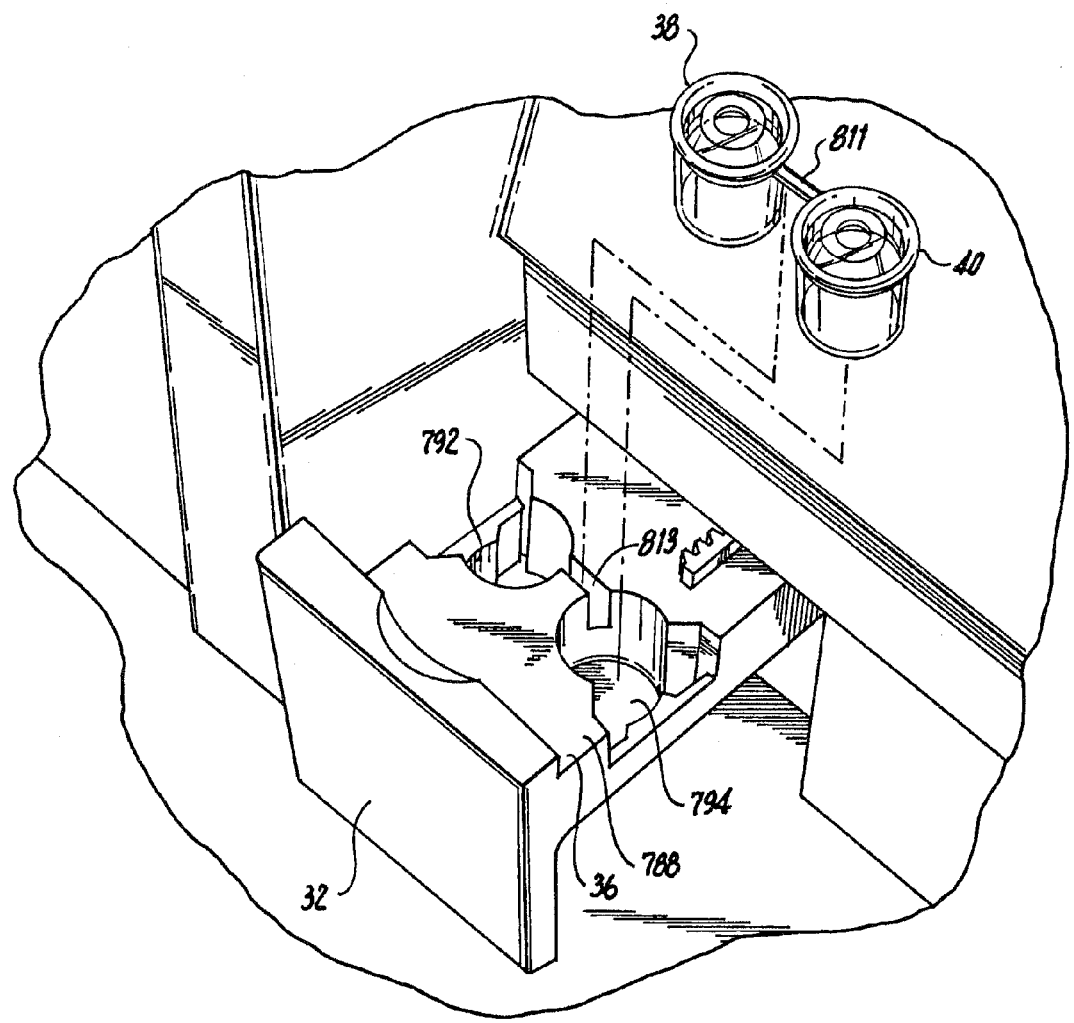
FIG. 39b is a top isometric view of the diluent cup and mixing cup drawer shown in FIGS. 39 and 39a extended outside the housing of the analyzer, and illustrating the placement of a diluent cup and mixing cup thereon.
Figure 41:
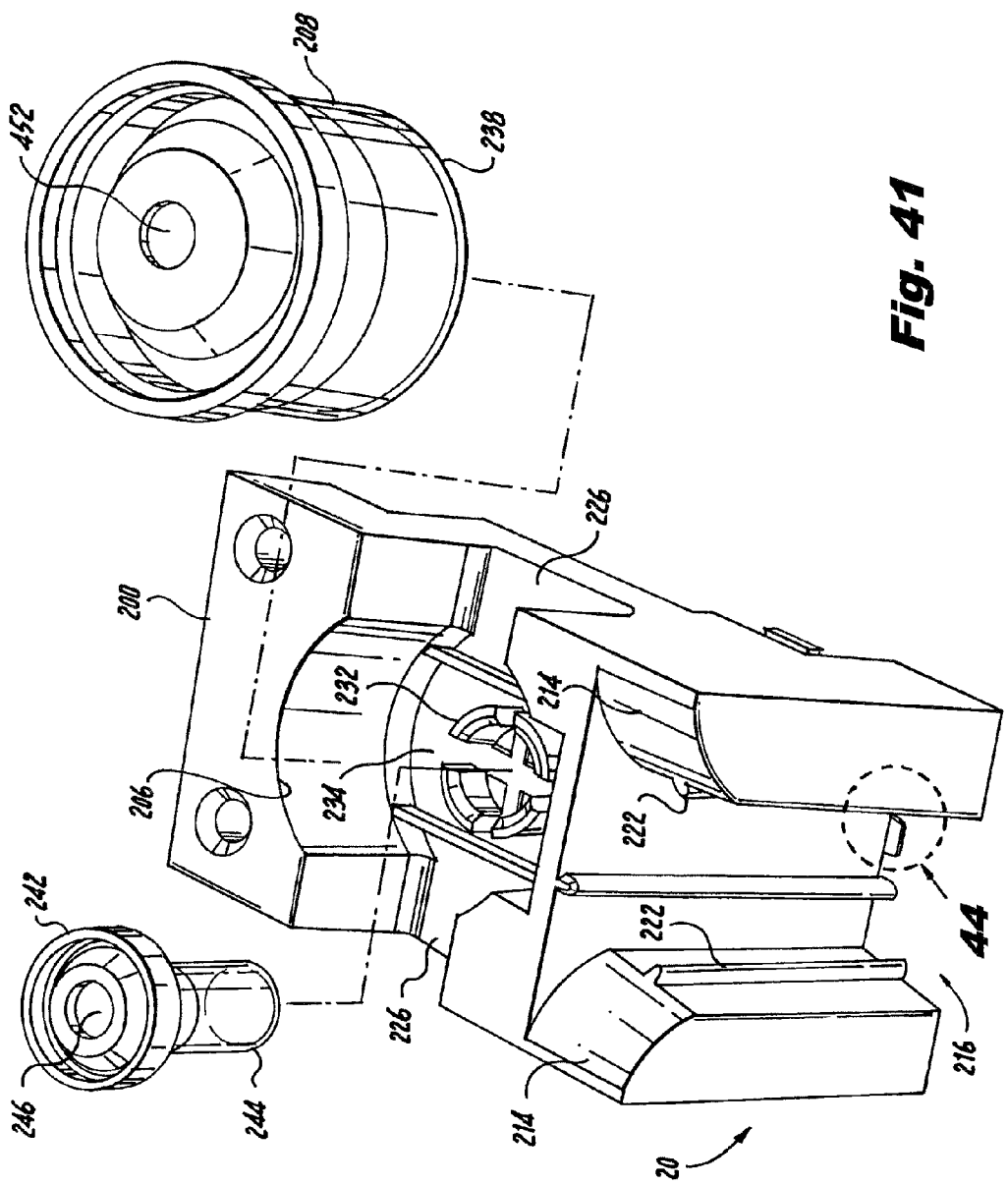
FIG. 41 is a front isometric view of a portion of the slide inserter mechanism shown in FIG. 9 and used in the chemical analyzer of the present invention, and illustrating the placement of either a centrifuge rotor or a sample vial thereon.
Figure 42:
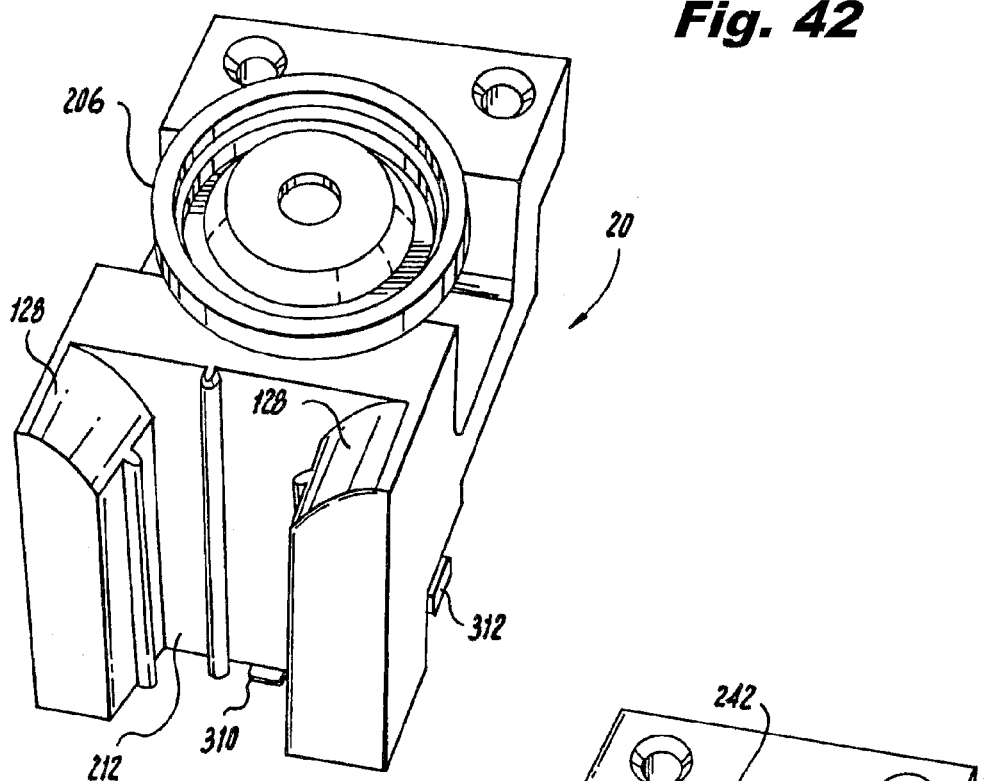
FIG. 42 is a front isometric view of the slide inserter mechanism of the present invention shown in FIG. 41, and illustrating the slide inserter mechanism holding a centrifuge rotor.
Figure 94:
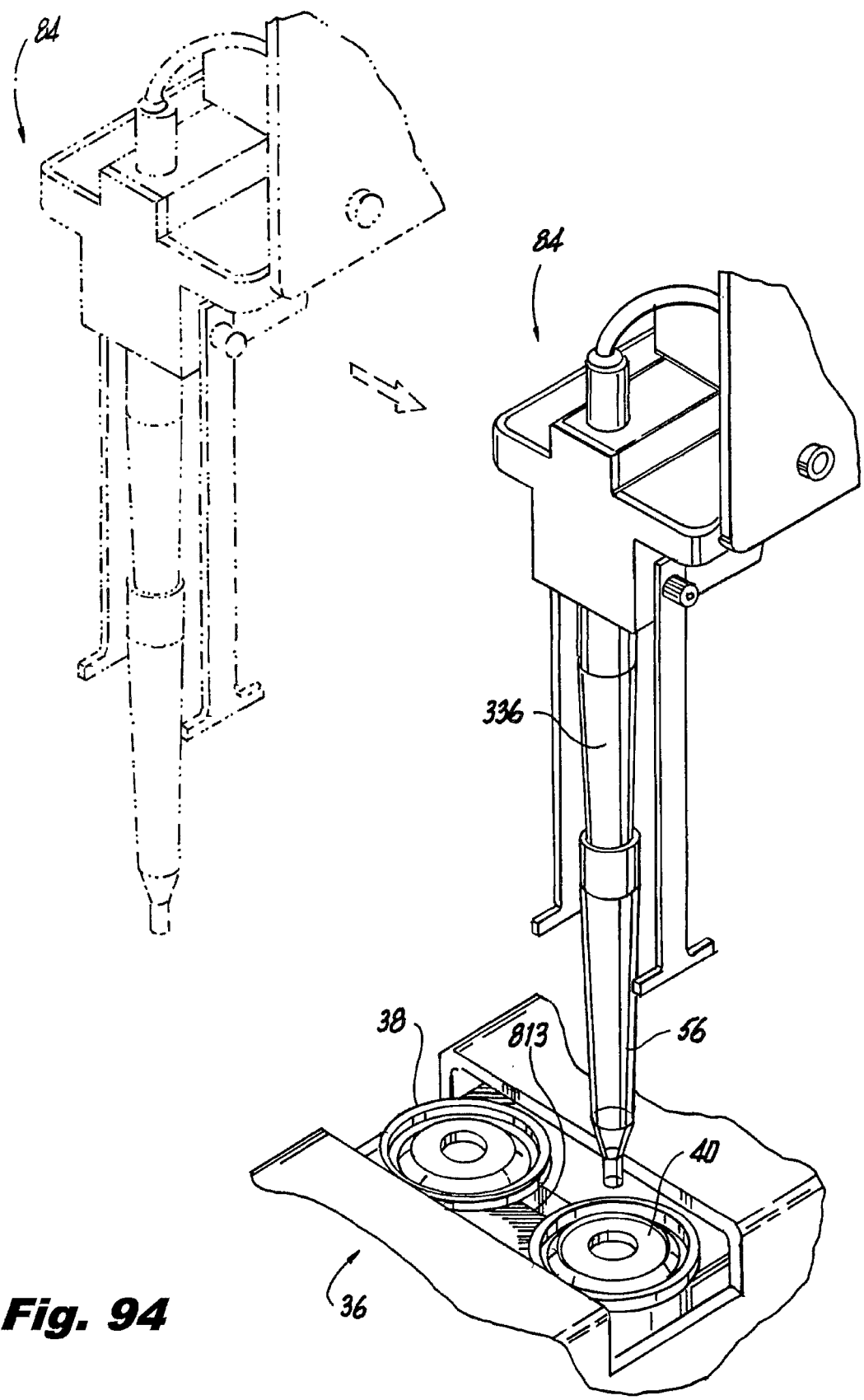
FIG. 94 is a top isometric view of a portion of the sample metering sub-assembly and a portion of the diluent cup and mixing cup drawer formed in accordance with the present invention, and illustrating in phantom one position of the sample metering sub-assembly and its movement to a second position, shown in solid lines, situated over the diluent cup and mixing cup drawer, the diluent cup and mixing cup drawer being further illustrated as having a diluent cup and mixing cup placed thereon.

A third door 32, preferably situated on the housing 6 to the right of the vertically sliding doors 16 behind which are situated the slide inserter mechanisms 20, is affixed to the front face 34 of an extendible and retractable spring loaded drawer 36 for receiving a diluent cup 38 and a mixing cup 40 (see FIGS. 39, 39a and 94). A mechanism 42 on the door 32 allows the clinician to press inwardly on the door 32 to unlatch the door 32 so that the drawer 36 will extend outwardly from the front face 34 of the housing 6 in a controlled manner under the force of a spring (not shown) to expose a pair of receptacles 46 formed in the drawer 36 and arranged side-by-side. The receptacles 46 are preferably provided to receive and hold firmly a cup 38 containing a diluent and another cup 40 for mixing the diluent with a blood sample. When the clinician has loaded the diluent cup 38 and the mixing cup 40 into the appropriate receptacles 46 in the drawer 36, the drawer 36 is closed by pushing on the outer face door 32 against the pressure of the spring (not shown) until the door 32 once again latches and is flush with the front face 18 of the housing 6.

Another door 52 is situated on the front face 18 of the chemical analyzer 2 of the present invention, and preferably positioned adjacent the diluent access door 32. This door 52 accesses a tray 54 holding a plurality of clean pipette tips 56, the use of which will be described in greater detail.

The door 52 to access the clean pipette tip tray 54 has a mechanical, spring loaded, latching mechanism similar to that used on the diluent door 32. The clinician presses inwardly on the door 52 to release the latch, and the tray 54 affixed to the rear surface 60 of the door may be extended from the front face 18 of the analyzer housing 6 by the clinician.

The tray 54 basically includes a pair of spaced apart, parallel bars 64 on and between which rests a row of clean pipette tips 56 (see FIG. 40). The clinician may add more pipette tips 56 to the tray 54 by simply placing the pipette tips 56 between the parallel bars 64 so that the proximal top end 66 of the pipette tips 56 (which are fitted onto the distal end 68 of the pipette 336) rests on and is supported by the parallel bars 64 of the tray 54. The clinician then pushes on the door 52 of the pipette tray 54 against the bias of a spring to retract the tray 54 into the analyzer housing 6 until the mechanical latching mechanism 62 secures the door 52 in a position that is flush with the front face 18 of the analyzer housing 6. A spring mechanism 70 having a constant force spring 71 and plate 73 joined to the spring 71 biases the clean pipette tips 56 resting on the parallel bars 64 of the pipette tip tray 54 so that adjacent clean pipette tips 56 are forced against one another, with no space therebetween, when the tray 54 is forced back into the analyzer housing 6. When the tray 54 is extended beyond the housing 6, the spring mechanism 70 relieves the pressure on the pipette tips 56 residing on the tray 54 to allow space between the pipette tips 56 so that more may be added between the parallel bars 64 of the tray 54.

The front face 18 of the housing 6 also includes a compartmentalized sliding drawer 74. The drawer 74 holds used chemical reagent test slides 14 as well as used pipette tips 56. The slides 14 have been ejected by the slide ejector mechanism 76 from the slide transport mechanism 26 after the analysis of the slides 14 has been completed by the analyzer 2, and the ejected slides 14 are directed to a first compartment 78 of the drawer 74 and held thereby (see FIG. 87).

The clinician may remove the drawer 74 from the front face 18 of the housing 6 and discard the reagent test slides 14 in an appropriate manner. The clinician then replaces the drawer 74 in the analyzer housing 6.

A second compartment 80 of the drawer 74 receives used pipette tips 56. As will be described in greater detail, pipette tips 56 are systematically removed from the pipette 336 of the sample metering sub-assembly 84 and directed to the second compartment 80 of the drawer 74 where the used pipette tips 56 are held. The clinician may remove the drawer 74 from the analyzer housing 6 in order to discard used pipette tips 56 in an appropriate manner. Then, the clinician replaces the drawer 74 into the analyzer housing 6.

Figure 2:
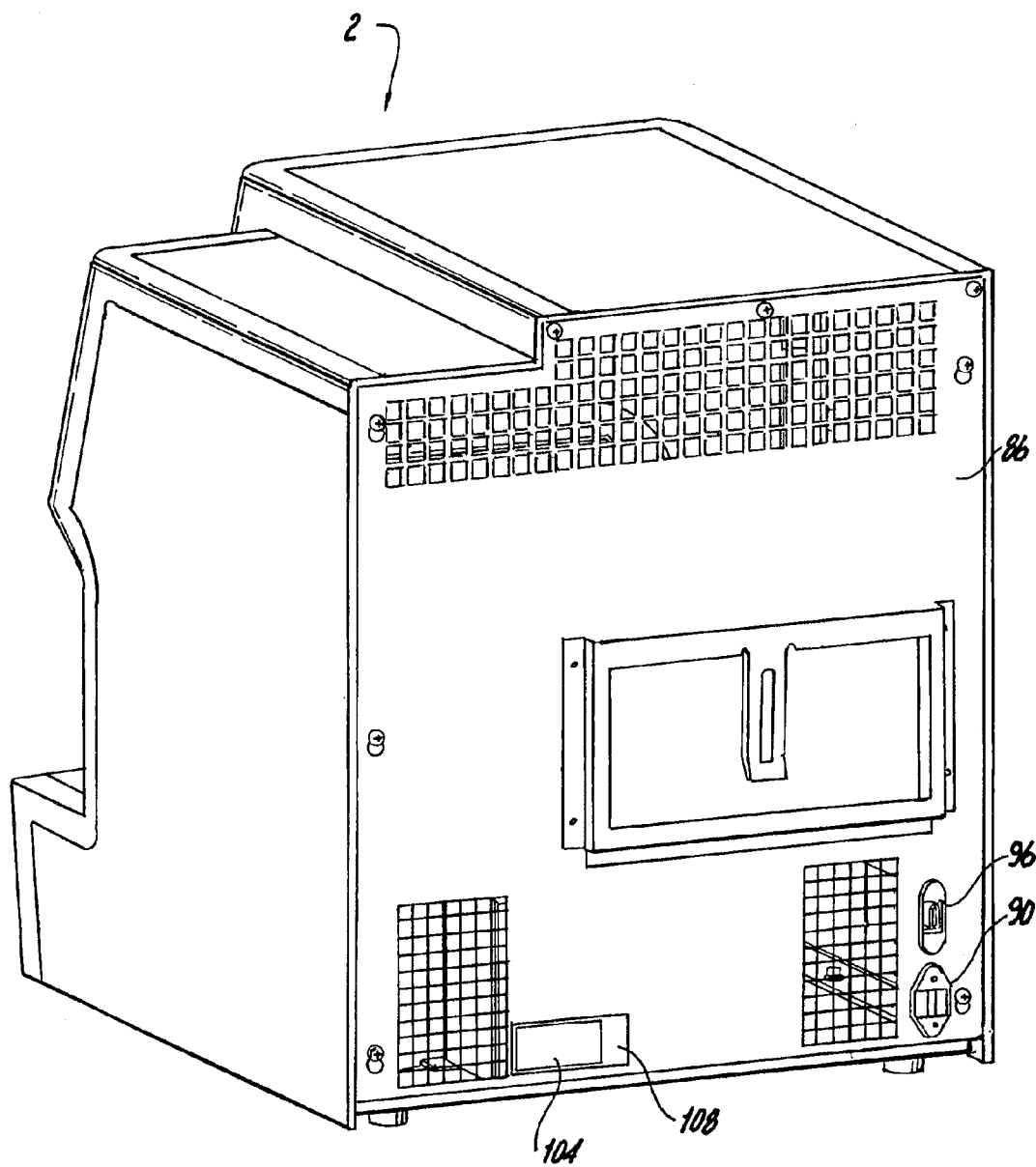
FIG. 2 is a rear isometric view of the chemical analyzer shown in FIG. 1 and formed in accordance with one form of the present invention.
Figure 3:
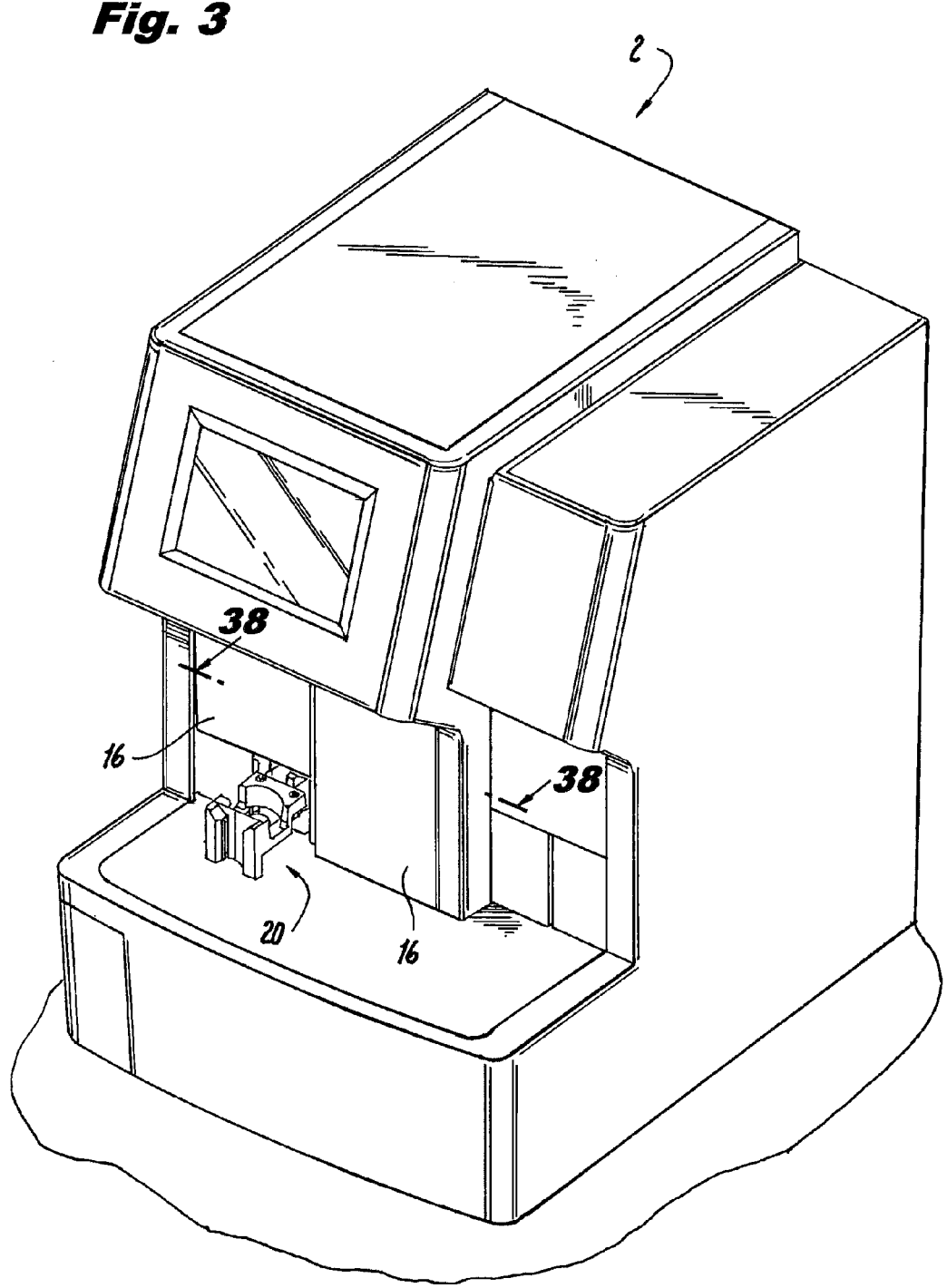
FIG. 3 is a front isometric view of the chemical analyzer shown in FIGS. 1 and 2, illustrating a first sliding door on the front face of the analyzer being open and a first slide inserter mechanism of the chemical analyzer extending beyond the front face of the analyzer housing.
Figure 4:
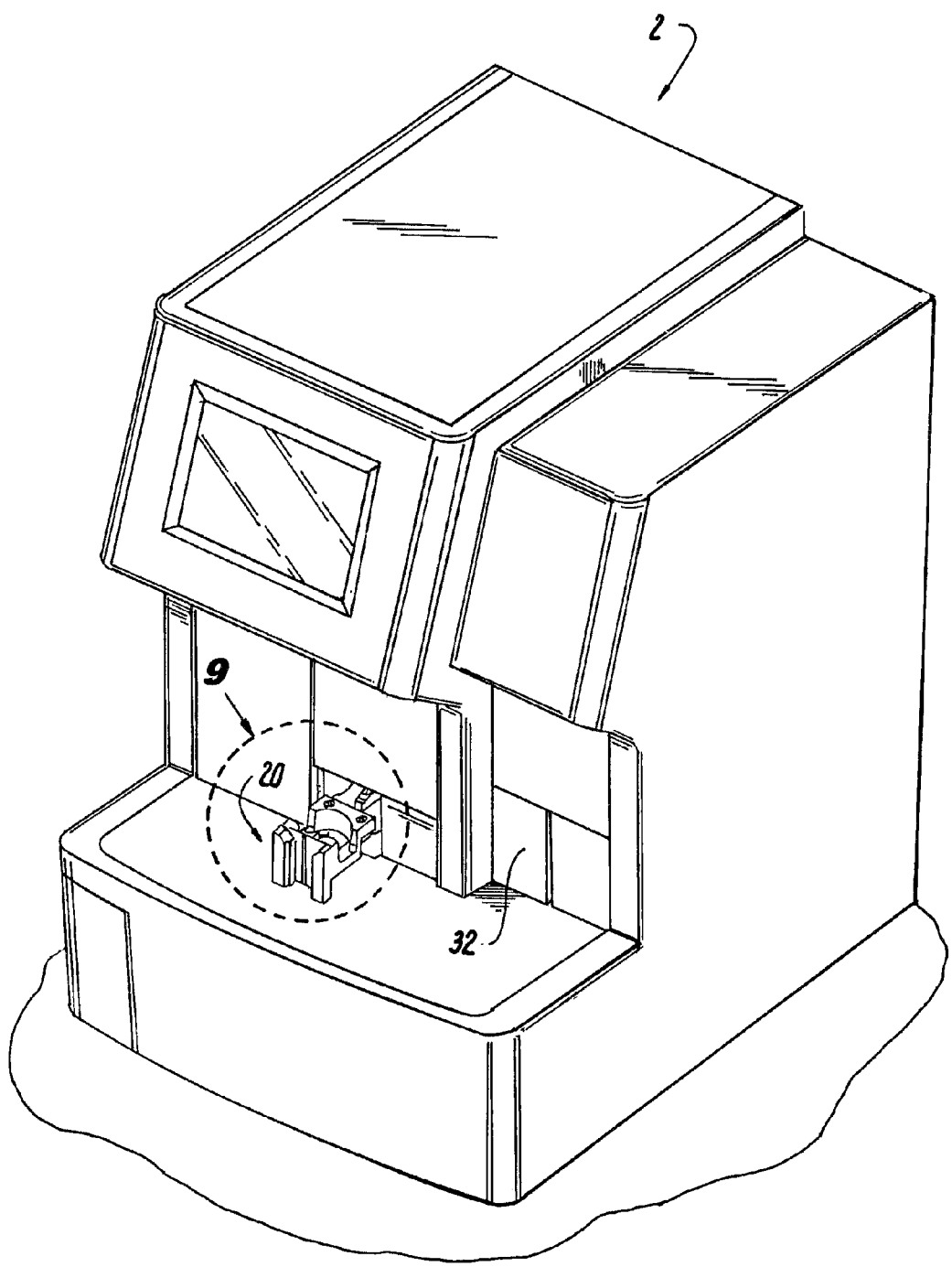
FIG. 4 is a front isometric view of the chemical analyzer shown in FIGS. 1 and 2, illustrating a second sliding door on the front face of the analyzer being open and a second slide inserter mechanism of the chemical analyzer extending beyond the front face of the analyzer housing.
Figure 5:
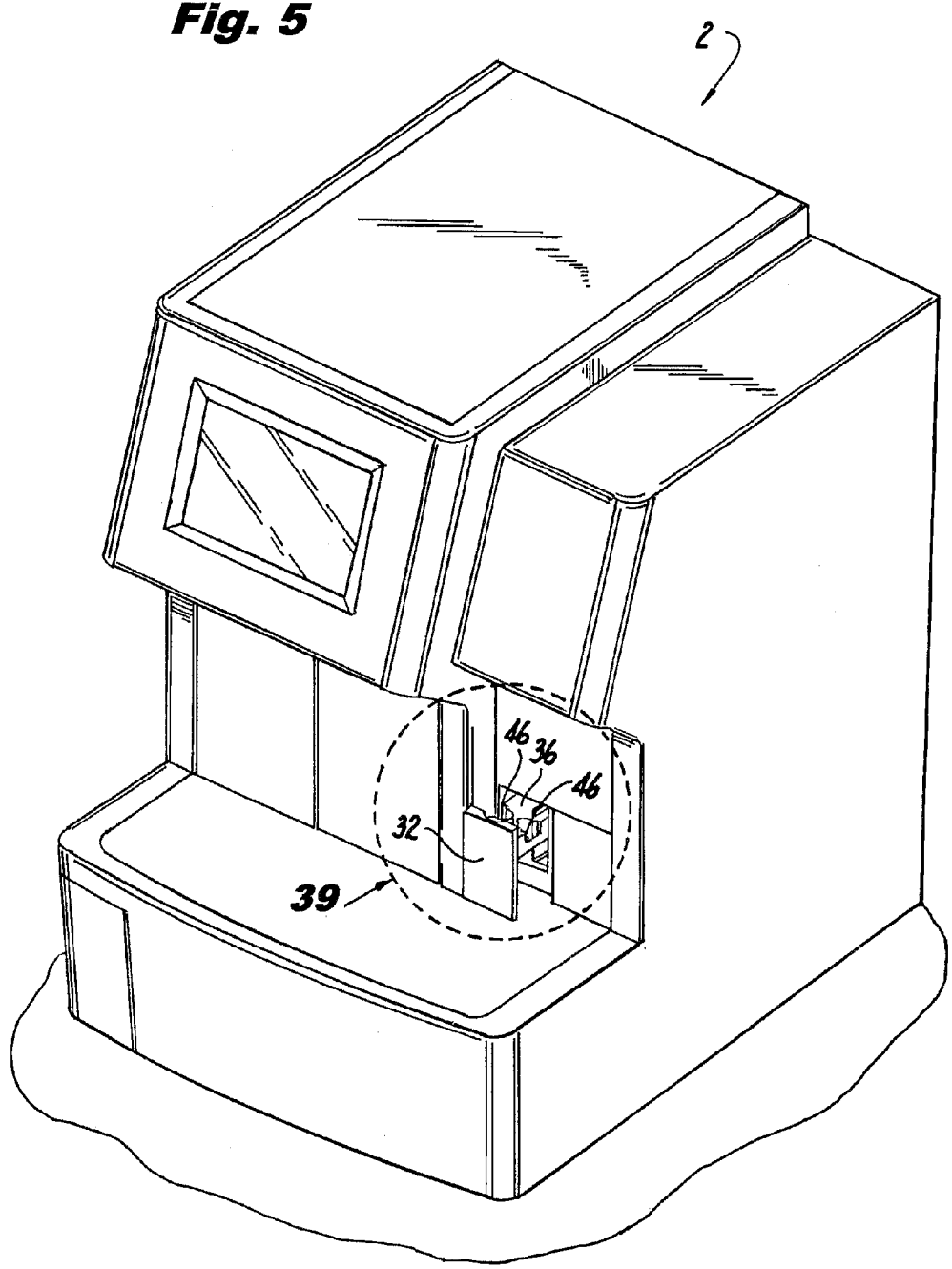
FIG. 5 is a front isometric view of the chemical analyzer of the present invention shown in FIGS. 1 and 2, and illustrating the extension from the front face of the analyzer housing of a tray for carrying a diluent and mixing cup.
Figure 6:
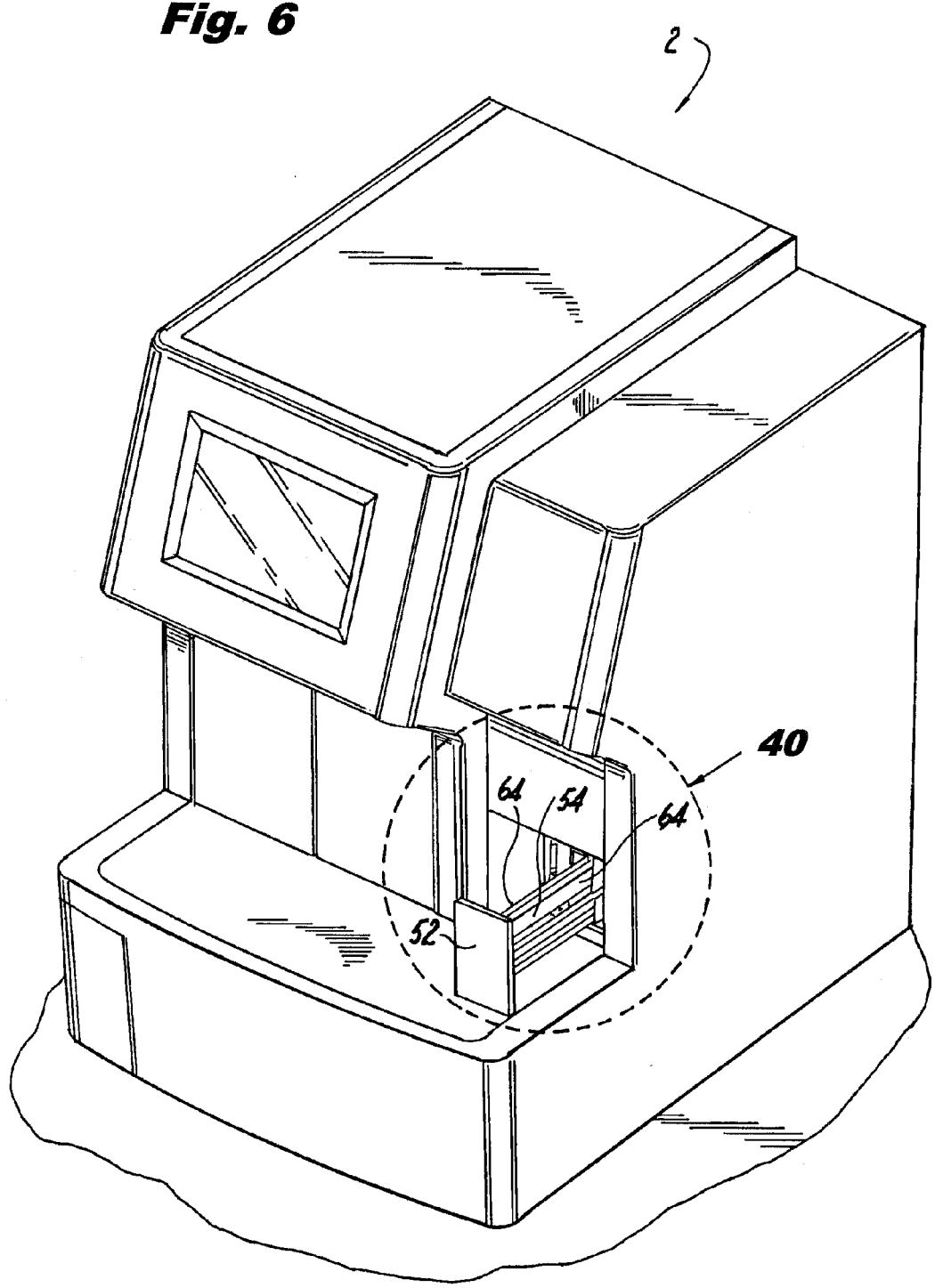
FIG. 6 is a front isometric view of the chemical analyzer of the present invention shown in FIGS. 1 and 2, and illustrating the extension of a clean pipette tip tray from the front face of the analyzer housing.
Figure 7:
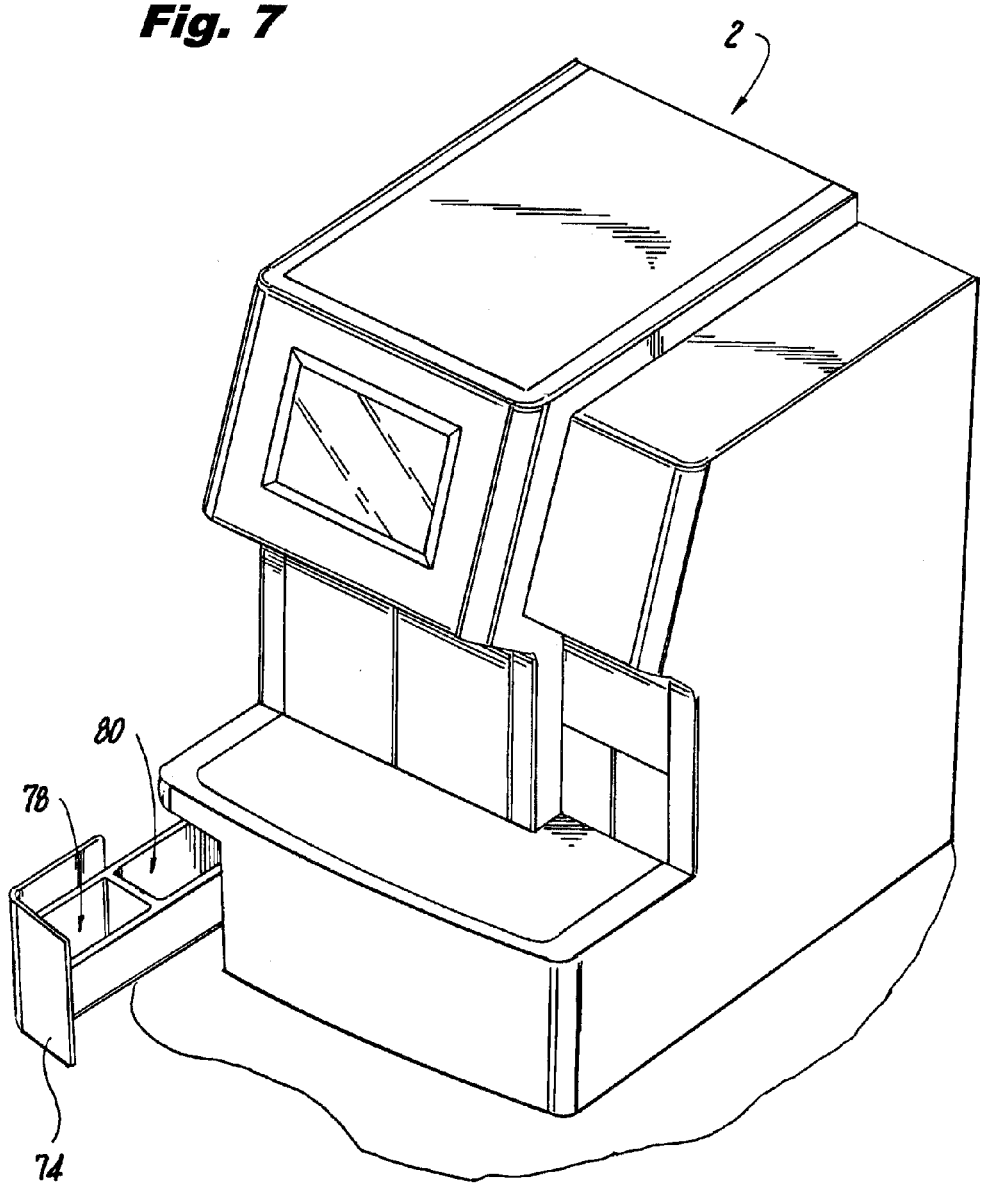
FIG. 7 is a front isometric view of the chemical analyzer of the present invention shown in FIGS. 1 and 2, and illustrating the extension of a drawer which holds used pipette tips and slides.

The rear face 86 of the housing 6 of the chemical analyzer 2, as shown in FIG. 2 of the drawings, preferably includes a number of connectors, including a standard male receptacle 90 which receives the mating female connector of a grounded power line cord (not shown), a female connector 96 which cooperatively mates with the male connector of a printer conduit (not shown) for a connection to a peripheral printer (not shown), and other connectors 104 (e.g., USB and Ethernet) for interfacing the chemical analyzer 2 with a hand-held, laptop or personal computer (not shown), or to a router and/or modem (not shown) so that information from the analyzer 2 may be transmitted over the Internet to a remote computer or processor (not shown). Also, an on/off switch 108 is mounted on the rear face 86 of the housing 6, which controls power to the analyzer 2.

It should be noted that the analyzer housing 6, including the touch screen display 4, is preferably completely sealed and water impermeable to allow the exterior of the analyzer 2 to be easily cleaned and to prevent any malfunctions in the event that a liquid is inadvertently spilled on the analyzer 2.

The Slide Inserter Mechanism

Figure 8:
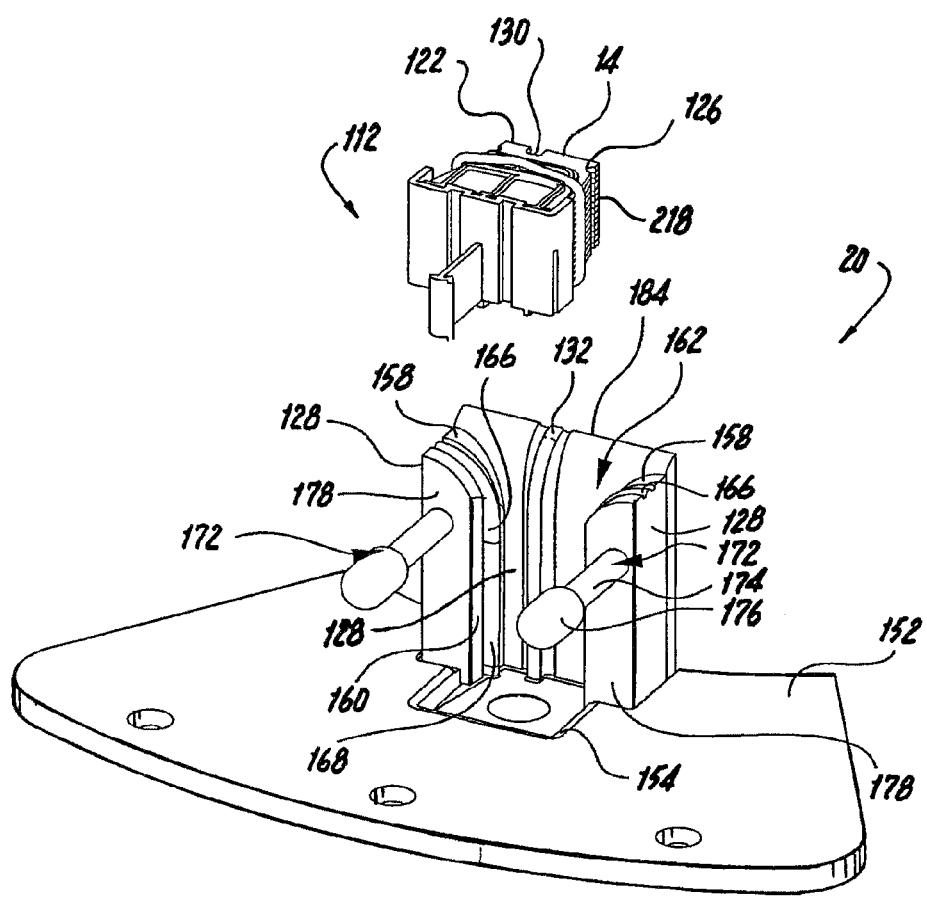
FIG. 8 is a front perspective view of a slide inserter mechanism formed in accordance with one form of the present invention, and showing a slide retaining clip for holding a plurality of reagent test slides cooperating with the slide inserter mechanism.
Figure 9:
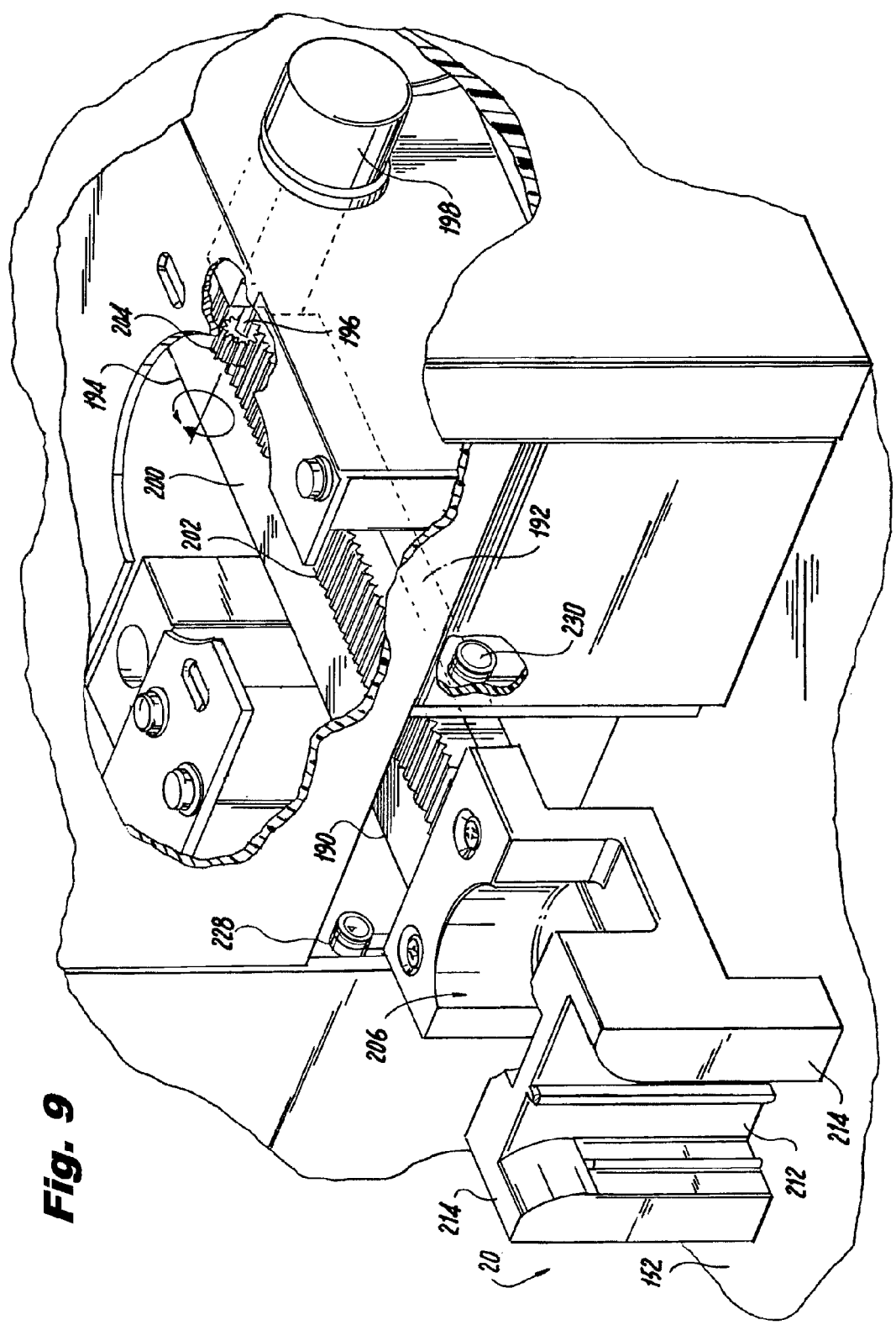
FIG. 9 is a top perspective view of another form of a slide inserter mechanism formed in accordance with the present invention, shown with the analyzer housing partially broken away.
Figure 10:
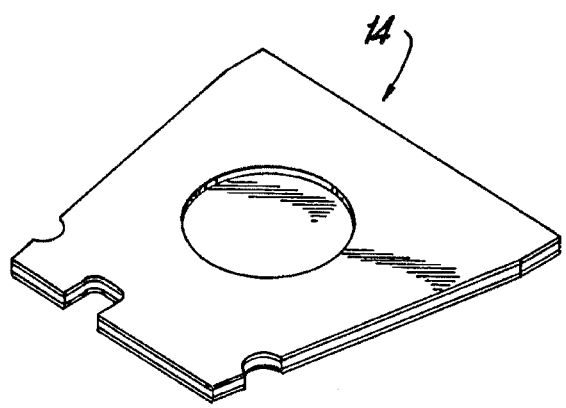
FIG. 10 is a top perspective view of a chemical reagent test slide preferably used with the chemical analyzer of the present invention.
Figure 11:
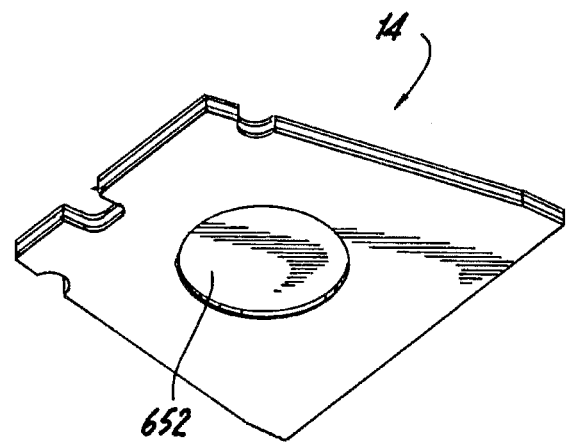
FIG. 11 is a bottom perspective view of the chemical reagent test slide shown in FIG. 1 and preferably used with the chemical analyzer of the present invention.
Figure 12:
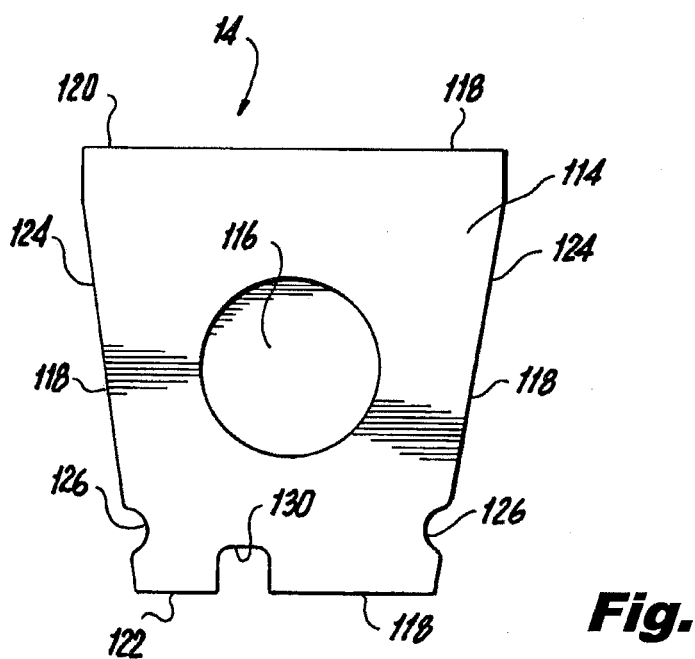
FIG. 12 is a top plan view of the chemical reagent test slide preferably used with the chemical analyzer of the present invention.
Figure 13:
FIG. 13 is a front elevational view of the preferred form of the chemical reagent test slide preferably used with the chemical analyzer of the present invention.
Figure 14:
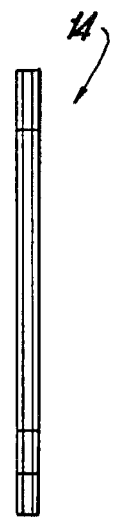
FIG. 14 is a right elevational view of the chemical reagent test slide preferably used with the chemical analyzer of the present invention.
Figure 15:
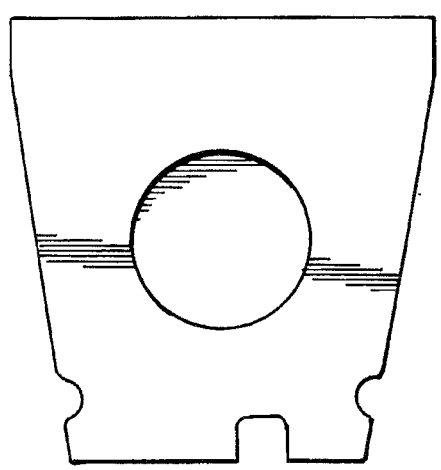
FIG. 15 is a bottom plan view of the chemical reagent test slide preferably used with the chemical analyzer of the present invention.
Figure 16:
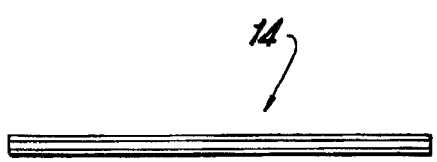
FIG. 16 is a rear elevational view of the chemical reagent test slide preferably used with the chemical analyzer of the present invention.
Figure 17:
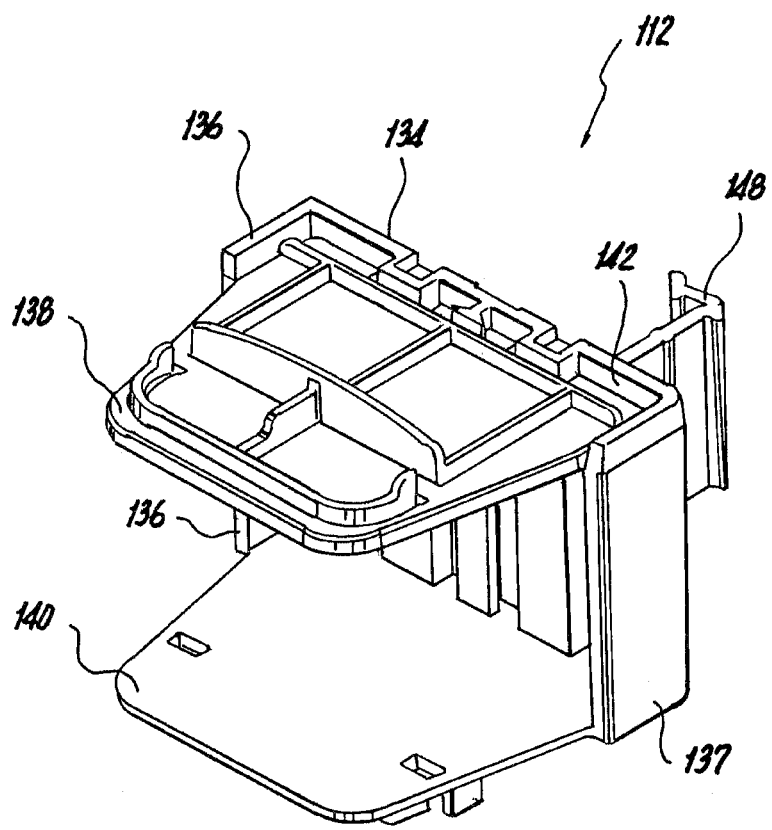
FIG. 17 is a front isometric view of a retaining clip preferably used with the chemical analyzer of the present invention.
Figure 18:
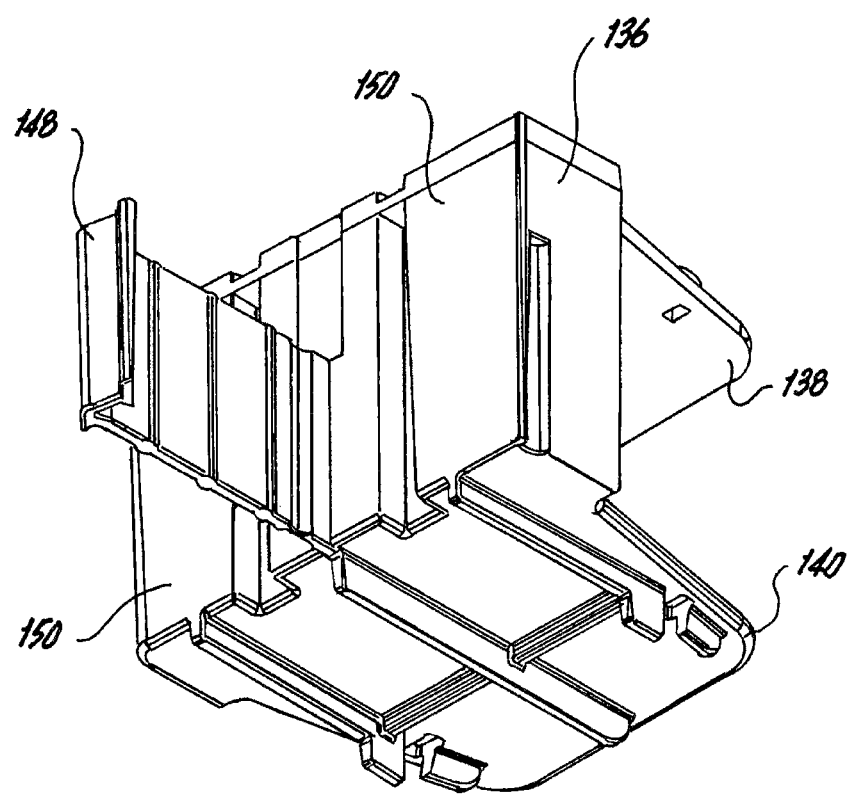
FIG. 18 is a rear isometric view of the retaining clip shown in FIG. 17.
Figure 19:
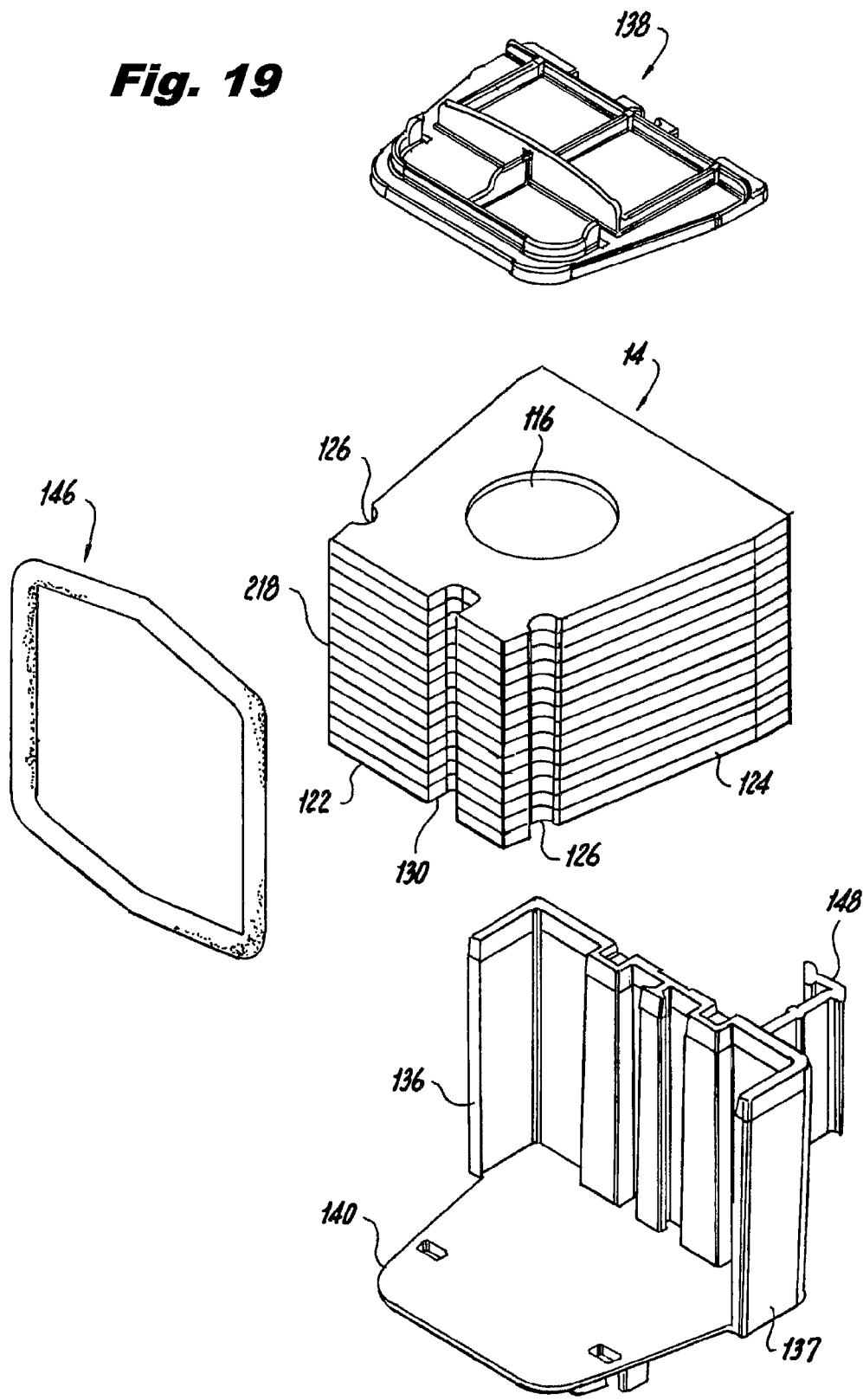
FIG. 19 is an exploded front isometric view of the retaining clip shown in FIG. 17.
Figure 20:
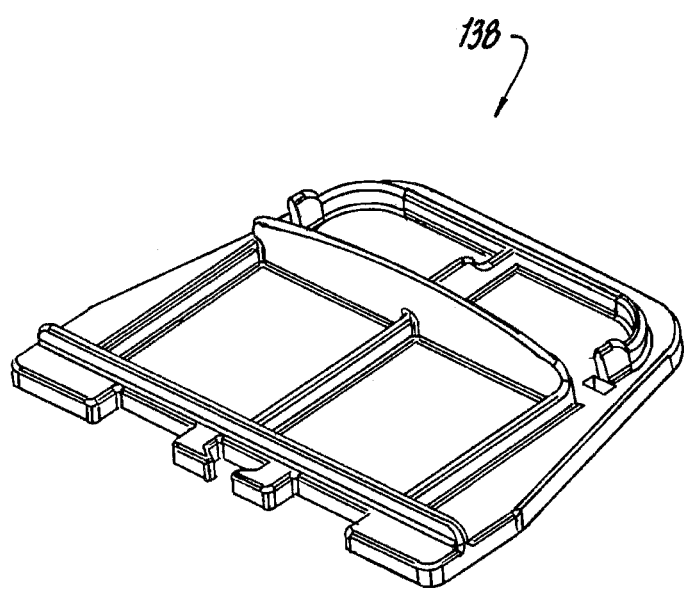
FIG. 20 a top isometric view of a first portion of the retaining clip shown in FIG. 17.
Figure 21:
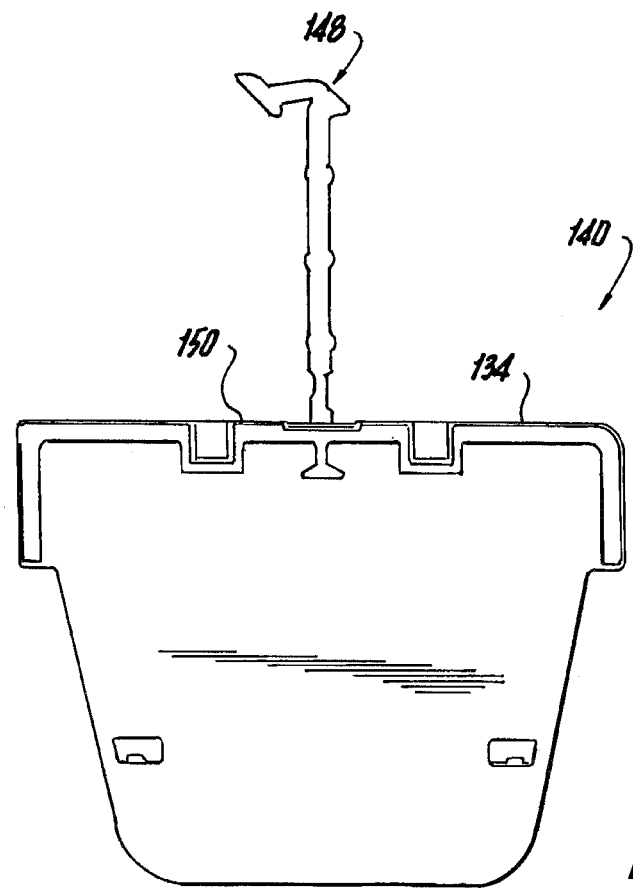
FIG. 21 is a top plan view of a first portion of the retaining clip shown in FIG. 17.
Figure 22:
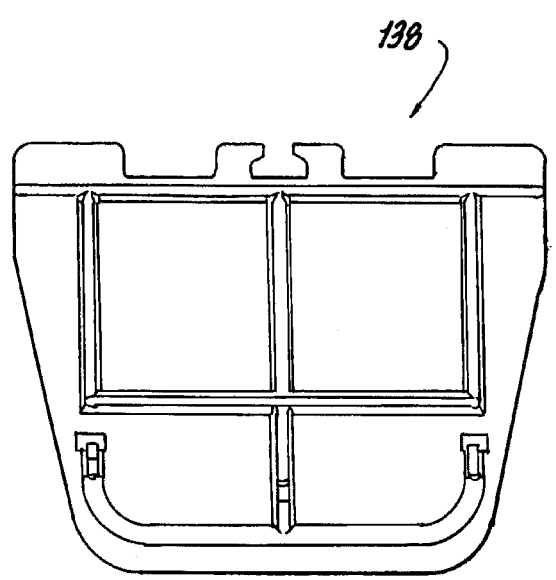
FIG. 22 is a top plan view of a second portion of the retaining clip shown in FIG. 17.
Figure 23:
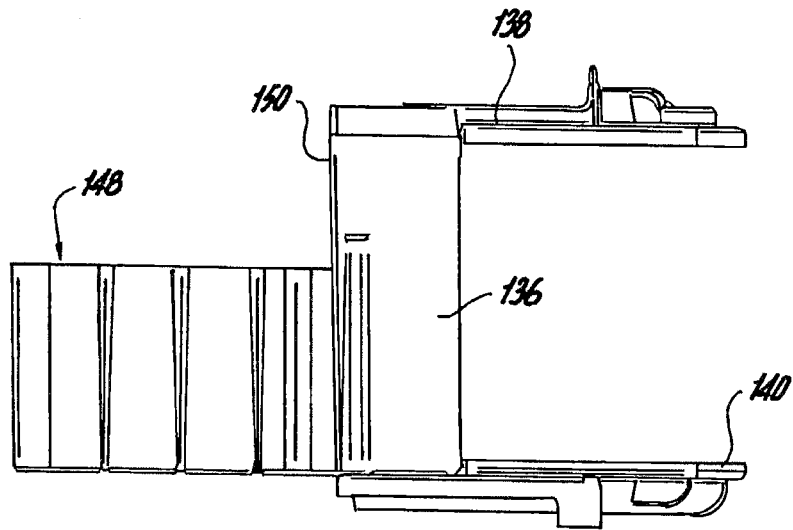
FIG. 23 is a side view of the retaining clip shown in FIG. 17.
Figure 24:
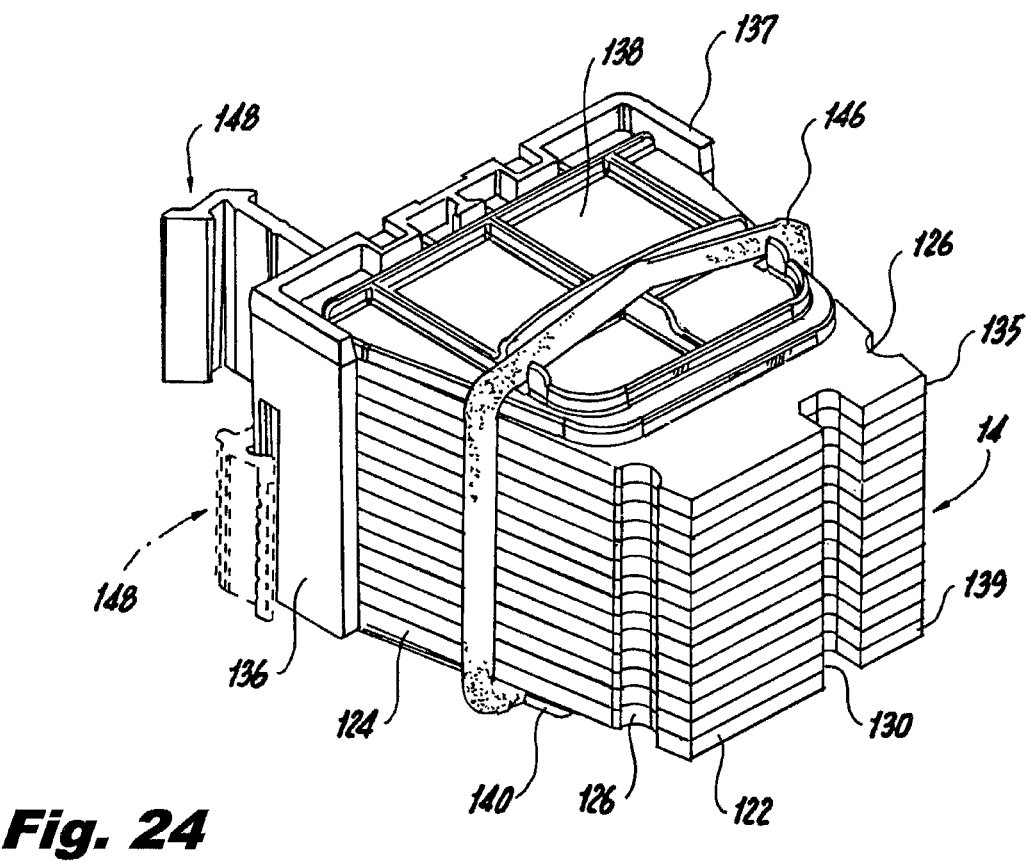
FIG. 24 is a front isometric view of the retaining clip shown in FIG. 17 and further shown holding a plurality of reagent test slides and having the handle thereof shown in an extended state (in solid lines) and in an unextended state (in dashed lines).
Figure 25:
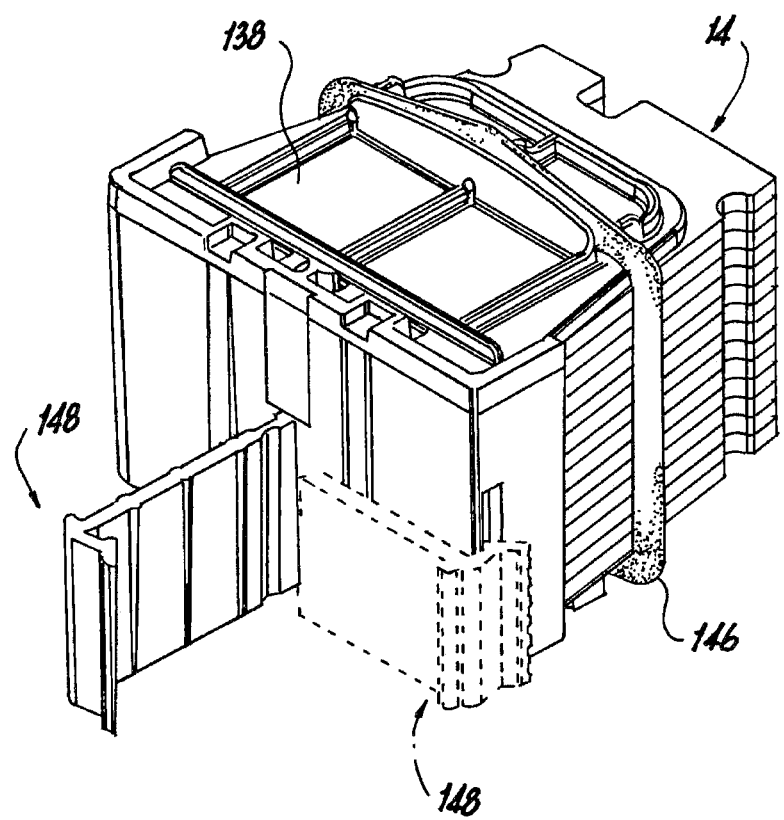
FIG. 25 is a rear isometric view of the retaining clip shown in FIG. 17 and shown holding a plurality of reagent test slides and having the handle thereof shown in an extended state (in solid lines) and in an unextended state (in dashed lines).
Figure 26:
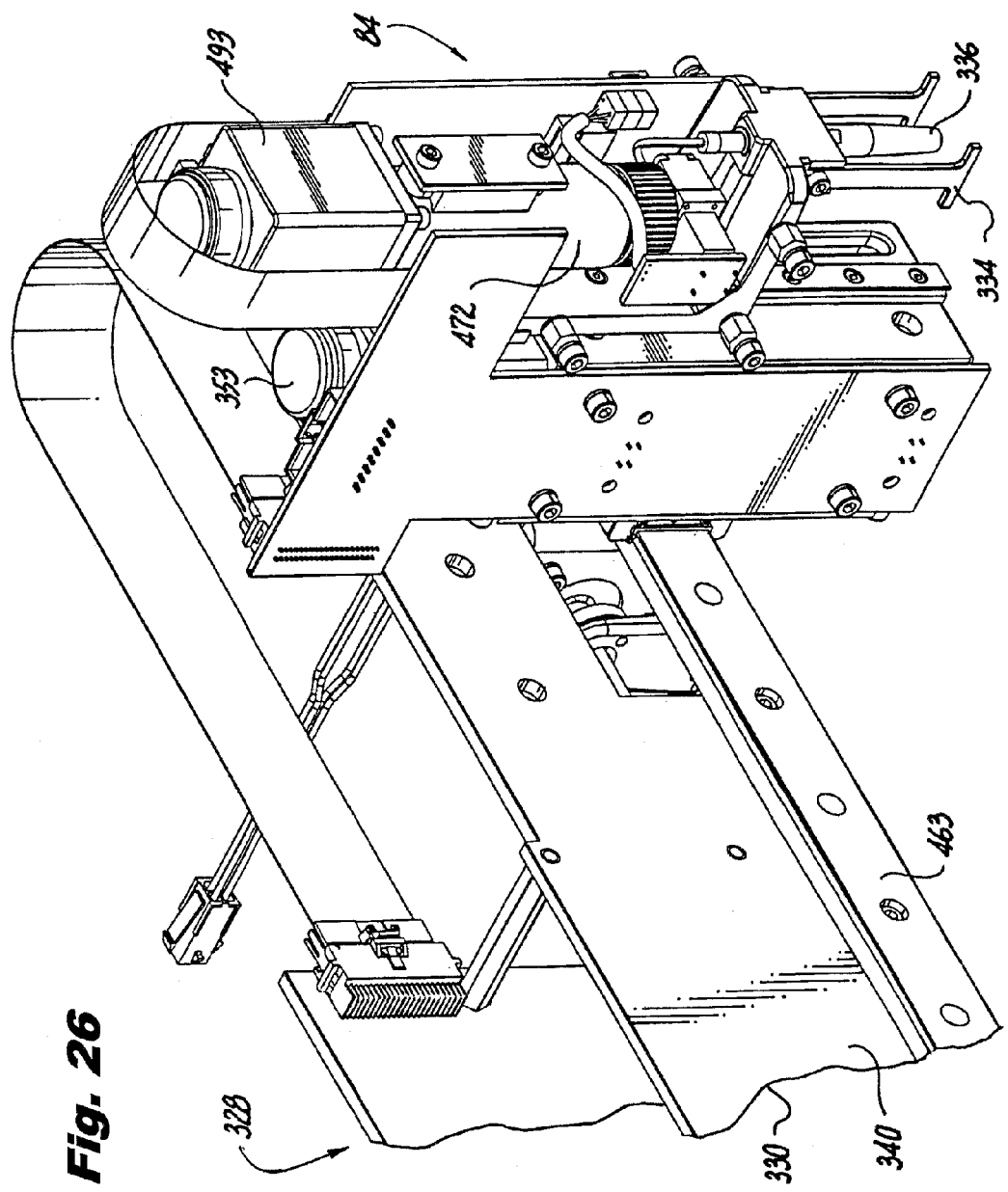
FIG. 26 is a front isometric view of a portion of the sample preparation station and sample metering sub-assembly mounted thereon of the chemical analyzer of the present invention.
Figure 27:
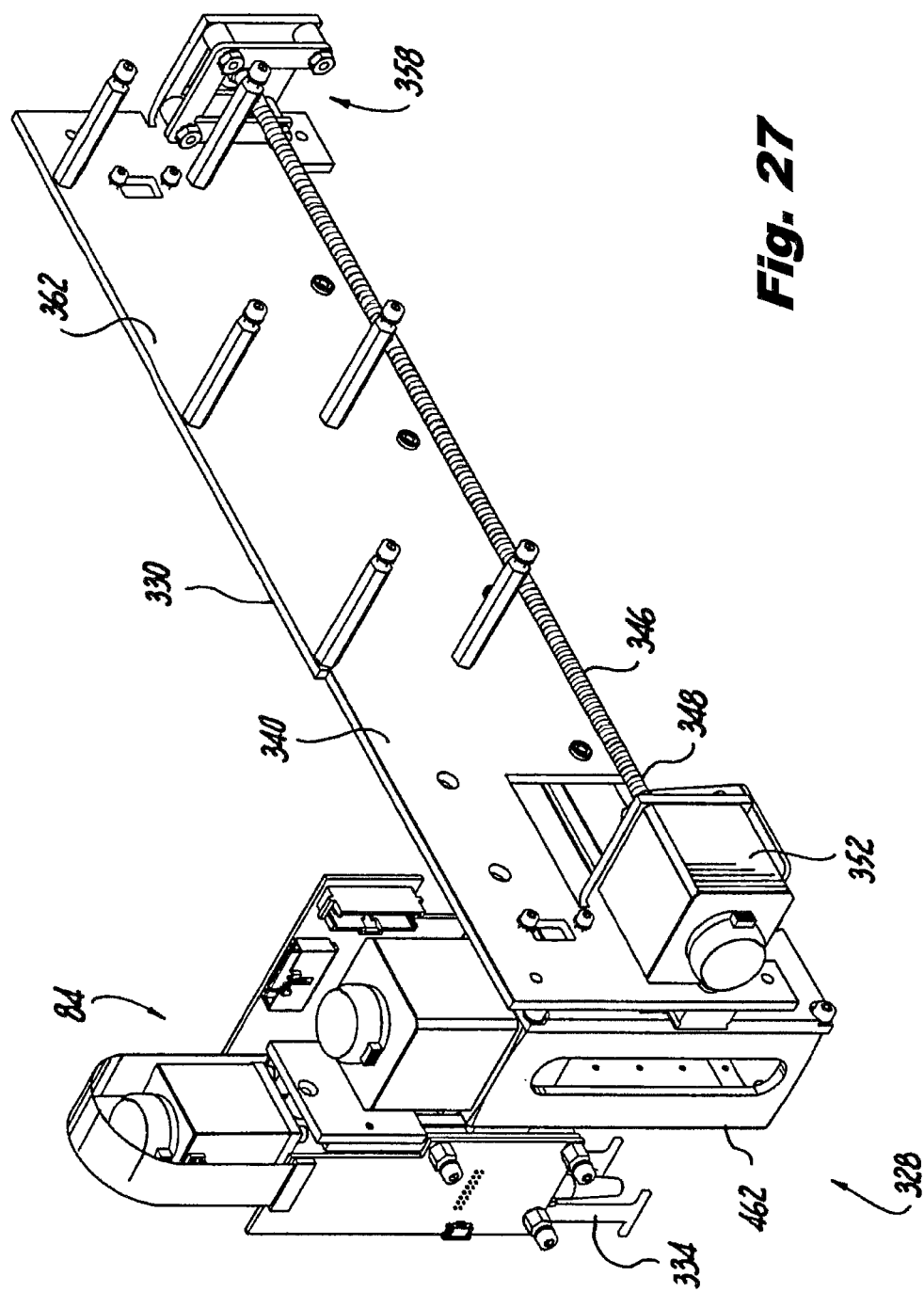
FIG. 27 is a rear isometric view of the sample preparation station and sample metering sub-assembly mounted thereon of the chemical analyzer of the present invention.
Figure 28A:
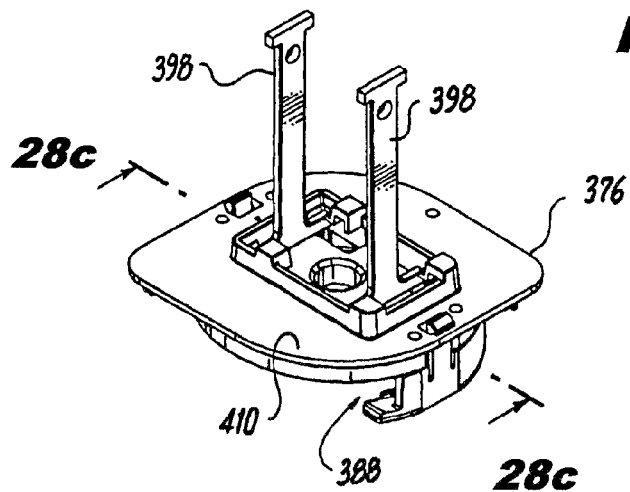
FIG. 28a is a top isometric view of a rotor carrier and a portion of a picker mechanism used in the sample preparation station of the chemical analyzer of the present invention.
Figure 28B:
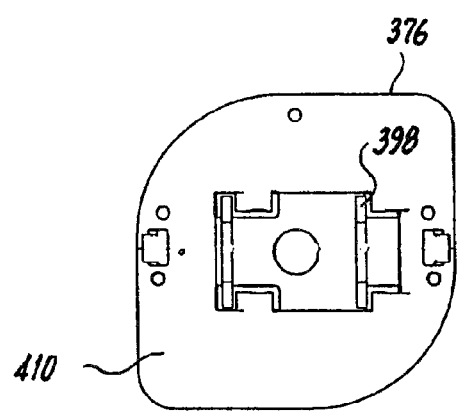
FIG. 28b is a top plan view of a rotor carrier and a portion of a picker mechanism used in the sample preparation station of the chemical analyzer of the present invention.
Figure 28C:
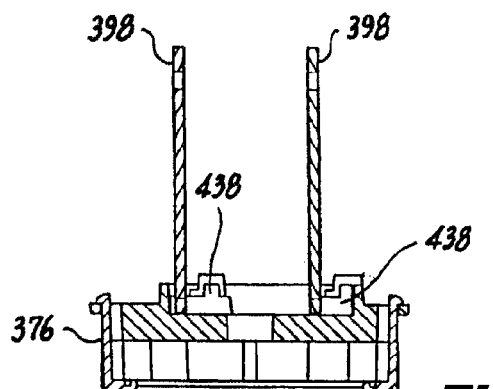

FIGS. 8, 9, and 9a show the preferred structure of the slide inserter mechanism 20 and its relative position with respect to the slide transport mechanism 26. As mentioned previously, the chemical analyzer 2 includes two separate slide inserter mechanisms 20 positioned side-by-side on the front face 18 of the housing 6 so that blood samples from two patients may be concurrently analyzed. Each mechanism 20 will be described in greater detail.

Before describing in detail the structure of the slide inserter mechanism 20, reference is now made to FIGS. 10-16 and FIGS. 17-25 which respectively illustrate a preferred form of the chemical reagent test slide 14 used in the chemical analyzer 2 of the present invention, and a retaining clip 112 for holding a plurality of reagent test slides 14 in a vertical stack 218 so that the reagent test slides 14, together as a stack 218 and not individually, are preferably loaded onto the slide inserter mechanism 20 without the clinician directly touching any of the individual slides 14.

More specifically, and as shown in FIGS. 10-16, each test slide 14 includes a frame 114 which is preferably trapezoidal in shape. The frame 114 surrounds and supports a circular film portion 116 situated interiorly of the edges 118 of the frame 114, which film portion 116 is coated with an analyte or chemical reagent, as is well known in the art. Common test slides used in biological fluid analysis include, for example, one for a calcium (Ca) test, another for an aspartate transminase (AST) test, and a third for a glucose (Glu) test.

The trapezoidal test slides 14 include a wider outer edge 120 and a narrower, opposite inner edge 122, and opposite lateral edges 124 which mutually converge toward the narrower inner edge 122. Preferably formed in the lateral edges 124 of the test slides 14, near the narrower inner edge 122, are recesses 126 which are preferably angled inwardly of each test slide 14 toward the narrower inner edge 122. The purposes of these recesses 126 is to allow the entire stack 218 of reagent test slides 14, held in place by the retaining clip 112, to be inserted into the slide inserter mechanism 20 of the chemical analyzer 2, which inserter mechanism 20 includes opposite, preferably dovetailed, vertical members 128, as will be described in greater detail, which are parallel to and spaced apart from one another a distance which corresponds to the width of each test slide 14 measured laterally in proximity to the opposite recesses 126.

An orientation notch 130 may be formed in one of the edges 118 of the slides 14, preferably the inner or front edge 122, and is offset from the center of the edge toward one lateral side or the other. As will be described in greater detail, the orientation notch 130 mates with a rib 132 or other projection, similarly located, on the slide inserter mechanism 20 to ensure that the slides 14 are properly oriented as they are being loaded onto the slide inserter mechanism 20.

This preferred form of a chemical reagent test slide 14 for use with the chemical analyzer 2 of the present invention is disclosed in U.S. Pat. No. D530,826, which issued on Oct. 24, 2006 to Carl Russell Rich et al., the disclosure of which is incorporated herein by reference.

A preferred form of a slide retaining clip 112, which carries a stack 218 of reagent test slides 14, is illustrated by FIGS. 17-25 of the drawings. The retaining clip 112 preferably includes a back wall 134, opposite lateral side walls 136, 137 extending preferably perpendicularly in the same direction from the back wall 134, and a bottom cover plate 140 affixed to the back wall 134 and extending preferably perpendicularly therefrom in the same direction as the lateral side walls 136. A top cover plate 138 is slidably attached to the back wall 134 of the retaining clip 112. The top cover plate 138 and the bottom cover plate 140 of the retaining clip 112 preferably at least partially conform to the general shape of the reagent test slides 14 held in place between them and extend outwardly from the front surface 142 of the back wall 134 a distance sufficient to cover the film portion 116 of the top and bottom reagent test slides 135, 139 in the stack of test slides 218 to help minimize evaporation of any analyte deposited thereon, but leave exposed the recesses 126 formed in the lateral edges 124 of the slides 14 and the orientation notch 130 formed in the front edge 122 of the slides 14 to allow the entire stack of reagent test slides 218, while still held by the retaining clip 112, to be transferred to the slide inserter mechanism 20 of the chemical analyzer 2.

An elastic band 146 to help secure the plurality of reagent test slides 14 in place on the retaining clip 112 between the lateral side walls 136, 137 and the top cover plate 138 and the bottom cover plate 140 is also included. The elastic band 146 rests and exerts pressure on the top cover plate 138 and the bottom cover plate 140 and ensures that the top and bottom cover plates tightly contact respectively the top and bottom slides 135, 139 of the stacked arrangements of slides 218 and to ensure that the top and bottom cover plates 138, 140 closely cover the film portion 116 of the top and bottom slides in the stack 218 to minimize any evaporation of the analyte deposited thereon.

The retaining clip 112 includes a handle 148 for grasping by the clinician. The handle 148 extends outwardly from the rear surface 150 of the back wall 134 of the retaining clip 112 in preferably a perpendicular direction therefrom. However, it may be folded and secured in place against or in proximity to the rear surface 150 of the back wall 134 when it is not being used, in order to reduce the overall dimensions of the retaining clip 112. Preferred and alternate forms of the retaining clip is described in greater detail in co-pending U.S. patent application Ser. No. 11/002,599, filed on Dec. 2, 2004, and entitled "Retaining Clip for Reagent Test Slides", and in U.S. patent application Ser. No. 11/001,994, filed on Dec. 2, 2004, and entitled "Retaining Clip for Reagent Test Slides", the disclosures of which are incorporated herein by reference.

FIGS. 8, 9, 9a and 41-45 illustrate two preferred forms of the slide inserter mechanism 20 of present invention. The slide inserter mechanism 20 includes structural components that interface with the test slides 14 to help remove the slides 14, in a stacked arrangement 218, from the retaining clip 112 described previously. Referring initially to FIG. 8 of the drawings, a first embodiment of a slide inserter mechanism 20 includes a pair of spaced apart, upstanding, vertically disposed guide blocks 128 between which a stack 218 of reagent test slides 14 is placed. The upstanding guide blocks 128 are situated perpendicularly on a support plate 152 through which an opening 154 is formed which is suitably dimensioned to receive therethrough individual reagent test slides 14 from the stack of slides 218 held in place between the upstanding guide blocks 128, with the guide blocks 128 being positioned on the support plate 152 on opposite lateral sides of the plate opening 154. The actual mechanism for moving the individual test slides 14 as they pass through the plate opening 154 to other stages of the chemical analyzer 2, such as the slide transport mechanism 26, is not shown or described herein, as any number of mechanisms may be employed, as would be well known to one skilled in the art, for example, a solenoid driven, reciprocatingly movable push rod or plate mounted under the support plate that engages the slides as they pass through the opening.

Each upstanding guide block 128 has a top surface 158, and an inner surface 160 which faces that of the other block 128. Portions of the top surfaces 158 and facing inner surfaces 160 of the guide blocks 128 may be inwardly curved to define a widened space 162 between the guide blocks 128 at their upper portions to help guide from above the blocks 128 the insertion of a stack 218 of reagent test slides 14 carried by the retaining clip 112 between the blocks 128. Preferably, each facing inner surface 160 of the guide blocks 128 includes a rib 166 projecting outwardly therefrom which extends along the length thereof. The ribs 166 are spaced apart from each other a predetermined distance such that they closely engage and are at least partially received by corresponding recesses 126 formed in the opposite lateral edges 124 of the test slides 14 held in a stacked arrangement 218 by the retaining clip 112, or individual test slides 14 that are inserted by the user between the guide blocks 128.

A portion 168 of the length of the ribs 166, or the entire length thereof, may be formed of a resilient material, such as plastic or metal, so as to be flexible in a transverse direction with respect to the inner facing surfaces 160 of the guide blocks 128. Such resilient rib portions 168 allow the clinician to load a stack 218 of test slides 14 held in place by the retaining clip 112, or individual test slides 14, onto the slide inserter mechanism 20 from the front of the mechanism 20 (as well as from atop the guide blocks 128) by pushing the slides 14 forward between the guide blocks 128 until the resilient portions 168 of the ribs 166 snap into the recesses 126 formed in the lateral edges 124 of the slides 14. The resiliency of the rib portions 168 may be uni-directional only, in the same forward direction of movement of the slides 14 as they are being inserted between the guide blocks 128, so that the slides 14 are captively received and held between the blocks 128 once the resilient rib portions 168 snap into the slide recesses 126. Alternatively, the resilient rib portions 168 may be flexible transversely bi-directionally, as long as the force required to unload the stack 218 of slides 14 from the retaining clip 112 is not greater than the holding force that the resilient rib portions 168 imparts on the test slides 14.

The slide inserter mechanism 20 may include posts 172 (generally referred to as slide retaining clip disengagement members) having shank portions 174 (generally referred to as first extended portions) and enlarged, bulbous free ends 176 (generally referred to as transverse end portions) extending perpendicularly outwardly from the front face 178 of each guide block 128 in the same parallel direction. The distance between the shank portions 174 of the posts 172 is equal to or slightly greater than the width of the retaining clip 112 so that the retaining clip 112 may be received between the posts 172 and guided thereby, as the clinician loads a stack 218 of test slides 14 held thereby from atop the guide blocks 128. The posts 172 are situated on the guide blocks 128 a distance above the support plate 152 that is at least slightly greater than the overall height of the retaining clip 112. Positioning and spacing the posts 172 as described above will prevent the clinician from inadvertently removing the retaining clip 112 at the upper portions of the guide blocks 128, where the spacing 162 between the blocks 128 is wider. At the upper portions of the guide blocks 128, the recesses 126 formed in the lateral edges 124 of the test slides 14 held by the retaining clip 112, especially for those slides toward the top of the stacked arrangement of slides 218, may not fully engage the projecting ribs 166, and, therefore, some slides may remain secured to the retaining clip 112 as it is pulled away from the slide inserter mechanism 20 when the user is unloading the slides 14. However, with the posts 172 and the enlarged post ends 176, the clinician is prevented from prematurely withdrawing the retaining clip 112 from the slide inserter mechanism 20 until the retaining clip 112 fully passes below the lowermost part of the enlarged post ends 176. This structure ensures that the projecting ribs 166 of the guide blocks 128 fully and securely engage the stacked arrangement of slides 218 at the slide recesses 126, which occurs at the lower portion of the guide blocks 128, before the clinician is permitted to withdraw the retaining clip 112 from the slide inserter mechanism 20.

If only a portion of each projecting rib 166 is made resilient, then that resilient portion 168 is preferably situated approximately above the top surface of the support plate 152 and below the lowermost extent of the enlarged ends 176 of the posts 172. In this manner, the clinician, when unloading the slides 14 from the retaining clip 112 at the front of the slide inserter mechanism 20, can only do so if he positions the retaining clip 112 below the posts 172 where the ribs are resilient. It should be realized, however, that structure other than posts 172 with enlarged ends 176 may be used to ensure the proper positioning of the retaining clip 112 on the slide inserter mechanism 20. For example, L-shaped brackets (not shown) extending outwardly from the front face 178 of the guide blocks 128 may be used in lieu of the posts 172. The L-shaped brackets would be arranged in mirrored symmetry, with their shorter legs directed toward each other and spaced apart a distance sufficient to allow the handle 148 of the retaining clip 112 to pass therebetween. The L-shaped brackets would help guide the retaining clip 112 into proper position on the slide inserter mechanism 20 and, like the posts 172 mentioned previously, would be positioned above the top surface of the support plate 152 a predetermined distance that would prevent the clinician from withdrawing the retaining clip 112 prior to the test slides 14 in the stacked arrangement 218 being fully engaged by the resilient rib portions 168 situated at the lower portions 180 of the guide blocks 128.

The clinician would grasp the handle 148 of the retaining clip 112 and insert the entire stack of slides 218 held thereby onto the slide inserter 20 between the two guide blocks 128, either by sliding the stack of slides 218 between the two blocks 128 from atop the blocks, or by pushing the retaining clip 112 forward until the recesses 126 in the lateral edges 124 of the slides 14 in the stack 218 engage the resilient portions 168 of the projecting ribs 166. Preferably, the user will hear an audible click from the resilient ribs 168 snapping into the slide recesses 126 and will know that the test slides 14, still held by the retaining clip 112, are properly mounted in place on the slide inserter mechanism 20. The clinician may now pull backward on the handle 148 of the retaining clip 112, and the entire stack of slides 218 held thereby will be removed from the retaining clip 112, as they are now held in place on the slide inserter mechanism 20.

If desired, the slide inserter mechanism 20 may include a back plate 184 situated opposite the front faces 178 of the guide blocks 128 and extending across the separation between the guide blocks 128. The back plate 184 may include another rib 186 extending outwardly perpendicularly from an exposed surface thereof toward the spacing between the guide posts 172 and longitudinally along the length thereof. This rib 186 is preferably not centered between the guide blocks 128, but rather is offset toward one guide block 128 or the other. The rib 186 is aligned with and, therefore, is received by the orientation notches 130 formed in the opposite inner edge 122 of the test slides 14 to ensure that the slides 14 are properly oriented as they are being loaded onto the slide inserter mechanism 20. If the slides 14 are being inserted on the slide inserter mechanism 20 upside down, the rib 186 will not be in alignment with the orientation notches 130 of the slides 14 and will not be received thereby. The height of the rib 186 above the exposed surface of the back plate 184 is such that, when the slides 14 are improperly oriented, the rib 186 engages the un-notched portion of the inner edge 122 of the slides 14 and prevents the recesses 126 from receiving the projecting ribs 166 of the guide blocks 128. Accordingly, the stack of slides 14 will be prevented from being unloaded from the retaining clip 112 if the slides 14 are in an improper orientation.

It should be further noted that either the top cover plate 138 or the bottom cover plate 140, or both, of the retaining clip 112 are preferably dimensioned so that they entirely cover the film portion 116 of the top and bottom end slides 14 in the stack 218, but also have a width which is less than the width of the test slides 14 measured across the slides 14 between the recesses 126 formed in the opposite lateral edges 124 so that at least portions of the lateral edges 124 of the slides 14 bearing the recesses 126 extend beyond the lateral sides of the top and bottom cover plates 138,140 to expose the recesses 126 and so that the recesses 126 may cooperate with and receive portions of the upstanding vertical members 128 of the slide inserter mechanism 20 while the test slides 14 are still retained by the retaining clip 112. As mentioned previously, the top and bottom cover plates 138,140 also preferably do not cover the orientation notch 130 formed in the front edge 122 of the test slides 14, so that the orientation notch 130 which is offset to one lateral side or the other, will be exposed to engage the cooperating orientation rib 186 of the slide inserter mechanism 20. The structure of the slide inserter mechanism 20 shown in FIG. 8 is disclosed in the aforementioned application Ser. No. 11/002,599.

The preferred form of the slide inserter mechanism 20 is shown in FIGS. 9, 9a and 41-45. Each slide inserter mechanism 20 is integrally formed at the distal end 190 of an elongated block-like, rectangular support member 192. The proximal end 194 of the support member 192 is operatively coupled to the shaft 196 of a motor 198 which, when energized, will extend or retract the slide inserter mechanism 20 situated at the distal end 190 of the support member 192 with respect to the front face 18 of the housing 6 when the sliding vertical doors are open 16. This allows easy access by the clinician to the slide inserter mechanism 20. The motors 198 which extend and retract the slide inserter mechanism 20 are controlled by the electronic circuitry (not shown) of the chemical analyzer 2 which, from the sensors (not shown) on the sliding vertical doors 16, knows when the doors are open or closed.

More specifically, a surface of each elongated support member 192, such as the top surface 200, has mounted thereon a toothed rack 202. A pinion gear 204 affixed to the shaft 196 of each motor 198 engages the toothed rack 202 of a corresponding slide inserter mechanism 20 to extend and retract the slide inserter mechanism 20.

A well or recess 206 is formed in the upper surface 200 of the support member 192 for each slide inserter mechanism 20, which acts as a receptacle for receiving and holding a centrifuge rotor 208 or a blood sample vial 242 placed thereon by a clinician. As will be described in greater detail below, the rotor 208 may be removed by the sample preparation station of the chemical analyzer 2 and placed on the high speed spin centrifuge 210 provided in the analyzer 2. Alternatively, a previously centrifuged blood sample may be contained in the sample vial 242 that is placed by the clinician on one or both of the slide inserter mechanisms 20 and deposited without further centrifugation by the sample metering sub-assembly 84 directly onto the reagent test slides 14 for analysis.

More specifically, the preferred form of the slide inserter mechanism 20 includes a front wall 212 and a pair of lateral, spaced apart vertical blocks 214 extending outwardly from the front wall 212, the blocks 214 defining a space 216 between them for receiving therein a stack 218 of reagent test slides 14. Each vertical block 214 has a surface 220 facing inwardly of the space, and a vertical rib 222 projecting outwardly from this surface 220 of each block 214 and into the space 216 between the blocks 214. The ribs 222, as described previously with respect to the embodiment of the slide inserter mechanism shown in FIG. 8, are in alignment with each other and are received by the recesses 126 formed in the opposite lateral sides 124 of the chemical reagent slides 14 (see FIGS. 10-16) when the slides 14 are placed on the slide inserter mechanism 20 either individually or in a stack 218. Since the preferred form of the test slides 14 is trapezoidal, the blocks 214 may be angled to mutually converge slightly toward the front face 212 of the slide inserter mechanism 20 so that they define the space 216 for receiving the slides 14 with a complementary trapezoidal shape. An orientation rib 132 projecting outwardly from the front face 212 of the slide inserter mechanism 20 and offset laterally from the vertical centerline thereof is received by the orientation notch 130 formed in the reagent test slides 14 (see FIGS. 10-16) when the slides 14 are mounted on the inserter mechanism 20 to ensure that the slides 14 are properly oriented (e.g., not upside down).

The well or recess 206 formed in the upper surface 200 of the support member 192 can accommodate either a centrifuge rotor 208, for blood samples not yet centrifuged, or a smaller vial 242 containing a pre-centrifuged blood sample. The overall shape of the well 206 is circular, defined by circularly-shaped, partial inner walls 224 of the support member 192. The side walls 224 of the support member 192, in the area of the well 206, include cutouts 226 formed therein which communicate with the well 206. The cutouts 226 are provided to allow a beam of light to pass therethrough and through the wells 206 to determine whether the clinician placed the larger diameter rotor 208 in the well 206, which is within the light path and would interrupt the light beam, or the smaller diameter sample vial 242, which would not interfere with the light beam passing through the side wall cutouts 226 and the well 206. The light beam is preferably generated by a light source 228, such as a light emitting diode, positioned inside the analyzer housing 6 to be in alignment with the cutout 226 formed in one side wall 224 of a respective slide inserter mechanism 20 when the mechanism 20 is in its fully retracted state. The light beam is preferably received by a light sensor 230, such as a photodiode, positioned also inside the analyzer housing 6 to be in alignment with the cutout 226 formed in the other side wall 224 of the slide inserter mechanism 20, opposite the light source 228, when the inserter mechanism 20 is fully retracted, to receive the light generated by the light source 228. The light sensor 230 generates an electrical signal that is indicative of whether light generated by the light source 228 is received thereby (and thus whether a centrifuge rotor 208 or a sample blood vial 242 has been placed in the well 206), and provides this signal to the electronic circuitry of the analyzer 2. Based on the state of this signal, the analyzer 2 recognizes that either a rotor 208 is in the well 206, and will execute a centrifugation operation in which the rotor 208 is removed from the well 206 and transported to a centrifuge 210 where the blood sample is centrifuged, or a sample vial 242 is in the well 206, in which case the analyzer 2 will omit the centrifugation operation and will draw the blood samples directly from the vial 242 for spotting the slides 14 (if it is not desired to mix the blood sample with a diluent, which involves an additional step).

In an even more preferred embodiment of the present invention, the light source 228 and light sensor 230 scan the well 206 formed in the slide inserter mechanism as the mechanism is being retracted into the analyzer housing. The signal generated by the sensor 230 in response to the larger diameter centrifuge rotor 208, when mounted on the slide inserter mechanism, will be different from the signal generated by the sensor 230 in response to scanning the well 206, with the light beam interrupted intermittently by the smaller diameter sample vial 242 mounted in the well 206. In this way, the electronic circuitry cannot only determine whether the centrifuge rotor 208 or the sample vial 242 is situated in the well 206 of each slide inserter mechanism, but also if neither the rotor 208 nor the sample vial 242 is situated in the well, as under such conditions, the light beam generated by the light source 228 and detected by the sensor 230 will be uninterrupted when the well 206 is scanned and the slide inserter mechanism is being retracted into the analyzer housing.

Figure 43:
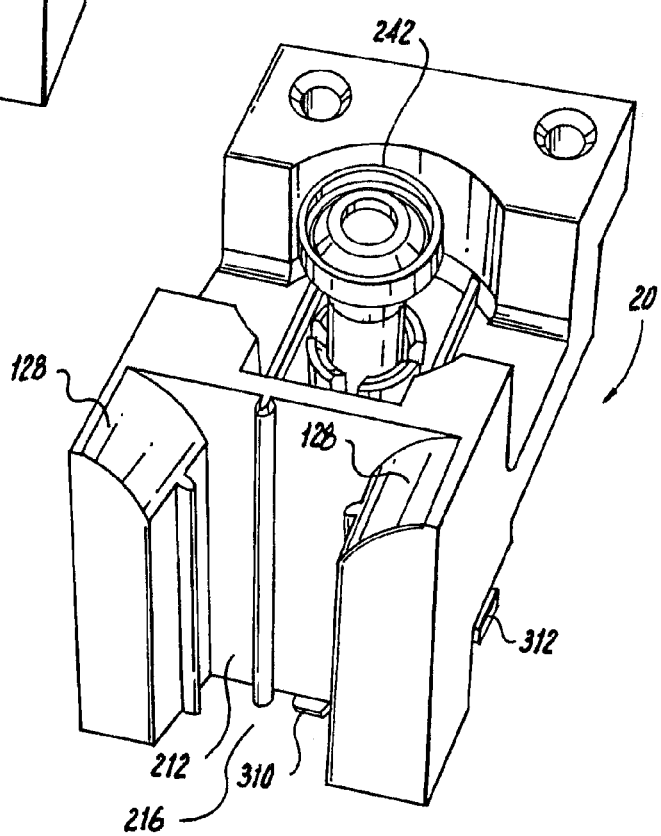
FIG. 43 is a front isometric view of the slide inserter mechanism shown in FIG. 41, and illustrating the slide inserter mechanism holding a sample vial.
Figures 46, 47:
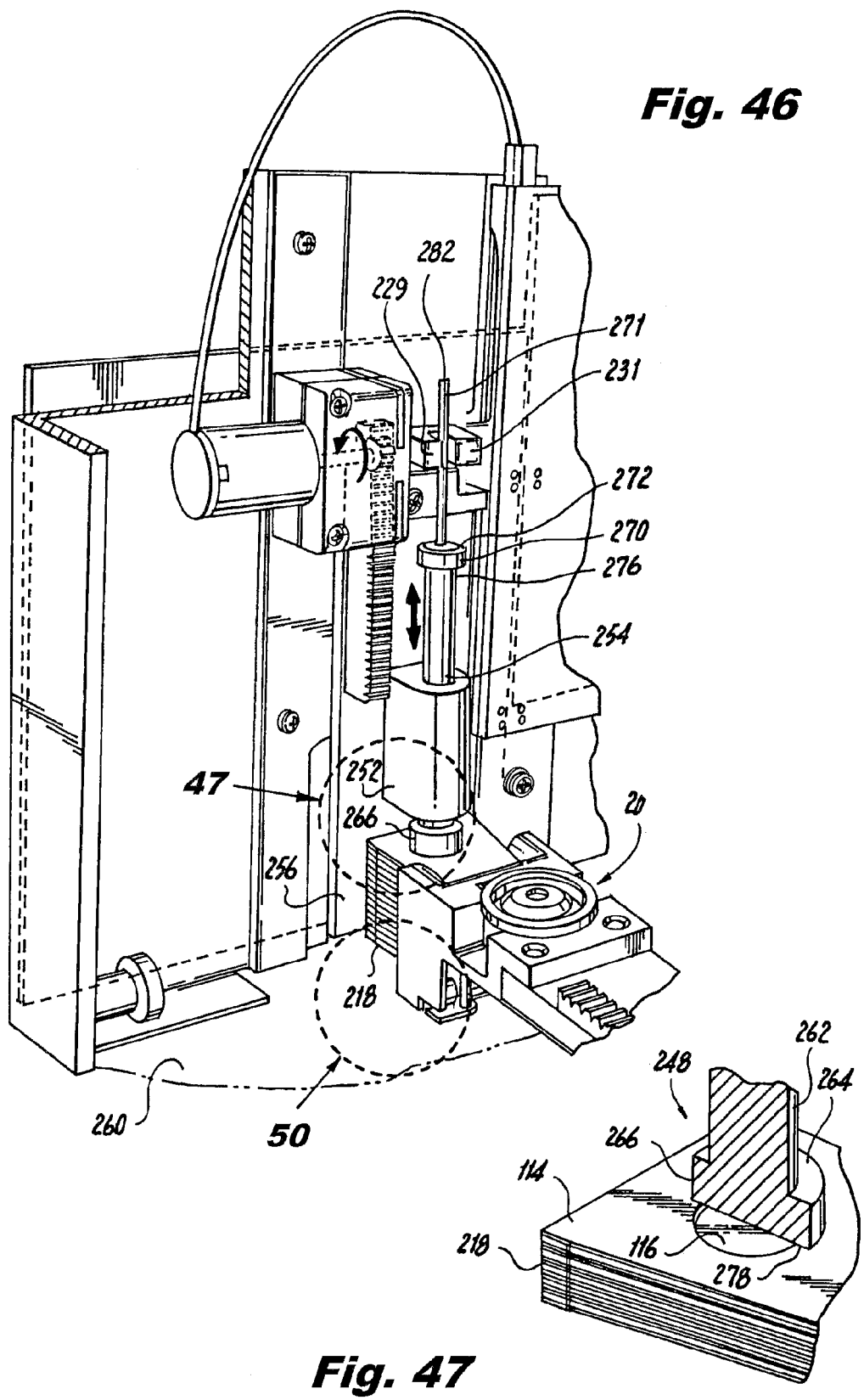
FIG. 46 is a rear isometric view of a portion of the chemical analyzer of the present invention, illustrating the operation of a gravity enhancer portion of the analyzer.
FIG. 47 is a partially cut away, detailed isometric view of the portion of the gravity enhancer shown encircled by dashed line 47 in FIG. 46.

A series of four circumferentially spaced apart resilient fingers 232 project upwardly from the top surface 236 of the bottom wall 234 of the elongated support member 192 of the slide inserter mechanism 20 which partially defines the rotor and sample vial receptacle or well 206. The spaced apart resilient fingers 232 are situated on the bottom wall 234 of the elongated support member 192 so that they do not interfere with a centrifuge rotor 208 placed in the well 206. More specifically, the resilient fingers 232 are positioned to be within the inner space 240 defined by the outer skirt 238 of the centrifuge rotor 208 if the rotor 208 instead of the sample vial 242 is placed in the well 206 (see FIG. 58). The resilient fingers 232 can closely and securely hold among them, interiorly of the fingers, the bottom portion 244 of the sample vial 242, such as shown in FIG. 43. When the vial 242 containing a pre-centrifuged sample of blood, for example, is used instead of the centrifuge rotor 208, the clinician places the sample vial 242 in the center of the resilient fingers 232, which holds the sample vial 242 in an upright position. The sample vial 242 has an open top end 246 so that the pipette 336 of the chemical analyzer 2 may withdraw a blood sample therefrom.

In a preferred form of the slide inserter mechanism 20 of the chemical analyzer 2, a weight 248 is provided which exerts a force on the top slide in the stack of slides 218 placed on the slide inserter mechanism 20. As can be seen from FIGS. 38, 38a, 46 and 47, this weight 248, also referred to herein as a "gravity enhancer", is in the form of an elongated rod 250 which is vertically slidably received by and mounted to a support member 252 having a bore 254 extending axially therethrough, which support member 252 is affixed to a bracket 256 on which each vertically sliding door 16 is mounted. The bracket 256 and support member 252 move vertically with the door 16 when it is raised and lowered.

There are preferably two gravity enhancers 248, each being positioned in alignment with a respective slide inserter mechanism 20, and positioned over the stack of slides 218 residing on the slide inserter mechanism 20 and above an opening 258 formed in an exposed slide support surface 260 (similar to the opening formed in the support plate for the embodiment of the slide inserter mechanism shown in FIG. 8) when the slide inserter mechanism 20 is in the fully retracted position. Each gravity enhancer 248 includes an elongated rod 250, as mentioned previously. An enlarged foot portion 264 in the form of a cylindrical disc 266 having a diameter which is greater than those of the rod 250 and the bore 254 of the bracket support member 252 is affixed to the lower axial end 262 of the rod 250. An enlarged head portion 270, also in the form of a cylindrical disc 272 having a diameter which is greater than those of the rod 250 and the bore 254 of the bracket support member 252 is affixed to the opposite upper axial end 276 of the rod 250. In this way, the gravity enhancer 248 is held captive in the bore 254 of its respective support member 252 but is freely slidable therein over the length of the rod 250 between the head and foot portions 270,264 of the enhancer 248. Of course, it is envisioned to be within the scope of the present invention to form the enlarged head and foot portions 270,264 with shapes other than that of a disc, such as a square or rectangular shape, or to eliminate the enlarged head portion 270 and substitute instead a transverse pin (not shown) extending diametrically through the top end of the rod 250 to ensure that the rod 250 of the gravity enhancer 248 is held captive but slidable within the bore 254 of the bracket support member 252.

Even more specifically, the diameter of the foot portion 264, preferably in the form of a disc 266, is greater than that of the film portion 116 of the reagent test slides 14 so that the bottom surface 278 of the foot portion 264 rests on the frame 114 of the top slide in the slide stack 218 and completely covers the film portion 116 of the top slide. Thus, the gravity enhancer 248, and in particular the disc-shaped foot portion 264 thereof, completely covers the film portion 116 of the top slide. Therefore, the gravity enhancer 248, and in particular the disc shaped foot portion 264 thereof, because it covers the film portion 116 of the top slide, minimizes any evaporation of the analyte on the film portion 116 of the slide, since it is the top slide in the stack 218 that is primarily exposed to the atmosphere, and respective middle and bottom slides in the stack of slides 218 mounted on the slide inserter mechanism 20 are protected from deleterious environmental effects by the slide directly resting above it.

When a stack of slides 218 is transferred by the clinician to a respective one of the preferably two slide inserter mechanisms 20, with either the centrifuge rotor 208 or sample vial 242 being placed in the corresponding well 206, the clinician signals the analyzer 2 by using the touch screen display 4 that this task has been completed, and the electronic circuitry 22 of the analyzer 2 energizes the motor 198 to retract the slide inserter mechanism 20 into the interior 570 of the housing 6. Once the slide inserter mechanism 20 is fully retracted, the motor 30 driving the toothed rack of the corresponding sliding door 16 lowers the door 16 and with it, the support member 252 and gravity enhancer 248, such that the foot portion 264 of the gravity enhancer 248 rests on the frame 114 of the top slide in the stack of slides 218 loaded onto the slide inserter mechanism 20, with the foot portion 264 thereof completely covering the film portion 116 of the top slide.

The weight of each gravity enhancer 248 bears down on the stack of slides 218 to keep the slides arranged vertically in alignment, especially during the slide insertion operation, and to help force the slides by gravity due to its weight from the inserter mechanism 20 into the opening 258 formed in the slide support surface 260 below the stack of slides 218.

Furthermore, the head portion 270 of each gravity enhancer 248, or more preferably, a member 271 which axially extends upwardly from the top surface 282 of the head portion 270, is positioned between a light source 229 and a light sensor 231, such as a light emitting diode and a photo detector, respectively. The light source 229 and light sensor 231 are mounted on the door frame bracket 284 and movable therewith. The light source 229 is aligned with the light sensor 231 to direct light emitted thereby onto the light sensor 231. The light source 229 and light sensor 231 are positioned on diametrically opposite sides of the gravity enhancer 248 or the member 271 extending axially therefrom so that the light path is selectively interrupted by the gravity enhancer 248 or the extended member 271, depending on the vertical position of the gravity enhancer 248 resting on the stack of slides 218.

As the slides from the stack of slides 218 loaded on the slide inserter mechanism 20 drops, one by one, into the opening 258 formed in the slide support surface 286, the gravity enhancer 248 resting by its weight on the stack of slides 218 is incrementally lowered. During the loading process, the gravity enhancer 248 or the member 271 extending axially from the head portion 270 thereof is positioned between the light source 229 and the light sensor 231 and interrupts the light path between the light source 229 and the light sensor 231. The light sensor 231, not receiving light from the light source 229 due to the interruption in the light path, provides an electrical signal to the electronic circuitry (not shown) of the analyzer 2, indicating that there are slides 14 remaining on the slide inserter mechanism 20 which have not yet been transferred to the slide transport mechanism 26 of the analyzer 2.

When the last (top) slide in the stack 218 passes through the opening 258 in the slide support surface 260, the top end 282 of the head portion 270 of the respective gravity enhancer 248, or the top end 282 of the extended member 271 thereof, drops below the light path between the light source 229 and light sensor 231 so that the light sensor 231 now receives light generated by the light source 229. The light sensor 231 thus provides an electrical signal to the electronic circuitry 22 of the analyzer 2, indicating that there are no more slides 14 remaining on the slide inserter mechanism 20.

Figure 50:
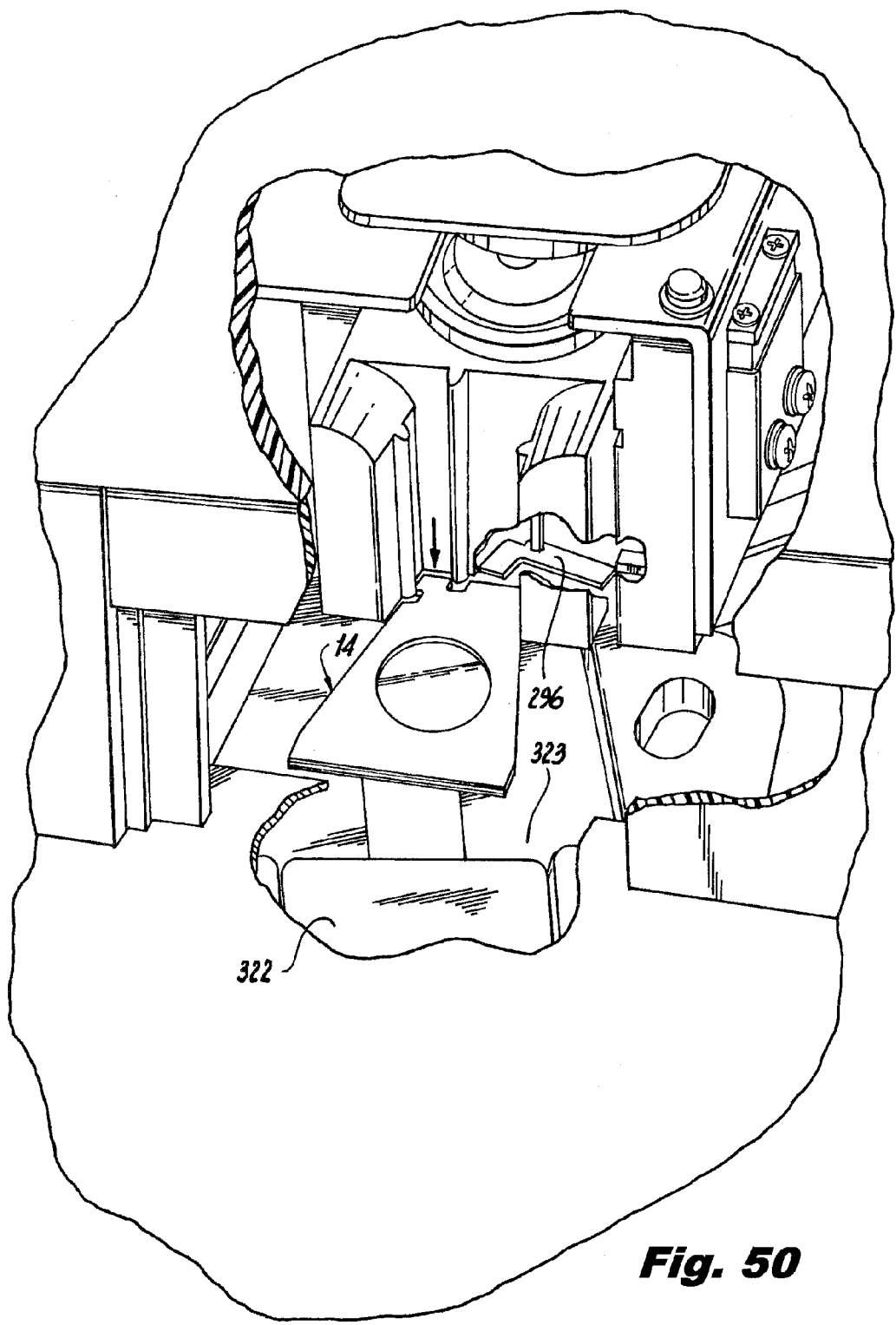
FIG. 50 is a front isometric view of the slide inserter mechanism shown in FIG. 49, with the inserter mechanism partially broken away to show the retraction of a tab which engages a chemical reagent test slide situated on the slide inserter mechanism, the analyzer housing being shown partially broken away.
Figure 51:
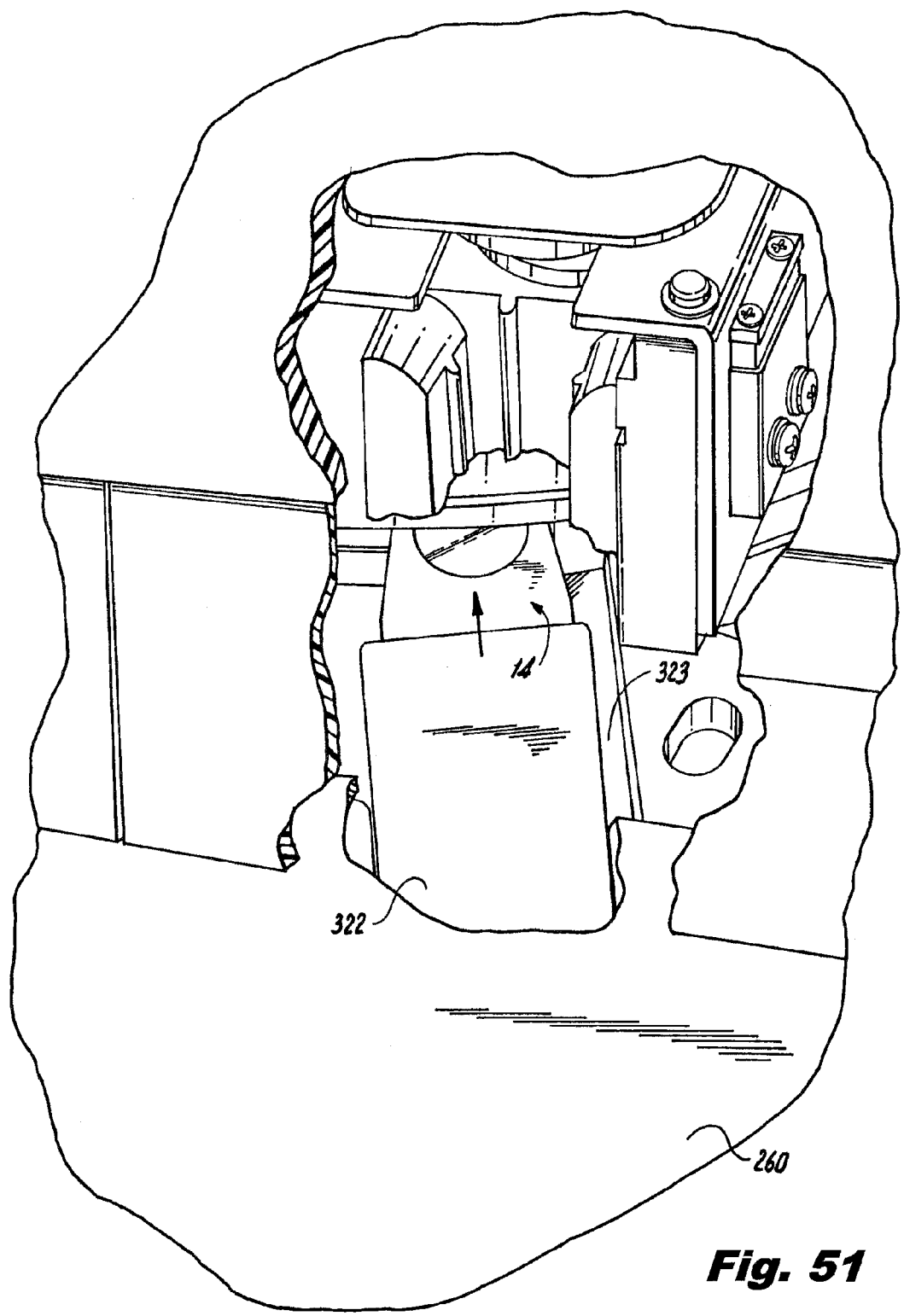
FIG. 51 is a front isometric view of the slide inserter mechanism shown in FIG. 50 through the analyzer housing which is shown partially broken away, and the engagement of a reagent test slide by a pusher plate forming part of the chemical analyzer of the present invention.

The slide support surface 260 is preferably situated both outside the housing 6 in front of the vertically slidable doors 16 and extends inside the housing 6, behind the doors 16, where the slide receiving openings 256 in the surface are situated. Actually, the slide support surface 260 is a plate under a portion of which is situated the mechanism 20 to insert the slides 14 which pass one at a time through the opening 258 into the slide transport mechanism 26, which in the preferred form of the invention includes a circular slide track 292 about which the slides 14 are moved. As mentioned previously, the mechanism for moving the individual test slides 14 as they pass through the opening 258 in the slide support surface 260 is not shown or described herein, and any number of mechanism known to those skilled in the art may be employed. However, in the preferred embodiment, there is a support plate 323 positioned under the opening 258 on which the slides 14 rest when they drop through the opening 258 in the slide support surface 260, and a reciprocatingly movable pusher plate 322 (see FIGS. 50 and 51) which slides on the support plate 323 that engages a slide on the support plate 323 and which is driven by a motor to move the individual slides from a respective slide inserter mechanism 20 to the slide track 292 forming part of the slide transport mechanism 26.

The slide inserter mechanism 20 reciprocatingly moves on the slide support surface 260 as it is extended outwardly of the housing 6 for ease of loading slides 14 thereon, such as from a retaining clip 112 holding the slides 14 in a stack 218, as shown in FIGS. 17-25, or retracted into the housing 6 through the raised door opening. As shown by FIGS. 48-51, the slides 14, loaded on the slide inserter mechanism 20 in a stacked arrangement, are drawn by the mechanism 20 over the slide support surface 260 to a position where they are in alignment with the slide opening 258 formed in the support surface 260, which leads to the mechanism below the surface for moving the individual slides 14 to the slide transport mechanism 26 (e.g., the slide track).

A retractable clip 296, which is shown in FIGS. 42-45, 48 and 50, is mounted on the lower portion 294 of each slide inserter mechanism 20 to ensure that the lowermost slide is raised slightly at its front edge 122 (see FIGS. 10-15) off the slide support surface 260 of the analyzer 2. Thus, when the slide inserter mechanism 20, loaded with a stack of slides 218, is retracted, the front edge 122 of the lowermost slide frame 114 remains lifted off the slide support surface 260 by the retractable clip 196, while the opposite rear edge 120 of the lowermost slide frame 114 is essentially pulled along and in contact with the surface 260, with the slides 14 being at a slight outwardly sloping angle to the slide support surface 260, toward the slide opening 258 in the surface 260.

In this way, the rear edge 120 of the lowermost slide drops into the side opening 258 in the support surface 260 first, and rests on the support plate 323 used in cooperation with reciprocatingly movable pusher plate 322 for moving the slide 14 to the slide transport mechanism 26, when the slide 14 is moved by the retracting slide inserter mechanism 20 to a position where it resides over the slide opening 258 in the support plate 260. The retractable clip 296 maintains the front edge 122 of the lowermost slide in a slightly raised position, so that the slide 14 drops into the opening 258 with its rear edge 120 first (see FIGS. 48-51).

As shown in FIGS. 44 and 45, the retractable clip 296 is, in its preferred form, a pivotable elongated member 302 that is pivotally mounted with a pivot pin 304 to the underside surface 294 of each slide inserter mechanism 20. One axial end 308 of the elongated member 302 includes a flattened tab 310 extending laterally therefrom, which tab 310 protrudes partially into the space 216 between the side blocks 128 of the slide inserter mechanism 20 in which the stack of slides 218 are placed, and below the lowermost edge of the front wall 212 of the slide inserter mechanism 20. The opposite axial side 312 of the elongated member 302, on the other side of the pivot pin 304, includes a laterally extending block 314 about which is mounted a compression spring 316. The spring 316 engages the inside surface 318 of one of the blocks 128 of the slide inserter mechanism 20, and normally biases the clip 296 in an outward direction to ensure that the member 302 is pivoted such that the tab 310 protrudes partially into the space and beneath the lowermost slide, so that the front edge 122 of the slide 14 rests on the tab 310.

However, when the slide inserter mechanism 20 is retracted slightly further, a stationary post or other structure (not shown) mounted within the interior of the housing 6 engages the spring loaded axial end 312 of the elongated member 302 to cause the member 302 to pivot in the opposite direction against the force of the spring 316, thereby moving the tab 310 out of the slide space 216 and from beneath the lowermost slide of the stack 218. Now, the front edge 122 of the lowermost slide in the stack 218 is free to drop into the opening 258 in the slide support surface 260 and onto the support plate 323 positioned under the opening 258. The retractable clip 296 thus minimizes the opportunity for the lowermost slide in the stack 218 to bind on the slide support surface 260 as it moves therealong as the slide inserter mechanism 20 is being retracted into the analyzer housing 6, or to become wedged between the edges of the slide opening 258 and the pusher bar 322 or support plate 323 when the slide inserter mechanism 20 is positioned in alignment with the opening 258 formed in the slide support surface 260. By having the lowermost slide drop into the opening 258 rear edge 120 first, the chance of it becoming wedged between the pusher bar 322 or support plate 323 and the edges of the opening 258 is minimized.

The clinician enters a command into the chemical analyzer 2 by using the touch screen display 4, and the electronic circuitry energizes the motor 30 coupled to the door 16 of a respective slide inserter mechanism 20 to lift the door 16. Then, the electronic circuitry energizes the motor 198 which extends the support member 192 and a slide inserter mechanism 20 affixed thereto beyond the front face 18 of the analyzer housing 6 so that the slide inserter mechanism 20 and the rotor/sample vial receptacle 206 is easily accessible. The clinician places a rotor 208 or vial 242 containing a blood sample on the support member 192, and loads a plurality of reagent test slides 14 on the slide inserter mechanism 20 either by using a slide retaining clip 112, as described previously, or by hand loading the slides 14 (see FIG. 48). The clinician then indicates to the analyzer 2 by using the touch screen display 4 that the slides 14 and rotor 208 or sample vial 242 have been loaded onto the slide inserter mechanism 20, and the electronic circuitry 2 in response energizes the motor 198 to retract the support member 192 on which the slide inserter mechanism 20 is affixed (see FIG. 48) and, when the slide inserter mechanism 20 is entirely retracted within the confines of the analyzer housing 6, energizes the motor 30 to close the access door 16 to the slider inserter mechanism 20 (see FIGS. 38 and 38a). The clinician then may repeat the same procedure with the second slide inserter mechanism 20 for an additional blood sample.

The Sample Preparation Station

FIGS. 26-28 and 53-56, show various views of the preferred form of a sample preparation station 328 of the chemical analyzer 2. The sample preparation station 328 includes a sample metering sub-assembly 84, which sub-assembly will be described in greater detail under a separate sub-heading.

The sample preparation station 328 of the chemical analyzer 2 preferably includes an overhead carriage 330 on which a pipette 336 and rotor picker mechanism 334 of the metering sub-assembly 84 are precisely linearly moved both horizontally and vertically. The overhead carriage 330 is positioned above the slide transport mechanism 26, which receives reagent test slides 14 from the slide inserter mechanism 20, the centrifuge 210 of the chemical analyzer 2, the clean pipette tip tray 54 and the used slide and pipette tip discard drawer 74. In this way, the pipette 336 of the sample metering sub-assembly 84 may be positioned over one of the slide transport mechanism 26, the centrifuge 210, the clean pipette tip tray 54 and the discard drawer 74, and may be raised and lowered to operatively cooperate with these other components in the operation of the chemical analyzer 2.

More specifically, the overhead carriage 330 includes a pair of upright, vertical stanchions or other supporting structure (not shown), which may be part of the analyzer housing or chasis, and a horizontally disposed bracket 340 supported at its opposite axial edges 343 by the upright stanchions or the like. The horizontally disposed bracket 340 includes a sample metering sub-assembly transport mechanism which is operatively linked to the structure of the sample metering sub-assembly 84 and is controlled by the electronic circuitry 22 of the chemical analyzer 2 to precisely position the pipette 336 (and rotor picker mechanism 334) over one of the slide transport mechanism 26, the centrifuge 210, the clean pipette tip tray 54 and the used pipette tip/slide drawer 74.

Even more specifically, the sample metering sub-assembly transport mechanism of the overhead carriage 330 includes a threaded lead screw 346 extending longitudinally across the length of the horizontal bracket 340. One axial end 348 of the lead screw 346 is coupled to the shaft of a stepping motor 352 so that the lead screw 346 turns a precise number of revolutions counter-clockwise and clockwise in response to the controlled selective energization of the stepping motor 352 by the electronic circuitry 22 of the analyzer 2. The opposite axial end 354 of the lead screw 346 engages a low friction bushing 356. Because of the relatively long length of the horizontal bracket 340 on which the sample metering sub-assembly 84 traverses, the lead screw 346, which is spaced apart from and disposed parallel with the bracket 340, might not remain truly parallel with the horizontal bracket 340 due to the effect of the sample metering sub-assembly 84 being coupled to and driven by the lead screw 346, had the lead screw 346 been rigidly affixed at each of its axial ends 348, 354 to the horizontal bracket 340, and this may have caused the sample metering sub-assembly 84 to bind or move erratically as it travels reciprocatingly on the horizontal bracket 340. This effect is minimized or avoided with the sample metering sub-assembly transport mechanism in its preferred form.

Figure 56:
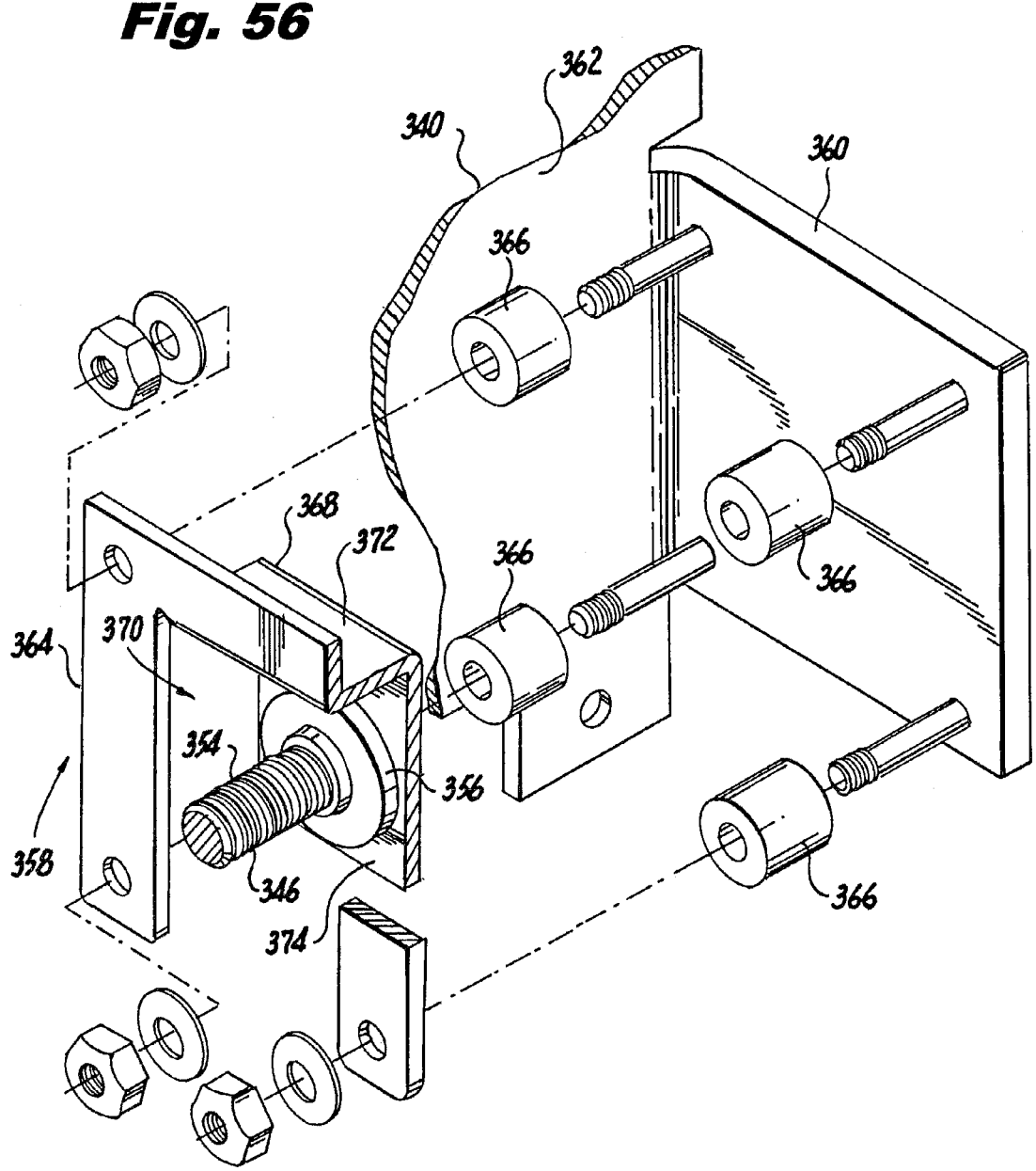
FIG. 56 is an exploded isometric view of a portion of the overhead carriage of the sample preparation station of the chemical analyzer of the present invention.

Preferably, and as shown in FIG. 56, the axial end 354 of the lead screw 346, opposite the end 348 attached to the stepping motor 352, engages the low friction bushing 356 that is fixedly mounted to a "floating" bracket 358. More specifically, a first bracket 360 is mounted to and extends perpendicularly from the rear surface 362 of the horizontal bracket 340 of the overhead carriage 330 on the same side of the horizontal bracket 340 on which the lead screw 346 is situated. A second bracket 364 is mounted to the first bracket 360, and spaced apart therefrom by preferably four flexible cylindrical standoffs 366 made from rubber or some other resilient material. This second bracket 364 includes an L-shaped center piece 368 situated in a cutout 370 formed through the thickness of the second bracket 364. The first leg 372 of the L-shaped center piece 368 is affixed to the second bracket 364, while the second leg 374, extending perpendicularly to the first leg 372 and preferably vertically when the overhead carriage 330 is assembled and properly situated in the analyzer 2, has mounted thereon the low friction bushing 356 which supports the axial free end 354 of the lead screw 346. The second bracket 364, being mounted to the first bracket 360 by the flexible standoffs 366, thus "floats" on the first bracket 360, i.e., it can move slightly in preferably three dimensions (the X, Y and Z axes) to compensate for any bowing or other non-linearity in the shape of the lead screw 346 over the longitudinal extent thereof as the sample metering sub-assembly 84 moves reciprocatingly on the horizontal bracket 340 of the overhead carriage 330 traversing the length thereof. The L-shaped center piece 368 of the second bracket 364 provides the capability to use a slightly longer lead screw 346 on the overhead carriage 330 so that the sample metering sub-assembly 84 can traverse a greater length of the horizontal bracket 340.

As will be described in greater detail, the sample metering sub-assembly 84, which includes the pipette 336, is coupled to the rotatable lead screw 346 of the overhead carriage 330 and includes structure which precisely raises and lowers the pipette and rotor picker mechanism 336, 334 vertically over the slide transport mechanism 26, the centrifuge 210, the clean pipette tip tray 54 and the used pipette tip/slide drawer 74 of the chemical analyzer 2 (see FIG. 52).

Figure 62:
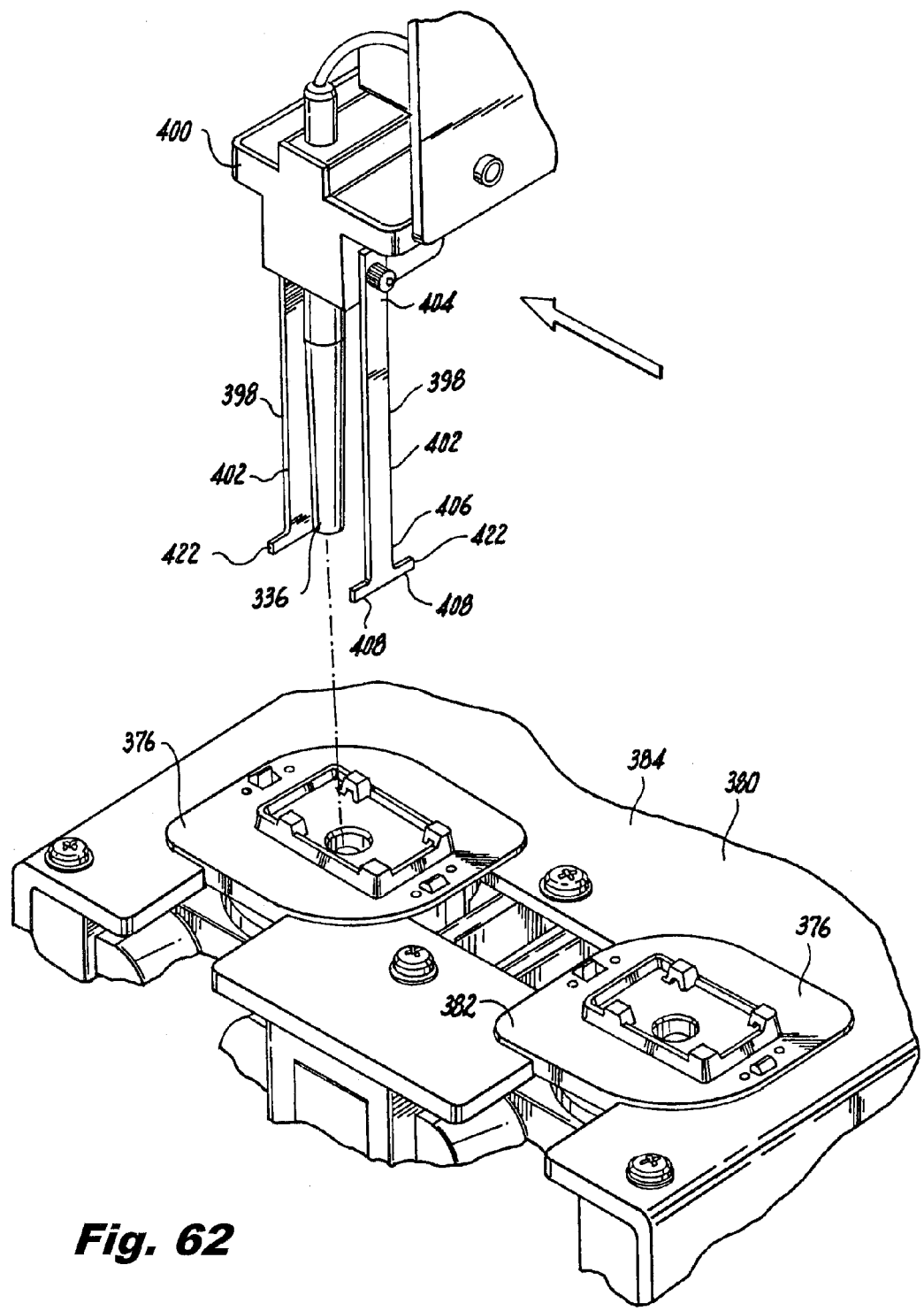
FIG. 62 is a top isometric view of a pair of rotor carriers and the picker mechanism of the sample metering sub-assembly, and illustrating the alignment of the sample metering sub-assembly with one of the rotor carriers.

In operation, the electronic circuitry of the chemical analyzer 2 moves the sample metering sub-assembly 84 linearly on the overhead carriage 330 until it is positioned over a rotor 208 residing in the receptacle 206 of one of the slide inserter mechanisms 20 (see FIG. 62). As will be described in greater detail, the rotor picker mechanism 334 affixed to the vertically moveable metering sub-assembly 84 removes the rotor 208 from the support member 192 on which the slide inserter mechanism 20 is situated and transports the rotor 208 to the high speed spin centrifuge 210 of the chemical analyzer 2 for centrifuging the blood sample contained therein.

At this point in the explanation of the structure of the sample preparation station 328, a more detailed description of the rotor picker mechanism 334 and its operation will now be provided.

Figure 48:
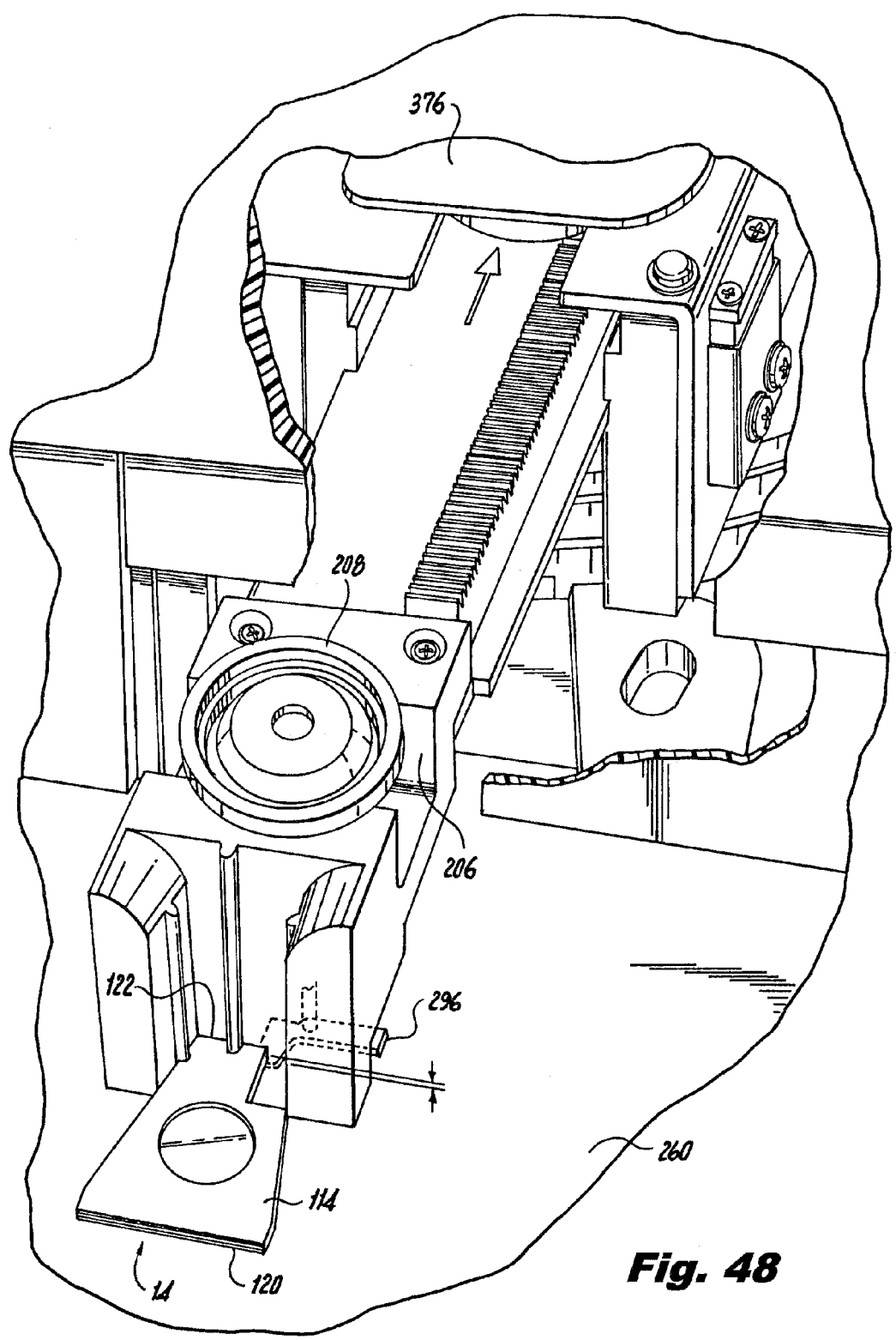
FIG. 48 is a front isometric view of the slide inserter mechanism shown in FIG. 9 and a chemical reagent test slide shown thereon, the slide inserter mechanism being depicted as being retracted into the analyzer housing which is partially broken away.
Figure 49:
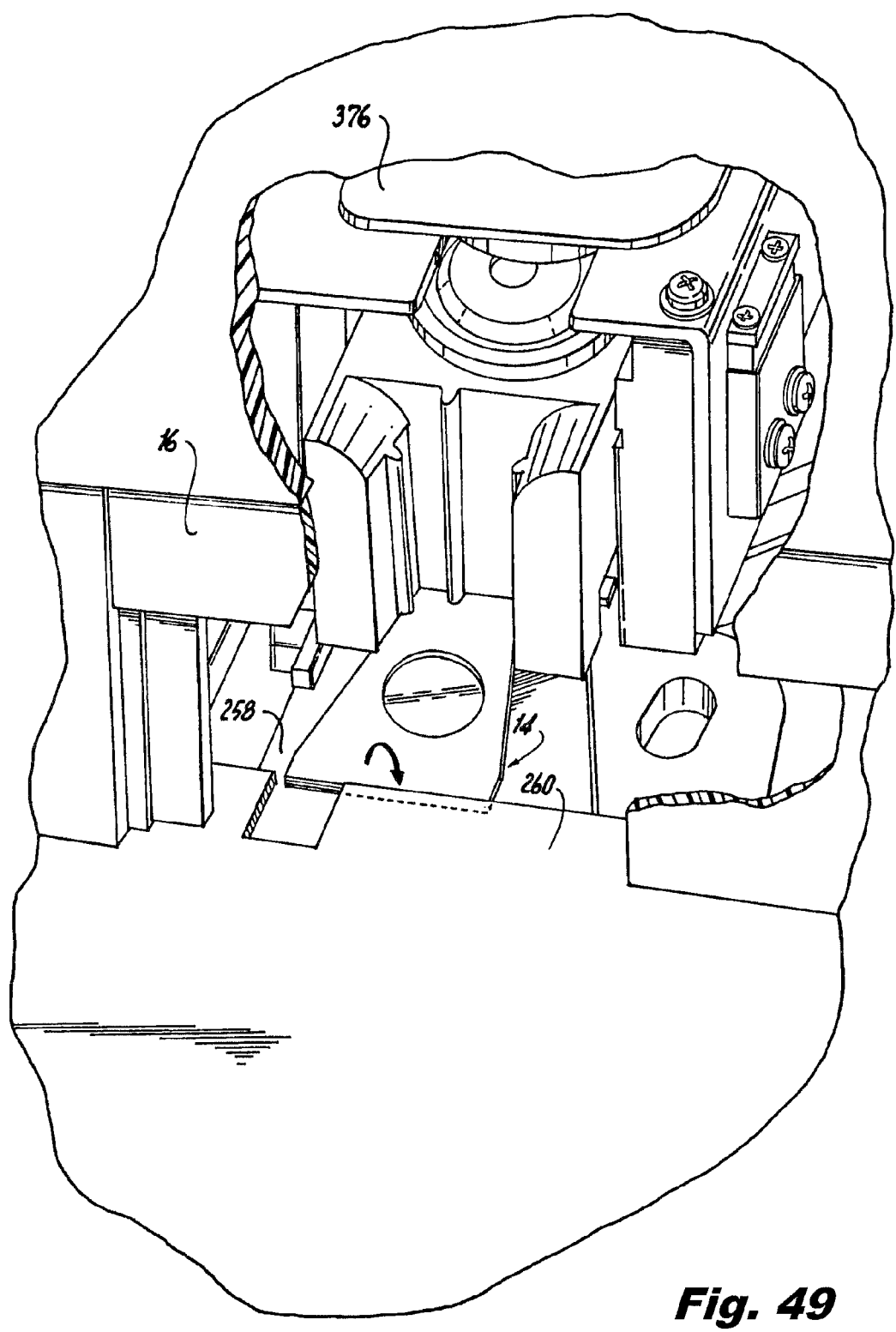
FIG. 49 is a front isometric view of the slide inserter mechanism shown in FIG. 48 in a retracted position within the analyzer housing, shown partially broken away.
Figure 57:
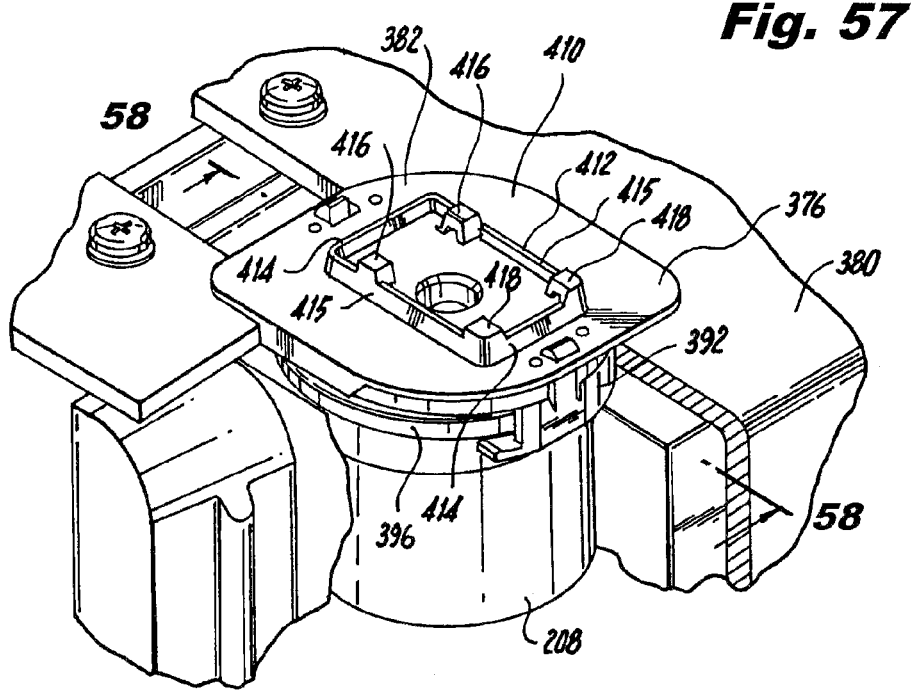
FIG. 57 is a top isometric view of a rotor carrier formed in accordance with the present invention and used in the chemical analyzer of the present invention, and illustrating the rotor carrier engaging a centrifuge rotor mounted on the slide inserter mechanism of the present invention.
Figure 63:
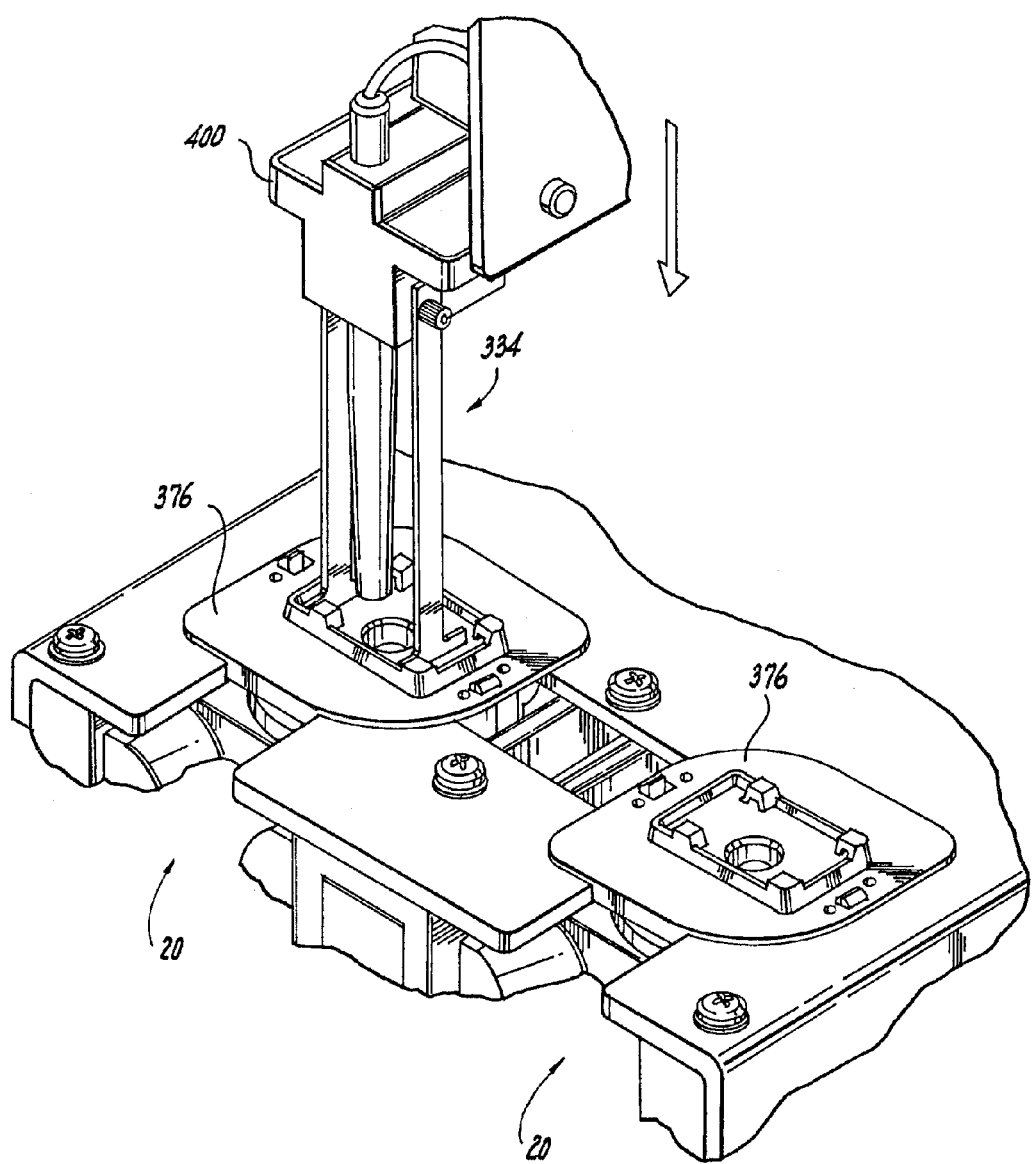
FIG. 63 is a top isometric view of the rotor carriers and picker mechanism of the sample metering sub-assembly shown in FIG. 62, and illustrating movement of the sample metering sub-assembly so that the picker mechanism engages one of the rotor carriers.

When the slide inserter mechanism 20 is retracted into the analyzer housing 6, with a rotor 208 resting in the receptacle 206 of the support member 192, as shown in FIGS. 48 and 49, the rotor 208 is forcibly received by a rotor carrier 376 that rests in an opening 378 formed in a support plate 380 that extends horizontally above each slide inserter mechanism 20 and in particular the support member 192 on which the slide inserter mechanism 20 is situated, as shown in FIG. 57. Thus, there are two rotor carriers 376, one for each rotor 208 placed in the well 206 or receptacle on the support member 192 of a slide inserter mechanism 20 (see FIGS. 62-64). As shown in FIGS. 57-61, each rotor carrier 376, situated above and in alignment with a respective rotor receptacle 206 formed in a corresponding slide inserter mechanism support member 192, generally includes a cover plate 382 that rests on the upper surface 384 of the support plate 380 that resides above the support members 192 of the slide inserter mechanisms 20, and which includes a C-shaped, semi-circular flange 386 that extends downwardly through the opening 378 in the supporting plate 380, which defines an open pocket 388 for receiving therein the top portion 390 of the rotor 208 residing in the support member 192 of the slide inserter mechanism 20.

More specifically, the flange 386 of the rotor carrier 376 includes a semi-circular partial sidewall 392 having a slightly radially inwardly extending shoulder 394 at its lowermost extent. The rotor 208, at its upper portion 390, includes a radially outwardly extending lip 396 which is received within the pocket 388 defined by the rotor carrier 376 above the shoulder 394 and below the cover plate 382. The diameter of the lip 396 is greater than the partial diameter of the shoulder 394 so that the lip 396 of the rotor 208 will be engaged by the shoulder 394 of the rotor carrier 376 when the rotor carrier 376 is removed from the opening 378 in the support plate 380 in which it resides.

Figure 58:
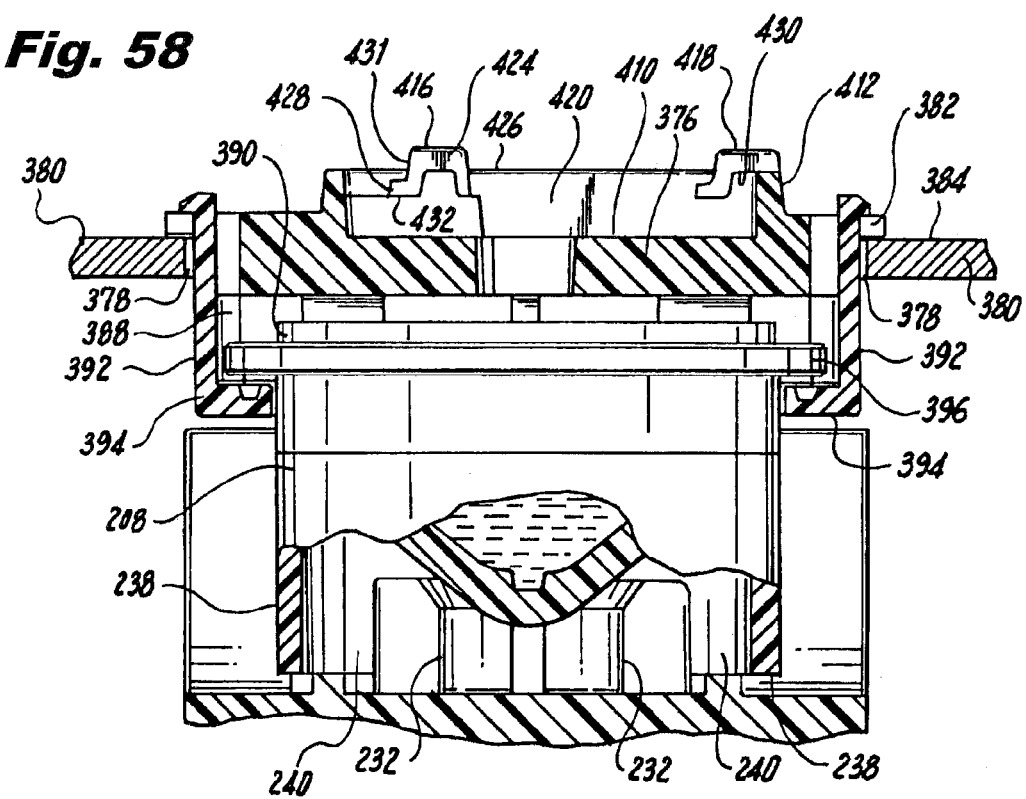
FIG. 58 is a cross-sectional view of the rotor carrier and centrifuge rotor mounted thereon shown in FIG. 57 and taken along line 58-58 of FIG. 57.
Figure 59:
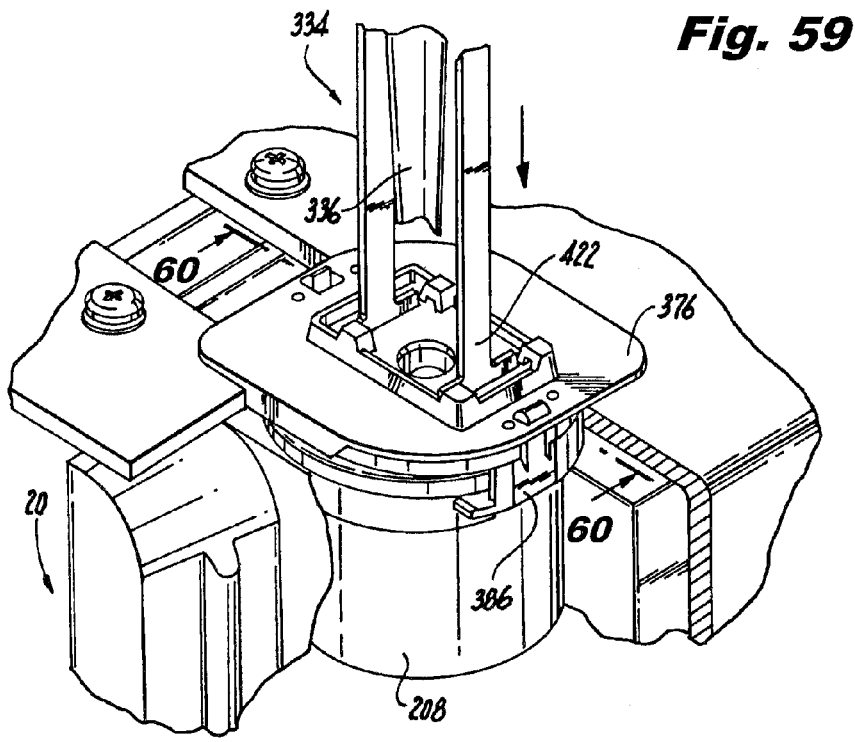
FIG. 59 is a top isometric view of the rotor carrier and centrifuge rotor shown in FIG. 58, and a portion of a picker mechanism of the sample metering sub-assembly engaging the rotor carrier.

The diameter of the cover plate 382 of the rotor carrier 376 is greater than that of the opening 378 in the support plate 380 on which it resides, and the semi-circular sidewall 392 of the rotor carrier 376 has a diameter which is less than that of the support plate opening 378 so that the rotor carrier 376 may loosely rest on the upper surface 384 of the support plate 380 and be removable therefrom, as shown in FIGS. 57 and 58. Similarly, the diameter of the rotor 208, including the outwardly extending lip 396, is less than that of the opening 378 formed in the rotor carrier support plate 380 so that, when the rotor carrier 376 is removed from the support plate 380, the rotor 208 received thereby is removed with it through the opening 378 in the support plate 380 from the receptacle 206 on the support member 192 of the slide inserter mechanism 20 on which it had been placed by the clinician.

As mentioned previously, the sample pipette sub-assembly 84 includes a rotor picker mechanism 334. Generally, the rotor picker mechanism 334 includes a pair of spaced apart, T-shaped members 398 extending in parallel downwardly from a vertically moveable bracket 400 of the sample metering sub-assembly 84, as can be seen from FIGS. 64 and 76. Each T-shaped member 398 includes an elongated central leg 402, which has a proximal end 404 that is attached to the vertically moveable pipette support bracket 400, and an opposite distal end 406 on which is formed a pair of shorter legs 408 extending in opposite directions from one another and perpendicularly to the elongated leg 402.

The pair of T-shaped members 398 is situated on diametrically opposite sides of the pipette 336 so that the pipette 336 resides therebetween.

Returning again to the structure of the rotor carrier 376, the upper surface 410 of the cover plate 382 of the rotor carrier 376 has a rectangular frame 412 formed of opposite transverse and longitudinal parallel walls 414 and 415, respectively, extending upwardly therefrom (see FIGS. 57-61). The spacing between the opposite longitudinal walls 415 is slightly greater than the total combined width of the shorter legs 408 of the T-shaped members 398 of the picker mechanism 334 so that the shorter picker legs 408 may be received between the walls 415. First and second pairs of hanger brackets 416,418 extend from the rectangular frame 412 above the upper surface 410 of the rotor carrier within the interior space 420 defined by the frame 412. More specifically, the hanger brackets 416 of the first pair are separated from each other so that they can respectively engage the free ends 422 of respective shorter legs 408 of one T-shaped member 398 of the picker mechanism 334. The hanger brackets 418 of the second pair are separated from one another, and from the first pair of hanger brackets 416 the same distance that the two T-shaped members 398 of the picker mechanism 334 are separated, so that they can engage the free ends 422 of the shorter legs 408 of the other T-shaped member 398 of the picker mechanism 334.

Each hanger bracket 416,418 includes a horizontal first portion 424 joined to a wall 426 of the frame 412 and a horizontal second portion 428, the first portion 424 being situated higher than the second portion 428 relative to the upper surface 410 of the rotor carrier 376. The first and second portions 424,428 are interconnected to each other by a vertical middle portion 431. Thus, the higher and lower first and second portions of each hanger bracket 416,418, residing over the upper surface 410 of the rotor carrier 376, define with the upper surface an L-shaped slot 430 for receiving respective free ends 422 of the oppositely extending shorter legs 408 of the T-shaped members 398 of the picker mechanism 334.

The spacing between the upper surface 410 of the rotor carrier 376 and the lower surface 432 of the second portion 428 of each hanger bracket 416,418 is equal to or just slightly greater than the height of the shorter legs 408 of the picker T-shaped member 398 so that the shorter legs 408 may be closely received between the upper surface 410 of the rotor carrier 376 and the lower surface 432 of the second portion 428 of each hanger bracket 416,418 to ensure that there is little or no vertical movement or play between the rotor carrier 376 and picker mechanism 334 and more specifically with respect to the T-shaped members 398 thereof. The spacing between the first portion 424 of each hanger bracket 416,418 and the upper surface 410 of the rotor carrier 376 is greater than that between the second portion 428 and the upper surface 410 of the rotor carrier 376 so that the shorter legs 408 of the T-shaped members 398 may be received in this spacing, with the lower surface 434 of the first portions 424 resting on the upper surfaces 436 of the shorter legs 408 of the T-shaped members 398, so that the T-shaped members 398 are held captive by the hanger brackets 416,418 within the L-shaped slots 430 defined thereby when positioned thusly.

Figure 60:
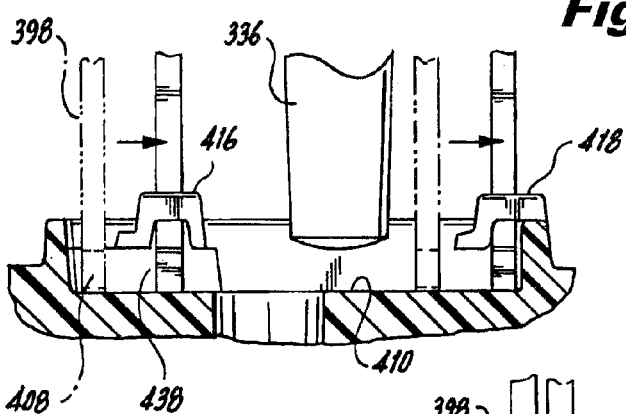
FIG. 60 is a cross-sectional view of a portion of the rotor carrier and picker mechanism shown in FIG. 59 and taken along line 60-60 of FIG. 59.
Figure 61:
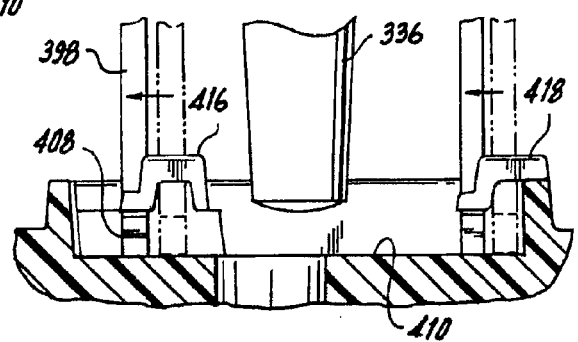
FIG. 61 is a cross-sectional view of a portion of the rotor carrier and picker mechanism shown in FIG. 60 and illustrating movement of the picker mechanism in relation to the rotor carrier.

From the foregoing description, it should be clear that each T-shaped member 398 of the rotor picker mechanism 334 may horizontally enter a respective L-shaped slot 430 defined by the hanger brackets 416,418 and the upper surface 410 of the rotor carrier 376 and be moved sideways on the rotor carrier 376 so that the distal free end 406 of the T-shaped member 398 is received by and held captive in the lateral extent 438 of the slot 430 directly under the first portions 424 of the hanger brackets 416,418, whereby the rotor carrier 376 is selectively attached to the rotor picker mechanism 334 and in particular the T-shaped members 398 thereof, in order to lift the rotor carrier 376, and the rotor 208 attached thereto, through the opening 378 in the support plate 380 on which the rotor carrier 376 rests, as shown by FIG. 60. The L-shaped slots 430 described above thus have a "hook" shape in cross-section to ensure that the picker T-shaped members 398 are captively received by the slots 430 of the rotor carrier 376.

Reference should now be made to FIGS. 59-68 of the drawings. After the clinician loads a sample-filled rotor 208 onto the support member 192 of a respective slide inserter mechanism 20, and the slide inserter mechanism 20 is retracted within the housing 6 of the analyzer 2, the rotor 208 lockingly engages with the rotor carrier 376 situated above the respective slide inserter mechanism 20. The rotor picker mechanism 334, which is attached to the sample metering sub-assembly 84, is moved on the overhead carriage 330 to a position where it is aligned with the respective rotor carrier 376. Then, the moveable bracket 400 on which the rotor picker mechanism 334 is attached is vertically lowered until the distal free ends 422 of the T-shaped members 398 of the rotor picker mechanism 334 are captively received by the L-shaped slots 430 defined by the hanger brackets 416,418 and the upper surface 410 of the cover plate 382 of the rotor carrier 376. The moveable bracket 400 of the sample metering sub-assembly 84 on which the rotor picker mechanism 334 is situated is then vertically retracted so that it pulls the rotor carrier 376 and the rotor 208 affixed thereto through the opening 378 formed in the support plate 380 until the rotor carrier 376 and the rotor 208 are raised clear of the support plate 380. The overhead carriage 330 then transports the rotor 208 containing the blood sample to the centrifuge 210 of the chemical analyzer 2 whereupon the moveable bracket 400 of the sample metering sub-assembly 84 is lowered until the rotor 208 is received by the centrifuge 210.

The centrifuge 210 includes a mandrel 440 in the form of upstanding resilient fingers 442 that engage the inner diameter 444 of the skirt 238 of the rotor 208 and releasably secure the rotor 208 thereto (see FIGS. 65-68). The resilient fingers 442 of the mandrel 440 extend upwardly within a protective outer cylindrical housing 446 of the centrifuge 210, the housing 446 having a top opening 448 for receiving the rotor 208. The rotor carrier 376 and in particular the cover plate 382 thereof acts as a cover for this cylindrical protective housing 446 and is held in place over the top opening 448 in the housing 446 by the rotor picker mechanism 334 during the centrifugation process.

More specifically, the centrifuge rotor 208 is secured to the resilient fingers 442 of the centrifuge 210. Then, the T-shaped members 398 of the rotor picker mechanism 334 are moved by the overhead carriage 330 and pipette sub-assembly 84 mounted thereon slightly downwardly so that the shorter legs 408 of the T-shaped members 398 no longer engage the lower surface 434 of the first portions 424 of the hanger brackets 416,418 of the rotor carrier 376, and then are moved slightly horizontally so that the shorter legs 408 are in alignment with the second portion 428 of the hanger brackets 416,418 and closely received within the spacing between the upper surface 410 of the rotor carrier 376 and the lower surface 432 of the second portion 428 of the hanger brackets 416,418, with little or no play between the picker T-shaped members 398 and the rotor carrier upper surface 410 and hanger brackets 416,418. Now, the pipette sub-assembly 84 lowers the picker mechanism 334 slightly to disengage the circumferential lip 396 of the centrifuge rotor 208 from the shoulder 394 of the rotor carrier 376 on which it had been resting when transported by the picker mechanism 334. This minimizes or eliminates any contact friction between the two when the rotor 208 is spun by the centrifuge 210.

Figure 64:
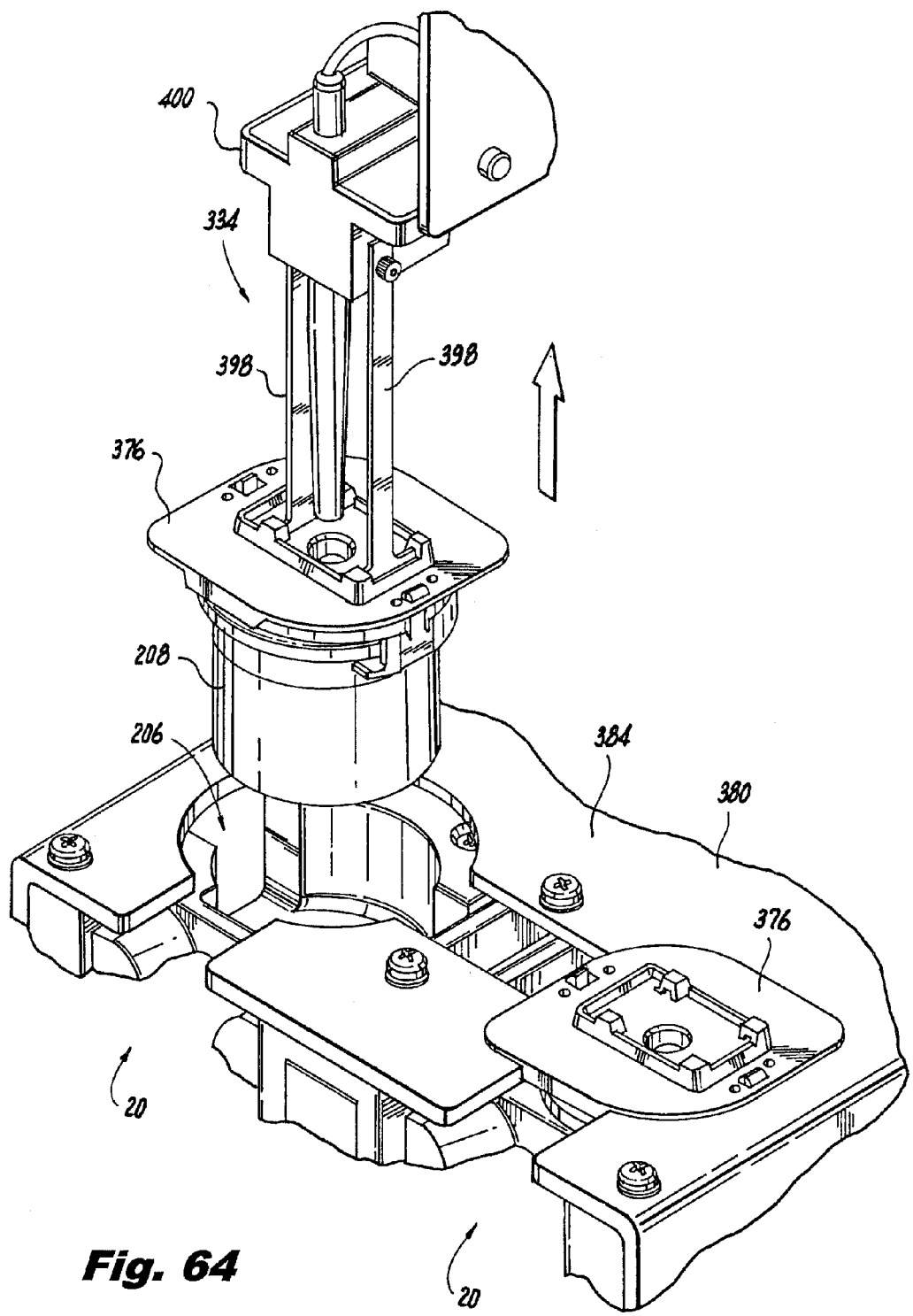
FIG. 64 is a top isometric view of the rotor carriers and picker mechanism of the sample metering sub-assembly shown in FIG. 63, and illustrating how the picker mechanism lifts one of the rotor carriers and a centrifuge rotor situated thereon from a slide inserter mechanism.
Figure 65:
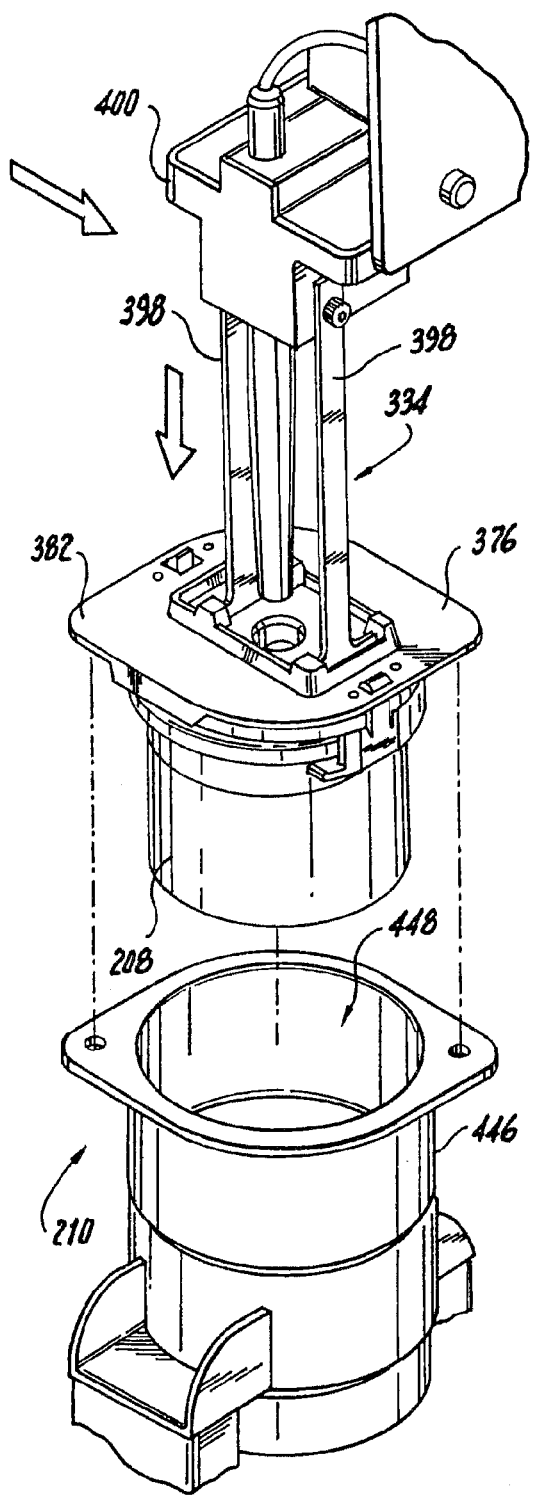
FIG. 65 is a top isometric view of the rotor carrier and picker mechanism of the sample metering sub-assembly shown in FIG. 64, and illustrating the movement of the sample metering sub-assembly to a position over a centrifuge used in the chemical analyzer of the present invention.
Figure 66:
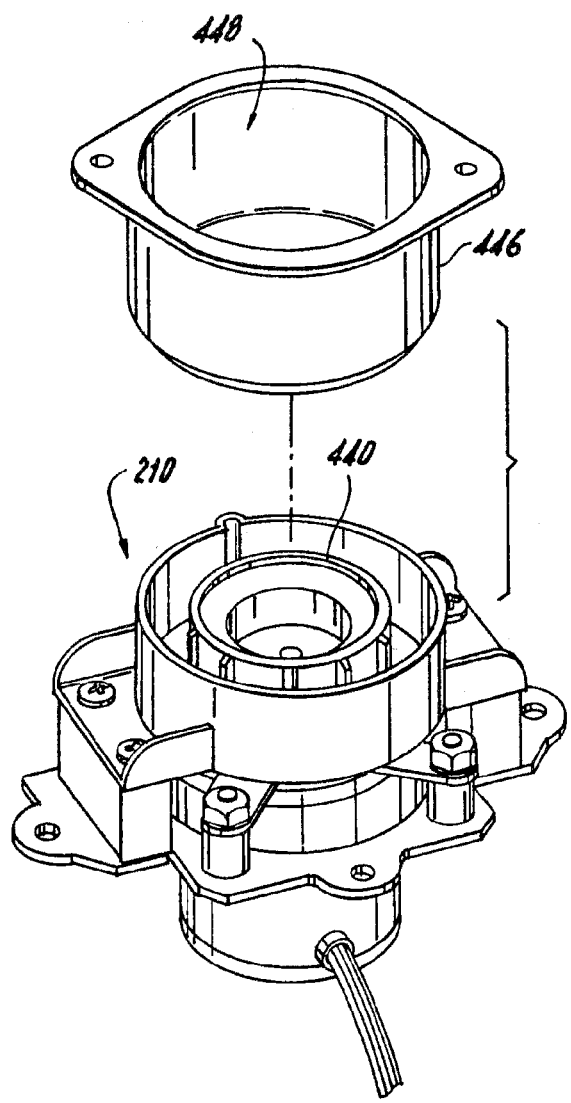
FIG. 66 is a partially exploded, top isometric view of the centrifuge used in the chemical analyzer of the present invention.

After the blood sample contained in the rotor 208 is centrifuged, the electronic circuitry 22 of the analyzer 2 causes the moveable bracket 400 of the sample metering sub-assembly 84 to retract vertically, lifting the rotor cover and the rotor 208 affixed thereto from the centrifuge 210, and in particular the resilient fingers 442 of the mandrel 440 of the centrifuge 210, and transports the rotor 208 horizontally to the opening 378 in the support plate 380 above the respective slide inserter mechanism 20 from which the rotor 208 was removed (see FIG. 64). The moveable bracket 400 of the sample metering sub-assembly 84 is then lowered until the cover plate 382 of the rotor carrier 376 rests on the upper surface 384 of the support plate 380 (see FIG. 63). Then, the sample metering sub-assembly 84 is moved slightly horizontally on the overhead carriage 330 to disengage the distal free ends 422 of the parallel T-shaped members 398 from the L-shaped receiving slots 430 defined by the hanger brackets 416,418 and the upper surface 410 of the rotor carrier 376 to release the rotor carrier 376 from the rotor picker mechanism 334, leaving the rotor carrier 376 and the rotor 208 affixed thereto resting on the upper surface 384 of the support plate 380 above the slide inserter mechanism 20 and extending through the opening 378 in the support plate 380 (see FIG. 62). This process of lifting the rotor 208, placing it on the centrifuge 210 and returning the rotor 208 to its respective resting opening 378 on the support plate 380 may be repeated for the rotor 208 placed on the support member 192 of the other slide inserter mechanism 20.

Figures 71, 72:
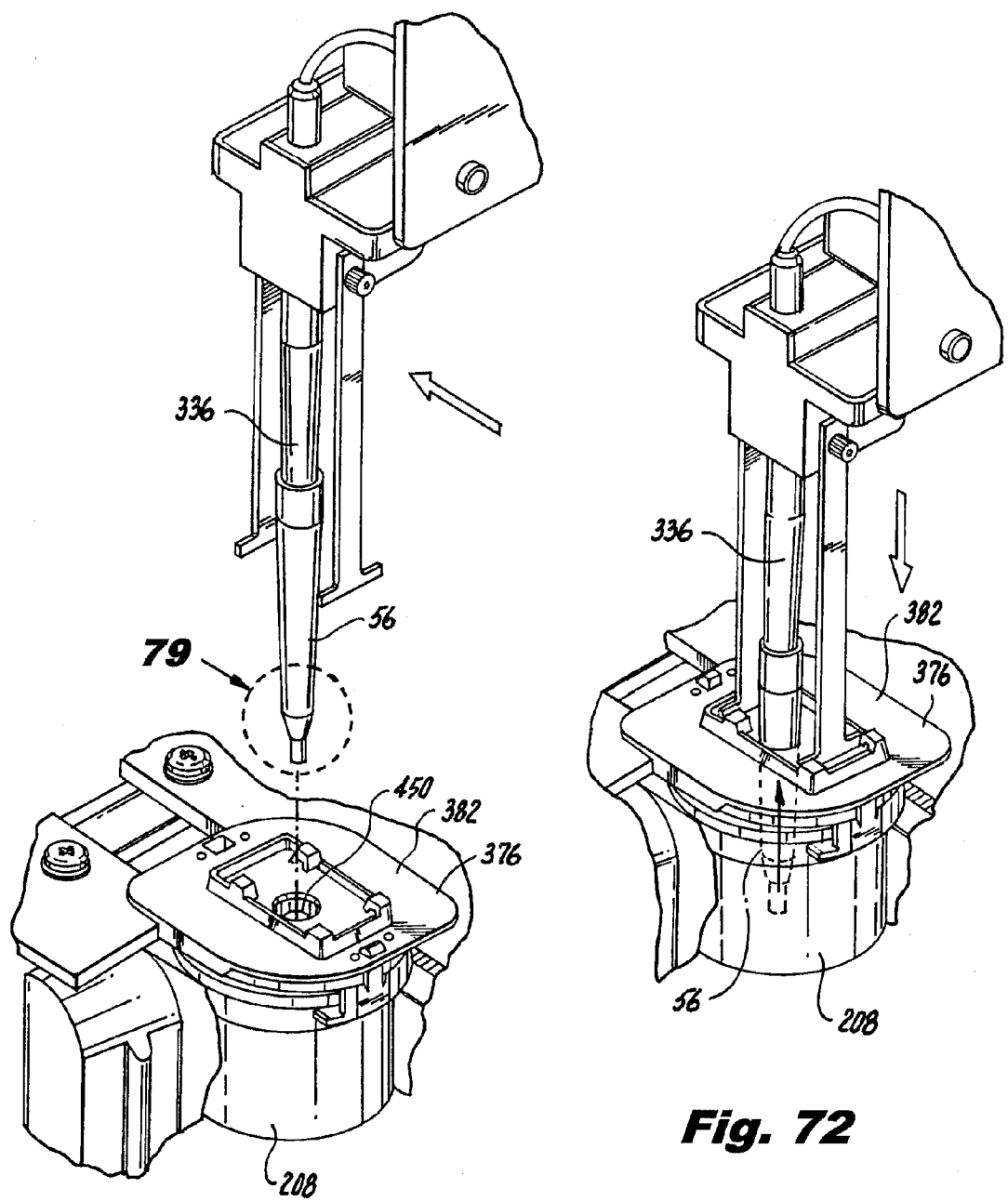
FIG. 71 is a top isometric view of a portion of the sample metering sub-assembly of the present invention and a portion of the rotor carrier and centrifuge rotor mounted thereon, and illustrating the alignment of the pipette tip mounted on the pipette of the sample metering sub-assembly shown in FIG. 70 with the rotor carrier.
FIG. 72 is a top isometric view of a portion of the sample metering sub-assembly, rotor carrier and centrifuge rotor shown in FIG. 71, and illustrating the movement of the sample metering sub-assembly over the centrifuge rotor to aspirate a blood sample therefrom.

As shown in FIGS. 71 and 72, the rotor carrier 376 includes a central opening 450 formed through the cover plate 382 thereof, which opening 450 is aligned with the fill port 452 of the rotor 208 so that the centrifuged blood sample contained in the rotor 208 may be accessed by a pipette tip 56 mounted on the pipette 336 of the sample metering sub-assembly 84 and withdrawn from the rotor 208 thereby. The central opening 450 in the cover plate 382 is also situated in alignment with a sample vial 242 residing in the well or receptacle 206 of the slide inserter mechanism support member 192 if the vial 242 is placed in the receptacle 206 rather than the rotor 208, so that the pipette tip 56 mounted on the pipette 336 of the sample metering sub-assembly 84 may pass through the opening 450 and draw sample from the vial 242 through the open top end 246 of the vial 242.

Figure 69:
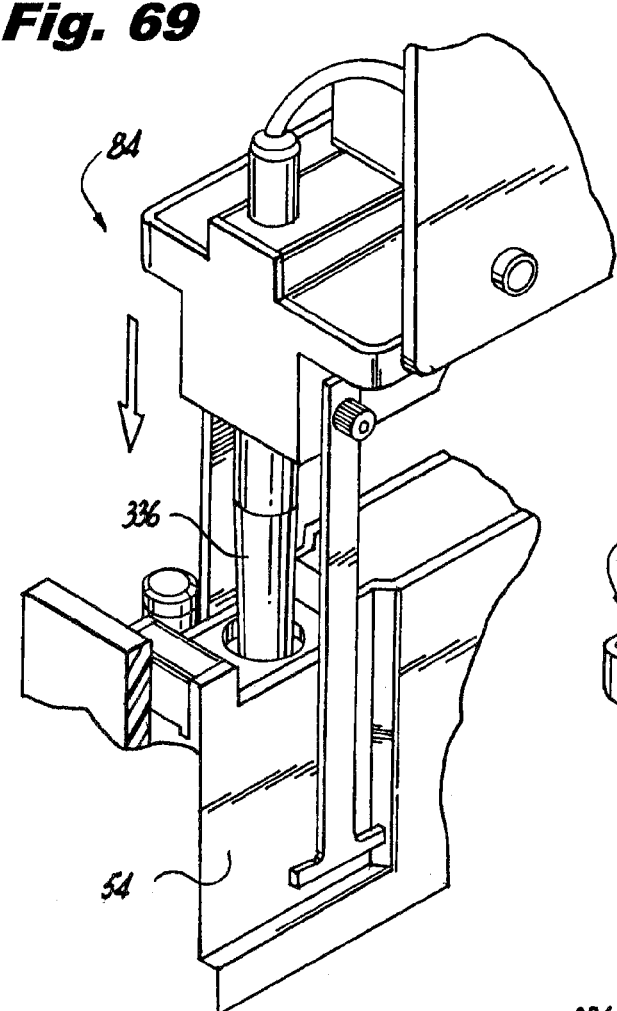
FIG. 69 is a top isometric view of a portion of the sample metering sub-assembly and a portion of the clean pipette tip tray, and illustrating the sample metering sub-assembly being lowered thereover.
Figure 70:
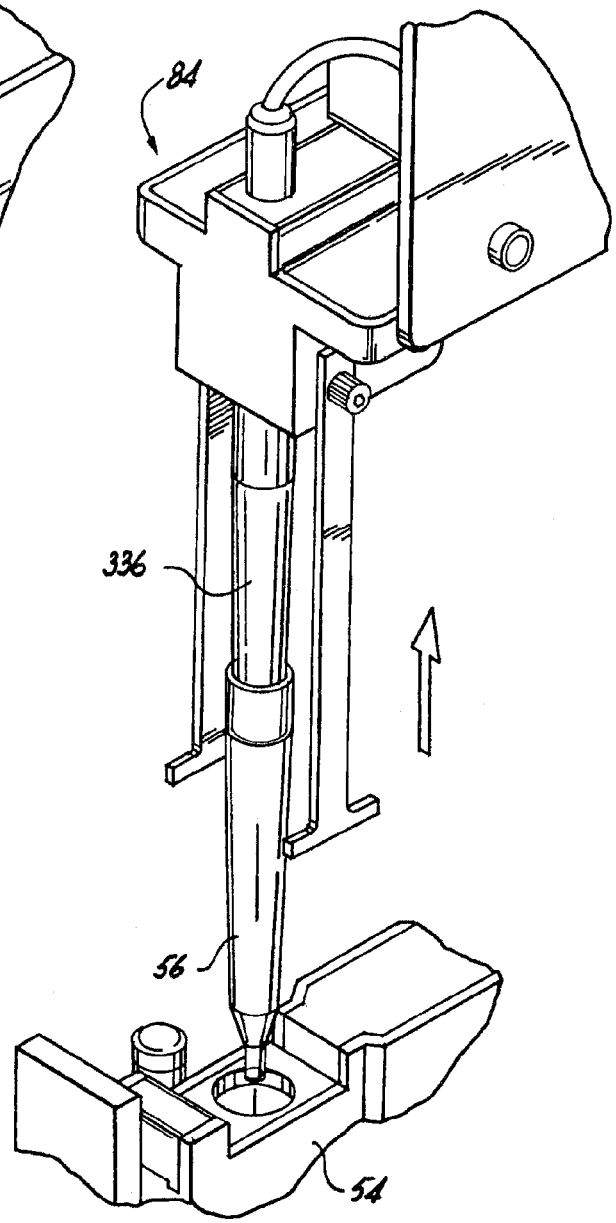
FIG. 70 is a top isometric view of a portion of the sample metering sub-assembly and a portion of the pipette tip tray, and illustrating the engagement between a pipette of the sample metering sub-assembly and a pipette tip carried by the pipette tip tray.

After the blood sample in rotor 208 has been centrifuged, the electronic circuitry of the chemical analyzer 2 moves the sample metering sub-assembly 84 linearly on the overhead carriage 330 until the pipette 336 affixed thereto is positioned over the clean pipette tip tray 54, whereupon the circuitry causes the structure of the metering sub-assembly 84 to lower the pipette 336 until the distal end 454 thereof is received by and lockingly engages one of the clean pipette tips 56 residing vertically on the pipette tip tray 54, as illustrated by FIGS. 69 and 70. The pipette 336, with the clean pipette tip 56 affixed thereto, is raised on the overhead carriage 330 and linearly horizontally transported to a position over one of the rotors 208 suspended by the rotor carriage 376 on the support plate 380, and in alignment with the opening 450 in the cover plate 382 of the rotor carrier 376 (see FIG. 71).

It should be understood here that the pipette 336 may be positioned over a sample vial 242 containing centrifuged blood placed on a support member 192 of one of the slide insertion mechanisms 20, if such a sample vial 242 is used instead of a rotor 208, should the blood sample have already been centrifuged prior to its placement on the analyzer 2. Then, of course, no further centrifugation of the blood sample need take place.

The electronic circuitry of the chemical analyzer 2 then lowers the pipette 336 such that the tip 56 contacts the centrifuged blood sample contained in the rotor 208 (or a sample vial 242 held by a support member 192 of a slide inserter mechanism 20) to extract by aspiration a predetermined volume of blood sample into the pipette tip 56 (see FIG. 72). Then, the pipette 336, with the specimen contained in the tip 56, is again moved on the overhead carriage 330 linearly horizontally and positioned over the slide transport mechanism 26 (see FIG. 73).

Figure 73:
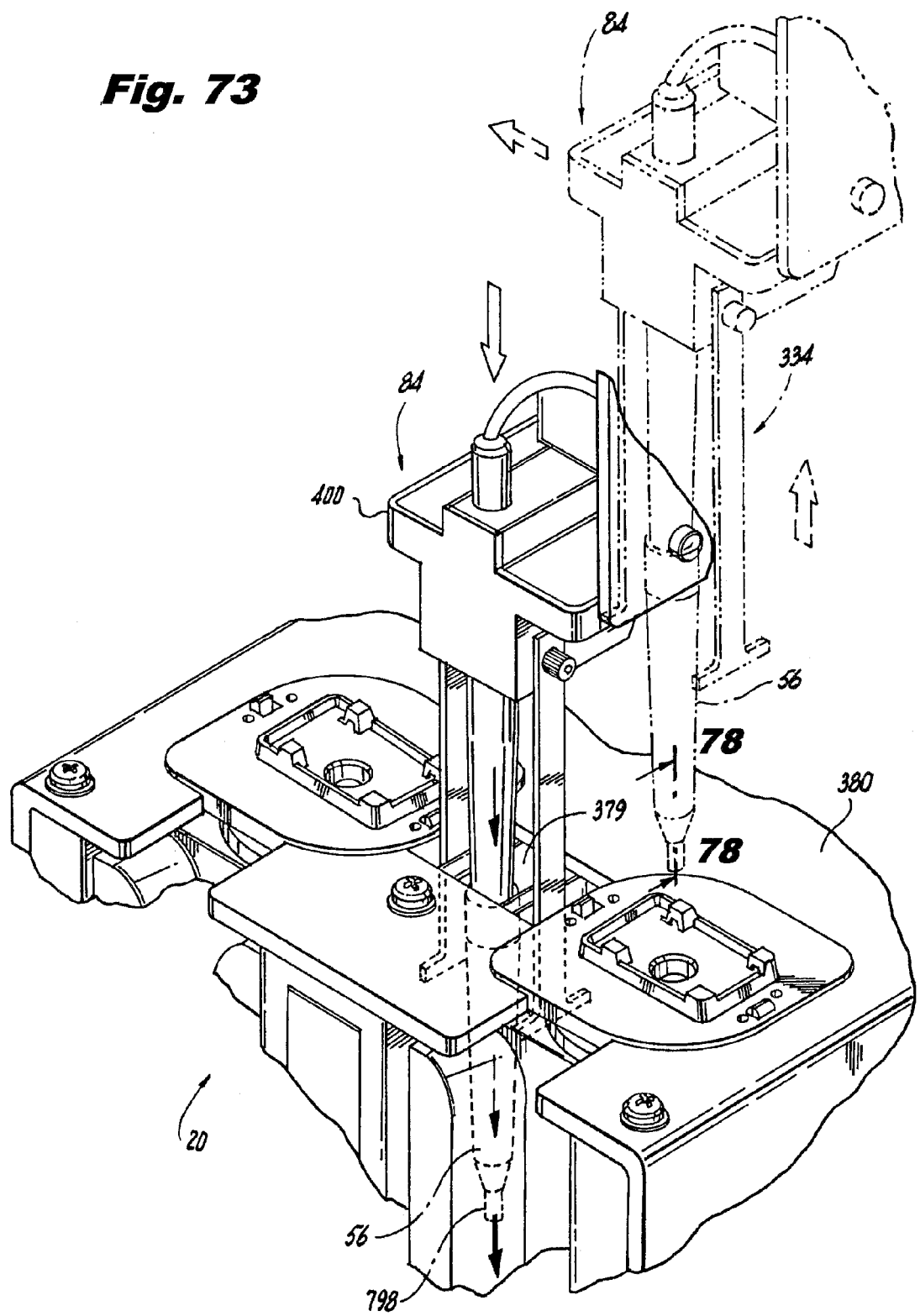
FIG. 73 is a top isometric view of a portion of the sample metering sub-assembly, shown in phantom in one position and in solid lines in a second position, and illustrating its alignment with an opening formed in a support plate on which a pair of rotor carriers rest to expel sample fluid from a pipette tip mounted on the sample metering sub-assembly onto a reagent test slide.

After the slides 14 have been loaded by the slide inserter mechanism 20 onto the slide transport mechanism 26, the electronic circuitry of the chemical analyzer 2 causes the pipette tip 56, filled with specimen, to be lowered and raised over the film portions 116 of the chemical reagent test slides 14 through an opening 379 formed in the support plate 380, as the test slides 14 are positioned by the slide transport mechanism 26, one at a time, beneath and in alignment with the pipette tip 56 so that the pipette 336 can meter a precise volume of specimen onto each reagent test slide 14 carried by the transport mechanism 26, as shown in FIG. 73.

Figure 52:
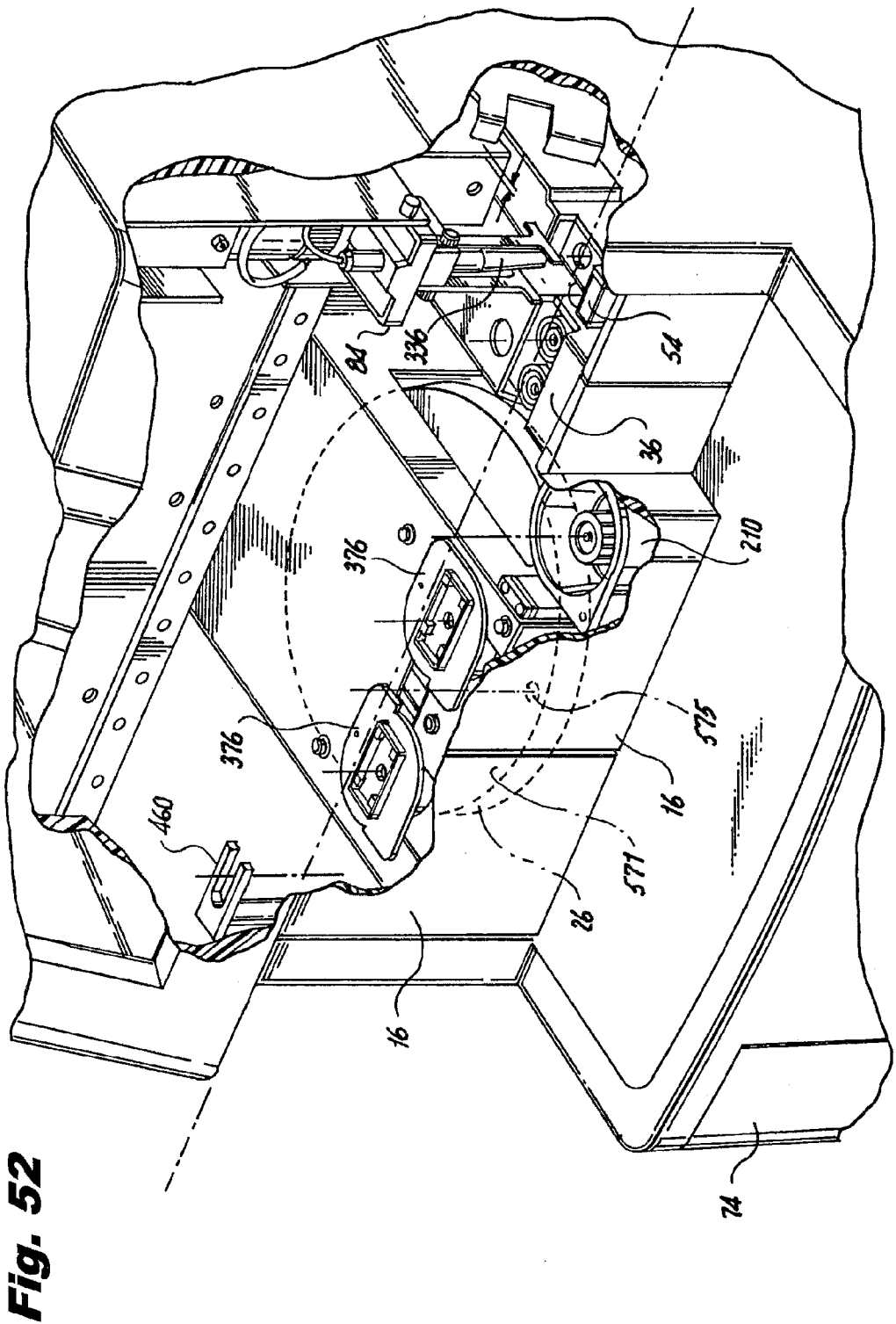
FIG. 52 is a front isometric view of the chemical analyzer, with the housing thereof partially broken away, and illustrating various components of the analyzer of the present invention.
Figure 53:
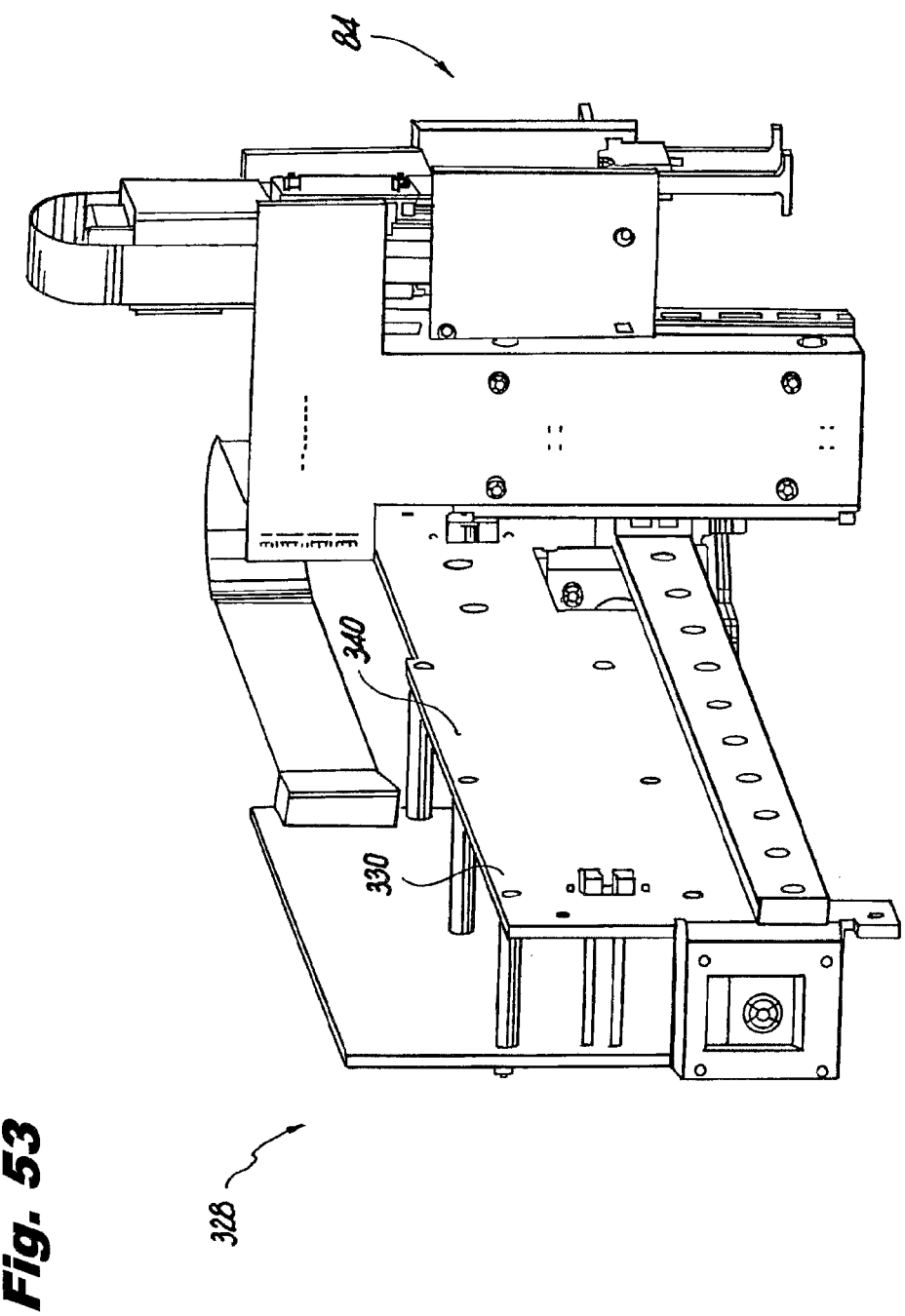
FIG. 53 is a front isometric view of a portion of the overhead carriage of the sample preparation station and the sample metering sub-assembly of the chemical analyzer of the present invention.
Figure 54:
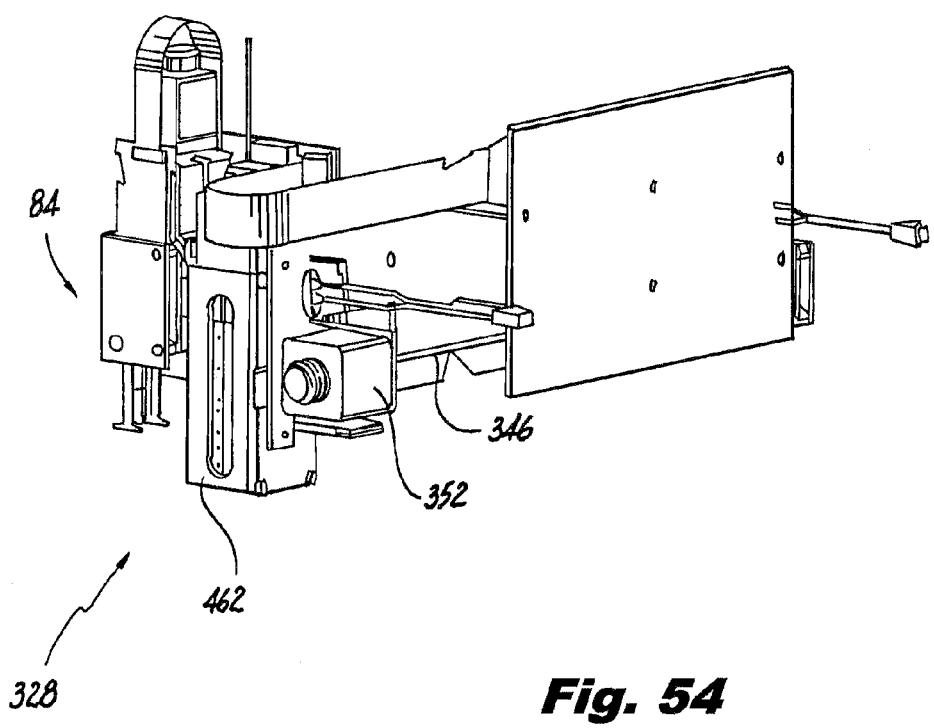
FIG. 54 is a rear isometric view of the overhead carriage of the sample preparation station and the sample metering sub-assembly shown in FIG. 53.
Figure 55:
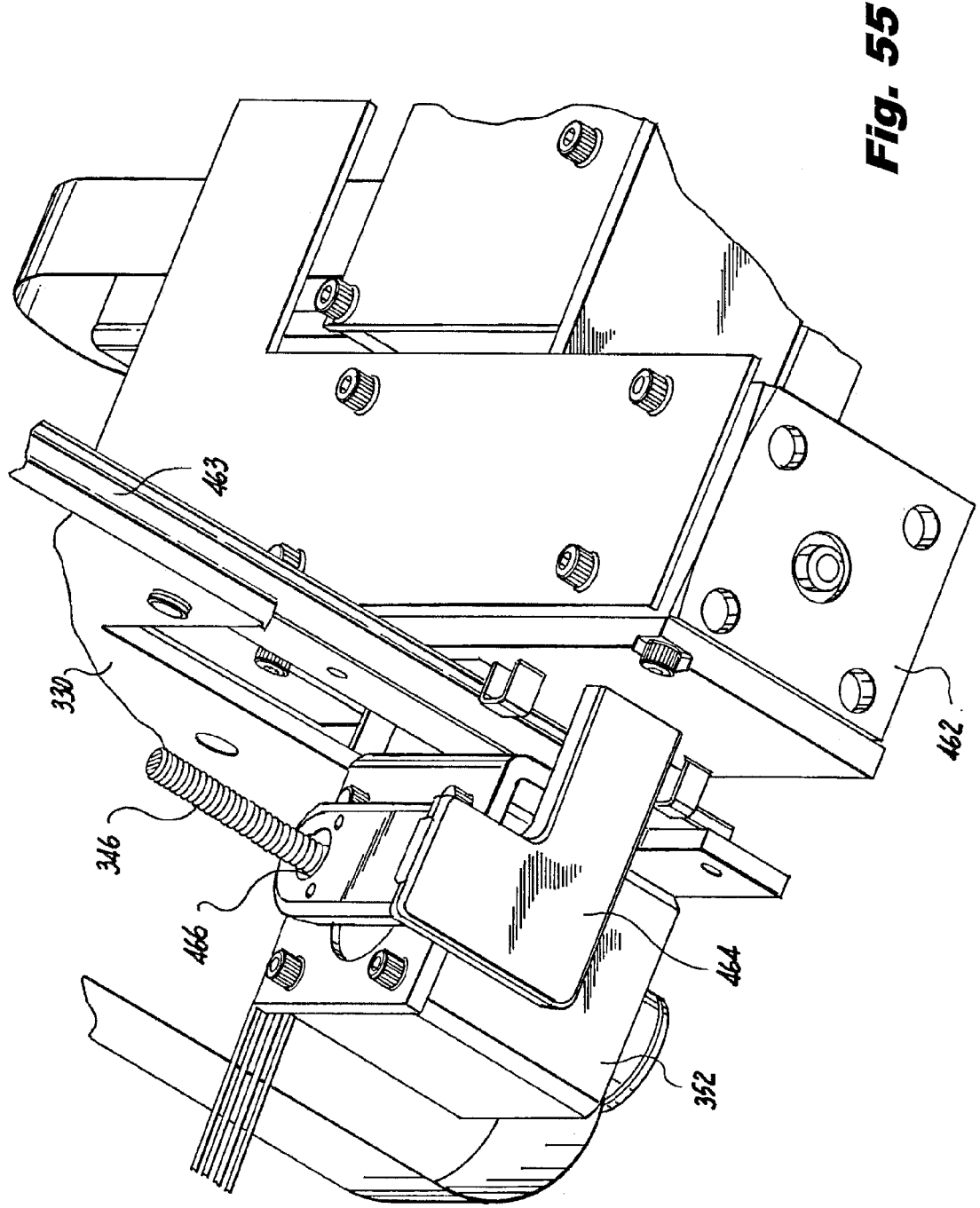
FIG. 55 is a detailed bottom isometric view of a portion of the overhead carriage of the sample preparation station and a portion of the sample metering sub-assembly shown in FIG. 54.

After completion of the metering step, the electronic circuitry of the chemical analyzer 2 causes the pipette 336 of the metering sub-assembly 84 to move on the overhead carriage 330 linearly horizontally to a position over and in alignment with the used pipette tip/slide drawer 74 (see FIG. 52). In this position, the top edge 456 of the pipette tip 56 is received between parallel prongs 458 of a forked member 460, as shown in FIGS. 74 and 75. The moveable bracket 400 of the sample metering sub-assembly 84 is then moved vertically upwardly so that the top edge 456 of the pipette tip 56 engages the prongs 458 of the forked member 460, which forces the pipette tip 56 to slip off the distal end 454 of the pipette 336 and fall into the used pipette tip/slide drawer 74. The used pipette tips 56 are collected in the drawer 74 and will be disposed of by the clinician in accordance with proper medical procedures. There is a sensor (not shown) operatively coupled to the used pipette tip/slide drawer 74 which detects the position of the used pipette/tip slide drawer 74, and which sends a signal to the electronic circuitry of the analyzer indicative of the position of the drawer 74 and in particular whether the drawer has been removed from the analyzer housing. The electronic circuitry of the analyzer will not initiate the procedure that removes the pipette tips 57 from the pipette 336 or the procedure that ejects slides from the slide transport mechanism if the used pipette tip/slide drawer 74 is not in its proper position within the housing to accept the discarded pipette tips 56 and test slides 14.

The Sample Metering Sub-Assembly

FIGS. 26, 27, 53-55, 76 and 76*a* illustrate a preferred form of the sample metering sub-assembly 84 of the chemical analyzer 2 of the present invention. As mentioned previously, the sample metering sub-assembly 84 is mounted on the overhead carriage 330 of the sample preparation station 328 and is reciprocatingly slidable thereon to be positioned precisely in alignment with the slide transport mechanism 26, each slide inserter mechanism 20 to aspirate a blood sample from a rotor 208 or vial 242 placed thereon, the clean pipette tip tray 54 and the used pipette tip/slide discard drawer 74.

Figure 76:
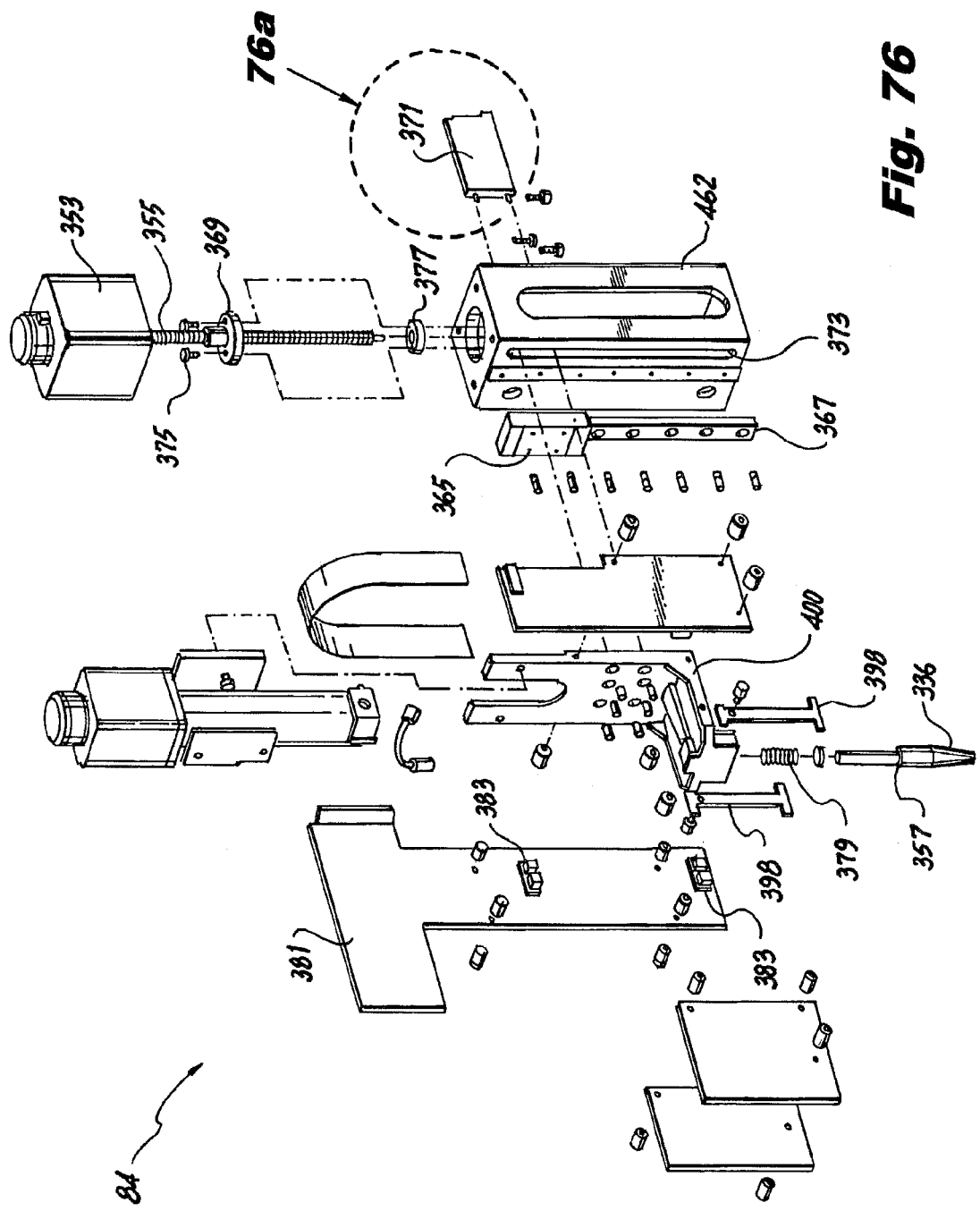
FIG. 76 is an exploded, front isometric view of one form of a sample metering sub-assembly constructed in accordance with the present invention.
Figure 76A:
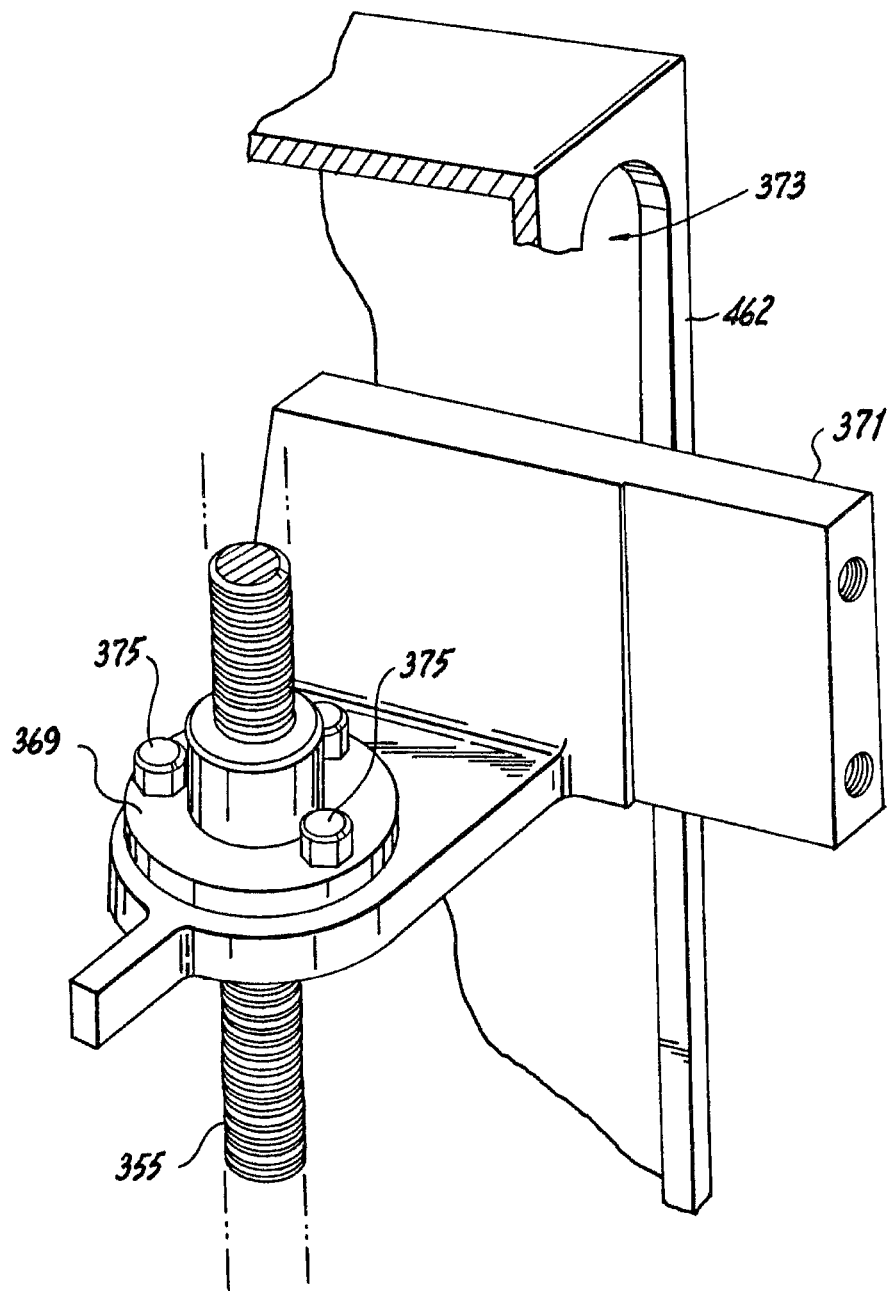
FIG. 76a is an isometric view of a portion of a sample metering sub-assembly constructed in accordance with the present invention and shown in FIG. 76.

As shown in FIG. 76, the sample metering sub-assembly 84 includes a first support bracket or box-like frame 462 which is slidably affixed to and rides on a rail 463 extending along the horizontal bracket 340 of the overhead carriage 330 of the sample preparation station 328 and is reciprocatingly movable thereon. An extending portion 464 of the first support frame 462 includes a threaded bore 466 which receives the lead screw 346 extending laterally across the width of the horizontal bracket 340 of the overhead carriage 330. As described previously, one axial end 354 of the lead screw 346 is rotatably mounted to the floating second bracket 358 of the overhead carriage 330 at one lateral side thereof. The opposite axial end 348 of the lead screw 346 is co-axially aligned with and joined to the shaft of the precision stepping motor 352. The electronic circuitry of the chemical analyzer 2 energizes and de-energizes the stepping motor 352 to rotate the lead screw 346, which rotational movement translates into a linear reciprocating movement of the sample metering sub-assembly 84 from one side of the overhead carriage 330 to the other.

An L-shaped second support bracket 400 is mounted on a side of the first support frame 462 and vertically movable thereon. More specifically, and as shown in FIG. 76, the rear side of the L-shaped second support bracket 400 is affixed to a plate 365 which is slidably mounted on a rail 367 mounted to a side of the first support frame 462.

A stepping motor 353 on the sample metering sub-assembly 84 is mounted on the first support frame 462. The shaft of this stepping motor 353 is operatively coupled to a lead screw 355 which extends longitudinally through the interior of the first support frame 462. A threaded follower 369 is threadingly mounted on the lead screw 355 and moves axially thereon in either direction when the lead screw 355 is rotated either clockwise or counterclockwise by the stepping motor 353.

The L-shaped second support bracket 400 includes an extended portion 371 which extends through a slot 373 formed in the side of the first support frame 462 and is coupled to the follower 369 by screws 375 passing through the extended portion 371 and into a securing ring 377 threadingly receiving the screws 375 on the other side so that the extended portion 371 is sandwiched between and movable with the follower 369 and the securing ring 377. Rotational movement of the lead screw 355 on the first support frame 462 translates to a reciprocating vertical movement of the second support bracket 400.

The pipette 336 of the metering sub-assembly 84, which is preferably spring loaded using coiled spring 379 situated on the outer surface of the pipette 336 and between the bottom portion of the L-shaped movable bracket 400 and a shoulder 357 formed radially inwardly of the outer surface of the pipette 336 to reduce inadvertent impact damage to the pipette, as well as preferably the pump 472 and the rotor picker mechanism 334, are mounted to the vertically moveable second bracket 400. Also, the first support frame 462 may include a plate 381 mounted thereon and having a pair of upper and lower positional sensors 383, each sensor 383 of the pair having a light source and a light detector, and being situated in proximity to the movable second support bracket 400 having a finger (not shown) extending therefrom to selectively interrupt the light beam of the pair of positional sensors 383 to signal the electronic circuitry of the analyzer when the upper and lower limits of travel of the second support bracket 400 on the first support frame 462 have been reached.

The electronic circuitry of the chemical analyzer 2 selectively energizes and de-energizes the precision stepping motor 353 of the sample metering sub-assembly 84 to cause the lead screw 355 to rotate in either a clockwise or counter-clockwise direction. The rotation of the lead screw 355 causes the second support bracket 400 to move reciprocatingly with respect to the first support frame 462 so that the pipette 336, and the pipette tip 56 selectively affixed thereto, can move vertically upwardly and downwardly a precise amount when aspirating the specimen from the centrifuge rotor 208 or from a sample vial 242, or when mixing the sample with diluent in the mixing cup 40, or when depositing the aspirated sample onto a chemical reagent test slide 14 carried by the slide transport mechanism 26, or to engage clean pipette tips 56 from the pipette tip tray 54.

Figure 77:
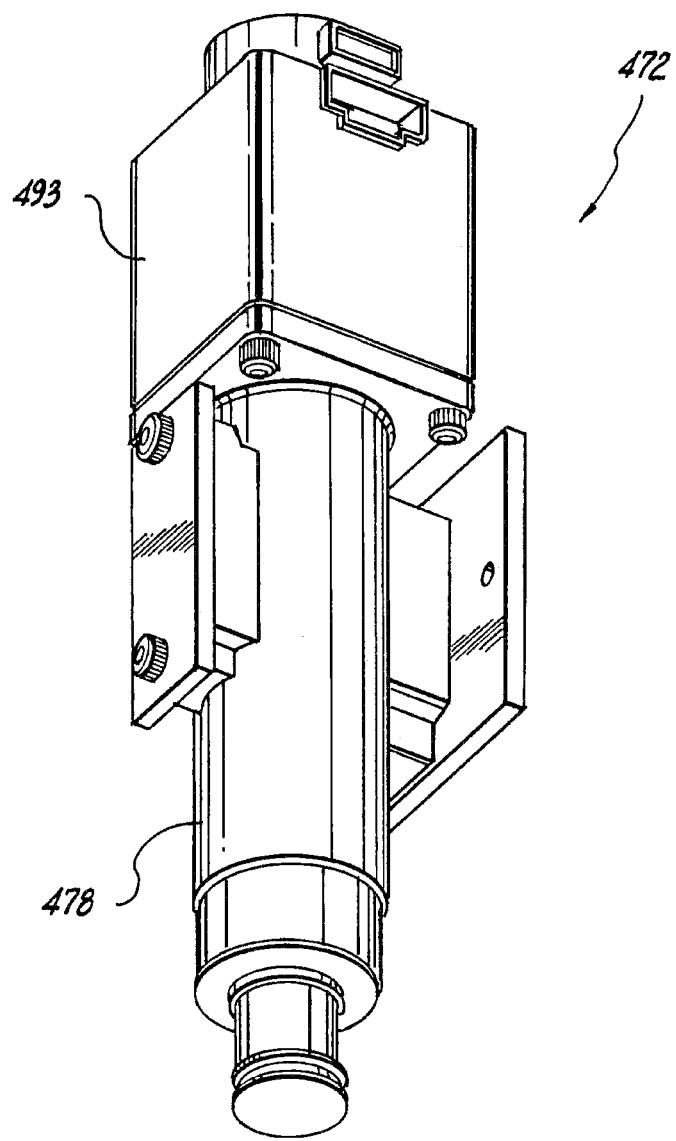
FIG. 77 is a pictorial illustration of a pump forming part of the sample metering sub-assembly constructed in accordance with the present invention.

As shown in FIG. 75, for example, the pipette 336 is an elongated member having an internal, axially extending bore 468. The pipette bore 468 communicates with a conduit 470 that is attached to an electrically operated mechanical pump 472 (see FIG. 77), which pump 472 is selectively energized and de-energized to create a negative air pressure or positive air pressure to respectively aspirate and expel a specimen from the pipette tip 56 fitted on the distal end 454 of the pipette 336.

Figure 77A:
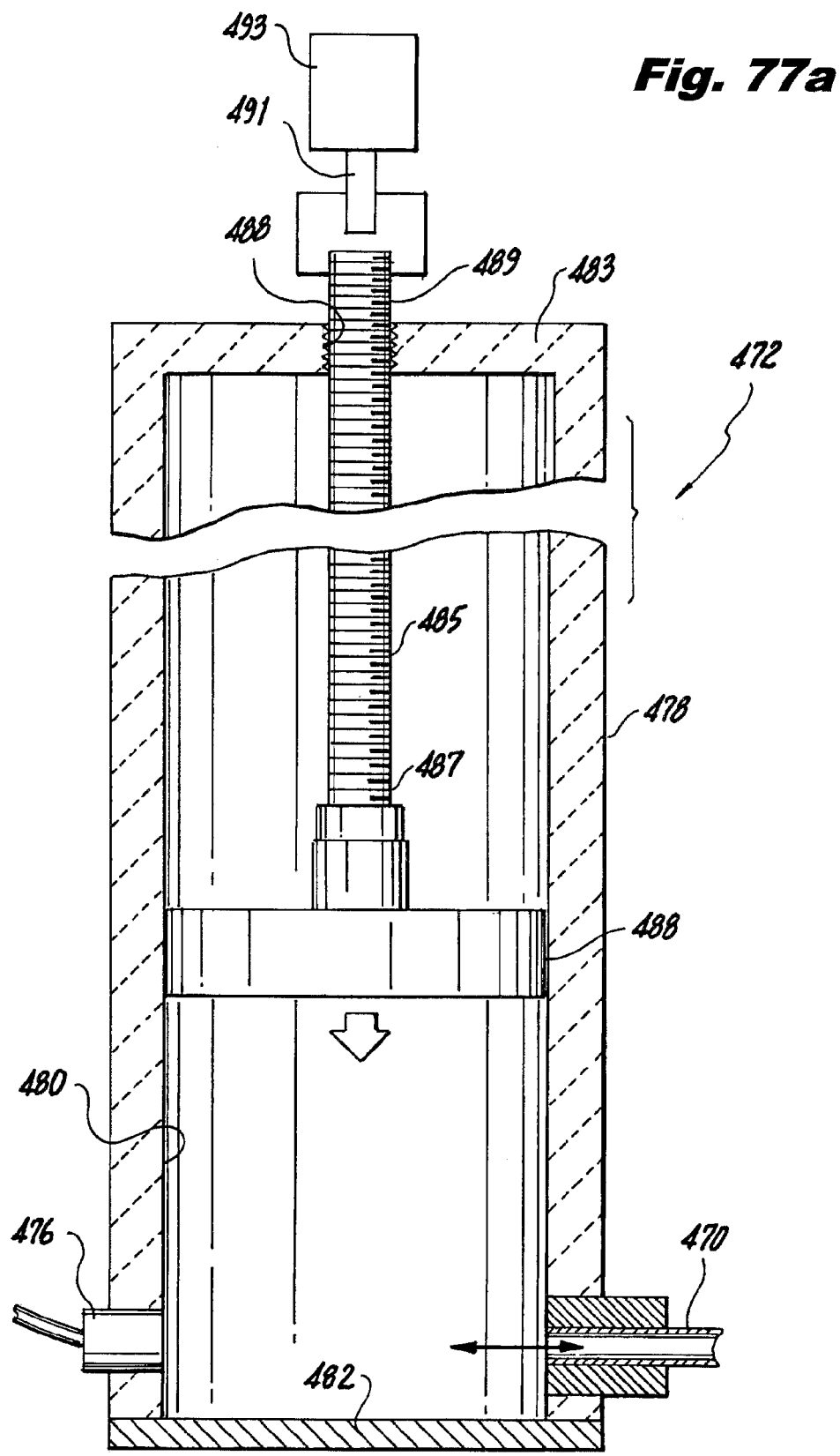
FIG. 77a is a cross-sectional illustrative view of a pump forming part of the sample metering sub-assembly constructed in accordance with the present invention and shown in FIG. 77.

Also included in the sample metering sub-assembly 84 is a pressure and/or temperature sensor 476 (see FIG. 77*a*) which communicates with the pipette bore 468, pump bore 480 and interconnecting conduit 470. As the temperature changes, pressure increases within the pipette bore 468 which could inadvertently force the liquid specimen out of the orifice 492 in the pipette tip 56. The pressure and/or temperature sensor 476 monitors the ambient conditions of the metering sub-assembly 84 and provides a signal to the electronic circuitry of the chemical analyzer 2 which, in accordance with the operational software programmed into the electronic circuitry, controls the pump 472 to increase or decrease the volume of air in the pipette tube bore 468 to increase or decrease the pressure of the air exerted on the fluid sample contained in the pipette tip 56.

As shown in FIGS. 26, 27, 76, 77 and 77*a*, the pump 472 and its associated components are mounted on the second, vertically moveable support bracket 400 of the sample metering sub-assembly 84. The pump 472 is preferably formed from a cylindrical tube 478 having a precisely formed bore 480 extending at least partially axially therethrough. One axial end 482 of the cylindrical tube 478 is fluidtightly connected to the conduit 470, the other end of the conduit 470 being coupled to the proximal or top end 486 of the pipette bore 468. The other axial end 485 of the tube includes an opening 488 that receives a portion of a lead screw 485. On the distal axial end 487 of the lead screw 485 opposite the proximal axial end 489 which is coupled to the shaft 491 of a stepping motor 493 is mounted a piston 488 which is closely received by the bore 480 of the cylindrical tube 478. The piston 488, when moved axially by the energization of the stepping motor 493, which is controlled by the electronic circuitry of the chemical analyzer 2, exerts pneumatic pressure within the pipette bore 468 on the specimen held by the pipette tip 56. Retracting the piston 488 within the cylindrical tube 478 relieves pressure on the specimen and causes air or specimen to be aspirated into the pipette tip 56, and rotation of the lead screw 485 in the opposite direction causes the piston 488 to move axially in the opposite direction in the cylindrical tube bore 480 and increases the air pressure within the cylindrical tube bore 480, which in turn exerts increased pressure on the specimen to expel precise volumes of liquid specimen from the pipette tip 56, such as when the specimen is being deposited on the chemical reagent test slides 14 carried by the slide transport mechanism 26.

Preferably, the cylindrical pump tube 478 is made from a ceramic material, and the piston 488 is also made from the same material as the cylindrical tube 478, that is, a ceramic material. Ceramic is preferred because it is substantially unaffected by temperature variations, and thus the dimensions of the tube 478 and piston 488 will not change appreciably, and tolerances between the two components will remain substantially constant over variations in anticipated ambient temperatures. Also, by making the piston 488 and cylindrical tube 478 of the same material, any changes to the dimensions of the two components due to temperature variations will track one another so that tolerances between the two components will remain precisely fixed. Furthermore, ceramic is a relatively hard material, the use of which results in negligible wear between the piston 488 and the walls of the pump tube 478.

The preferred volume of sample fluid that may be aspirated by the piston's movement in the pump cylindrical tube 478 is 200 microliters (µl). This means that for a 200 step motor 493 driving the piston 488 axially through the cylindrical tube 478, a sample fluid can be aspirated or expelled from the pipette tip 56 at precise volumetric quantities of one microliter per step.

Also, the tube 470 connecting the end of the pump cylindrical tube 478 to the pipette 336 (also referred to herein as a proboscis) is preferably formed of a Teflon™ material, which will not substantially expand or contract under anticipated temperature variations. The inner diameter of the tube 470 is preferably 0.012 inches.

Very small and precise amounts of liquid specimen are deposited on the film portion 116 of the chemical reagent test slides 14. Preferably, only about five (5) microliters to about ten (10) microliters, plus or minus 0.119 microliters standard deviation, is deposited on each test slide 14.

Furthermore, the method of depositing liquid specimen on each test slide 14 by the metering sub-assembly 84 of the present invention differs from that of the VETTEST® chemical analyzer. With the present invention, liquid specimen is propelled from the orifice 492 formed in the pipette tip 56, also referred to herein as "injection metering", to avoid tip backwetting. The VETTEST® chemical analyzer, on the other hand, forms a drop at the orifice of the pipette tip, which is drawn to the slide by capillary action when the pipette tip is lowered to the reagent test slide so that the drop contacts the film portion of the slide.

Even more preferably, the pipette tip 56 is lowered by the sample metering sub-assembly 84 (see FIG. 73) to about 0.035 inches above the film portion 116 of each slide 14 positioned under it in the slide transport mechanism 26. Then, a stream of fluid sample is ejected from the pipette tip 56 onto the slide 14 by the pump 472. The pipette tip 56 is relatively quickly withdrawn from its proximity to the slide 14 so that no capillary drawing of fluid to the slide 14 or backwetting of the exterior surface 798 of the pipette tip 56 occurs. The next slide is positioned under the pipette tip 56, and the above-described metering process is repeated until all of the slides 14 have been spotted with fluid specimen.

Additionally, the electronic circuitry of the chemical analyzer 2 can precisely adjust the axial movement of the pump piston 488 to adjust the amount of liquid specimen deposited on each test slide 14, as some test slides 14 require more or less than a nominal volume of liquid sample. As will be described in greater detail, a UPC (Universal Product Code) 494 or other information is imprinted on each test slide 14, which is read by the chemical analyzer 2 using a code reader 642, and the electronic circuitry can adjust the volume of liquid specimen expelled from the pipette tip 56 accordingly.

Figure 79:
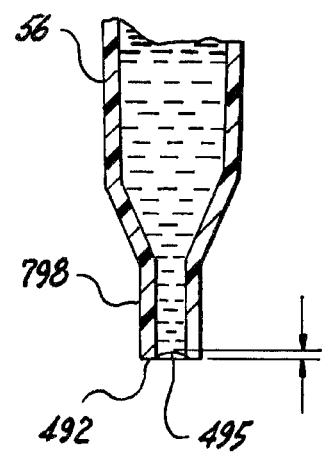
FIG. 79 is a cross-sectional view of the pipette tip containing liquid and showing a concave meniscus of liquid formed at the orifice of the pipette tip taken along line 79-79 of FIG. 73.
Figure 80:
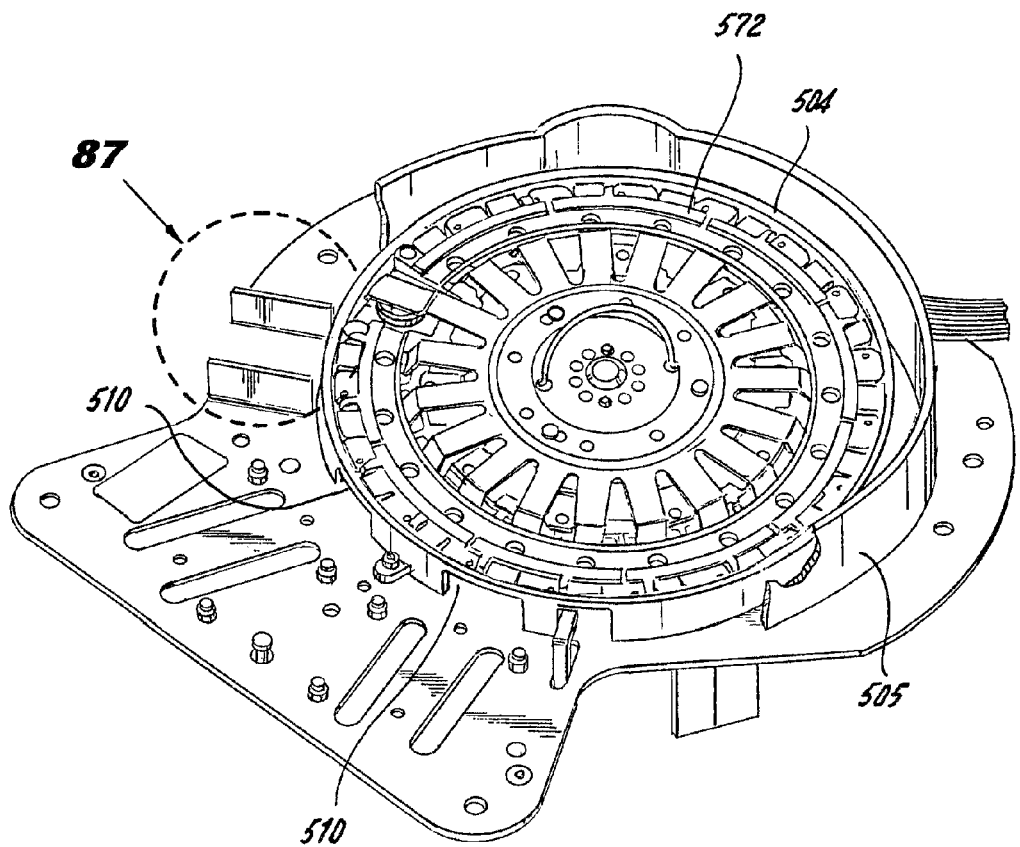
FIG. 80 is a top isometric view of a portion of the slide transport mechanism formed in accordance with the present invention and used in the chemical analyzer of the present invention.

The electronic circuitry of the chemical analyzer 2 controllably energizes the precision stepping motor 493 driving the piston 488 of the pump 472 to withdraw the piston 488 slightly in the tube bore 480 after each time liquid specimen is deposited on a reagent test slide 14. By doing this, a concave meniscus 495 of liquid specimen is formed at the orifice 492 of the pipette tip 56, as shown in FIG. 79. The concave meniscus 495 minimizes the possibility of wetting the outer surface 798 of the pipette tip 56 with the liquid specimen contained therein, which may have otherwise affected the accuracy and repeatability of depositing a predetermined volume of liquid specimen on each chemical reagent test slide 14. Furthermore, if the ambient temperature does vary, with such variation affecting the pressure within the pump's tube bore 480 that may have otherwise inadvertently forced liquid specimen from the orifice 492 of the pipette tip 56, the concave meniscus 495 provides a buffer volume of air which may be occupied by the liquid specimen as the ambient temperature and concomitant pressure within the pump tube bore 480 vary.

Figure 78:
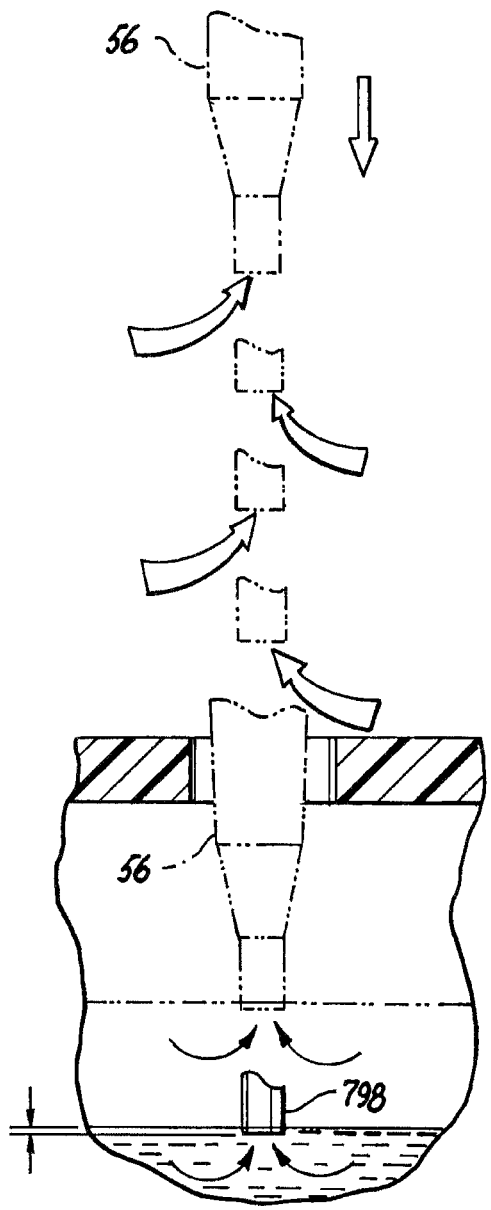
FIG. 78 is a cross-sectional view of a portion of the pipette tip of the sample metering sub-assembly and a portion of a vessel containing a liquid, such as a blood sample, and depicting movement of the pipette tip and the operation thereof in accordance with the present invention to detect the level of the liquid contained in the vessel.

Another feature of the sample metering sub-assembly 84 is its ability to continuously lower the pipette tip 56 in the centrifuge rotor 208 as liquid specimen is being aspirated into the pipette tip 56 from the rotor 208 or sample vial 242 (see FIG. 78). As the liquid specimen is removed from the centrifuge rotor 208 or sample vial 242, the level of the volume remaining in the rotor 208 or vial 242 decreases. The electronic circuitry of the chemical analyzer 2 causes the sample metering sub-assembly 84 to position a minimal portion of the pipette tip 56 below the surface level of the liquid specimen contained in the rotor 208. This is to ensure that no air, and just liquid specimen, is aspirated into the pipette tip 56 through the orifice 492 thereof.

As the level of the liquid specimen in the rotor 208 falls, the electronic circuitry energizes the precision stepping motor 353 of the sample metering sub-assembly 84 to continually lower the pipette tip 56 in order to maintain a minimal portion of the pipette tip 56 below the decreasing surface level of the liquid specimen in the rotor 208, until a volume of liquid specimen required for the particular test being conducted is aspirated into the pipette tip 56.

More specifically, and as mentioned previously, the pump mechanism 472 of the sample metering sub-assembly 84 may include pressure and/or temperature sensors 476. One such pressure sensor 476 is preferably situated at the end portion 482 of the pump cylinder 478 diametrically opposite the location of the end of the connection tube 470 to the proboscis (pipette 336). This pressure sensor 476 can detect minute changes in pressure within the pipette tip 56 fluidtightly affixed to the pipette 336, and thus can detect whether air or sample is being aspirated by the pipette 336, one purpose of which will be explained below.

It is desired that when aspirating a fluid sample, either from the centrifuge rotor 208 or from the sample vial 242, little or no wetting of the exterior surfaces 798 of the pipette tip 56 occurs; it is possible that significant wetting of the pipette tip exterior surfaces 798 could affect the desired volume of fluid sample metered onto the reagent test slides 14. Accordingly, it is desired to submerge the pipette tip 56 into the sample vial 242 or centrifuge rotor 208 preferably no more than about one millimeter (mm) below the surface of the fluid sample contained therein.

In order to determine the surface height of the volume of fluid sample in the fluid vial 242 or rotor 208, the sample metering sub-assembly 84 continually aspirates small volumes of air as the pipette tip 56 is lowered into the sample vial 242 or rotor 208, and monitors the pressure within the pump cylinder 478 and interconnected pipette 336 in fluid communication therewith sensed by the pressure sensor 476, as shown in FIG. 78. As the pipette 336 is being lowered into the sample vial 242 or centrifuge rotor 208, an increase in pressure may be detected by the pressure sensor 476, which indicates that fluid sample rather than air has been aspirated. The electronic circuitry 22 is signaled by the pressure sensor 476 to indicate that the surface of the fluid sample in the vial 242 or rotor 208 has been reached. The analyzer 2 has pre-programmed into a memory circuit of the electronic circuitry the overall interior geometry and thus volume of the sample vial 242 and rotor 208. Furthermore, the rate at which fluid sample is withdrawn from the sample vial 242 or rotor 208 by the sample metering sub-assembly 84 is also monitored by the electronic circuitry. Therefore, as the fluid sample is withdrawn from the sample vial 242 or rotor 208, the pipette tip 56 is controllably lowered by the sample metering sub-assembly 84 into the sample vial 242 or rotor 208 so that the depth of the pipette tip 56 is maintained at about 1 millimeter (mm) below the surface level of the fluid sample.

To put this feature into perspective, the sample vial 242, in its preferred form, is truncated conically shaped in longitudinal cross-section. As the pipette tip 56 is submerged about one millimeter below the surface of the fluid sample, the sample is aspirated by the pipette 336 at a constant rate. Since the surface level of the fluid sample in the vial 242 falls more rapidly the lower it is in the vial 242, due to the geometry of the vial 242, the software of the analyzer 2, knowing this geometry, adjustably increases the velocity at which the pipette tip 56 is lowered into the sample vial 242 to maintain the pipette tip 56 at a depth preferably no more than one millimeter below the surface of the fluid sample. The electronic circuitry stops the pump 472 when the desired volume of fluid sample has been aspirated.

The Slide Transport Mechanism

FIGS. 29-31 and 80-83 illustrate a preferred form of a transport mechanism 26 for transporting the reagent test slides 14 from one station of the chemical analyzer 2 to another, and for incubating the slides 14 before and during the colorimetric tests performed on the slides 14.

More specifically, the slide transport mechanism 26 includes a non-rotatable slide track 500 which is circular in shape and which includes an inner radial vertical sidewall 502, an outer radial vertical sidewall 504 and a bottom wall 506 disposed between the inner radial sidewall 502 and the outer radial sidewall 504. The inner radial sidewall 502, outer radial sidewall 504 and bottom wall 506 of the slide track 500 together define a U-shaped circular channel 508 in which the reagent test slides 14 are received and about which the slides 14 are moved in a circular path. The transport mechanism 26 may further include a third outermost radial vertical wall 505 on which a cover plate may be attached to define with the outermost wall 505 an incubator in which the slide track 500 resides.

A slot 510 is formed in the outer radial vertical sidewall 504 near the bottom wall 506 of the slide track 500 and is aligned with one of the slide inserter mechanisms 20 so that test slides 14 placed on the slide inserter mechanism 20 may be received through the slot 510 by a pusher plate 322 or other structure of the slide inserter mechanism 20 and into the U-shaped channel 508 of the slide track 500. As mentioned previously, two side-by-side slide inserter mechanisms 20 are preferably provided with the chemical analyzer 2 of the present invention. Accordingly, and as shown in FIG. 29, two slots 510 may be formed in the radially outer vertical sidewall 504 of the slide track 500, each slot 510 being in alignment with a respective slide inserter mechanism 20 and each slot 510 communicating with the U-shaped channel 508 of the slide track 500 to receive slides 14 therethrough and into the U-shaped channel 508. Alternatively, a single slot (not shown) extending angularly over a portion of the outer vertical sidewall 504 of the slide track 500 and in radial alignment with both slide inserter mechanisms 20 or pusher plates 322 to receive inserted slides 14 from each mechanism 20 may be provided. Preferably, the non-moveable slide track 500 has its sidewalls 502, 504 made from Delrin® material, and its bottom wall 506 made from aluminum impregnated with polytetrafluoroethylene, so that the slides 14 may be moved within the slide track 500 with little or no friction between the slide frame 114 and the inner and outer radial sidewalls 502,504 and bottom wall 506 of the slide track 500. Each of the slots 510 has a width which is slightly greater than that of the reagent test slides 14 to allow the reagent test slides 14 to freely pass therethrough and into the U-shaped channel 508 defined by the slide track 500.

A third slot 514, also having a width which is slightly greater than that of the reagent test slides 14, is formed in the outer sidewall 504 of the slide track 500 in alignment with the used slide drawer 74. A pusher bar 744, which is radially retractable and extendable and operatively coupled to a solenoid or motor 516 (preferably a motor) which is selectively energized by the electronic circuitry of the chemical analyzer 2, selectively passes through a slot 518 formed in the inner radial sidewall 502 of the slide track 500 and rides in a recessed track 519 formed in the bottom wall 506. When the solenoid or motor 516 is energized by the electronic circuitry, the pusher bar 744 engages the front edge 122 of a chemical reagent test slide 14 situated in alignment with and between the third slot 514 formed in the outer radial sidewall 504 and the slot 518 formed in the inner radial sidewall 502 to eject the so-aligned reagent test slide 14 through the outer sidewall slot 514 and into the used slide drawer 74 of the chemical analyzer 2, as illustrated by FIG.

87. A chute or ramp 520 extending from the outer surface 522 of the outer radial sidewall 504 of the slide track 500 and positioned beneath and in alignment with the third slot 514 may be provided to ensure that the used reagent test slides 14 are properly directed to fall into the slide drawer 74 for discarding by the clinician.

Figure 81:
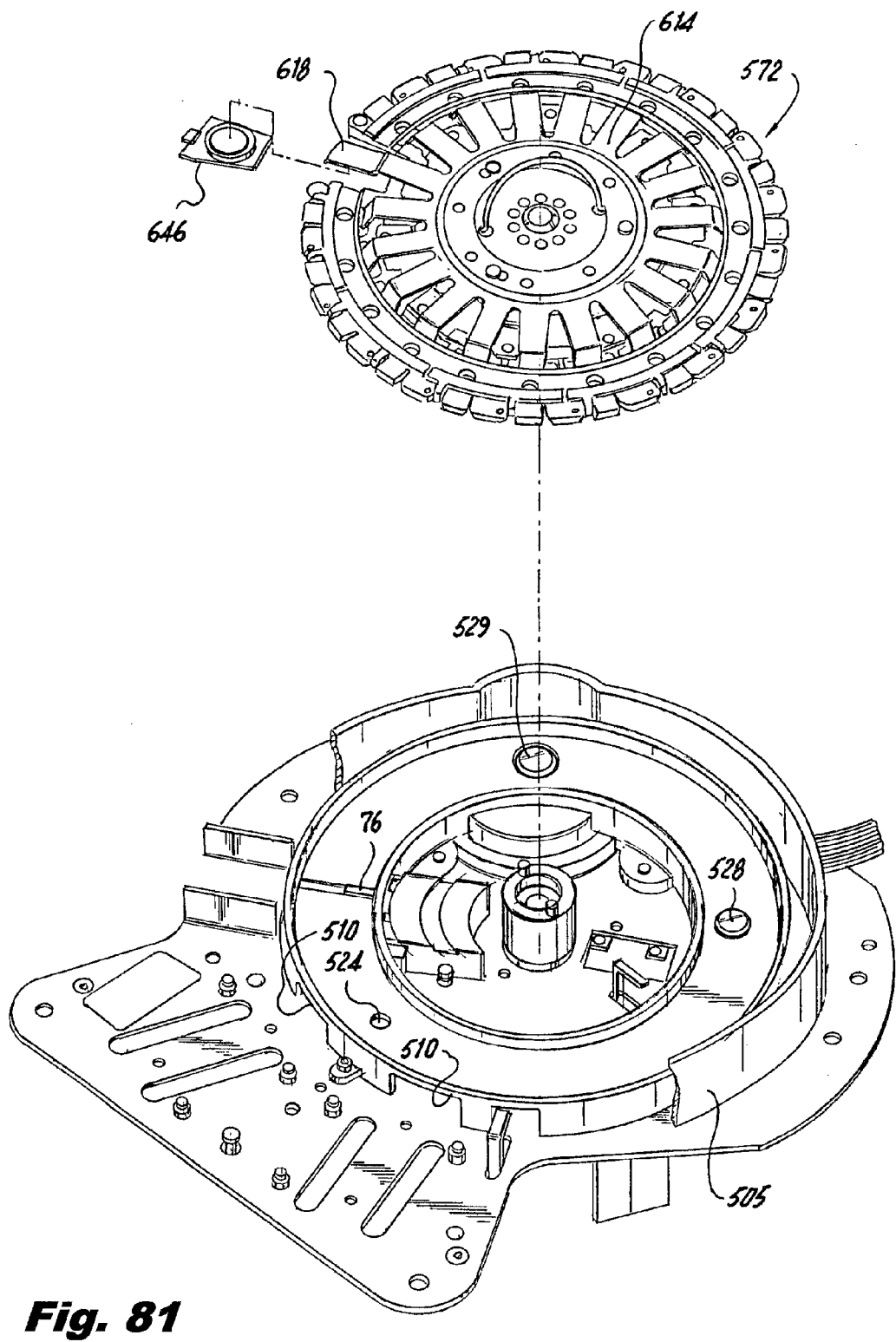
FIG. 81 is a partially exploded, top isometric view of the slide transport mechanism shown in FIG. 80.
Figure 82:
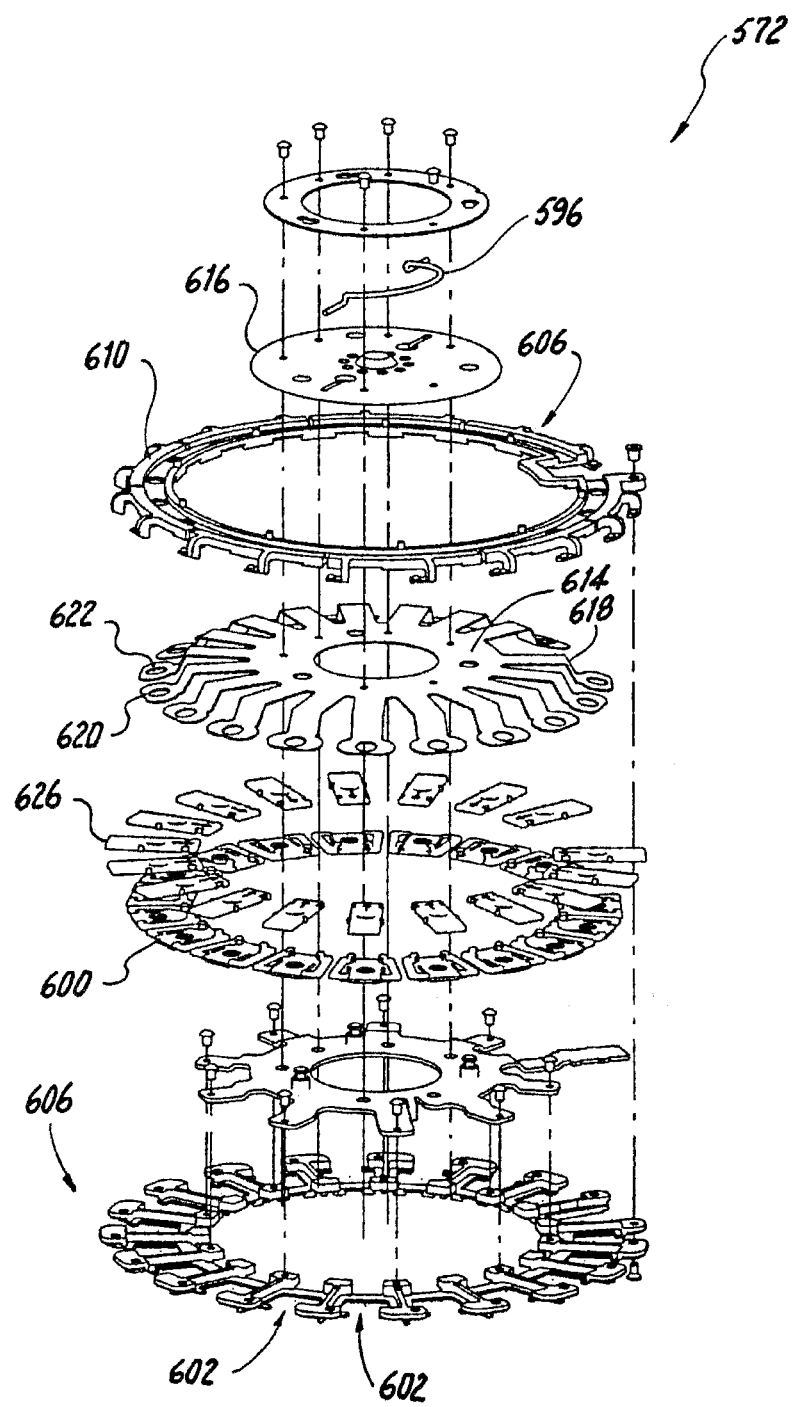
FIG. 82 is an exploded, top isometric view of the slide carousel portion of the slide transport mechanism constructed in accordance with the present invention and used in the chemical analyzer of the present invention.
Figure 82A:
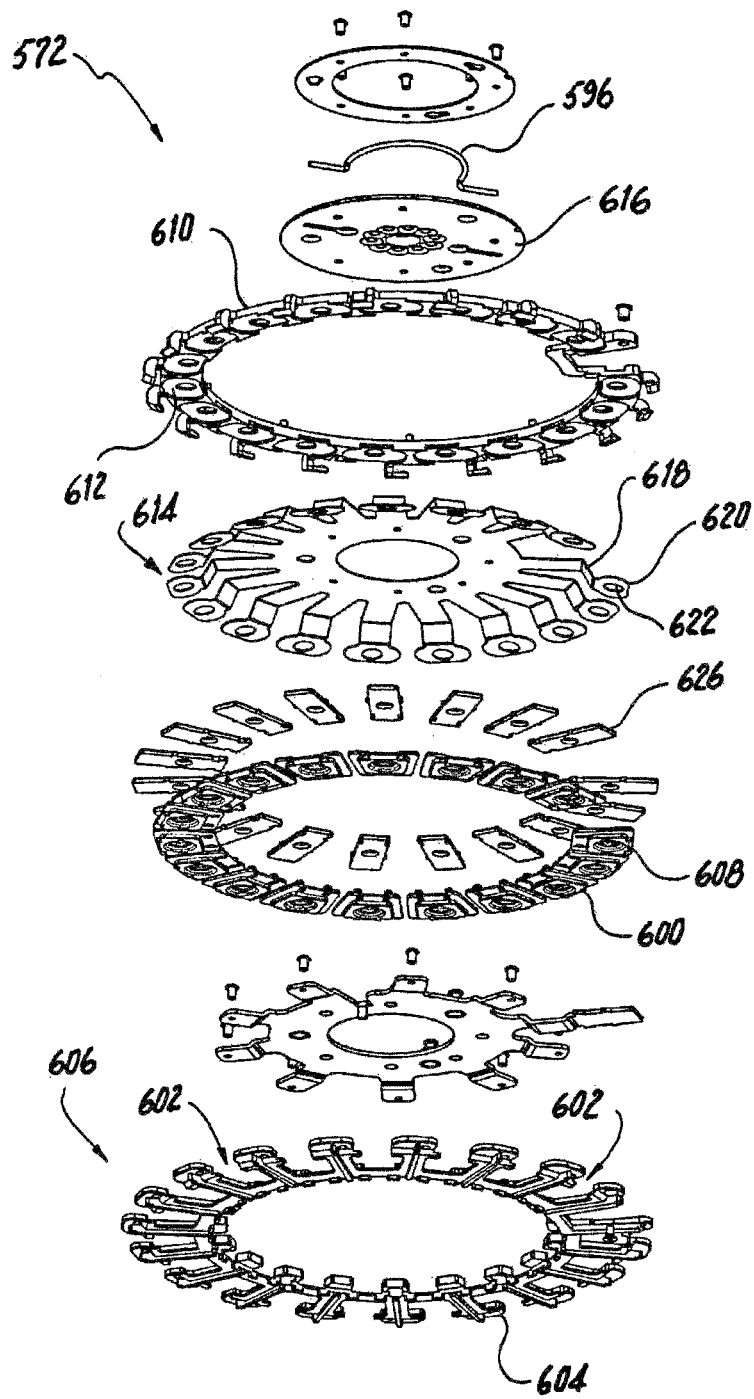
FIG. 82a is an exploded, bottom isometric view of the slide carousel portion of the slide transport mechanism constructed in accordance with the present invention and used in the chemical analyzer of the present invention.
Figure 82B:
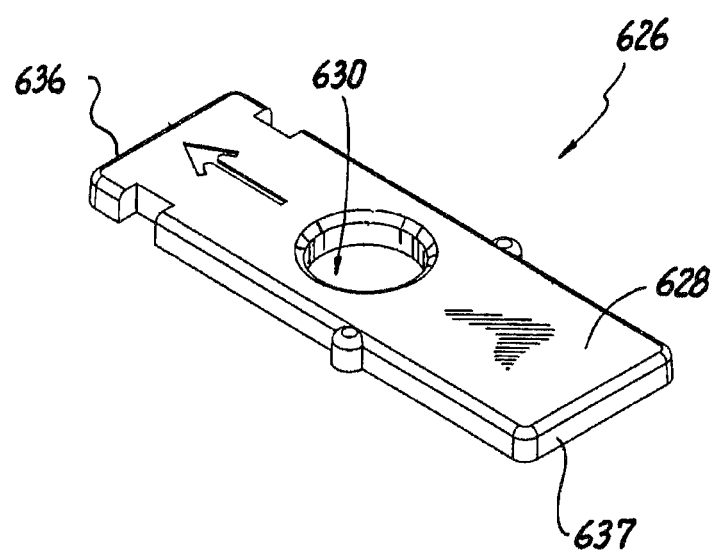

Preferably, a first opening 524 is formed through the thickness of the bottom wall 506 of the slide track 500 (see FIGS. 29 and 81). This opening 524 is provided in the unlikely event that any fluid deposited on a reagent test slide 14 drips onto the slide track 500. Such dripped fluid would pass through the opening 524 in the bottom wall 506 of the slide track 500 and be removed from the U-shaped channel 508 as the reagent test slides 14 move about the U-shaped channel 508.

Figure 86:
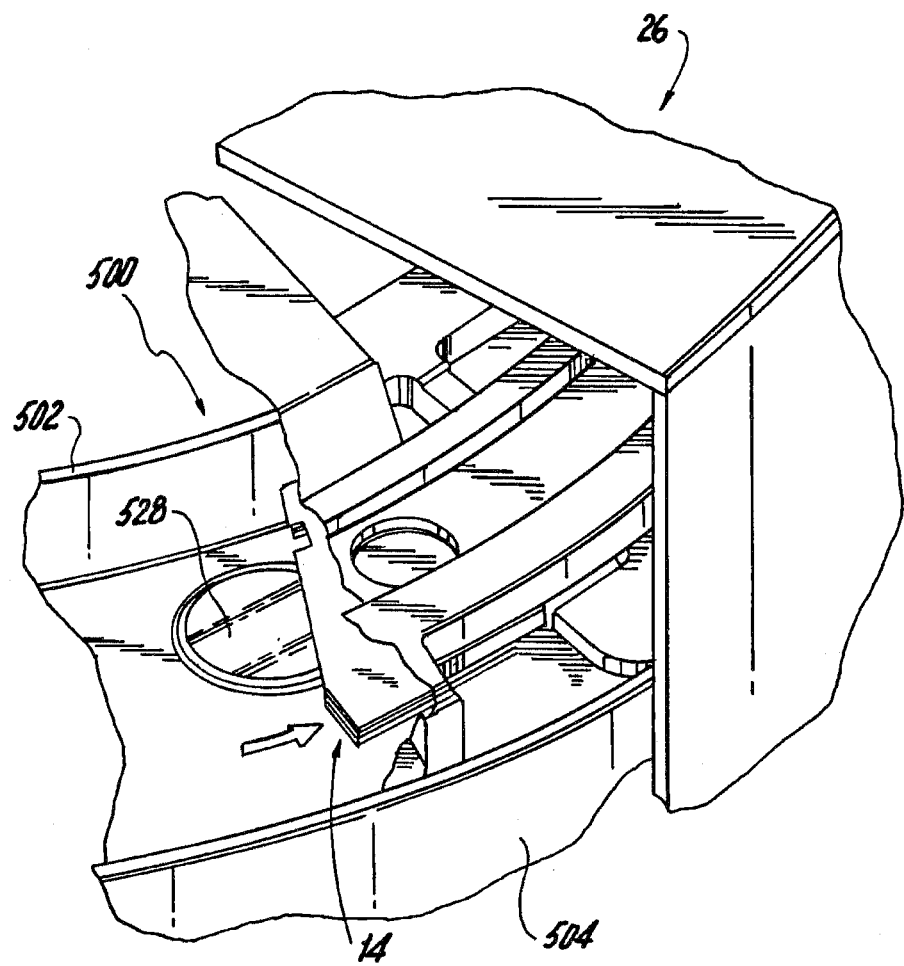
FIG. 86 is a top isometric view of a portion of the slide transport mechanism of the present invention and a partially cut away reagent test slide received thereby, and illustrating how the reagent test slide cleans a window of either a fluorometer or a reflectometer situated in the slide transport mechanism of the present invention.

A second opening 526 is formed through the thickness of the bottom wall 506 of the slide track 500. This opening 526 includes a transparent plastic or glass window 528 which is received therein, and is situated over and coupled to the reflectometer/fluorometer station 530 of the chemical analyzer 2, as will be described in greater detail. However, it is preferred that the glass or plastic window 528 is raised slightly off the surface of the bottom wall 506 of the slide track 500, preferably a few thousands of an inch. The advantage of doing this is that the transparent window 528 is always wiped clean by the frames 114 of the passing slides 14 as the slides 14 move about the U-shaped channel 508 of the slide track 500, as shown in FIG. 86 of the drawings.

If the chemical analyzer 2 uses a reflectometer and fluorometer that are separate and spaced apart from one another under the slide track 500, then the second opening 526 and transparent window 528 is used for one of the reflectometer and fluorometer, and a third opening 532 formed in the slide track 500 and a second transparent window 529 received thereby, also raised slightly in the slide track 500 for being wiped clean by the passing slides 14, is provided for and forms part of the other of the reflectometer and fluorometer (see FIGS. 29 and 81).

Figure 83:
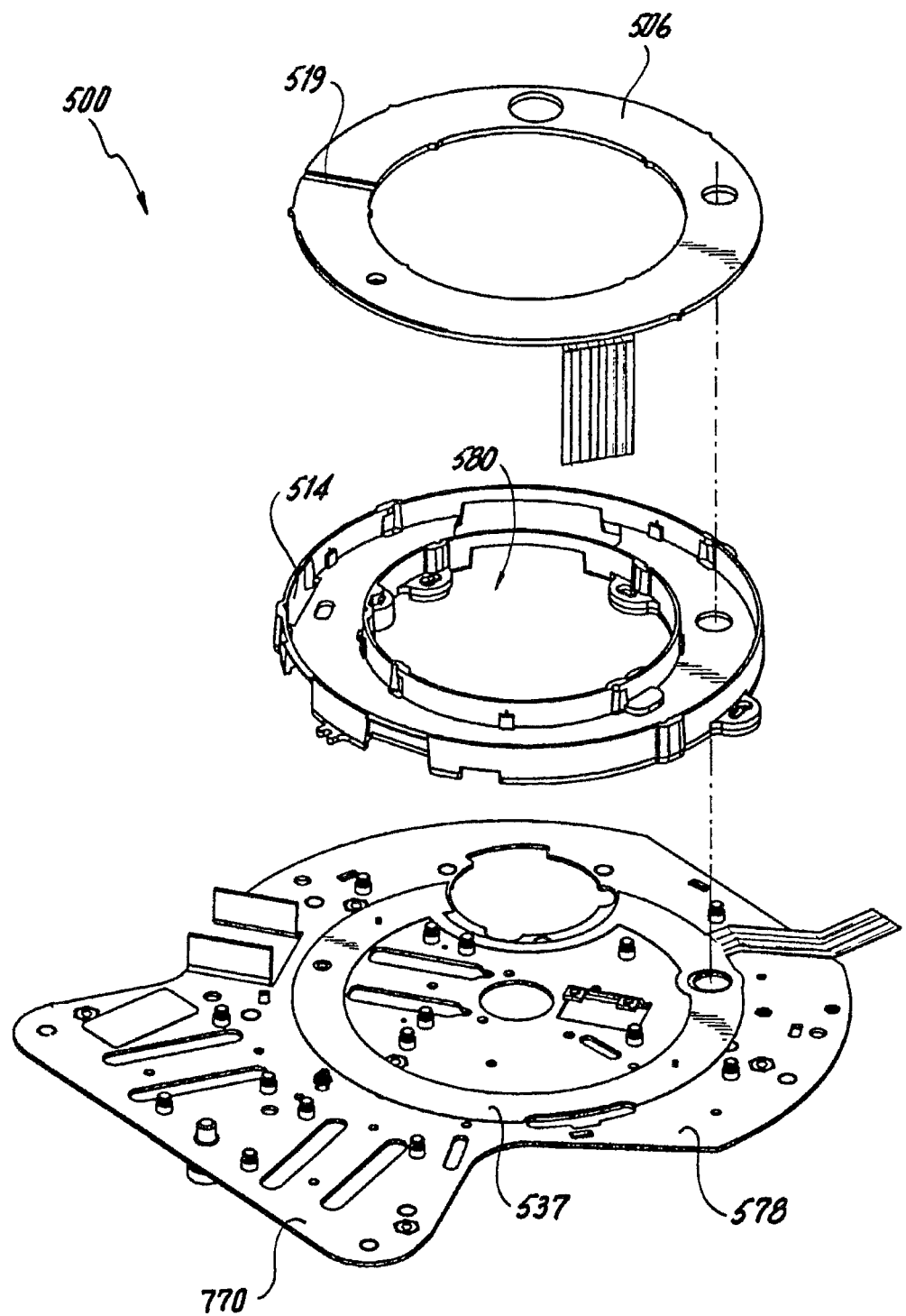
FIG. 83 is a partially exploded, top isometric view of the slide transport mechanism formed in accordance with the present invention and used in the chemical analyzer of the present invention.
Figure 83A:
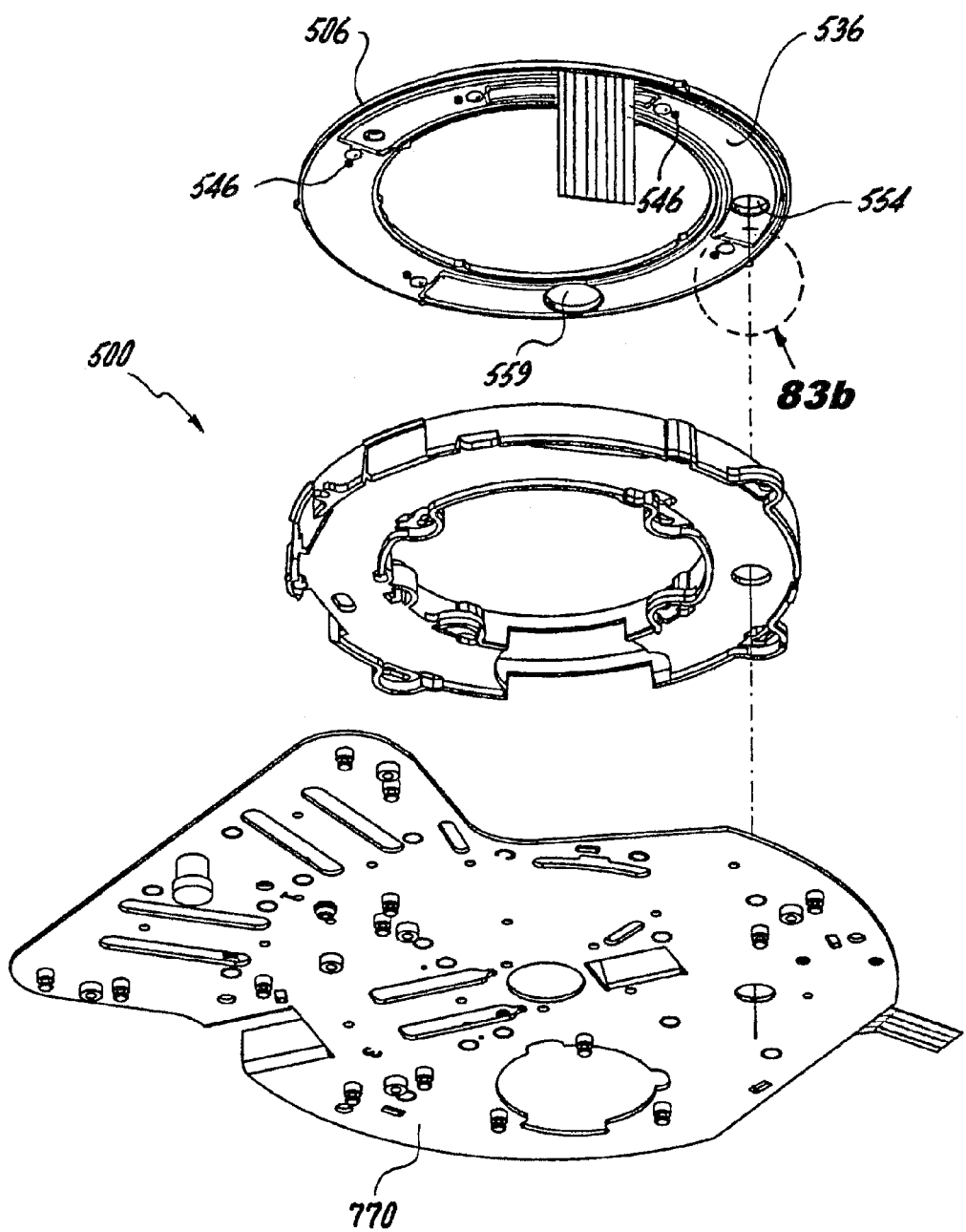
FIG. 83a is a partially exploded, bottom isometric view of the slide transport mechanism formed in accordance with the present invention and used in the chemical analyzer of the present invention.
Figure 83B:
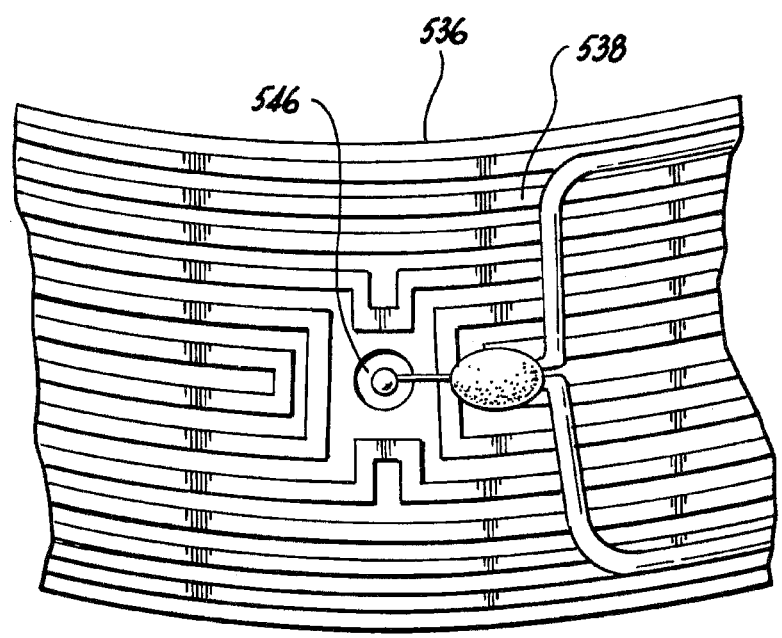
FIG. 83b is a top plan view of a portion of a heating ring forming part of the slide transport mechanism formed in accordance with the present invention and used in the chemical analyzer of the present invention.

On the underside surface 534 of the bottom wall 506 of the slide track 500 is situated a ring-shaped, thin, flexible printed circuit board 536, as shown in FIG. 83a. The printed circuit board 536 is formed as a flexible substrate sandwiched between two thermally conductive but electrically insulative layers of material, such as Kapton® film. The substrate has a plurality of heating element lands 538 situated in a circuitous, undulating or serpentine pattern. The heating ring 536 is situated in close proximity to, and preferably in contact with (preferably, adhesively affixed to), the underside of the bottom wall 506 of the slide track 500 and so that heat generated by the heating elements 538 of the heating ring 536 is transferred by conduction and/or convection to the bottom wall 506 of the slide track 500 so that the slides 14 moving rotatably within the U-shaped channel 508 are incubated and maintained at a specific temperature. The heating ring 536 includes one or more temperature sensors 546 positioned as needed thereon (preferably, there are five thermistors periodically spaced circularly about the heating element printed circuit board 536 under the slide track), which are used to maintain the temperature within the U-shaped channel 508 to within a specific range, which is 37° Celsius (98.6° Fahrenheit) within the incubator defined by the U-shaped channel 508 in which the slides 14 reside, the tolerance being preferably plus or minus 0.2° Celsius. The temperature sensors 546 detect the temperature within the U-shaped channel 508 (i.e., the slide incubator), and provide signals to the electronic circuitry of the chemical analyzer 2 which, in response, selectively energize or de-energize at least selected portions of the heating elements 538 on the heating ring 536.

Preferably, two heating zones, independently controlled by the electronic circuitry and software of the analyzer 2, are provided by the heating element printed circuit board 536, the temperature of each zone being detected by one or more of the thermistors mentioned previously. One zone is located near where the slides 14 are loaded into the slide track 500. The other zone is located near the test area for the slides 14, that is, where the reflectometer and/or fluorometer are situated. Of course, it is envisioned to be within the scope of the present invention to have a lower or greater number of heating zones, each independently controlled by the electronic circuitry of the analyzer, to maintain a suitably constant temperature for the slides 14 as they move about the slide track 500.

The heating element printed circuit board 536 also includes openings 554 formed through the thickness thereof for receiving therethrough the upper portion of the reflectometer and fluorometer and the windows 528, 529 thereof. Preferably, one or more printed circuit lands 538 are disposed near these openings 554 and windows 528, 529 and preferably at least partially encircle these windows 528, 529 to help maintain the reflectometer and fluorometer at a near constant temperature.

Another thin, flexible, ring-shaped printed circuit board 537 of similar structure to printed circuit board 536, with a flexible substrate having heating element lands situated thereon and sandwiched between two Kapton® film layers, is used to heat the "skull plate" 770 inside the analyzer housing on which this printed circuit board 537 rests or is in close proximity thereto and to help maintain the temperature generally within the interior space of the housing 6 to a near constant temperature (preferably thirty-five (35) degrees Celsius, as stated below). A single heating zone on printed circuit board 537, controlled by the electronic circuitry, may be provided for heating the skull plate 770 and interior space of the analyzer housing 6, although it is envisioned to be within the scope of the present invention to have more than one controllable heating zone or additional heating elements for the interior of the housing 6.

One or more temperature sensors, such as thermisters 539 on printed circuit board 537, or elsewhere in the analyzer, are also provided within the housing 6 of the chemical analyzer 2 to detect the interior temperature. Preferably, and as stated above, the interior temperature inside the enclosure 6 of the chemical analyzer 2 is maintained at 35° Celsius, which temperature is maintained regardless of the ambient temperature of the laboratory where the chemical analyzer 2 is used. The temperature sensor or sensors 546 (preferably there are two thermistors situated on the lower printed circuit board 537 in contact with the skull plate 770) detect the temperature of the interior of the chemical analyzer 2 and provide corresponding signals to the electronic circuitry which, in response thereto, selectively energizes the heating elements on the printed circuit board 537 (or a separate heating block (not shown) situated within the interior space of the housing 6) in order to maintain the interior of the housing 6 at the desired temperature.

A ring-shaped slide carousel 572 is at least partially rotatably received within the U-shaped channel 508 of the slide track 500, as shown in FIGS. 30, 31 and 80-83 of the drawings. A precision stepping motor and coupler assembly 574 is used to rotate the slide carousel 572 within the U-shaped channel 508 of the slide track 500. The stepping motor and coupler assembly 574 is preferably mounted on the upper surface 578 of the skull plate 770 on which is also mounted the slide track 500, the stepping motor 574 being preferably positioned at the center of the interior space 580 defined by the inner radial sidewall 502 of the slide track 500. The shaft of the stepping motor 574 is operatively coupled directly to the slide carousel 572, or indirectly by gearing, belt, chain and sprocket, or like mechanisms to the slide carousel 572 to cause the slide carousel 572 to rotate in at least one direction within the U-shaped channel 508 of the slide track 500.

A plurality of ribs 584 extend outwardly from the lower surface 586 of the slide carousel 572 and radially from the inner radial edge 588 to the outer radial edge 590 of the slide carousel 572. Adjacent ribs 584 are spaced apart from one another a predetermined distance to closely receive therebetween a respective reagent test slide 14 which, as mentioned previously, is preferably trapezoidal in overall shape. The ribs 584 extend sufficiently outwardly from the lower surface 586 of the slide carousel 572 to engage the lateral edges 124 of the reagent test slides 14, but not so far as to touch the upper surface 592 of the bottom wall 506 of the slide track 500. As the carousel 572 is rotated by the stepping motor and coupler assembly 574, it moves the reagent test slides 14 situated within the U-shaped channel 508 of the slide track 500.

Adjacent ribs 584 and the lower surface 586 of the slide carousel 572 define with the upper surface 592 of the bottom wall 506 of the slide track 500 an incubated chamber 594 for receiving a respective reagent test slide 14 therein and holding the test slide 14 captive within the chamber 594 when the slides 14 are loaded onto the slide track 500 through the slot or slots 510 provided in the outer radial sidewall 504 of the slide track 500 by the slide inserter mechanism 20 or mechanisms. Thus, the slide carousel 572 moves the reagent test slides 14 within the U-shaped channel 508 as the slide carousel 572 is rotated by the stepping motor 574 coupled thereto. The slide carousel 572 includes a D-ring 596 on its upper surface 598 that may be grasped by the clinician so that the slide carousel 572 may be lifted free of the motor and coupler assembly 574 and removed from the chemical analyzer 2 for cleaning.

The slide carousel 572 includes a plurality of "floating", generally trapezoidally-shaped slide covers 600 positioned in complementary-shaped recesses 602 formed in the lower surface 604 of the main body 606 of the slide carousel 572 and loosely receivable in the recesses 602. The slide covers 600 rest on top of the reagent test slides 14 situated in the U-shaped channel 508 of the slide track 500 and between adjacent ribs 584 of the carousel 572. Each floating slide cover 600 includes an opening 608 formed through the thickness thereof. These openings 608 are aligned with respective openings 612 formed in the upper surface 610 of the main body 606 of the slide carousel 572, which main body openings 612 extend from the upper surface 610 of the main body 606 to the recesses 602 that receive the floating slide covers 600. The openings 612 in the main body 606 of the carousel 572, and the openings 608 in the slide covers 600, are positioned to reside over the film portion 116 of a chemical reagent test slide 14 situated in the slide track 500 between adjacent ribs 584. The openings are provided for allowing the liquid specimen to be deposited through the openings onto the film portion 116 of the reagent test slides 14 by the sample metering sub-assembly 84. As the slide carousel 572 is rotated, a reagent test slide 14 moved thereby on the slide track 500 is positioned below and in alignment with the pipette 336 of the sample metering sub-assembly 84, which deposits a predetermined volume of fluid specimen on each slide 14 as they are sequentially positioned in alignment with the pipette tip 56.

The slide carousel 572 includes a spider spring 614 mounted to the hub 616 and which is formed with a plurality of resilient leaf springs 618 which extend radially therefrom. The free end 620 of each leaf spring 618 includes an opening 622 formed through the thickness thereof through which passes the liquid specimen deposited on each reagent test slide 14 by the pipette 336 of the sample metering sub-assembly 84. Each free end 620 of the leaf springs 618 is situated above a respective floating slide cover 600 and exerts a downward force thereon so that the slide covers 600 closely engage the top surface of a respective reagent test slide 14 situated below it in the slide track 500.

More specifically, each slide cover 600, floating within its corresponding recess 602 formed in the main body 606 of the slide carousel 572, closely engages the test slide frame 114 surrounding the film portion 116 to form a seal therewith and to ensure that the reagent test slide 14 closely contacts the upper surface 592 of the bottom wall 506 of the slide track 500 to minimize or eliminate any Z-axis variability in the position of the film portion 116 over the reflectometer and fluorometer optical substations of the chemical analyzer 2 in order to assure more accurate colorimetric measurements. A plurality of shutters 626, each in the form of a radially slidable plate 628 having an opening 630 formed through the thickness thereof, are received between the free end 620 of each leaf spring 618 and a respective slide cover 600 so as to selectively cover and uncover (i.e., close and open) the opening 608 in each slide cover 600. Preferably, the shutters 626 are formed of a fluorescent material, and thus may be used as a reference for calibrating the fluorometer.

Figure 29A:
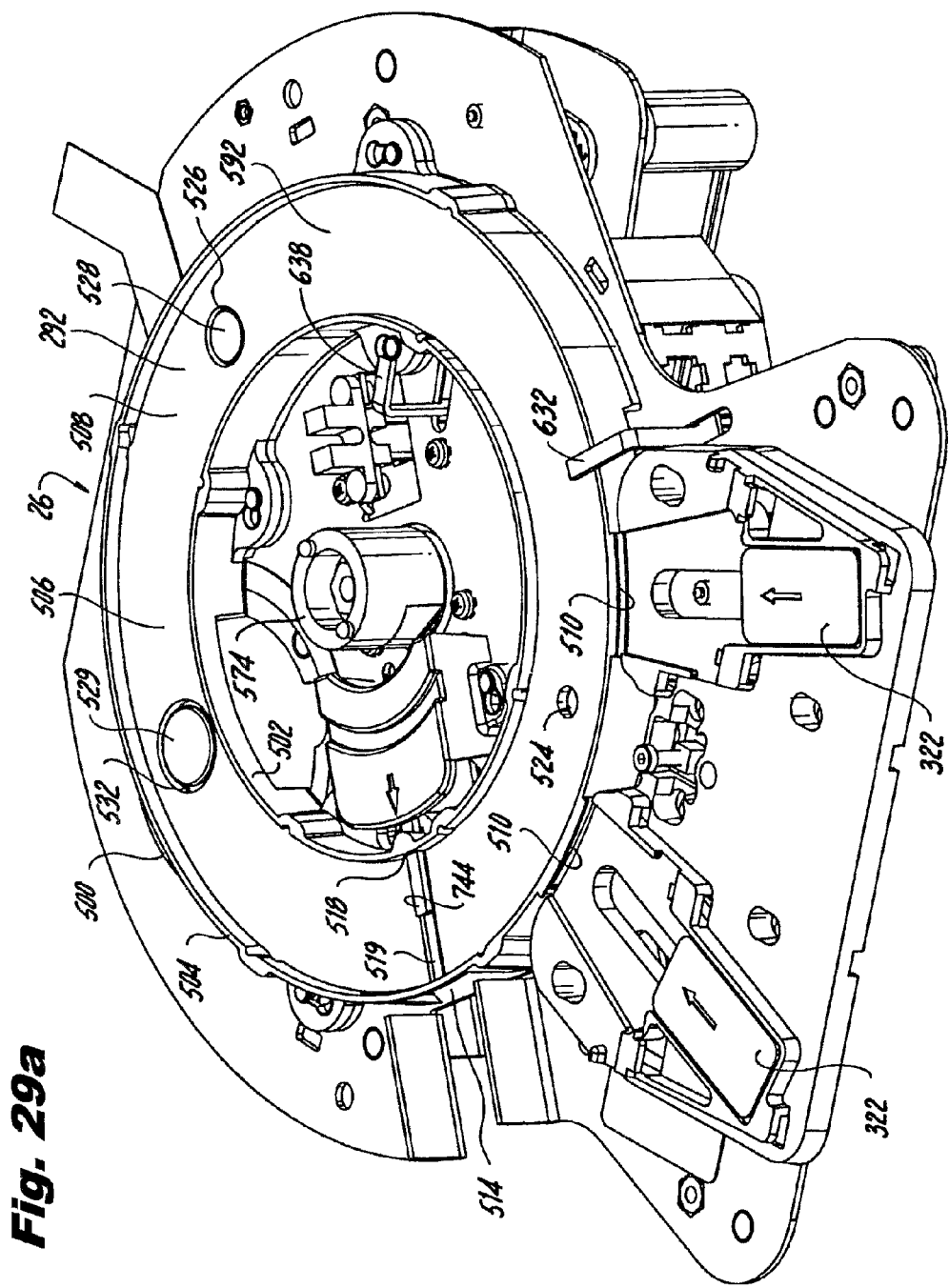
FIG. 29a is an isometric view of the slide transport mechanism, slide ejector mechanism, and first and second bar actuators for covering and uncovering reagent test slides used in the chemical analyzer of the present invention.
Figure 29B:
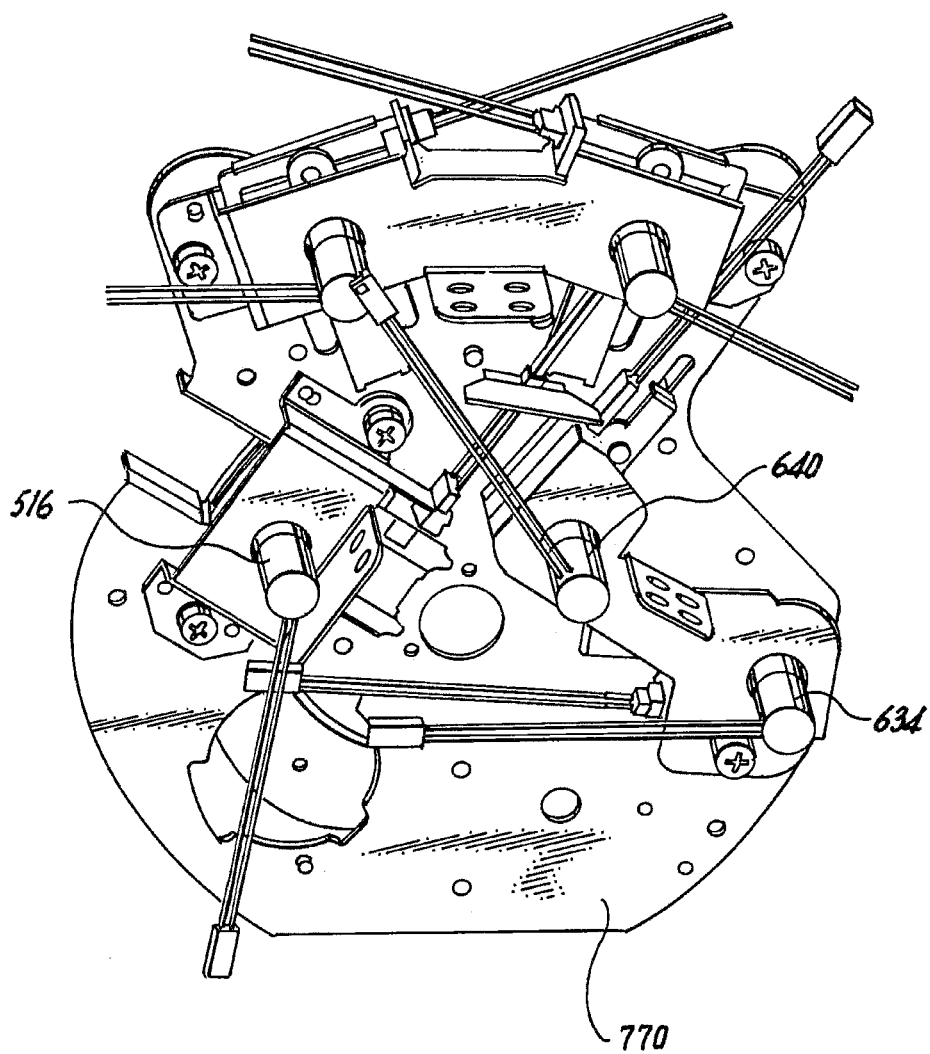
FIG. 29b is a pictorial illustration of the underside of the skull plate on which is mounted the slide transport mechanism, slide ejector mechanism and first and second bar actuators for covering and uncovering reagent test slides used in the chemical analyzer of the present invention.

As shown in FIGS. 29 and 29a, a first, radially moveable actuator bar 632 which is operatively coupled to a motor 634, solenoid or the like (preferably, a motor is used), is situated on one radial side of the slide track 500. As the reagent test slides 14 are moved about the slide track 500 by the carousel 572, the first actuator bar 632 operatively driven by the motor 634 or the like, the energization of which is controlled by the electronic circuitry, will push on an exposed end 636 of the shutter plate 628 of a slide cover 600 situated over a reagent test slide 14 positioned in alignment with the first actuator bar 632 to open the slide cover 600. The shutter plate 628 is moved by the first actuator bar 632 such that the opening 630 therein is aligned with corresponding openings 612 in the main body 606 of the slide carousel 572, the respective leaf spring 618 of the spider spring 614 and the slide cover 600, to expose the film portion 116 of a respective reagent test slide 14. The test slide 14 is moved under the pipette tip 56 of the sample metering sub-assembly 84, whereupon a minute volume of blood sample is deposited through the openings onto the reagent test slide 14.

After a blood sample is deposited on the reagent test slide 14, the slide 14 is then moved on the slide track 500 in alignment with a second moveable actuator bar 638 positioned on the other radial side of the slide track 500 (see FIG. 29). The second actuator bar 638 is operatively coupled to a motor 640, solenoid or the like (again, preferably, a motor is used), so that it is radially moveable, like the first actuator bar 632. The second actuator bar 638, operatively driven by the motor 640 or the like, the energization of which is controlled by the electronic circuitry, pushes on an exposed opposite end 637 of the shutter plate 628 of a slide cover 600 of the reagent test slide 14 positioned in alignment with the second actuator bar 638 to close the slide cover 600. The shutter plate 628 is thereby moved by the second actuator bar 638 in an opposite direction such that the opening 630 in the shutter plate 628 is misaligned with the corresponding openings 612, 622, 630 in the main body 606 of the slide carousel 572, the respective leaf spring 618 of the spider spring 614 and the slide cover 600, to thereby cover the film portion 116 of the respective reagent test slide 14 to minimize evaporation or contamination of the blood sample or wetted reagent on the film portion 116 of the slide 14.

With the Vet Test® chemical analyzer disclosed in the aforementioned Heidt et al. patent (U.S. Pat. No. 5,089,229), the slide cover rotates to uncover the film portions of each reagent test slide situated on the rotatable turntable simultaneously and for the duration of the fluid sample metering operation. With the chemical analyzer 2 of the present invention, each reagent test slide 14 situated within the slide track 500 is individually covered and uncovered as the reagent test slide 14 passes under the pipette 336 of the sample metering sub-assembly 84. Accordingly, the chemical analyzer 2 of the present invention shortens the time each reagent test slide 14 is exposed to air and thus minimizes or eliminates evaporation of either the analyte on the reagent test slide 14 or the liquid specimen deposited thereon by the sample metering sub-assembly 84.

Figure 84:
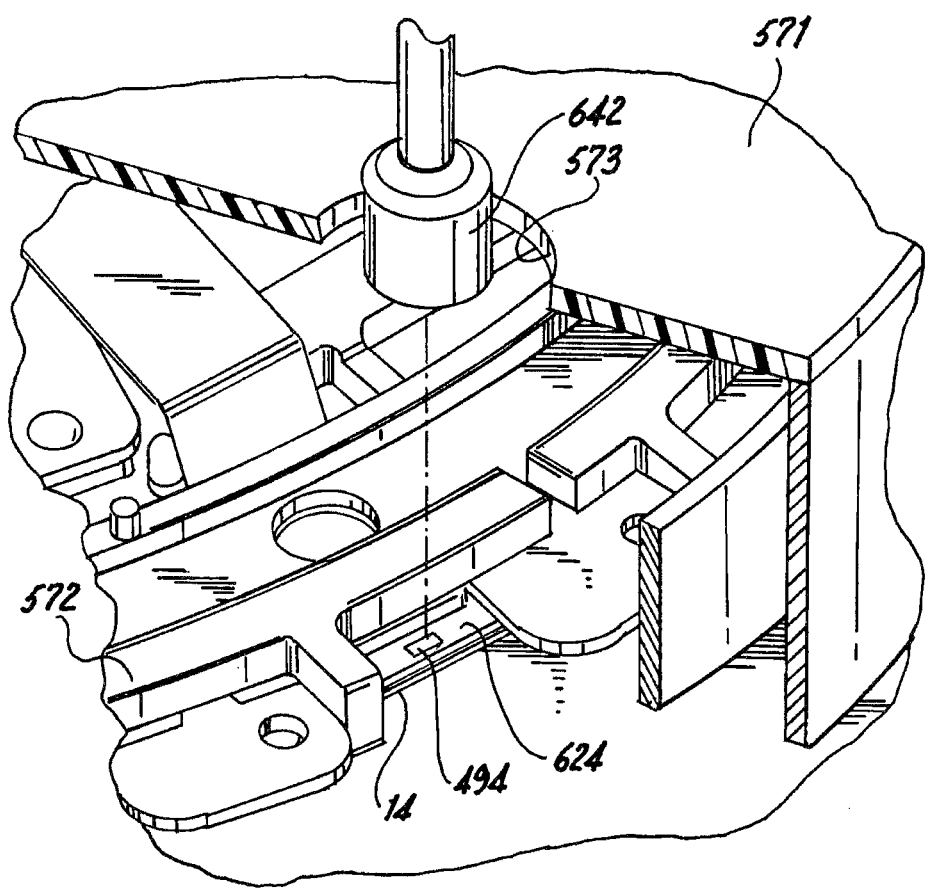
FIG. 84 is a top isometric view of a portion of the slide carousel of the slide transport mechanism of the present invention, and of an optical code reader in optical alignment with a code imprinted on a reagent test slide mounted on the slide transport mechanism of the present invention.

As shown in FIG. 84, each reagent test slide 14 has an optical code 494 (e.g., a universal product code, or UPC, or other bar code) imprinted on the top surface 624 of the slide frame 114, the bar code identifying the type of slide it is (e.g., calcium, glucose, AST (aspartate transminase) test slides). This bar code 494 is preferably printed on the slide 14 near the wider rear edge 298 thereof, which bar code 494 is read by a bar code reader 642 or other optical sensor placed in an optical path in alignment with the test slides 14 as they are transported about the slide track 500 by the slide carousel 572. Because each slide cover 600 of the carousel 572 covers most if not all of a respective test slide 14, the UPC or other code 494 is situated on each slide 14 such that it is in alignment with the shutter plate 628, which may be moved out of the way of the optical path of the code reader 642 by the first actuator bar 632 to uncover the UPC 494 or other code of the test slide 14 as the slides 14 are sequentially moved on the slide track 500 in alignment with the first actuator bar 632.

Accordingly, after the test slides 14 have been initially loaded onto the slide track 500, and before they are spotted with specimen, the analyzer 2 conducts a "dry read" of the slides 14 after the clinician indicates to the analyzer 2 by using the touch screen display 4 that all of the slides 14 have been loaded. The slides 14 are sequentially transported first in alignment with the first actuator bar 632, which pushes the shutter plate 628 over the slide radially inwardly to uncover the UPC 494 or other code imprinted on the slide frame 114. This optical code 494 is now read by the bar code reader 642. The slide 14 is then moved on the slide track 500 in alignment with the second actuator bar 638, which pushes on the shutter plate 628 in a radially outward direction to return the shutter plate 628 to its closed position covering the film portion 116 of the test slide 14 and the UPC 494 or other code previously read.

Figure 30:
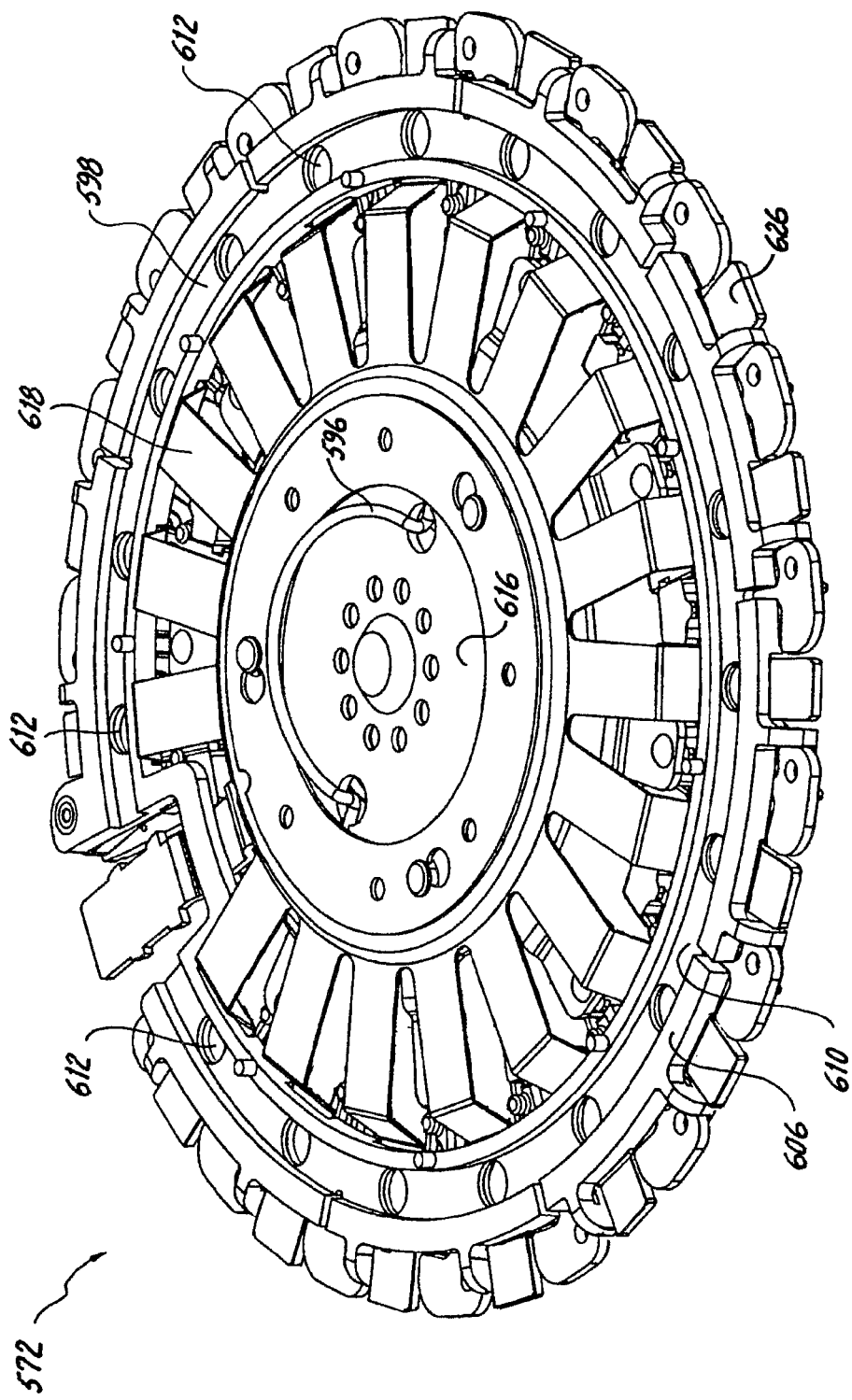
FIG. 30 is a pictorial illustration of the top side of one form of a slide carousel used in the chemical analyzer of the present invention.
Figure 30A:
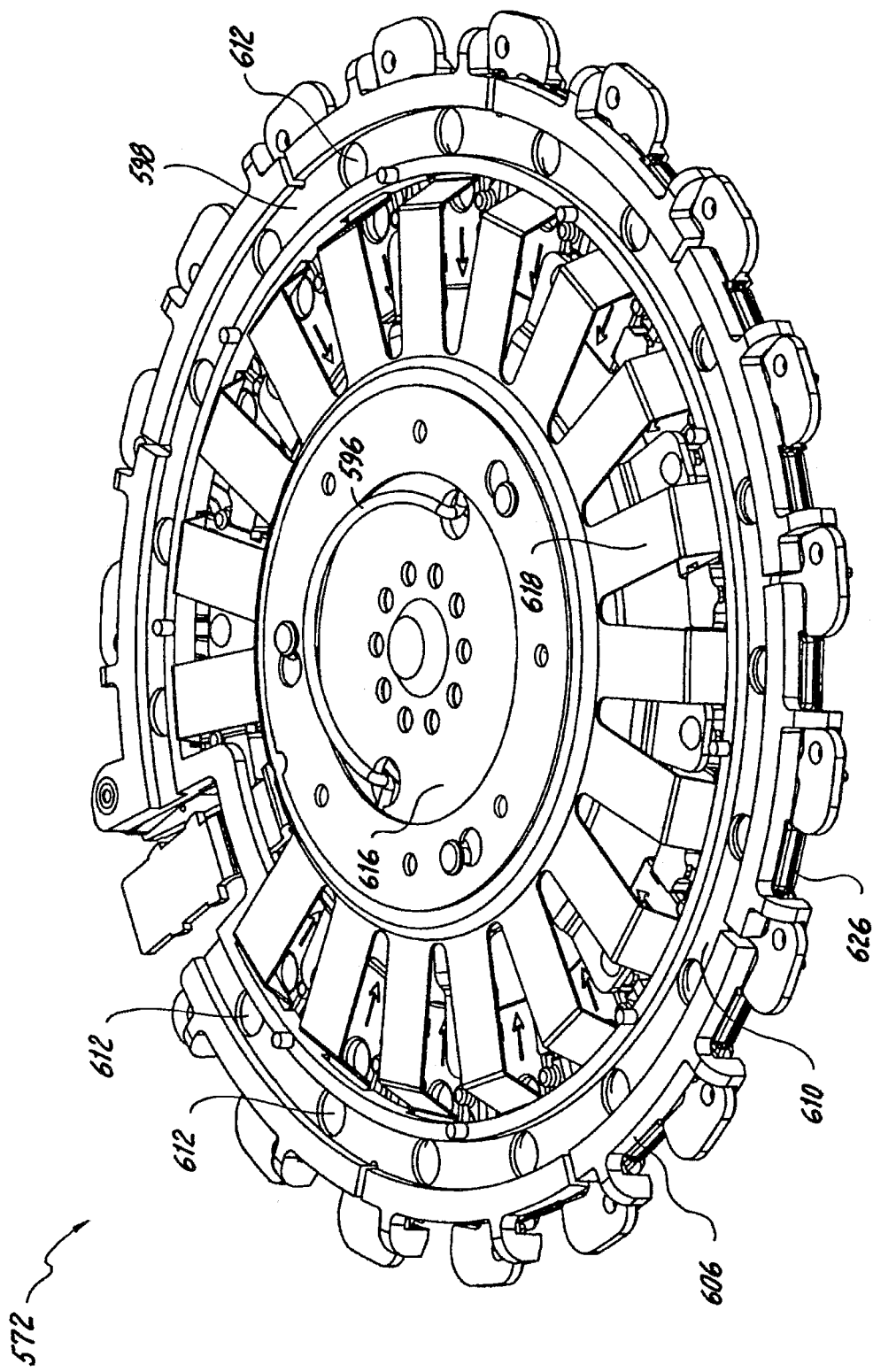
FIG. 30a is an isometric view of the top side of one form of a slide carousel used in the chemical analyzer of the present invention.
Figure 31:
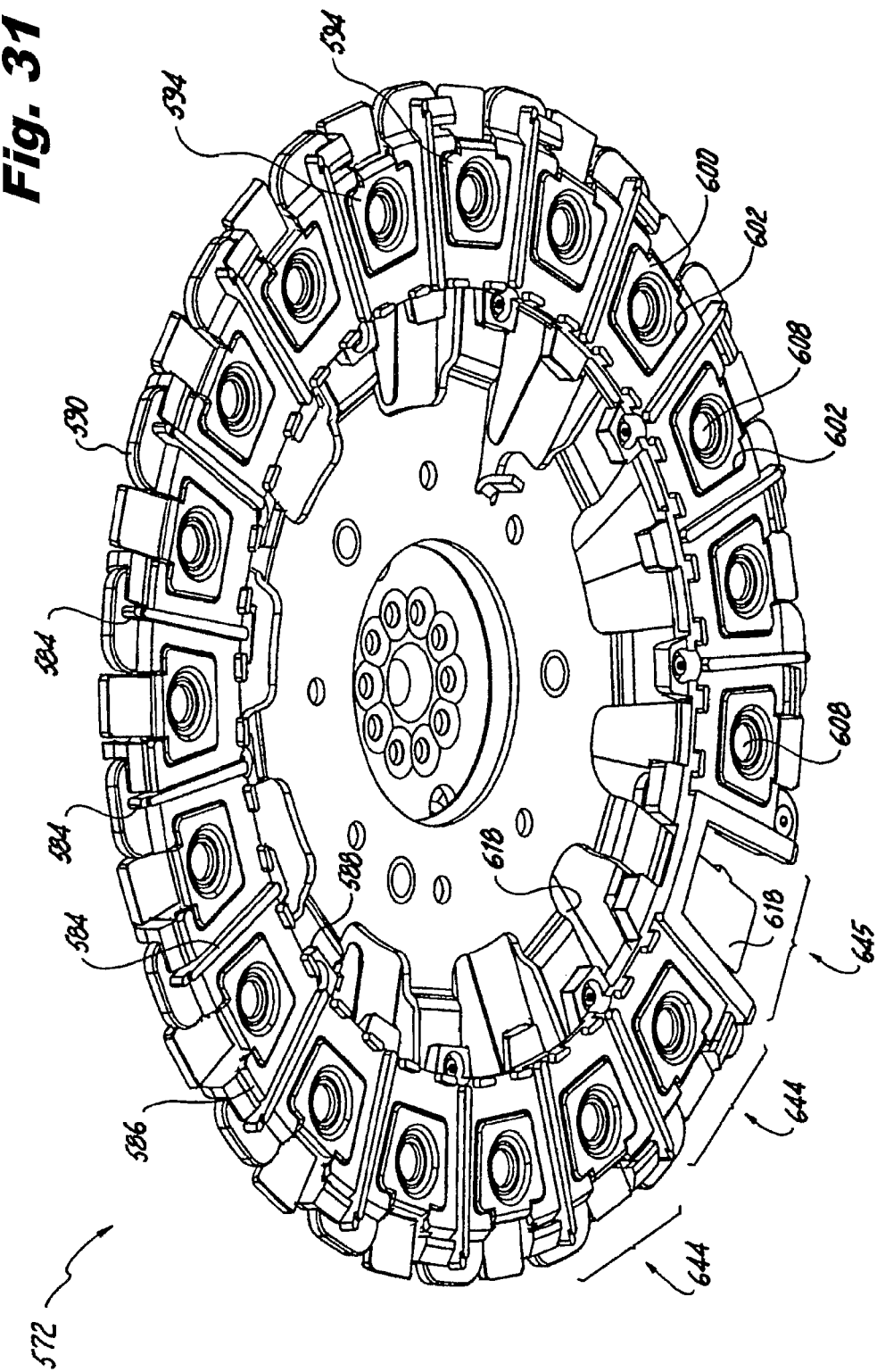
FIG. 31 is pictorial illustration of the bottom side of the slide carousel shown in FIG. 30 and used in the chemical analyzer of the present invention.
Figure 31A:
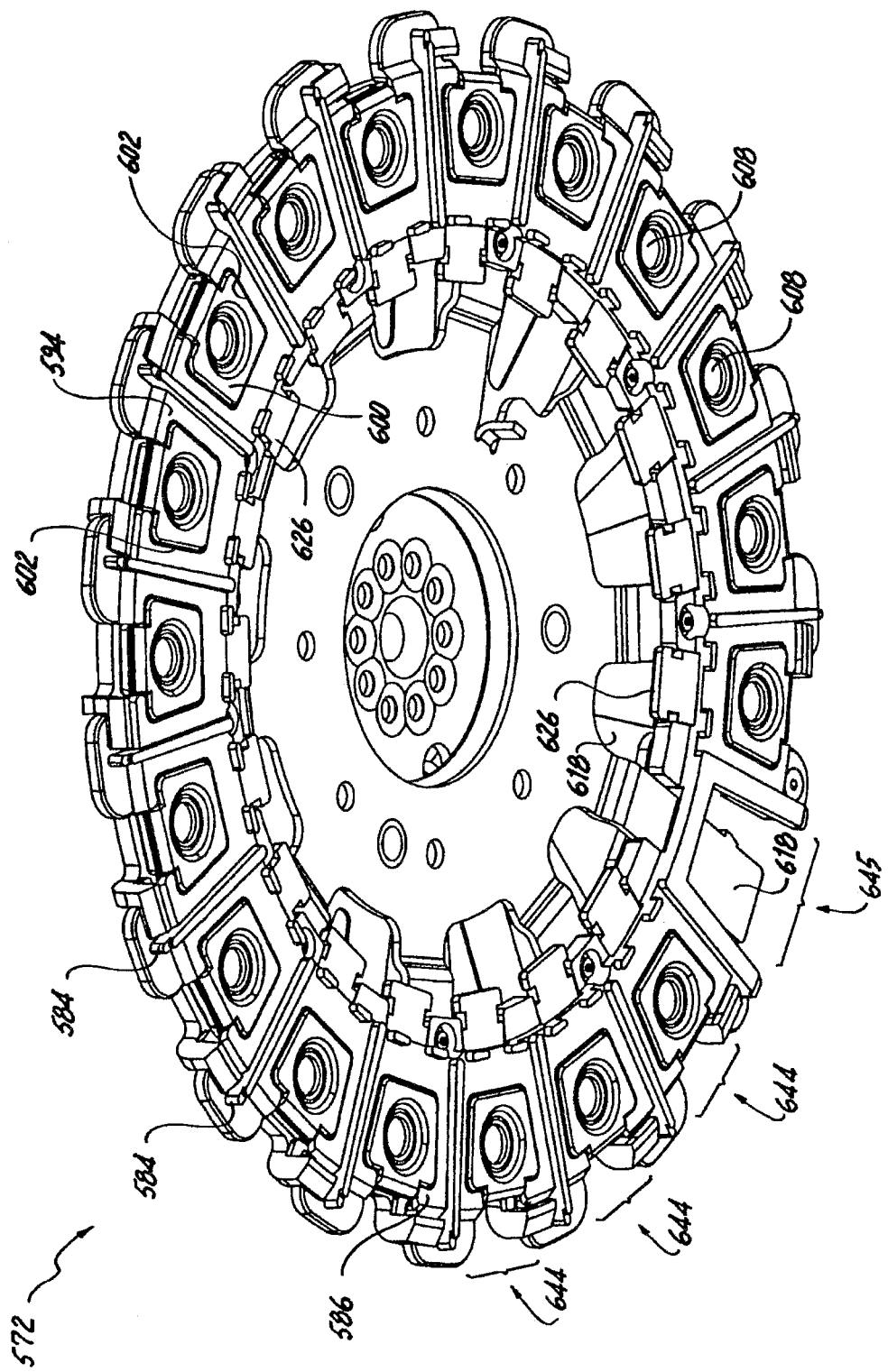
FIG. 31a is an isometric view of the bottom side of the slide carousel shown in FIG. 30 and used in the chemical analyzer of the present invention.

As can be seen from FIGS. 30 and 31, there are preferably nineteen (19) equally spaced segments 644 provided on the slide carousel 572, that is, eighteen slide covers 600 and associated components to accept eighteen test slides 14, and one blank segment 645 for receiving a glazed ceramic calibration tile 646 (see FIG. 81). The calibration tile 646 is preferably removably received by the slide carousel 572 and held in place thereon by one of the leaf spring fingers 618 of the spider spring 614.

A leaf spring finger 618 of the spider spring 614 exerts a force on the calibration tile 646 to hold it in place on the slide carousel 572, but unlike the slides 14, the calibration tile 646 does not contact the top surface 592 of the bottom wall 506 of the slide track 500 as it is moved about the slide track 500 over the reflectometer window 528, in order to keep the surface of the calibration tile clean. A ceramic tile 646 is preferably used, as opposed to a blank test slide 14 having no film portion 116 and just a polyester frame, because it is not likely for the ceramic tile 646 to absorb any impurities or change its reflectance characteristics over time and extended use in the analyzer 2.

Figure 87:
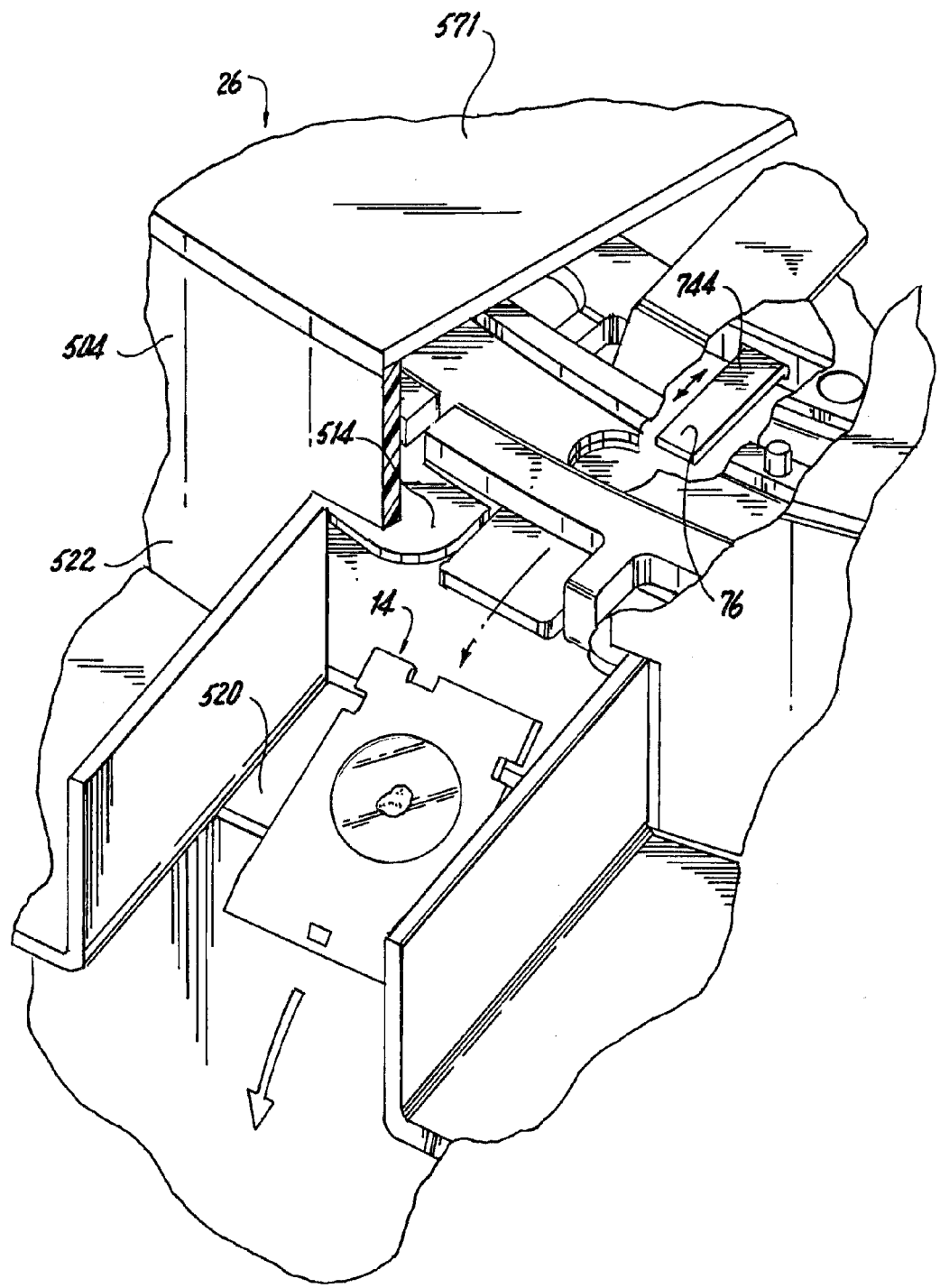
FIG. 87 is a top isometric view of a portion of the slide transport mechanism of the present invention, and illustrating the operation of a slide ejector mechanism to eject reagent test slides from the slide transport mechanism.
Figure 88:
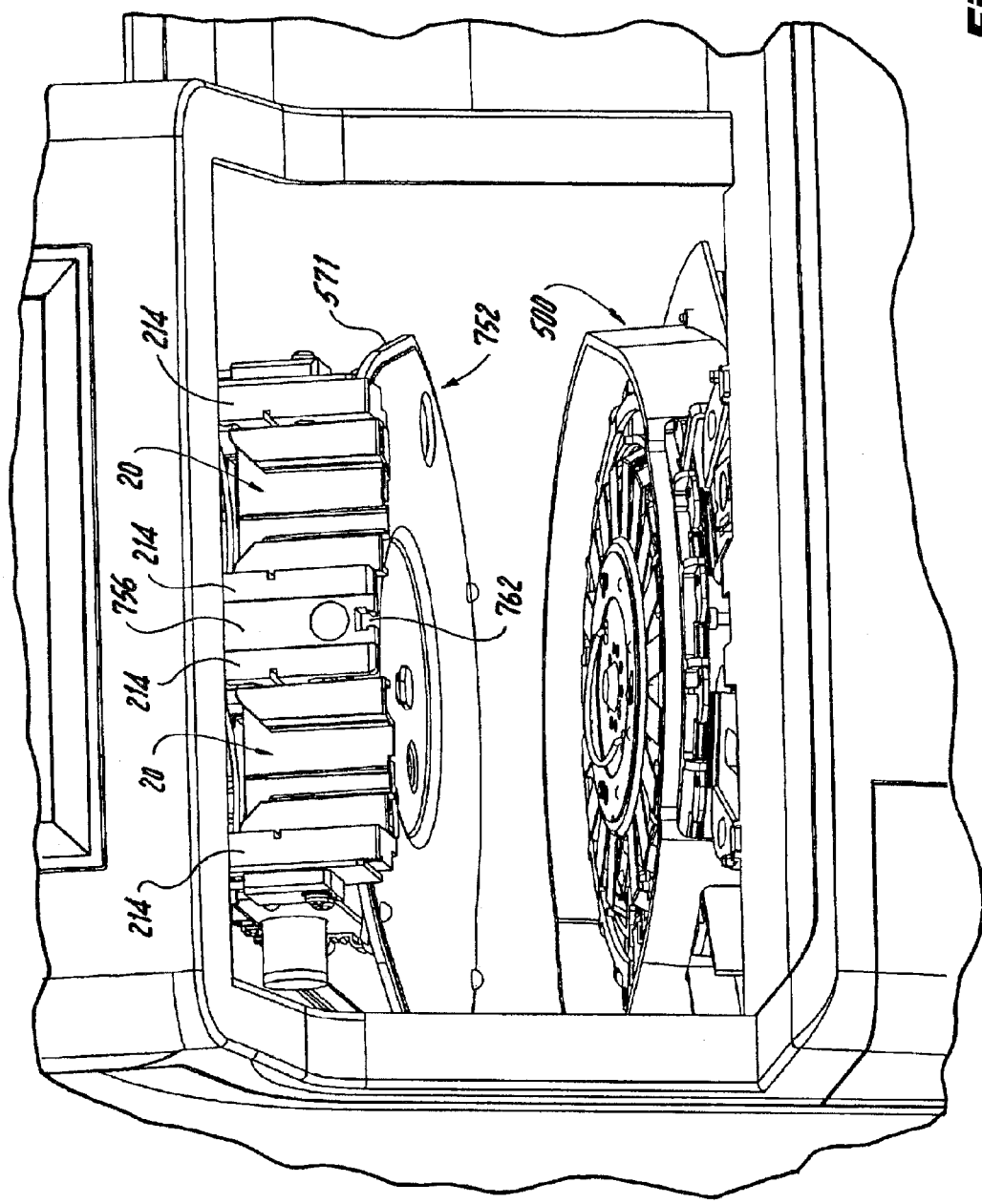
FIG. 88 is a front view of a portion of the chemical analyzer of the present invention, and illustrating a sub-assembly of the chemical analyzer in a raised position over the slide transport mechanism of the present invention.
Figure 89:
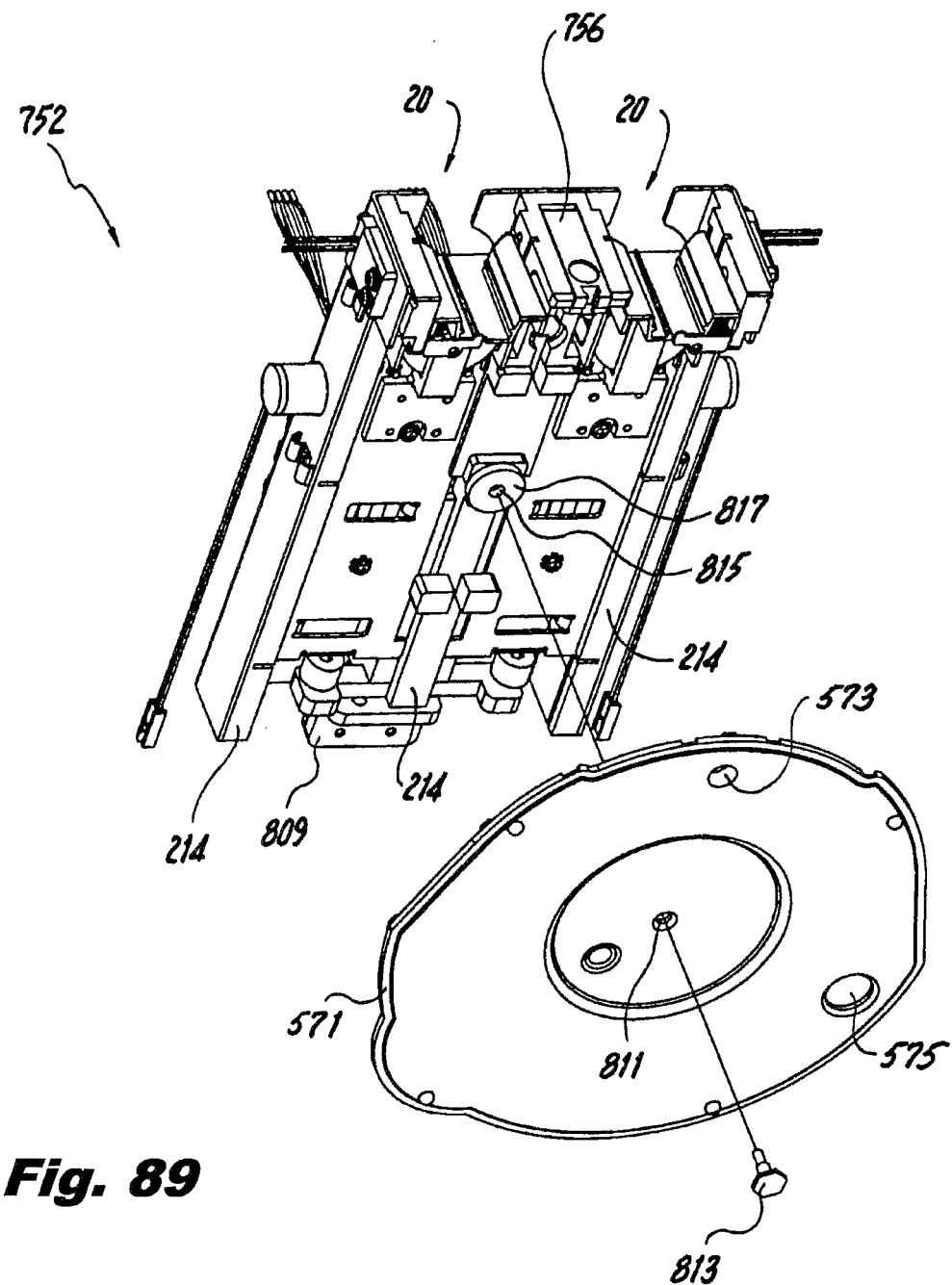
FIG. 89 is a partially exploded, bottom isometric view of the sub-assembly shown in FIG. 88 and constructed in accordance with the present invention.

As can be seen in FIGS. 87, 88 and 89, the slide transport mechanism 26 further includes a slide track cover plate 571. The slide track cover plate 571 is a relatively thick plate formed from a suitable material having preferably insulative properties, or more broadly, properties that retain heat within the U-shaped channel 508, such as, for example, a Delrin® material. The cover plate 571 is positioned over the slide track 500 and rests on the top edges of one or both of the outer radial vertical sidewall 504 and the inner radial vertical sidewall 502 of the slide track 500 or at the top edge of outermost radial vertical wall 505. The cover plate 571 together with slide track 500 define a controlled temperature incubator for the test slides situated within the U-shaped channel 508 of the slide track 500.

The cover plate 571 preferably includes at least two openings 573, 575 formed through the thickness thereof (see FIG. 89). The first opening 573 is to allow an optical code reader (see FIG. 84) to read a UPC (Universal Product Code) or other code imprinted on the reagent test slides through the first opening 573. This first opening 573 may have a window formed of a transparent material situated therein to minimize the escape of any heat from within the incubator defined by the slide track cover plate 571 and the slide track 500. A second opening 575 is provided to allow the pipette tip 56 mounted on the end of the pipette 336 of the sample metering sub-assembly 84 to pass therethrough to deposit a fluid sample on each reagent test slide 14 situated in the U-shaped channel 508 of the slide track.

As will be described in greater detail, and as shown in FIG. 88, the slide track cover plate 571 is removable from atop the slide track 500 to allow the clinician to gain access to the slide carousel 572, to remove the carousel, and to thereby gain access to the slide track 500 to clean the track and U-shaped channel 508 thereof.

The Reflectometer and Fluorometer Sub-Assemblies

As the reagent test slides 14 are moved by the slide carousel 572 on the slide track 500, they pass over the window or windows 528, 529 situated on the bottom wall 506 of the slide track 500 (see FIG. 86). Light of predetermined wavelengths is emitted by a reflectometer and/or a fluorometer and passes through the window or windows 528, 529 to impinge on the underside of the film portion 116 of the reagent test slide 14 situated in alignment with the windows 528, 529. A certain amount of the light is reflected (or fluoresced) by the test slide 14, which reflected (or fluoresced) light passes through the windows 528, 529 and is received by one or more photodiodes (not shown) of the reflectometer/fluorometer sub-assemblies. The photodiodes will provide a signal indicative of the amount of light reflected (or fluoresced) by the slides 14 to the associated electronic circuitry of the chemical analyzer 2. The slides 14 used in the analyzer 2 cause a change in the intensity of the reflected (or fluoresced) light (at certain known wavelengths) in accordance with the concentration of the chemistry in the serum being tested. The analyzer 2 will read the change in light intensity and derive the concentration accordingly.

Various tests require various test slides 14, each test slide 14 carrying a different dry analyte. The various test slides 14 must be exposed to light of selected wavelengths in order to conduct a reflectometry or fluorometry test. The type of test slide 14, for example, for a calcium test, is provided by the bar code information 494 on the top surface 624 of the frame 114 of the slide 14, which information is read by the bar code optical scanner 642 and which is provided to the associated electronic circuitry of the chemical analyzer 2. In a memory of the electronic circuitry, the analyzer 2 will track the location of each reagent test slide 14 during its movement on the slide track 500 and will energize an appropriate light source emitting a particular wavelength during the analysis operation when the slide 14 is positioned over the light transmissive window or windows 528, 529 in the slide track 500.

Figure 32:
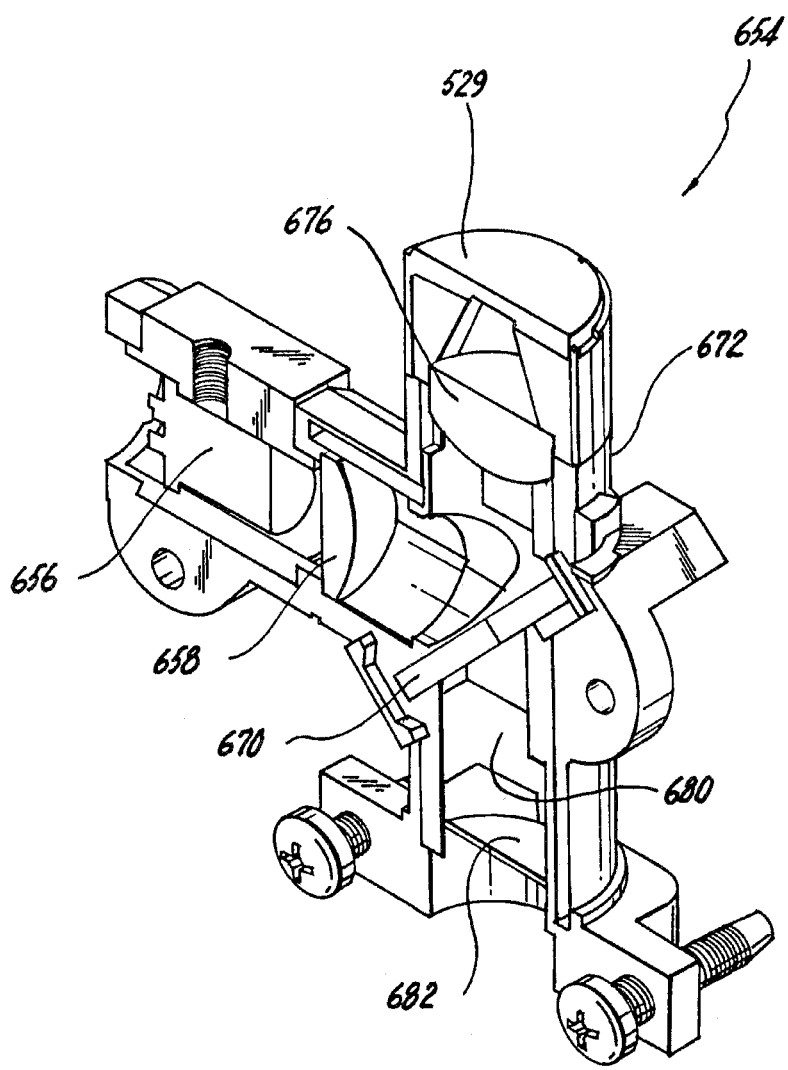
FIG. 32 is a cut-away pictorial illustration of a fluorometer used in the chemical analyzer of the present invention.
Figure 37:
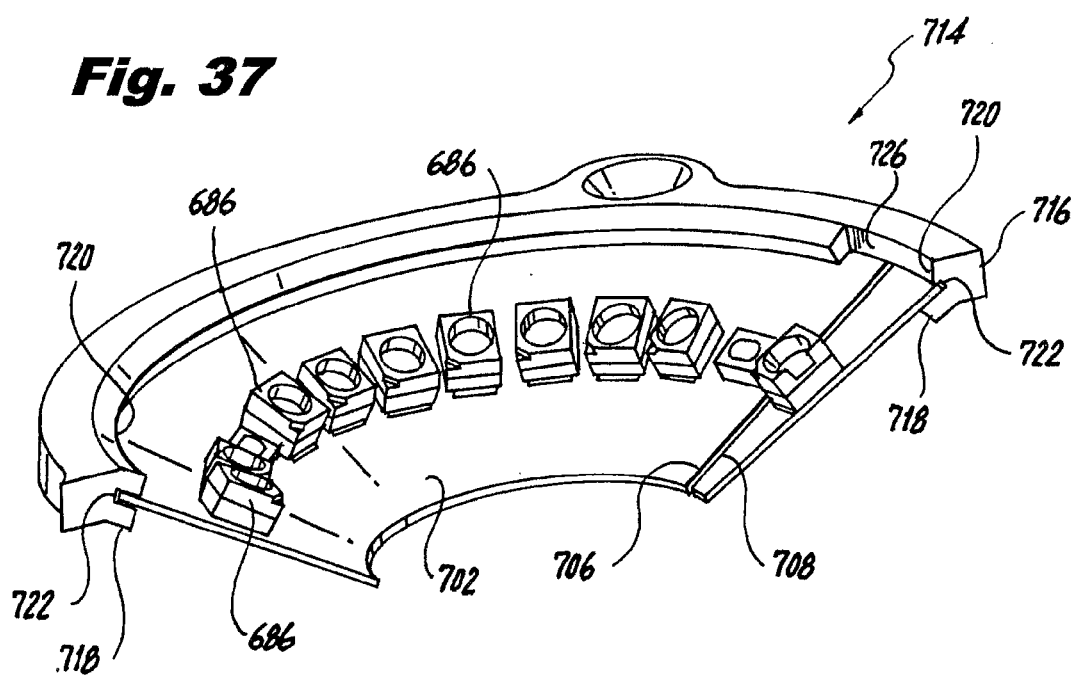
FIG. 37 is a perspective view of a cutaway portion of the mounting fixture of the present invention shown in FIG. 36.
Figure 37A:
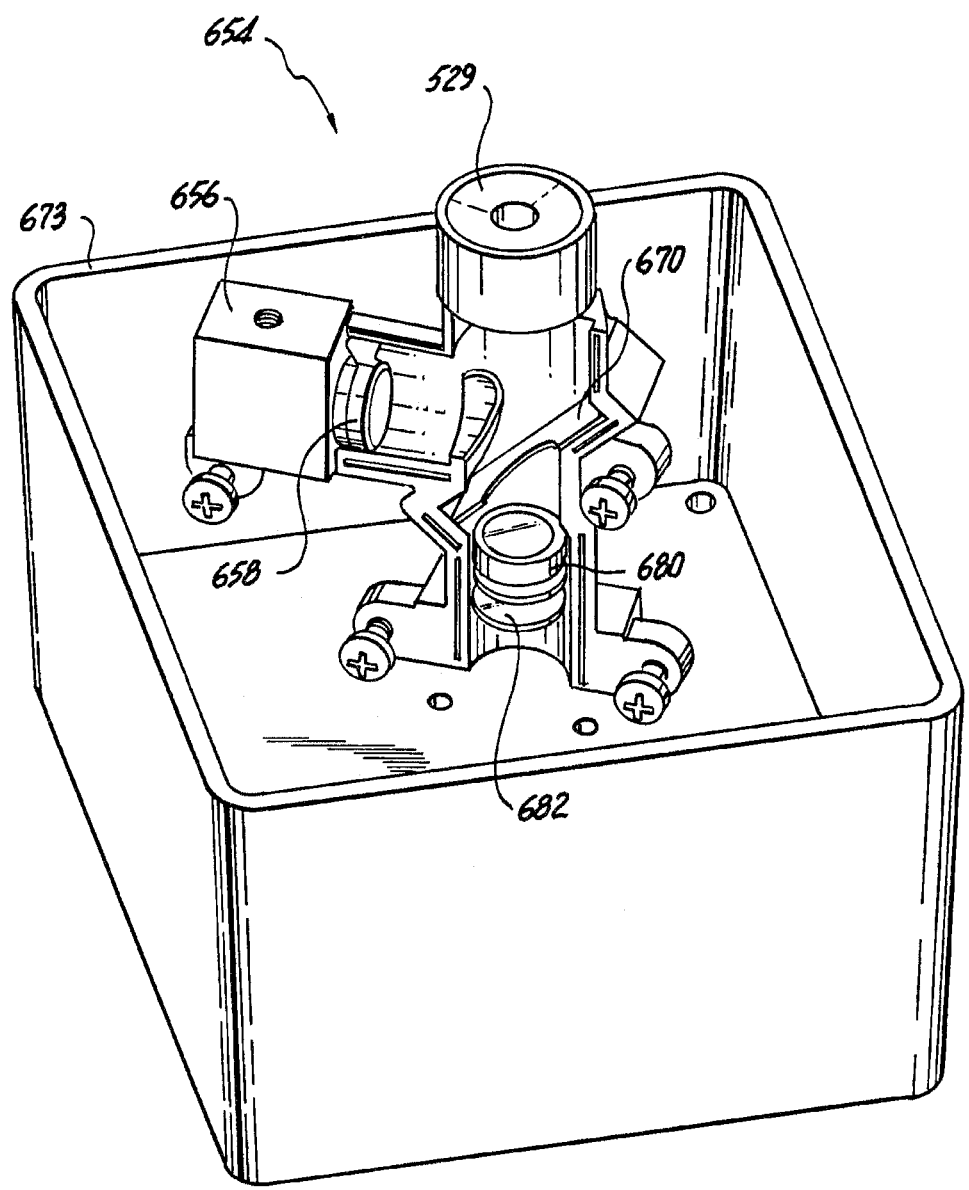
FIG. 37a is a cut-away pictorial illustration of the fluorometer shown in FIG. 32, situated in a housing.

A preferred form of a fluorometer 654 for electrolytes is shown in FIGS. 32 and 37*a*. The fluorometer 654 includes an LED 656 (light emitting diode), which emits light of a selected wavelength, a collimating lens 658 positioned in front of the LED 656, and a beam splitter 670 disposed at an angle to the collimating lens 658 and LED 656. The fluorometer 654 is preferably enclosed by a housing 672, with the window 529 that is closely fitted into the opening in the slide track 500 being mounted on the upper portion 674 of the fluorometer housing 672, 673. Light from the LED 656, passing through the collimating lens 658, impinges on the beam splitter 670 and is directed upwardly through another lens 676 and through the fluorometer window 529 positioned in the slide track 500 to impinge on the lower side 652 of the film portion 116 of a reagent test slide 14 positioned above the window 529. Light fluoresced from the film portion 116 passes through the window 529 and lens 676 positioned below the window 529, and further passes through the beam splitter 670 to another filter 680 and lens 682 positioned below the beam splitter 670. The fluoresced light that passes through this last lens 682 is received by a photodiode or other optical detector (not shown), which generates a signal corresponding to the fluoresced light that it detects. This signal is provided to the electronic circuitry of the chemical analyzer 2 for processing.

A preferred version of a reflectometer 684 formed in accordance with the present invention is illustrated by FIGS. 33-37 and 85. In this embodiment, a plurality of light emitting devices 686, such as light emitting diodes, at least some of which emit light of different wavelengths, is used as the light source for the reflectometer 684. The light emitting devices 686 are arcuately arranged about a circle having a predetermined diameter for those sources with substantially the same wavelengths and viewing angles. Sources emitting light of substantially different viewing angles need not be arranged at the same diameter. The light emitting devices 686 are positioned to direct light emitted therefrom on a plane through which passes the reagent test slides 14 so that the light from the light emitting devices 686 impinges on the film portion 116 thereof. Adjacent light emitting devices 686 are spaced from each other a predetermined distance. At least two of the light emitting devices emit light of the same wavelength and are illuminated simultaneously to provide a volume of substantially homogeneous light irradiance at the plane through which the reagent test slides 14 pass as they move about the slide track 500.

Figure 33:
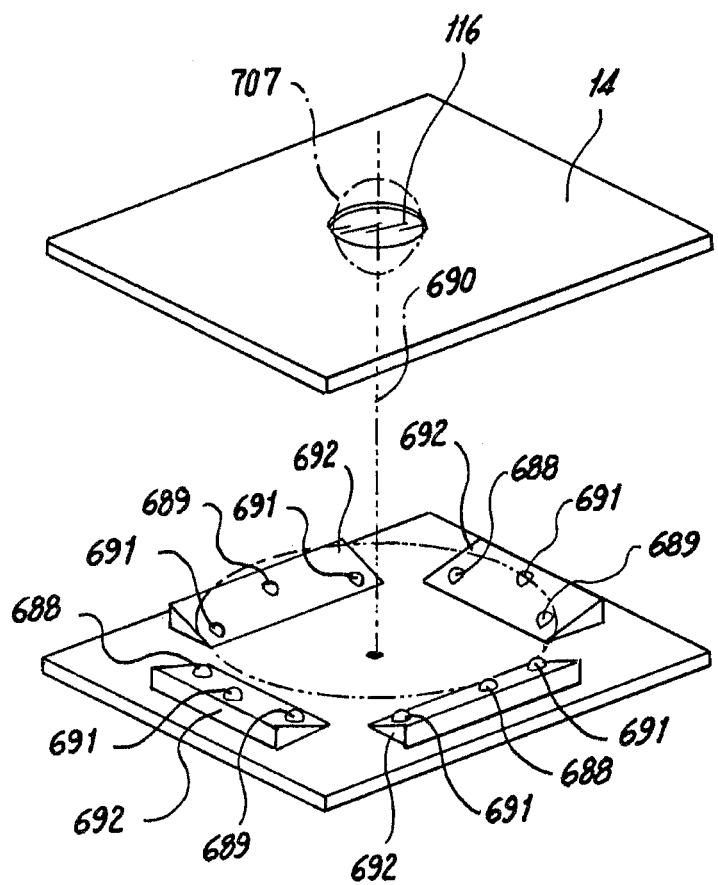
FIG. 33 is a top perspective view of one form of a support on which light emitting devices of the light source of a reflectometer used in the chemical analyzer of the present invention are mounted.

More specifically, and as shown in FIG. 33, positioned radially about the reflectometer optical axis and spaced arcuately apart from one another are a plurality of red, blue and green LEDs 688, 689, 691. Preferably, there are three blue LEDs 689 which are spaced arcuately apart from one another by 120 degrees. There are also three red LEDs 688 which are similarly spaced apart arcuately from one another by 120 degrees.

It may happen that some LEDs, for example, green LEDs 691, are manufactured with a lower radiant flux than similarly manufactured LEDs of other wavelengths. Accordingly, if these lower intensity LEDs are used in the light source of the reflectometer of the present invention, then more of these LEDs than the higher intensity LEDs are used to illuminate the plane in which the reagent test slide resides 14. Accordingly, and as shown in FIG. 33, preferably six of the lower radiant flux (e.g., green) LEDs 691 are used, with adjacent of these LEDs being spaced apart arcuately from each other by 60 degrees. All LEDs 688, 689, 691 are positioned such that the light emitted from each is directed to a common plane, which corresponds to where the film portion 116 of the chemical reagent test slide 14 is situated.

The plurality of LEDs 688, 689, 691 is preferably mounted on a substrate provided for supporting the LEDs 688, 689, 691. The substrate may include one or more printed circuit boards 692, such as shown in the top perspective view of FIG. 33, where the LEDs 688, 689, 691 are arranged radially about the system optical axis 690 of the LEDs 688, 689, 691, and with each LED of a given type (for example, green) spaced at approximately the same radius from the optical axis. The printed circuit boards 692 may reside in the same plane, with the LEDs 688, 689, 691 being mounted angularly on each board 692 so that their light beams are directed toward a single plane. Preferably, the printed circuit boards 692 themselves may be angled such that a common plane illuminated by multiple LEDs 688, 689, 691 situated on at least two circuit boards 692 intersects a volume of substantially homogeneous illumination.

Even more preferably, there are twenty-four (24) light emitting diodes (LEDs) 688, 689, 691 arranged circularly about the substrate, with LEDs that emit light of the same wavelength being spaced apart equi-distantly from each other. The preferred selection of LEDs include three LEDs emitting light at a wavelength of about 365 nanometers (nM), three LEDs emitting light at a wavelength of about 405 nM, three LEDs emitting light at a wavelength of about 470 nM, six LEDs emitting light at a wavelength of about 560 nM, three LEDs emitting light at a wavelength of about 587 nM, three LEDs emitting light at a wavelength of about 645 nM, and three LEDs emitting light at a wavelength of about 680 nM. One or more of these LEDs may include filters (not shown) situated in their optical paths, especially preferably the 680 nM wavelength LEDs which are energized for conducting calcium tests, because the wavelength for conducting such tests should be precisely controlled and should not vary from analyzer to analyzer.

During initial calibration or periodically during operation of the analyzer 2, the electronic circuitry of the analyzer 2 tests the condition of the reflectometer 684 by energizing each LED 688, 689, 691, and reading the intensity of light reflected from the calibration tile 646. For a given current provided to the selected energized LED 688, 689, 691, the software of the electronic circuitry knows the intensity of light that is normally reflected and sensed by the photodetector of the reflectometer. If, for example, the intensity of the reflected light is greater or less than that which is normally expected, the electronic circuitry of the analyzer 2 can adjust the current provided to the LEDs 688, 689, 691 to bring the reflected intensity in line with that which is desired and expected. Furthermore, if one of the LEDs 688, 689, 691 that emit the same wavelength burns out, the electronic circuitry of the analyzer 2 can adjust the current of the remaining same wavelength LEDs 688, 689, 691 to bring the intensity of the reflected light resulting from the simultaneous energization of the LEDs 688, 689, 691 to a desired level. Such measures could minimize the need for replacing the reflectometer 684 or servicing the analyzer 2.

In practice, it will be easiest to select the LED mounting radius (perpendicular distance from the system optical axis 690), and vertical spacing and mounting angle (relative to the desired illumination plane) based in part on the emission profile of the LEDs 688, 689, 691 selected. LEDs 688, 689, 691 are commonly available in 120, 60, 30 and 15 degree "viewing angles," although other values are also commercially available. Typically, LED manufacturers specify the "viewing angle" as the angle of the circular sector within which the LED intensity is half that of the maximum emitted intensity. This sector will include the LED's axis of symmetry or the normal to its face. For an LED 686 with a smooth emission profile, the maximum intensity often occurs normal to the LED's face or parallel to its axis of symmetry. For this invention, LEDs of wider viewing angles (e.g., 60-140 degrees) will be more effective toward forming an adequate volume of substantially homogeneous irradiance and are therefore preferred when the vertical spacing and LED mounting radius are on the order of 100 mm or less. In general, optimal LED viewing angle width and LED-to-illuminated object spacing are inversely related. Also, LEDs with smooth and consistent emission profiles are preferred for ease of placing them optimally relative to the desired volume of substantially homogeneous irradiance. However, neither wide viewing angles nor smooth nor highly consistent illumination is required to attain the improvements described in this invention to some degree, but optimization of these characteristics will help maximize the improvement of providing a more substantial and more consistent volume of homogeneous irradiance.

Figure 34:
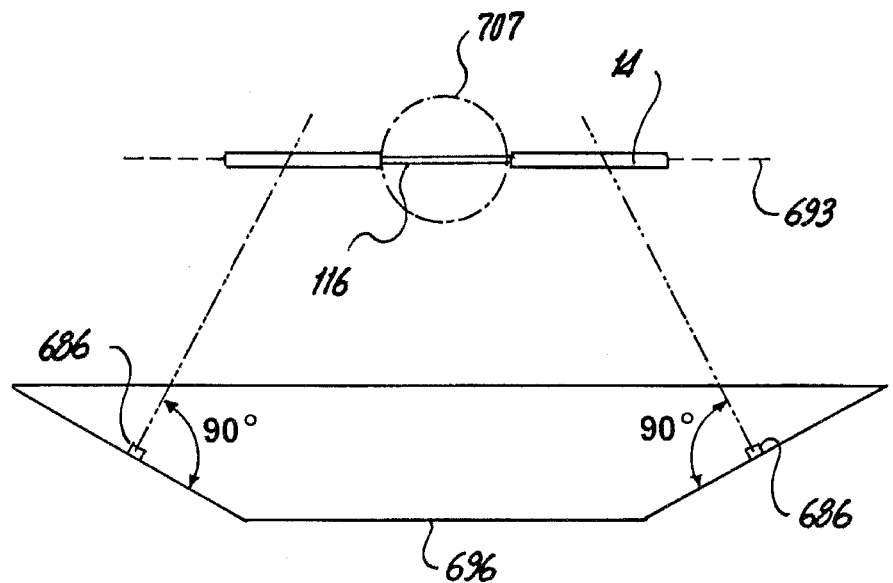
FIG. 34 is a side view of another form of a support for light emitting devices of the light source of a reflectometer used in the chemical analyzer of the present invention.

Even more preferably, for irradiating a circular object, the substrate on which the LEDs 688, 689, 691 are mounted may include a conically-shaped supporting structure 696, as shown in FIG. 34. The surface on which the LEDs 686 are mounted is angled toward the illumination plane 693. The normal to the semiconductor die of each LED 686, which in most cases is along the axis of peak light intensity, is also shown in FIG. 34.

Figure 35:
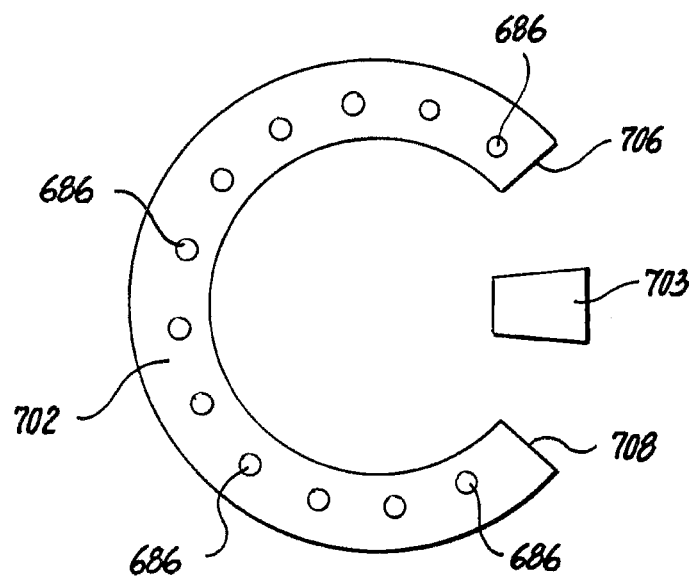
FIG. 35 is a top plan view of a support for mounting light emitting devices of the light source of a reflectometer used in the chemical analyzer of the present invention.

One way of forming the conically-shaped supporting structure 696, in accordance with the present invention, is by using a planar C-shaped member 702 having a surface 704 on which the LEDs 686 are mounted, as shown in FIG. 35. The C-shaped member 702 has a first end 706 and a second end 708 circumferentially opposite the first end 706. The first end 706 and the second end 708 are brought together by a stable holding means 703, such as shown in FIG. 35 and described in greater detail below, defining the LED supporting structure with a truncated conical shape, i.e., the frustum of a right circular cone, such as shown in FIG. 34. The C-shaped member 702 thus is preferably flexible, and may be, in one form of the present invention, a semi-rigid or flexible printed circuit board. Holding means, such as plate 703, and C-shaped member 702 are shown in FIG. 35.

More specifically, the first and second ends 706,708 of the C-shaped member 702 may be joined together by adhesive or a holding piece in the form of an elongated plate 703 that bridges the first and second ends 706,708 of the C-shaped member 702 and preferably extends along the full length of the first and second ends 706,708. The holding plate 703 is affixed to the first and second ends 706,708 of the C-shaped member 702 by adhesive, hardware or the like, and has sufficient torsional rigidity that, when attached to the first and second ends 706,708 of the C-shaped member 702, maintains the conical shape of the supporting structure especially at the juncture of the first and second ends 706,708. Preferably, the C-shaped member 702 is held in about its circumference by a fixture 714 that is designed to force the member into a frustum shape, at the designed radius and angle. An example of such a holding means in shown in FIGS. 36 and 37.

Figure 36:
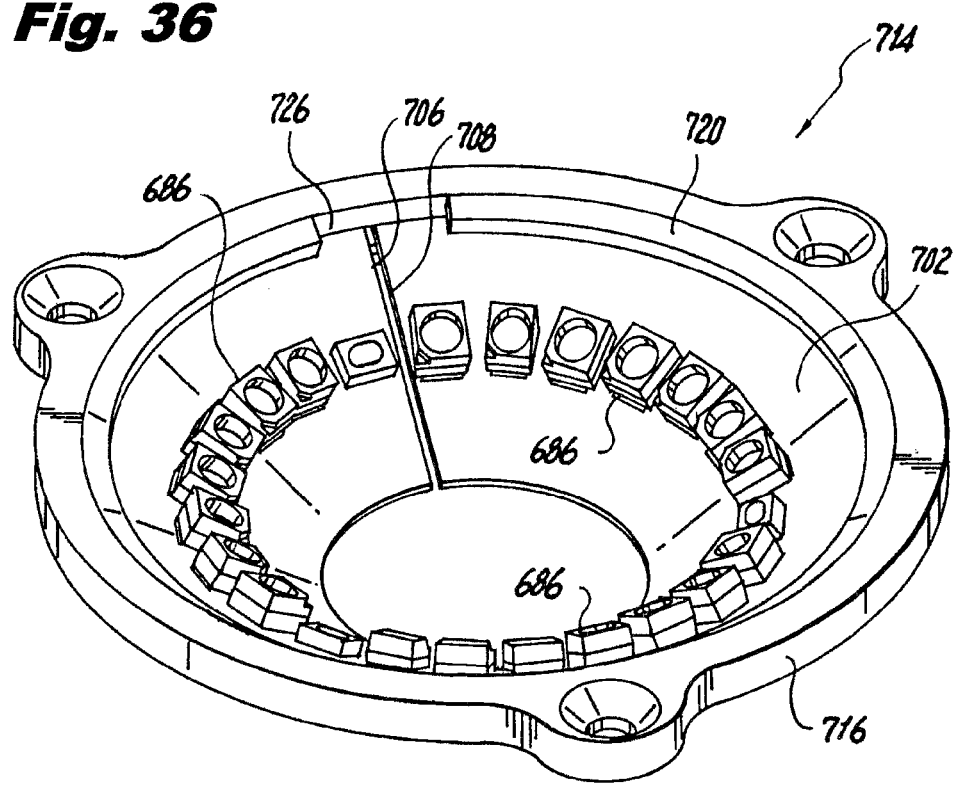
FIG. 36 is a perspective view of a light source fixture formed in accordance with the present invention for use in the chemical analyzer for supporting the C-shaped printed circuit board shown in FIG. 35 in the shape of the frustum of a right circular cone.

More specifically, and with reference to FIGS. 36 and 37, a fixture 714 for supporting the C-shaped printed circuit board 702 on which are mounted a plurality of LEDs 686 or other light sources includes a circularly extending rim 716 having a radially inwardly extending lower shoulder 718 and a radially inwardly extending upper shoulder 720 situated in overlying relationship to the lower shoulder 718. The upper and lower shoulders 718, 720 are slightly spaced apart from one another to define a circular slot 722 therebetween, which is preferably angled downwardly from the radial plane in which the rim 716 and shoulders 718, 720 reside, for at least partially receiving therein the outer radial edge portion of the printed circuit board 702. The upper shoulder 720 is preferably formed with a notch 726, or removed section, to facilitate the insertion of the printed circuit board outer edge portion into the receiving slot 722.

Preferably, the printed circuit board 702 is mounted to the fixture 714 by inserting the outer edge of the circuit board 710 nearest one end portion 706 thereof into the fixture slot 722, starting at the notch 726 formed in the upper shoulder 720. The remainder of the outer edge of the circuit board 702 is then worked circularly from the end portion 706 into the slot 722 until the entire outer edge of the printed circuit board 706 is properly seated in the slot 722, with the two end portions 706, 708 of the circuit board 706 in proximity to or abutting each other, as shown in FIGS. 36 and 37. The printed circuit board 706 is thus secured to the mounting fixture 714, and fixedly held in a frustum shape at a desired radius and angle. It should be noted here that the particular embodiment of the printed circuit board 706 of the present invention shown in FIGS. 36 and 37 includes twenty-four LEDs 686 or other miniature light sources (for examples, optical fiber outputs, or miniature lenses or apertures) mounted thereon for illuminating the test slide 14. However, the present invention should not be construed as being limited to a particular number of LEDs.

Figure 85A:
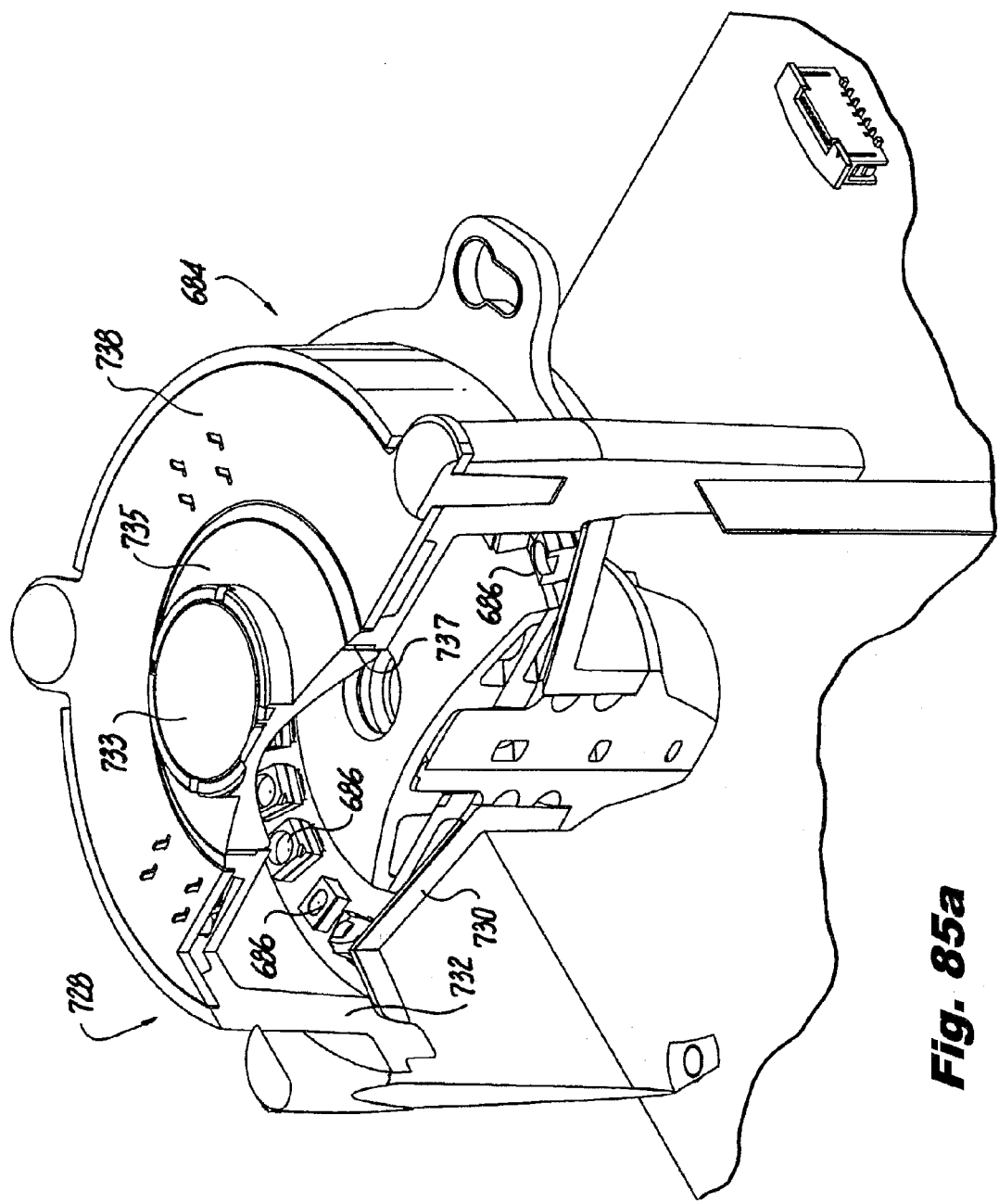
FIG. 85a is a top isometric view of a reflectometer constructed in accordance with the present invention and used in the chemical analyzer of the present invention, with portions of the reflectometer partially broken away.

Preferably, the printed circuit board 706 and mounting fixture 714 are situated in (or effectively formed within) a protective housing 728, which includes a lower portion 730 and an upper hood 732 mounted on the lower portion 730, as shown in FIGS. 85 and 85*a*.

The hood 732 has the window 733 situated in a mounting piece 735 that is received by a threaded opening 737 formed in its upper portion 738, which window 733 is received by the corresponding opening 528 in the bottom wall 506 of the slide track 500. The mounting piece 735 is also threaded on an exposed surface thereof and may be turned on the upper hood portion 738 of the reflectometer housing 728 so that the mounting piece 735 may be adjusted axially in its position on the upper portion 738, and with the mounting piece 735, the window 733 situated thereon. In this way, the window 733 received by the opening 528 in the slide track 500 may be adjusted in height above the top surface 592 of the bottom wall 506 of the slide track 500 to ensure that the frames 114 of the test slides 14 moved about the slide track 500 will contact and wipe the window clear of any impurities or dust that may have otherwise settled thereon and obscured the path of light passing therethrough and impinging on and reflected from the slides 14.

Accordingly, the use of multiple LEDs 686, simultaneously illuminated and having the same wavelength, provides a substantially even distribution of light and a volume 707 of substantially homogenous irradiance, which accounts for some or most of the z-axis variability, as well as variability in the (x,y) plane, arising from either positioning or development of the chemical reagent test slide 14 at the illumination plane 693 of the light source 686 of the reflectometer 684. Thus, it is envisioned that more accurate optical readings will occur when this light source 686 of the reflectometer 684 of the present invention is used in the chemical analyzer 2 to direct light on reagent test slides 14.

It should be noted that the intensity of one or more of the LEDs 686 of one wavelength relative to the other LEDs or LEDs of the same wavelength may be changed, in order to improve the consistency of the volume of substantially homogeneous irradiance provided by the simultaneous illumination of the LEDs 686. This may be accomplished by providing the capability for individually changing the drive current for each LED 686. The intensity of the LEDs 686 may also be made stronger or weaker by moving the substrate on which the LEDs 686 are mounted closer to or farther from the reagent test slide 14 being illuminated. This would, of course, entail adjusting the geometry of the light source 686, as it is still desired to have the illumination plane of optimum homogeneity coincide with the film portion 116 of the reagent test slide 14 being tested.

A more detailed description of this particular embodiment of the reflectometer 684 of the present invention is found in co-pending U.S. patent application Ser. No. 11/286,079, filed Nov. 23, 2005, the disclosure of which is incorporated herein by reference.

The Slide Ejector Mechanism

FIGS. 29 and 87 illustrate one form of a slide ejector mechanism 76 of the present invention which removes the reagent test slides 14 from the slide track 500 of the slide transport mechanism 26 after tests have been completed.

The slide ejector mechanism 76 includes a pusher bar 744, as mentioned previously, which is radially retractable and extendible and operatively coupled to a solenoid or motor 746 (preferably, a motor is used) which is selectively energized by the electronic circuitry of the chemical analyzer 2. The pusher bar 744 selectively passes through a slot 518 formed in the inner radial sidewall 502 of the slide track 500. When the solenoid or motor 746 is energized by the electronic circuitry, the pusher bar 744 engages the front edge 122 of a chemical reagent test slide 14 situated in alignment with and between the ejection slot 514 formed in the outer radially sidewall 504, as mentioned previously, and the slot 518 formed in the inner radial sidewall 502 to eject the so-aligned reagent test slide 14 through the outer sidewall slot 514 and into the used slide drawer 74 of the chemical analyzer 2. As mentioned previously, a ramp 520 extending from the outer surface 522 of the outer radial sidewall 504 of the slide track 500 and positioned beneath and in alignment with the ejection slot 514 may be provided to ensure that the used reagent test slides 15 are properly directed to fall into the slide drawer 74 for discarding by the clinician.

Other Features of the Analyzer

Returning to FIG. 1, which illustrates the front face 18 of the housing 6 of the chemical analyzer 2, a door 748 under a ledge of the housing portion 6 where the display 4 resides may be opened to gain access to an override mechanism (not shown). The override mechanism, when activated by the clinician, unlatches the doors 16 of the slide inserter mechanisms 20 to allow the clinician to raise the two vertical doors 16 simultaneously (see FIGS. 38 and 38a). The clinician then may reach into the housing 6 and remove the slide carousel 572 for cleaning by lifting it off the motor 574 by the D-ring 596 provided on the carousel's upper surface 598 and passing it through the door openings (see FIGS. 80, 81 and 88). The slide track 500 within the housing 6 is then also exposed for cleaning.

The slide carousel 572 is then repositioned over the slide track 500 to engage the motor 574, and the override mechanism is deactivated, which will allow the sliding vertical doors 16 to close by gravity, with the door latch now being engaged to prevent the doors from being manually raised. The ledge door 748 is then closed by the clinician.

As can be seen from FIGS. 88 and 89, a pivotable sub-assembly 752 is formed of the slide inserter mechanisms 20 and support plate 378 on which the rotor carriers 376 reside. More specifically, the slide inserter mechanisms 20 ride in corresponding tracks formed in vertically disposed side blocks 214, at least partially over the slide track 500 and slide carousel 572 of the slide transport station 26. The side blocks 214 are preferably mounted on, and extend perpendicularly outwardly from, the lower surface of the support plate 378. The support plate 378 is hingedly affixed near the rear edge thereof to a bracket 809 using a friction hinge mechanism to maintain the sub-assembly 752 in a pivoted raised position above the slide track 500 and carousel 572. When the sub-assembly 752 is in this raised position, the clinician may easily reach in beneath the sub-assembly 752 to grasp the D-ring 596 or handle 754 of the slide carousel 572 to remove the carousel 572 and gain access to the slide track 500 to clean each, as mentioned previously. When the slide carousel 572 is returned to its position over the slide track 500 in operative engagement with the stepping motor 574, the clinician pushes down on the front edge of the support plate 378 to lower the sub-assembly 752 to its working position over the slide track 500 and slide carousel 572. A pivotable locking post 756, which is spring biased outwardly from the front of the sub-assembly 752, is operatively pivotally mounted on its upper axial end to the support plate 378 (or another member affixed thereto) and has formed in its lower axial end a T-shaped groove 762 for removably receiving the enlarged head and shank of a machine screw (not shown) adjustably mounted to the front portion of the skull plate 770 on which the slide track 500 rests. The clinician maneuvers the post 756 as he or she lowers the sub-assembly 752 to engage the machine screw to lock the sub-assembly 752 in its lowered position.

As can also be seen from FIGS. 88 and 89, the slide track cover plate 571 is affixed to the bottom of the pivotable sub-assembly 752, and to the lower surfaces of side blocks 214. Alternatively, and as shown in FIG. 89, the cover plate 571 has an opening 811 formed through its thickness which receives a bolt 813 that is threadingly received in a corresponding threaded hole 815 formed in a boss 817 of a supporting member situated on the underside of the pivotable sub-assembly 752 so as to removably retain the slide cover 571 on the underside of the sub-assembly 752. Thus, when the sub-assembly 752 is pivoted to a raised position, the cover plate 571 is also lifted off the slide track 500 so that the clinician can gain access to the slide carousel 572 and the U-shaped channel of the slide track 500.

Another feature of the analyzer of the present invention is the inclusion of a vacuum test post 774 to determine if the pipette tip 56 is fluidtightly affixed to the pipette 336 (probiscus). After the pipette 336 is lowered over the pipette tip tray 54 to engage a pipette tip 56 thereon and remove the same from the tip tray 54, as shown in FIGS. 69 and 70, the overhead carriage 330 moves the sample metering sub-assembly 84 thereon so that the pipette 336 is situated directly over and in alignment with the vacuum test post 774.

As shown in FIGS. 90 and 91, the vacuum test post 774 includes an elongated, vertically disposed member 776 affixed to a sidewall 778 of the pipette tip tray 54, and has an exposed top portion 780 on which is affixed a bead or tip 782 made from a urethane, silicone or other relatively soft, resilient material. The pipette 336, with the newly attached pipette tip 56, is lowered by the sample metering sub-assembly 84, controlled by the electronic circuitry of the analyzer 2, until the pipette tip 56 engages the resilient tip 782 of the vacuum test post 774. The soft tip 782 of the vacuum test post 774 completely covers the orifice 492 in the pipette tip 56 and forms an airtight seal therewith. Then, the pump motor 493 is energized to aspirate and create a vacuum (or negative pressure) within the pipette 336 and cylindrical tube 470, and the pressure sensor 476 within the pump cylindrical tube 478 is monitored to determine if air is leaking between the pipette tip 56 and the outer sidewall 784 of the pipette 336 (proboscis) on which the pipette tip 56 is mounted. If air leakage is detected by a higher than expected pressure sensed by the pressure sensor 476, then the electronic circuitry causes the overhead carriage 330 to transport the pipette 336 to the forked member 460 to remove the defective pipette tip 56 from the pipette 336. Then, the overhead carriage 330 moves the sample metering sub-assembly 84 over the pipette tip tray 54 to pick up a new pipette tip 56 therefrom, and the vacuum testing procedure is repeated to ensure that the new pipette tip 56 is fluidtightly attached to the pipette 336.

Another feature of the analyzer 2 related to the above is that the analyzer 2 includes a mechanical interlock mechanism 24 operatively linked to the clean pipette tip tray 54. More specifically, and as shown in FIGS. 92, 93 and 93a, the frame 783 of the pipette tip tray 54 includes a plate 785 pivotally mounted on a sidewall 787 of the frame 783 by a pivot pin and bracket assembly 795. An upwardly extending member 799 of the pivotal plate 785, situated on a first side of the pivot pin and bracket assembly 795, extends beyond the top wall of the frame and includes an exposed free end 801 having a perpendicularly extending tab 803. A bent leg 789 extending perpendicularly from a surface of the plate 785 on the opposite second side of the pivot pin and bracket assembly 795 is received through an opening 791 formed through the sidewall 787 and selectively engages a wall 793 of the structure of the tray 54 which moves reciprocatingly with respect to the frame 783. The bent leg 789 has wrapped about it a coiled compression spring 797, which is positioned between the sidewall 787 of the frame 783 and the pivotal plate 785. The spring 797 biases the free end of the bent leg 789 in disengagement with the wall 793 of the movable structure of the pipette tip tray 54 to allow the pipette tip tray 54 to be extended from the front face of the analyzer housing when the sample metering sub-assembly 84, and in particular the pipette 336 thereof, is not positioned over and in alignment with the pipette tip tray 54.

However, when the sample metering sub-assembly 84 is positioned over and in alignment with the clean pipette tip tray 54, a bracket 805 of the sample metering sub-assembly 84 engages and pushes against the tab 803 on member 799 of pivotal plate 785 against the bias of spring 797, forcing the bent leg 789 inwardly of opening 791 to engage, or block the path of movement of, wall 793 of the pipette tip tray 54, which prevents the tray 54 from being opened by the clinician. This ensures that the tray 54 is closed and a pipette tip 56 is in proper alignment with and situated directly under the pipette 336 (proboscis) by the biasing spring 786 in the pipette tip tray 54 at the time when the pipette tip 56 is being loaded onto the pipette 336.

Yet another feature of the analyzer 2 of the present invention relates to the drawer 36 holding the diluent cup 38 and mixing cup 40, as shown in FIGS. 39, 39a and 94 and described previously. If it is desired to dilute the blood sample in the rotor 208 or sample vial 242, the electronic circuitry causes the sample metering device 84 to aspirate a desired volume of blood sample from the vial 242 or rotor 208 by energizing the pump motor 493, moves the sample metering sub-assembly 84 on the overhead carriage 330 so that the pipette tip 56 is positioned directly over and in alignment with the mixing cup 40 loaded by the clinician beforehand onto the tray, causes the sample metering sub-assembly 84 to lower so that the pipette tip 56 is received by or situated over the mixing cup 40, and energizes the pump motor 493 to deposit the blood sample into the mixing cup 40. Then, the electronic circuitry moves the sample metering sub-assembly 84 on the overhead carriage 330 to a position thereon where the pipette tip 56 is positioned directly over the diluent cup 38, causes the sample metering sub-assembly 84 to lower so that the pipette tip 56 contacts the diluent contained in the diluent cup 38 loaded by the clinician beforehand onto the tray, and energizes the pump motor 493 to aspirate a desired volume of diluent from the diluent cup 38.

The electronic circuitry then moves the sample metering sub-assembly 84 on the overhead carriage 330 again over the mixing cup 40, whereupon the pipette tip 56 is lowered over or into the mixing cup 40. The pump motor 493 is energized to expel the diluent in the pipette tip 56 into the mixing cup 40.

The sample metering sub-assembly 84 advantageously is used to mix the blood sample and diluent in the mixing cup 40. The pipette tip 56 is lowered into the mixing cup 40, and the electronic circuitry repeatedly energizes the pump motor 493 to sequentially turn in opposite rotational directions to aspirate and expel the mixture of blood sample and diluent contained in the mixing cup 40 several times to ensure that the diluent and blood sample are mixed to a sufficient degree. Then, a desired volume of the mixture may be withdrawn by the sample metering sub-assembly 84 from the mixing cup 40 either by using the same pipette tip 56, or more preferably, a clean pipette tip 56 loaded onto the pipette 336 after the previously used pipette tip 56 has been discarded, and metered onto the reagent test slides 14 in a manner as described previously.

The two receptacles or wells 790 formed in the upper surface 788 of the diluent cup and mixing cup tray may have different sizes and/or shapes, and similarly, the diluent cup 38 and mixing cup 40 may be formed with different shapes and/or sizes, so that the diluent cup 38 may only be received by the diluent cup receptacle 792, and the mixing cup 40 may only be received by the mixing cup receptacle 794. In this way, the clinician is prevented from inadvertently placing the diluent cup 38 filled with a diluent in the mixing cup receptacle 794, and the mixing cup 40 in the diluent cup receptacle 792.

Alternatively, the diluent cup 38 and the mixing cup 40 may be of the same size and shape but joined together on their outer surfaces by an elongated connection member 811.

The connection member 811 is preferably joined to the diluent cup 38 and mixing cup 40 tangentially to their outer surfaces or at least off-center from their respective diameters. A slot 813 formed in the upper surface 788 of the diluent cup and mixing cup drawer 36 interconnects the diluent cup receptacle 792 with the mixing cup receptacle 794, and this slot 813 is also positioned either tangentially to the outer circumference of the receptacles 792, 794 or off-center from their respective diameters in the same fashion as the connection member 811 is positioned with respect to the cups 38, 40. Accordingly, the diluent cup 38 and mixing cup 40, rigidly tethered together by the offset connection member 811, are placed together on the drawer 36 in their respective receptacles 792, 794, with the offset connection member 811 being received by the offset interconnecting slot 813. If the mixing cup 40 were positioned inadvertently by the clinician over the diluent cup receptacle 792, and the diluent cup 38 positioned over the mixing cup receptacle 794, the connection member 811 would not be in alignment with and would not be receivable by the offset interconnecting slot 813 so that the cups 38, 40 could not be received by the wrong receptacles 792, 794. Thus, this structure prevents the diluent cup 38 and mixing cup 40 from being incorrectly placed in the mixing cup receptacle 794 and the diluent cup receptacle 792, respectively.

The chemical analyzer 2 of the present invention is designed to be user friendly. More specifically, the chemical analyzer 2 will provide not only the test results of the analysis and a diagnosis of the possible ailments of the animal or human whose blood is being tested, but also will provide instructions on its LCD display 4 for the user to follow during operation of the analyzer 2.

The diluent cup and mixing cup drawer 36 may also include an electrical interlock or a mechanical interlock, such as the same or similar structure of the interlock described previously and used on the pipette tip tray 54, to prevent the drawer 36 from being inadvertently opened by the clinician when the sample metering sub-assembly 54 is positioned over the diluent cup and mixing cup drawer 36.

The chemical analyzer 2 of the present invention provides real time information to the user as the tests are run by displaying a plot of reflectance versus time so that a knowledgeable clinician can spot potential blood problems before the test is complete. The slide transport mechanism 26 used in the chemical analyzer 2 moves the test slides 14 circularly in a U-shaped channel 508 defined by the slide track 500, without the necessity of having a rotatable turntable, as included in the earlier VETTEST® chemical analyzer. During incubation of the test slides 14 on the slide transport mechanism 26, the temperature of the slides 14 is controlled precisely, with a minimal tolerance of plus or minus 0.2° Celsius. The slides 14 are uncovered sequentially, one at a time, to minimize evaporation during the metering operation, and for this purpose, include individual covers 600, where each cover 600 closes within two slide movements. With the slide transport mechanism 26 of the chemical analyzer 2, no slip rings are required, unlike the VETTEST® chemical analyzer.

The precise placement of the heating elements 538 and temperature sensors 566 in the slide transport mechanism 26 and within the housing 6 of the chemical analyzer 2 results in a precise temperature control of the slides 14 before and during performance of the colorimetric tests and analysis. The slide transport mechanism 26 also minimizes or eliminates any smearing of the specimens deposited on test slides 14 during their transport about the slide track 500.

The slightly raised reflectometer and fluorometer windows, which more specifically are raised in the slide track by approximately 0.002 inches, are wiped clean by the passing frames of the reagent test slides for maximum transmission of light therethrough and for accurate colorimetric measurements. The "spit" hole 524 formed in the slide track 500 removes spilled fluid or specimen, in the unlikely event that fluid gets on the slide track 500. The slide covers 600 of the transport mechanism 26 does not smear the sample deposited on the slides 14.

The chemical analyzer 2 includes test slide recognition electronics (including the optical code reader 642) that are situated in optical alignment with the transport mechanism 26. Also, a large number of slides 14, which is preferably eighteen (18), for a relatively small diameter slide track 500, is provided with the chemical analyzer 2 of the present invention, especially when trapezoidally-shaped reagent test slides 14 are used.

The sample metering sub-assembly 84 provides a more automated aspiration and metering of fluid samples. A more accurate aspiration of the sample from the centrifuge rotors 208 or sample vials 242 into the pipette tip 56 is achieved by the metering sub-assembly 84. Only about fifty (50) microliters dead volume of air is used in the pipette tip 56 during the aspiration of the fluid sample from the centrifuge rotors 208 or sample vials 242, which leads to greater precision and a more accurate deposition of sample onto the reagent test slide 14 is achieved with the metering sub-assembly 84 of the present invention.

The motion of the pipette 336 and the pipette tip 56 affixed to the distal end 454 thereof in relation to each reagent test slide 14 provides a full wetting of the slides 14. Also, the action of the metering sub-assembly 84 when depositing the fluid sample on each reagent test slide 14 minimizes or eliminates any capillary action that may wet the outer sidewall 796 of the pipette tip 56 which may have otherwise affected the accuracy and consistency of the volume of fluid sample deposited on each reagent test slide 14.

The pipette tip storage tray 54 structure is convenient for the clinician to use. Clean pipette tips 56 are loaded into the chemical analyzer 2, and each pipette tip 56 is automatically retrieved and placed on the distal end 454 of the pipette 336 without intervention by the clinician.

Furthermore, the sample metering sub-assembly 84 accurately deposits a desired volume of fluid sample on each reagent test slide 14, and this volume may be adjusted depending on the type of analyte or reagent used on the slide 14. The pump mechanism 472 and structure of the sample metering sub-assembly 84 accurately meters a desired volume of sample fluid on each test slide 14.

The sample metering sub-assembly 84 can deposit relatively minute volumes of sample on each slide 14, on the order of about five (5) to about ten (10) microliters, with a plus or minus 0.119 microliter standard deviation, so that the slides 14 are not overwetted, and a smaller volume of fluid sample is required for the chemical analyzer 2 to run a complete diagnostic check on the subject animal or human. Additionally, the method of depositing a specimen on each reagent test slide 14 minimizes or eliminates any backwetting on the outer surface 796 of the pipette tip 56, which could have otherwise affected the repeatability of depositing a consistent volume of sample on each slide 14.

The reflectometer 684 and other optics used in the chemical analyzer 2 of the present invention provide an accurate colorimetric measurement of the reagent test slides 14 for analysis by the chemical analyzer 2. The off-angle LED illumination of the slides 14 ensures more accurate readings, in spite of Z-axis variability in the position of the slides with respect to the reflectometer 684. Furthermore, unlike the VETTEST® chemical analyzer, no white (blank) reference slide is required with the chemical analyzer 2 of the present invention; the reference is preferably a tile 646 situated on the transport mechanism 26 and appropriately sensed by the reflectometer 684. The optics include an fluorometer 654 for electrolytes, as well as a reflectometer 684 for analyte slides, such as those used in the VETTEST® chemical analyzer.

The sample preparation station 328 of the present invention simplifies the operation of the analyzer 2 and requires little, if any, intervention by the clinician. A single centrifugation station is used for single or multiple patients. A unique centrifuge rotor 208, having an overfill indicator, is preferably employed in the chemical analyzer 2 of the present invention. Even though one centrifuge 210 is used, the chemical analyzer 2 of the present invention has a two patient loading system comprising two side-by-side slide inserter mechanisms 20.

The sample preparation station 328 includes a single, linear drive mechanism to retrieve and load a clean pipette tip 56 on the distal end 454 of the pipette 336 of the sample metering sub-assembly 84, aspirate a sample from the centrifuge rotors 208 and sample vials 242, deposit the specimen on the reagent test slides 14 situated on the slide transport mechanism 26, and discard the used pipette tip 56 in the pipette tip/slide discard drawer 74.

Each slide inserter mechanism 20 of the present invention cooperates with reagent test slide retaining clips 112 so that the clinician need not directly touch or handle any of the slides 14. The slide inserter mechanism 20 has the capability of intermixing stacks 218 of different test slides 14, and can accomplish batching and cueing of reagent test slides 14. The slide inserter mechanism 20, in cooperation with the particular trapezoidal shape of the reagent test slides 14, ensures that the slides 14 are loaded properly and in the correct orientation onto the slide transport mechanism 26.

The slide ejector mechanism 76 of the chemical analyzer 2 uses a simple, single pusher bar 744 which cooperates with a slot 514 formed in the transport mechanism 26 to eject the slides 14 from the slide track 500. The ejected slides 14 are directed to a slide drawer 74, which may be completely removed from the analyzer housing 6 by the clinician for their proper disposal.

The housing 6 of the chemical analyzer 2 includes electrically interlocked (by their connection to their respective driving motors) sliding doors 16 behind which are housed the slider inserter mechanisms 20 to ensure that the user of the chemical analyzer 2 does not have access to any of the stations or components in the interior of the housing 6 during the operation of the chemical analyzer 2.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method of maintaining an end of a pipette tip mounted to a pipette of a sample metering sub-assembly below the surface level of a fluid contained in a fluid container having an open end and a variable diameter in longitudinal cross-section at a substantially constant depth in the fluid relative to the surface level of the fluid as the fluid is being aspirated into the pipette tip and as the surface level of the fluid contained in the fluid container is decreasing using a chemical analyzer, wherein the chemical analyzer includes the sample metering sub-assembly, the sample metering sub-assembly having the pipette which is vertically movable, and a pump operatively coupled to the pipette, the pipette including an elongated member having a bore extending axially therein, the pump being in fluid communication with the pipette bore and selectively creating one of a negative air pressure and a positive air pressure within the pipette bore, the pipette including a first axial end operatively coupled to the pump, and a second axial end opposite the first axial end for fluidtightly receiving the pipette tip, the interior geometrical dimensions of the fluid container being known, wherein the method comprises the steps of:

pre-programming the known interior geometrical dimensions of the fluid container into the chemical analyzer;

positioning the pipette of the sample metering sub-assembly over the open end of the fluid container, the pipette having mounted thereon the pipette tip, the open end of the fluid container being dimensioned to receive at least a portion of the pipette tip and to allow the pipette tip to contact the fluid contained therein;

vertically lowering the pipette of the sample metering sub-assembly toward the surface level of the fluid contained in the fluid container;

detecting the surface level of the fluid contained in the fluid container by performing the sub-steps of:

creating a negative air pressure within at least one of the bore of the pipette and the pump in fluid communication with the pipette bore as the pipette is being vertically lowered toward the fluid container;

sensing the pressure within at least one of the pump and the bore of the pipette of the sample metering sub-assembly as the pipette is being vertically lowered toward the surface level of the fluid contained in the fluid container; and detecting a change in the pressure sensed in the at least one of the pipette bore and the pump in fluid communication with the pipette bore, the change in pressure being indicative of the pipette tip mounted on the pipette contacting the surface level of the fluid contained in the fluid container;

calculating the variable position of the surface level of the fluid within the fluid container as a desired volume of fluid is removed therefrom by aspirating the fluid into the pipette tip at a substantially constant rate based on the known interior geometric dimensions of the fluid container;

positioning the end of the pipette tip mounted on the pipette of the sample metering sub-ssembly at a desired depth below the detected surface level of the fluid;

aspirating into the pipette tip a volume of fluid from the fluid container at the substantially constant rate; and vertically lowering the pipette of the sample metering sub-assembly below the detected surface level of the fluid at an adjustable rate based on the first detected surface level of the fluid, the calculated variable position of the surface level of the fluid and the known interior geometrical dimensions of the fluid container as fluid is aspirated into the pipette tip from the fluid container at a constant rate to maintain the end of the pipette tip below the surface level of the fluid at the substantially constant relative depth.

2. A method of maintaining an end of a pipette tip mounted to a pipette of a sample metering sub-assembly below the surface level of a fluid as defined by claim 1, wherein the substantially constant depth at which the end of the pipette tip is maintained below the surface level of the fluid contained in the fluid container is about one millimeter.

3. A method of maintaining an end of a pipette tip mounted to a pipette of a sample metering sub-assembly below the surface level of a fluid as defined by claim 1, wherein the fluid container is one of a centrifuge rotor, a sample vial and a diluent cup.

* * * * *